United States Patent
Khvorova et al.

(10) Patent No.: US 10,233,449 B2
(45) Date of Patent: *Mar. 19, 2019

(54) METHODS AND COMPOSITIONS FOR SELECTING SIRNA OF IMPROVED FUNCTIONALITY

(71) Applicant: Thermo Fisher Scientific Inc., Lafayette, CO (US)

(72) Inventors: Anastasia Khvorova, Northborough, MA (US); Angela Reynolds, Conifer, CO (US); Devin Leake, Denver, CO (US); William Marshall, Boulder, CO (US); Steven Read, Denver, CO (US); Stephen Scaringe, Lafayette, CO (US)

(73) Assignee: Thermo Fisher Scientific Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/705,650

(22) Filed: Sep. 15, 2017

(65) Prior Publication Data

US 2018/0119144 A1 May 3, 2018

Related U.S. Application Data

(63) Continuation of application No. 14/965,816, filed on Dec. 10, 2015, now Pat. No. 9,777,270, which is a continuation of application No. 14/097,551, filed on Dec. 5, 2013, now Pat. No. 9,228,186, which is a continuation-in-part of application No. 10/940,892, filed on Sep. 14, 2004, which is a continuation of application No. PCT/US2004/014885, filed on May 12, 2004, which is a continuation-in-part of application No. 10/714,333, filed on Nov. 14, 2003, now Pat. No. 8,090,542.

(60) Provisional application No. 60/502,050, filed on Sep. 10, 2003, provisional application No. 60/426,137, filed on Nov. 14, 2002.

(51) Int. Cl.
| | |
|---|---|
| *C12N 15/113* | (2010.01) |
| *A61K 31/713* | (2006.01) |
| *C12N 15/10* | (2006.01) |
| *C12N 15/11* | (2006.01) |

(52) U.S. Cl.
CPC .......... *C12N 15/113* (2013.01); *A61K 31/713* (2013.01); *C12N 15/1048* (2013.01); *C12N 15/111* (2013.01); *C12N 15/1135* (2013.01); *C12N 15/1136* (2013.01); *C12N 15/1137* (2013.01); *C12N 15/1138* (2013.01); *C12Y 113/12007* (2013.01); *C12Y 502/01008* (2013.01); *C12N 2310/14* (2013.01); *C12N 2320/10* (2013.01); *C12N 2320/11* (2013.01)

(58) Field of Classification Search
None
See application file for complete search history.

(56) References Cited

U.S. PATENT DOCUMENTS

| | | |
|---|---|---|
| 5,958,773 A | 9/1999 | Monia et al. |
| 6,001,992 A | 12/1999 | Ackermann et al. |
| 6,046,319 A | 4/2000 | Power et al. |
| 6,111,086 A | 8/2000 | Scaringe |
| 6,150,092 A | 11/2000 | Uchida et al. |
| 6,172,216 B1 | 1/2001 | Bennett et al. |
| 6,291,642 B1 | 9/2001 | Weinstein |
| 6,506,559 B1 | 1/2003 | Fire et al. |
| 6,566,127 B1 | 5/2003 | Pavco et al. |
| 6,590,093 B1 | 7/2003 | Scaringe |
| 6,770,633 B1 | 8/2004 | Robbins et al. |
| 6,965,025 B2 | 11/2005 | Gaarde et al. |
| 6,994,979 B2 | 2/2006 | Reed et al. |
| 7,022,831 B1 | 4/2006 | Reed |
| 7,022,837 B2 | 4/2006 | Harding et al. |
| 7,033,830 B2 | 4/2006 | Karras et al. |
| 7,074,769 B2 | 7/2006 | Stein et al. |
| 7,157,570 B2 | 1/2007 | Yun |
| 7,176,304 B2 | 2/2007 | McSwiggen et al. |
| 7,250,496 B2 | 7/2007 | Bentwich |
| 7,371,735 B2 | 5/2008 | Harel-Bellan et al. |
| 7,399,853 B2 | 7/2008 | Freier et al. |
| 7,427,605 B2 | 9/2008 | Davis et al. |
| 7,459,547 B2 | 12/2008 | Zamore et al. |
| 7,507,811 B2 | 3/2009 | Khvorova et al. |
| 7,511,132 B2 | 3/2009 | Khvorova et al. |
| 7,514,550 B2 | 4/2009 | Khvorova et al. |
| 7,521,191 B2 | 4/2009 | Khvorova et al. |
| 7,541,453 B2 | 6/2009 | Khvorova et al. |

(Continued)

FOREIGN PATENT DOCUMENTS

| | | |
|---|---|---|
| EP | 1 637 144 | 3/2006 |
| EP | 2 344 639 | 7/2011 |

(Continued)

OTHER PUBLICATIONS

Abeliovich, et al. (2000) Mice Lacking Alph-Synuclein Display Functional Deficits in the Nigrostriatal Dopamine System. Neuron v.25:239-52.

(Continued)

*Primary Examiner* — Richard A Schnizer
(74) *Attorney, Agent, or Firm* — Fenwick & West LLP

(57) ABSTRACT

Efficient sequence specific gene silencing is possible through the use of siRNA technology. By selecting particular siRNAs by rational design, one can maximize the generation of an effective gene silencing reagent, as well as methods for silencing genes. Methods, compositions, and kits generated through rational design of siRNAs are disclosed including those directed to nucleotide sequences for TTR.

12 Claims, 43 Drawing Sheets

Specification includes a Sequence Listing.

(56) References Cited

U.S. PATENT DOCUMENTS

| | | |
|---|---|---|
| 7,550,572 B2 | 6/2009 | Khvorova et al. |
| 7,569,684 B2 | 8/2009 | Khvorova et al. |
| 7,576,196 B2 | 8/2009 | Khvorova et al. |
| 7,576,197 B2 | 8/2009 | Khvorova et al. |
| 7,579,457 B2 | 8/2009 | Khvorova et al. |
| 7,579,458 B2 | 8/2009 | Khvorova et al. |
| 7,582,746 B2 | 9/2009 | Khvorova et al. |
| 7,582,747 B2 | 9/2009 | Khvorova et al. |
| 7,589,191 B2 | 9/2009 | Khvorova et al. |
| 7,592,442 B2 | 9/2009 | Khvorova et al. |
| 7,592,443 B2 | 9/2009 | Khvorova et al. |
| 7,592,444 B2 | 9/2009 | Khvorova et al. |
| 7,595,387 B2 | 9/2009 | Leake et al. |
| 7,595,388 B2 | 9/2009 | Khvorova et al. |
| 7,595,389 B2 | 9/2009 | Khvorova et al. |
| 7,598,369 B2 | 10/2009 | Khvorova et al. |
| 7,598,370 B2 | 10/2009 | Khvorova et al. |
| 7,605,250 B2 | 10/2009 | Khvorova et al. |
| 7,605,252 B2 | 10/2009 | Khvorova et al. |
| 7,608,706 B2 | 10/2009 | Khvorova et al. |
| 7,608,707 B2 | 10/2009 | Khvorova et al. |
| 7,612,196 B2 | 11/2009 | Khvorova et al. |
| 7,615,541 B2 | 11/2009 | Khvorova et al. |
| 7,619,081 B2 | 11/2009 | Khvorova et al. |
| 7,632,938 B2 | 12/2009 | Khvorova et al. |
| 7,632,939 B2 | 12/2009 | Khvorova et al. |
| 7,635,770 B2 | 12/2009 | Khvorova et al. |
| 7,635,771 B2 | 12/2009 | Khvorova et al. |
| 7,638,621 B2 | 12/2009 | Khvorova et al. |
| 7,638,622 B2 | 12/2009 | Khvorova et al. |
| 7,642,349 B2 | 1/2010 | Khvorova et al. |
| 7,645,869 B2 | 1/2010 | Khvorova et al. |
| 7,645,870 B2 | 1/2010 | Khvorova et al. |
| 7,655,788 B2 | 2/2010 | Khvorova et al. |
| 7,655,789 B2 | 2/2010 | Khvorova et al. |
| 7,662,950 B2 | 2/2010 | Khvorova et al. |
| 7,666,853 B2 | 2/2010 | Khvorova et al. |
| 7,674,896 B2 | 3/2010 | Khvorova et al. |
| 7,678,896 B2 | 3/2010 | Khvorova et al. |
| 7,691,997 B2 | 4/2010 | Khvorova et al. |
| 7,691,998 B2 | 4/2010 | Khvorova et al. |
| 7,696,344 B2 | 4/2010 | Khvorova et al. |
| 7,709,629 B2 | 5/2010 | Khvorova et al. |
| 7,718,629 B2 | 5/2010 | Bumcrot et al. |
| 7,737,267 B2 | 6/2010 | Khvorova et al. |
| 7,741,470 B2 | 6/2010 | Khvorova et al. |
| 7,745,610 B2 | 6/2010 | Khvorova et al. |
| 7,745,611 B2 | 6/2010 | Khvorova et al. |
| 7,745,612 B2 | 6/2010 | Khvorova et al. |
| 7,781,575 B2 | 8/2010 | Khvorova et al. |
| 7,795,420 B2 | 9/2010 | Khvorova et al. |
| 7,795,421 B2 | 9/2010 | Khvorova et al. |
| 7,803,933 B2 | 9/2010 | Khvorova et al. |
| 7,807,819 B2 | 10/2010 | Khvorova et al. |
| 7,807,820 B2 | 10/2010 | Khvorova et al. |
| 7,816,512 B2 | 10/2010 | Khvorova et al. |
| 7,820,809 B2 | 10/2010 | Khvorova et al. |
| 7,829,696 B2 | 11/2010 | Khvorova et al. |
| 7,833,989 B2 | 11/2010 | Khvorova et al. |
| 7,834,170 B2 | 11/2010 | Khvorova et al. |
| 7,897,754 B2 | 3/2011 | Khvorova et al. |
| 7,898,754 B2 | 3/2011 | Liao |
| 7,935,813 B2 | 5/2011 | Khvorova et al. |
| 7,951,935 B2 | 5/2011 | Khvorova et al. |
| 7,977,471 B2 | 7/2011 | Khvorova et al. |
| 7,985,854 B2 | 7/2011 | Khvorova et al. |
| 7,999,097 B2 | 8/2011 | Khvorova et al. |
| 8,000,902 B2 | 8/2011 | Khvorova et al. |
| 8,008,474 B2 | 8/2011 | Khvorova et al. |
| 8,013,145 B2 | 9/2011 | Khvorova et al. |
| 8,090,542 B2 | 1/2012 | Khvorova et al. |
| 8,168,775 B2 | 5/2012 | Sah et al. |
| 8,741,866 B2 | 6/2014 | Sah et al. |
| 9,228,186 B2 | 1/2016 | Khvorova et al. |
| 9,234,196 B2 | 1/2016 | Sah et al. |
| 2002/0081578 A1 | 6/2002 | Plowman et al. |
| 2002/0086321 A1 | 7/2002 | Craig |
| 2002/0086356 A1 | 7/2002 | Tuschl et al. |
| 2002/0150945 A1 | 10/2002 | Finney et al. |
| 2002/0160394 A1 | 10/2002 | Wu |
| 2003/0072794 A1 | 4/2003 | Boulikas |
| 2003/0087249 A1 | 5/2003 | Glucksmann |
| 2003/0087259 A1 | 5/2003 | Clancy et al. |
| 2003/0105051 A1 | 6/2003 | McSwiggen |
| 2003/0142597 A1 | 7/2003 | Finney et al. |
| 2003/0143597 A1 | 7/2003 | Finney et al. |
| 2003/0143732 A1 | 7/2003 | Fosnaugh et al. |
| 2003/0157030 A1 | 8/2003 | Davis et al. |
| 2003/0170891 A1 | 9/2003 | McSwiggen |
| 2003/0224512 A1 | 12/2003 | Dobie |
| 2003/0228597 A1 | 12/2003 | Cowsert et al. |
| 2003/0229037 A1 | 12/2003 | Massing et al. |
| 2004/0006365 A1 | 1/2004 | Brady et al. |
| 2004/0014956 A1 | 1/2004 | Woolf et al. |
| 2004/0029275 A1 | 2/2004 | Brown et al. |
| 2004/0054155 A1 | 3/2004 | Woolf et al. |
| 2004/0063654 A1 | 4/2004 | Davis et al. |
| 2004/0077574 A1 | 4/2004 | Klinghoffer et al. |
| 2004/0101857 A1 | 5/2004 | Ward et al. |
| 2004/0101915 A1 | 5/2004 | Deveraux et al. |
| 2004/0102391 A1 | 5/2004 | Dean et al. |
| 2004/0137471 A1 | 7/2004 | Vickers et al. |
| 2004/0180357 A1 | 9/2004 | Reich et al. |
| 2004/0191818 A1 | 9/2004 | O'Toole et al. |
| 2004/0192629 A1 | 9/2004 | Xu et al. |
| 2004/0204380 A1 | 10/2004 | Ackermann et al. |
| 2004/0219671 A1 | 11/2004 | McSwiggen et al. |
| 2004/0248296 A1 | 12/2004 | Beresford et al. |
| 2004/0248299 A1 | 12/2004 | Jayasena et al. |
| 2004/0259247 A1 | 12/2004 | Tuschl et al. |
| 2005/0048529 A1 | 3/2005 | McSwiggen |
| 2005/0106726 A1 | 5/2005 | McSwiggen et al. |
| 2005/0107328 A1 | 5/2005 | Wyatt et al. |
| 2005/0130181 A1 | 6/2005 | McSwiggen |
| 2005/0176025 A1 | 8/2005 | McSwiggen et al. |
| 2005/0181382 A1 | 8/2005 | Zamore et al. |
| 2005/0186586 A1 | 8/2005 | Zamore et al. |
| 2005/0227935 A1 | 10/2005 | McSwiggen et al. |
| 2005/0239731 A1 | 10/2005 | McSwiggen et al. |
| 2005/0244869 A1 | 11/2005 | Brown-Driver et al. |
| 2005/0245475 A1 | 11/2005 | Khvorova et al. |
| 2005/0255487 A1 | 11/2005 | Khvorova et al. |
| 2005/0261485 A1 | 11/2005 | Uchida |
| 2005/0272680 A1 | 12/2005 | Bhanot et al. |
| 2005/0276804 A1 | 12/2005 | Smith et al. |
| 2006/0008910 A1 | 1/2006 | MacLachlan et al. |
| 2006/0025372 A1 | 2/2006 | Bhanot et al. |
| 2006/0069056 A1 | 3/2006 | Feinstein et al. |
| 2006/0083780 A1 | 4/2006 | Heyes et al. |
| 2006/0134189 A1 | 6/2006 | MacLachlan et al. |
| 2006/0135460 A1 | 6/2006 | Widder et al. |
| 2006/0240093 A1 | 10/2006 | MacLachlan et al. |
| 2006/0263435 A1 | 11/2006 | Davis et al. |
| 2006/0286575 A1 | 12/2006 | Farrell et al. |
| 2007/0004664 A1 | 1/2007 | McSwiggen et al. |
| 2007/0021360 A1 | 1/2007 | Nyce et al. |
| 2007/0021369 A1 | 1/2007 | Doucette-Stamm et al. |
| 2007/0031844 A1 | 2/2007 | Khvorova et al. |
| 2007/0039072 A1 | 2/2007 | Khvorova et al. |
| 2007/0135372 A1 | 6/2007 | MacLachlan et al. |
| 2007/0207974 A1 | 9/2007 | Khvorova et al. |
| 2007/0254850 A1 | 11/2007 | Lieberman et al. |
| 2007/0269395 A1 | 11/2007 | Christiano |
| 2007/0275465 A1 | 11/2007 | Woppmann et al. |
| 2007/0281899 A1 | 12/2007 | Bumcrot et al. |
| 2007/0281901 A1 | 12/2007 | Yanni et al. |
| 2008/0108583 A1 | 5/2008 | Feinstein |
| 2008/0113351 A1 | 5/2008 | Naito et al. |
| 2008/0124370 A1 | 5/2008 | Marx |
| 2008/0188675 A1 | 8/2008 | Chen et al. |
| 2008/0287382 A1 | 11/2008 | Feinstein et al. |
| 2009/0023215 A1 | 1/2009 | Jessee et al. |
| 2009/0023673 A1 | 1/2009 | Manoharan et al. |
| 2009/0082291 A1 | 3/2009 | Feinstein et al. |

(56) References Cited

U.S. PATENT DOCUMENTS

| | | | |
|---|---|---|---|
| 2009/0082300 A1 | 3/2009 | Brown-Driver et al. |
| 2009/0105173 A1 | 4/2009 | Feinstein |
| 2009/0149403 A1 | 6/2009 | MacLachlan et al. |
| 2009/0247608 A1 | 10/2009 | Manoharan et al. |
| 2009/0291131 A1 | 11/2009 | MacLachlan et al. |
| 2010/0029746 A1 | 2/2010 | Feinstein |
| 2010/0120893 A1 | 5/2010 | Sah et al. |
| 2010/0130588 A1 | 5/2010 | Yaworski et al. |
| 2010/0324120 A1 | 12/2010 | Chen et al. |
| 2011/0015250 A1 | 1/2011 | Bumcrot et al. |
| 2011/0237646 A1 | 9/2011 | Smith et al. |
| 2011/0294868 A1 | 12/2011 | Monia et al. |
| 2012/0052487 A9 | 3/2012 | Khvorova et al. |
| 2012/0149109 A1 | 6/2012 | Brown-Driver et al. |
| 2012/0225927 A1 | 9/2012 | Sah et al. |
| 2012/0244207 A1 | 9/2012 | Fitzgerald et al. |
| 2012/0294905 A1 | 11/2012 | Sah |
| 2013/0143732 A1 | 6/2013 | Aoki |
| 2013/0281510 A1 | 10/2013 | Ando et al. |
| 2014/0194493 A1 | 7/2014 | Sah et al. |

FOREIGN PATENT DOCUMENTS

| | | |
|---|---|---|
| EP | 2 496 238 | 9/2012 |
| WO | WO 98/00532 | 1/1998 |
| WO | WO 99/38965 | 8/1999 |
| WO | WO 99/54459 | 10/1999 |
| WO | WO 99/55910 | 11/1999 |
| WO | WO 00/20645 | 4/2000 |
| WO | WO 00/21559 | 4/2000 |
| WO | WO 00/32765 | 6/2000 |
| WO | WO 00/44194 | 7/2000 |
| WO | WO 00/44895 | 8/2000 |
| WO | WO 00/76497 | 12/2000 |
| WO | WO 01/36646 | 5/2001 |
| WO | WO 01/68836 | 9/2001 |
| WO | WO 02/44321 | 6/2002 |
| WO | WO 02/055693 | 7/2002 |
| WO | WO 02/55693 | 7/2002 |
| WO | WO 02/059300 | 8/2002 |
| WO | WO 03/035869 | 5/2003 |
| WO | WO 03/035870 | 5/2003 |
| WO | WO 03/046176 | 6/2003 |
| WO | WO 03/062394 | 7/2003 |
| WO | WO 03/064625 | 8/2003 |
| WO | WO 03/064626 | 8/2003 |
| WO | WO 03/070897 | 8/2003 |
| WO | WO 03/070910 | 8/2003 |
| WO | WO 03/070918 | 8/2003 |
| WO | WO 03/070969 | 8/2003 |
| WO | WO 03/646625 | 8/2003 |
| WO | WO 03/072704 | 9/2003 |
| WO | WO 03/074654 | 9/2003 |
| WO | WO 2004/031237 | 4/2004 |
| WO | WO 2004/031327 | 4/2004 |
| WO | WO 2004/045543 | 6/2004 |
| WO | WO 2004/046324 | 6/2004 |
| WO | WO 2004/048511 | 6/2004 |
| WO | WO 2004/080406 | 9/2004 |
| WO | WO 2004/090105 | 10/2004 |
| WO | WO 2004/090108 | 10/2004 |
| WO | WO 2004/094636 | 11/2004 |
| WO | WO 2004/111191 | 12/2004 |
| WO | WO 2005/001043 | 1/2005 |
| WO | WO 2005/062937 | 7/2005 |
| WO | WO 2005/078095 | 8/2005 |
| WO | WO 2005/089224 | 9/2005 |
| WO | WO 2005/117991 | 12/2005 |
| WO | WO 2005/120152 | 12/2005 |
| WO | WO 2006/006948 | 1/2006 |
| WO | WO 2006/015389 | 2/2006 |
| WO | WO 2006/110813 | 10/2006 |
| WO | WO 2007/012191 | 2/2007 |
| WO | WO 2007/087451 | 8/2007 |
| WO | WO 2008/042973 | 4/2008 |
| WO | WO 2009/001359 | 12/2008 |
| WO | WO 2009/044392 | 4/2009 |
| WO | WO 2009/086558 | 7/2009 |
| WO | WO 2009/127060 | 10/2009 |
| WO | WO 2010/042877 | 4/2010 |
| WO | WO 2010/048228 | 4/2010 |
| WO | WO 2010/053572 | 5/2010 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/147992 | 12/2010 |
| WO | WO 2011/056883 | 5/2011 |
| WO | WO 2011/123468 | 10/2011 |

OTHER PUBLICATIONS

Abifadel et al. Mutations in PCSK9 cause autosomal dominant hypercjolesterolemia. (2003) Nature Genetics, vol. 34, pp. 154-156.

Agrawal, S., et al., "Antisense oligonucleotides: towards clinical trials." Trends in Biotechnology. Oct. 1996, vol. 14, pp. 376-387.

Akinc, A., et al., "A combinatorial library of lipid-like materials for delivery of RNAi therapeutics." Nature Biotechnology, 2008, vol. 26, pp. 561-569.

Almeida, M.-R., et al., "Small Transthyretin (TTR) Ligands as Possible Therapeutic Agents in TTR Amyloidoses," Current Drug Targets—CNS & Neurological Disorders, Oct. 2005, pp. 587-596, vol. 4, No. 5.

Amarzguioui M et al, Tolerance for mutations and chemical modifications in a siRNA Nucleic Acids Research vol. 31, No. 2, Jan. 15, 2003 pp. 589-595 , XP002270887 ISSN: 0305-1048.

Amarzguloui, Mohammed et al. Secondary structure prediction and in vitro accessibilty of mRNA as tools in the selection of target sites for ribozymes 2000 Oxford University Press, Nucleic Acid Research, 2000, vol. 28, No. 21 pp. 4113-4124.

Bass, B., "The short answer," Nature, May 24, 2001, pp. 428-429, vol. 411.

Benson, M., et al., "Targeted suppression of an amyloidogenic transthyretin with antisense oligonucleotides," Muscle & Nerve, Jan. 18, 2006, pp. 609-618, vol. 33, No. 5.

Betrand (2002) Comparison of Antisense Oligonucleotides and siRNAs in cell culture and in vivo, Biotechnical and Biophysicial Research Communication 296:1000-1004.

Boutla et al., Short 5'-phosphorylated double-stranded RNAs induce RNA interference in *Drosophila*, 2001, Current Biology, vol. 11, pp. 1776-1780.

Brown et al. (1997) Identification and cDNA Cloning of a Novel Mammalian C2 Domain-Containing Phosphoinositide 3-kinase, HsC2-PI3K. Biochemical and Biophysical Research Communications. 233, 537-544.

Brummelkamp et al. A System for Stable Expression of Short Intereferring RNAs in Mammalian Cells, Science vol. 296 pp. 550-553 (2002).

Cahill et al. (1999) Genomics. 58:181-187.

Caplen et al. Gene 2000, vol. 252, p. 95-105.

Caplen et al. Specific inhibition of gene expression by small double-stranded RNAs in invertebrate systems, Proc. Natl. Acad. Sci USA vol. 98, pp. 9742-9747 (2001).

Caplen, RNAi as a gene therapy approach, Expert Opin. Biol. Ther. 2003, vol. 3, p. 575-586 (2003).

Caplen. dsRNA-mediated gene silencing in cultured *Drosophila* cells: a tissue culture model for analysis of RNA interference. Gene, vol. 252, p. 95-105 (2000).

Chalk, A.M et al. (2005) siRNAdb: a database of siRNA sequences. Nucleic Acids Res. 33:D131-134.

Chalk, et al. (2004) Improved and automated prediction of effective siRNA. Biochem Biophys Res Comm 319:264-274.

Chen et al. (2005) TSSK5, A Novel Member of the Testis-Specific Serine/Threonin Kinase Family, Phosphorylates CREB at Ser-122, and Stimulates the CRE-CREB Responsive Pathway. Biochemical and Biophysical Research Communications. 333: 742-749.

(56) References Cited

OTHER PUBLICATIONS

Cherry, Michael J. (1995) Computer Manipulation of DNA and Protein Sequences. Current Protocols in Molecular Biology. 7.7.1-7.7.23.

Chi, J.-T. et al. (2003) Genome wide view of gene silencing by small interfering RNAs. Proc. Natl. Acad. Sci. USA 100/11:6343-6346.

Chinault, Overlap Hybridization Screening: Isolation and Characterization of Overlapping DNA Framgments Surroungin the leu2 Gene on Yeast Chromosome III (1979), 5(2):111-26.

Daniel et al., Specific association of Type I with Ran GTPase in lipopolysacchardie-mediated differentiation, Oncogene 2001, vol. 20: 2618-2625.

Dodelet et al. (2000) Eph Receptors and Ephrin Ligands: embryogenesis to tumorigenesis. Oncogene 19:5614-5619.

Domin et al.(1997) Cloning of Human Phosphoinositide 3-Kinase with a C2 Domain that Displays Reduced Sensitivity to the Inhibitor Wortmannin. Biochem. J., v.325:139-47.

Dottori, et al. (1998) EphA4 (Sek1) receptor tyrosine kinase is required for the development of the corticospinal tract, Proc. Natl. Acad. Sci. vol. 95, pp. 13248-13253, Neurobiology.

Ekholm, et al.,(2004) Deregulation of Cyclin E in Human Cells Interferes with Prereplication Complex Assembly, The Journal of Cell Biology. vol. 165, pp. 789-800.

El Touny, et al. (2006) Identification of Both Myt-I and Wee-I as Necessary Mediators of the P2I-Independent Inactivation of the Cdc-2/Cyclin BI complex and Growth Inhibition of TRAMP Cancer Cells by Genistein. The Prostate, vol. 66:1542-1555.

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.

Elbashir, S., et al., "RNA Interference is Mediated by 21-and 22 Nucleotide RNAs," Genes & Development, 2001, pp. 188-200, vol. 15.

European Patent Office, Communication pursuant to Article 94(3) EPC for European Patent Application No. 09 810 834.3, dated Feb. 15, 2012, 6 pages.

European Patent Office, Office Action dated Nov. 15, 2007. Application No. 03 786 798.3, 6 pages.

Examination Report dated Jun. 14, 2011, for New Zealand Patent Application No. 592867, 2 Pages.

Extended European Search Report for European Patent Application No. EP 10829034.7, dated Aug. 30, 2013, 10 Pages.

Far, R. K.-K. et al. (2003) The activity of siRNA in mammalian cells is related to structural target accessibility: a comparison with antisense oligonucleotides. Nucleic Acids Res. 31/15:4417-4424.

Feng, et al. (2003) Inhibiting the Expression of DNA Replication-Initiation Proteins Induces Apoptosis in Human Cancer Cells. Cancer Research, vol. 63, pp. 7356-7364.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in Caenorhabditis elegans," Nature, Feb. 19, 1998, pp. 806-811, vol. 391.

Fox, et al. (1995) cDNA Cloning and Tissue Distribution of Five Human EPH-like Receptor Protein-tyrosine kinases, Oncogene; 10(5):897-905.

Futami et al. (2002) Induction of Apoptosis in Hela Cells With siRNA Expression Vector Targeted Against BCL-2. Nucleic Acids Research Supplement No. 2:251-252.

Gautam et al. Heparin-binding protein (HBP/CAP37): A missing link in neutrophil-evoked alteration of vascular permeability, Nature Medicine 2001, vol. 7, pp. 1123-1127.

Genbank Accession NM 001790 Oct. 10, 2008 http://www.ncbi.nlm.nih.gov/entrez/viewer.fcgi?db=nuccore&id=12562539.

Genbank Accession No. NM.sub.—138578, http://www.ncbi.nlm.nih.gov/entrez/viewer.fcgi?db=nuccore&id=20336334. Accessed on Aug. 11, 2008.

GenBank Accession No. NM.sub.—000371.2, "*Homo sapiens* transthyretin (TTR), mRNA," Dec. 21, 2008, three pages.

GenBank Accession No. NM.sub.—000371.3, "*Homo sapiens* transthyretin (TTR), mRNA," Sep. 23, 2012, four pages.

Genbank Accession No. NM.sub.—002645.2, http://www.ncbi.nlm.nih.gov/entrez/viewer.fcgi?db=nuccore&id=157671928. Accessed on Jul. 31, 2008.

GenBank Accession No. NM.sub.—012681.1, "Rattus norvegicus transthyretin (TTR), mRNA," Feb. 14, 2010, two pages.

GenBank Accession No. NM.sub.—013697.2, "Mus musculus transthyretin (TTR), mRNA," Apr. 5, 2007, three pages.

Genbank Accession Z15005.1 (1993).

Hammond et al., Post-transcriptional gene silencing by double-stranded RNA, Nature Reviews, 2001, vol. 2, 110-119, MacMilan Magazines Ltd.

Hao, et al. (2004) Expression Analysis of the Human Testis-specific Serine/Threonine Kinase (TSSK) Homologues. A TSSK member is Present in the Equatorial Segment of Human Sperm. Molecular Human Reproduction, vol. No. 6 pp. 433-444.

Hara, R., et al., "Impact of Liver Transplantation on Transthyretin-Related Ocular Amyloidosis in Japanese Patients," Arch Ophthalmol, Feb. 2010, pp. 206-210, vol. 128, No. 2.

Harborth et al. Identification of Essential Genes in Cultured Mammalian Cells Using Small Interfering RNAs. (2001) J. Cell. Sci. 114:4557-4565.

Heyes, et al., "Cationic lipid saturation influences intracellular delivery of encapsulated nucleic acids," Journal of Controlled Release, 2005, pp. 276-287, vol. 107.

Ho, Nucleic Acids Research, vol. 24: 1901-1907 (1996).

Holen, et al. (2002) Positional Effects of Shorts Interfering RNAs Targeting the Human Coagulation Trigger Tissue Factor. Nucleic Acids Research, vol. 30, No. 8, pp. 1757-1766.

Hornung, V., et al., "Sequence-specific potent induction of IFN-.alpha. by short interfering RNA in plasmacytoid dendritic cells throughTLR7," Nature Medicine, Mar. 2005, pp. 263-270, vol. 11, No. 3.

Human Neuropeptide Y Blast results, http://www.ncbi.nlm.nih.gov/blast, accessed on Mar. 18, 2008.

IHOP [online] [retrieved on Sep. 9, 2008]. Retrieved from the Internet. <http://www.ihop-net.org/UniPub/iHOP/bng1119248.html?list=0>.

Iliakis et al. (1990) Induction and Repair of DNA Strand Breaks in Radiation-resistant Cells Obtained by Transformation of Primary Rat Embryo Cells with the Oncogenes H-ras and v-myc. Cancer Research, 50, pp. 6575-6579.

International Search Report for PCT/US04/14885, dated Sep. 24, 2007 (Brusca).

Ishibashi et al., A Novel Dual Specificity Phosphatase Induced by Setum Stimulation and Heat Shock, (1994) J. Biol. Chem. 47: 2897-2902.

Ishimi et al., Enhanced expression of Mcm proteins in cancer cells derived from uterine cervix, 2003, European Journal of Biochemistry, vol. 270, pp. 1089-1101.

Jackson, et al., Expression profiling reveals off-target gene regulation by RNAi, Nature Biotechnology, vol. 21, pp. 635-637 (2003).

Jiang, Bcl-2 constitutively suppresses p53-dependent apoptosis in colorectal cancer cells, Genes & Development 17:832-837 (2003).

Kalra et al., Central Administration of Antisense oligodeoxynucleotides to neuropeptide Y (NPY) mRNA reveals the critical role of newly synthesized NPY in regulation of LHRH release, 1995, Regulatory Peptides, vol. 59, pp. 215-220.

Kasif, Simon et al, A computational framework for optimal masking in the synthesis of oligonucleotide micrarrays 2002 Oxford University Press, Nucleic Acid Research, 2002, vol. 30, No. 20 e106.

Khvorova, A. et al. (2003) Functional siRNAs and miRNAs Exhibit Strand Bias. Cell 115:209-216.

Kretscmer-Kazemei, The Activity of siRNA in mammalian cells is related to structural target accessibility: a comparison with antisense oligonucleoitdes (2003).

(56) References Cited

OTHER PUBLICATIONS

Kumar, R. et al. (2003) High-Throughput Selection of Effective RNAi Probes for Gene Silencing. Genome Res. 13:2333-2340.
Kurosawa, T., et al., "Selective silencing of a mutant transthyretin allele by small interfering RNAs" Biochem Biophys Res Commun., Nov. 25, 2005, vol. 337, No. 3, pp. 1012-1018.
Laitala et al., Inhibition of Bone Resorption in Vitro by Antisense RNA and DNA Molecules Targeted against Carbonic Anhydrase II or Two Subuntis of Vacuolar H + ATPase, Journal of Clinical Investigation 1994, vol. 93, pp. 2311-2318.
Lapidot-Lifson, et al. (1992) Cloning and Antisense Oligodeoxynucleotide Inhibition of a Human Homolog of cdc2 required in Hematopoiesis, Proc. Natl. Acad. Sci. vol. 89, pp. 579-583.
Levenkova, N. et al. (2004) Gene specific siRNA selector. Bioinformatics 20/3:430-432.
Lindgren, et al. (2002) Contribution of Known and Unknown Susceptibility Genes to Early-Onset Diabetes in Scandinavia, Diabetes vol. 51, 1609-1617.
Love, K., et al., "Lipid-like materials for low-dose, in vivo gene silencing," PNAS, Feb. 2, 2010, pp. 1864-1869, vol. 107, No. 5.
Lshimi et al., Enhanced expression of Mcm proteins in cancer cells derived from uterine cervix, 2003, European Journal of Biochemistry, vol. 270, pp. 1089-1101.
Lu, et al., The Human AQP4 gene: Definition of the locus encoding two water channel polypeptides in brain, Proc. Natl Acad. Sci vol. 93, pp. 10908-10912 (Oct. 1996).
Maeda, S., "Use of genetically altered mice to study the role of serum amyloid P component in amyloid deposition," Amyloid, 2003, vol. 10, Suppl. 1, pp. 17-20.
Marathi et al. RAD1, A Human Structural Homolog of the Schizosaccharomyces pombe RAD1 Cell Cycle Checkpoint Gene, 1998, Genomics, vol. 54, pp. 344-347.
McManus and Sharp (2002) Gene silencing in mammals by small interfering siRNAs. Nature Reviews Genetics 3:737-747.
Miller, V M et al., "Allele-specific silencing of dominant disease genes" Proceedings of the National Acadamy of Sciences of USA, vol. 100, No. 12, Jun. 10, 2003, pp. 7195-7200, XP002276730.
Miyagashi et al. (2003) Comparison of the Suppressive Effects of Antisense Oligonucleotides and siRNAs Directed Against the Same Targets in Mammalian Cells. Antisense and Nucleic Acid Drug Development 13:1-7.
Morales, S. et al., "Collagen gel contraction by ARPE-19 cells is mediated by a FAK-Src dependent pathway," Experimental Eye Research, 2007, pp. 790-798, vol. 85.
Morrissey, D., et al., "Potent and persistent in vivo anti-HBV activity of chemically modified siRNAs," Nature Biotechnology, Aug. 1, 2005, vol. 23, pp. 1002-1007.
Murphy, et al. (2000) Synucleins are Developmentally Expressed, and Alpha-Synuclein Regulates the Size of the Presynaptic Vesicular Pool in Primary Hippocampal Neurons. The Journal of Neuroscience, vol. 20(9):3214-20.
Naito, Y. et al. (2004) siDirect: highly effective, target-specific siRNA design software for mammalian RNA interference. Nucleic Acids Res. 32:W124-W129.
NCBI Nucleotide Result for NM-002609, http://www.ncbi.nlm.nih.gov/sites/entrez, accessed on Jul. 14, 2008.
NCBI Sequence Viewer v2.0 for NM-000905, http://www.ncbi.nlm.nih.gov/entrez/viewer, accessed on Mar. 18, 2008.
NCBI Sequence Viewer v2.0 for NM-004438, http://www.ncbi.nlm.nih.gov/entrez/viewer.fcgi?db=nuccore&id=45439363, accessed on Jul. 3, 2008.
Nguyen T. et al. Current Opin. Molec Ther. vol. 10, No. 2, pp. 158-167 (2008).
Oishi, et al., Identification and Characterization of PKN Beta, a Novel Isoform of Protein Kinase PKN: Expression and Arachiodonic Acid Dependency Are Different from those of PKN alpha, 1999 Biochemical and Biophysical Research Communication, 261, pp. 808-814.
Olie et al, A Novel Antisense Oligonucleotide Targeting Survivin Expression Induces Apoptosis and Sensitizes Lung Cancer Cells to Chemotherapy, Cancer Research 2000, vol. 60: pp. 2805-2809.
Pan, et al. (2005) Calmodulin-dependent protein kinase IV regulates nuclear export of Cabin1 during T-cell activation, The EMBO Journal, 24, 2104-2113.
PCT International Search Report and Written Opinion for International Patent Application No. PCT/US2010/055311, dated Mar. 2, 2011, 17 pages.
PCT International Search Report and Written Opinion, PCT/US2009/061381, dated Jul. 26, 2010, 15 pages.
PCT International Search Report and Written Opinion, PCT/US2011/030392, dated Jun. 27, 2011, 10 pages.
PCT International Search Report for International Application No. PCT/US03/36787, dated Feb. 25, 2005.
PCT International Search Report and Written Opinion for PCT/US03/36787, dated Sep. 25, 2005, 4 pages.
PCT International Search Report for International Application No. PCT/US04/14885, dated Sep. 24, 2007.
PCT Invitation to Pay Additional Fees and, Where Applicable, Protest Fee, PCT/US2009/061381, dated Apr. 27, 2010, 7 Pages.
Promega (2003) siRNA Target Designer—Version 1.1, Silentgene U6 Cassette RNA Interference System. http://www.promega.com/siRNADesigner/program.
Promega siRNA Target Designer—Version 1.51, http:///www.promega.com/siRNADesigner/program/default.asp. Accessed Jun. 24, 2008.
Rabert et al. (1998) A Tetrodextrin-Resistant Voltage-gated Sodium Channel from Human Dorsal Root Ganglia, hPN3/SCN10A. Pain, 78, pp. 107-114.
Rashid et al. Decreased plasma cholesterol and hypersensitivity to statins in mice lacking PCSK9, 2005 PNAS, vol. 102, pp. 5374-5379.
Reynolds, A. et al. (2004) Rational siRNA design for RNA interference. Nature Biotechnology 22/3:326-330.
Robbins, M., et al., "Stable expression of shRNAs in human CD34.sup.+ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Ross, et al. (2001) Inhibition of Kirsten-ras Expression in Human Colorectal Cancer Using Rationally Selected Kirsten-ras Antisense Oligonucleotides, Molecular Cancer Therapeutics vol. 1, 29-41.
Scherer and Rossi. (2003) Approaches for the sequence specific knockdown of mRNA. Nat. Biotechnol. 21 (12):1457-1465.
Scherer and Rossi. (2004) Therapeutic Applications of RNA Inferferences: Recent Advances in siRNA Design. Advances in Genetics 22:1-21. Duplicate.
Sekijima, Y., et al., "Pathogenesis of and Therapeutic Strategies to Ameliorate the Transthyretin Amyloidoses," Current Pharmaceutical Design, Jan. 1, 2008, pp. 3219-3230, vol. 14, No. 30.
Semizarov, D. et al. (2003) Specificity of short interfering RNA determined through gene expression signatures. Proc. Natl. Acad. Sci. USA 100/11:6347-6352.
Shi et al. (1995), Abl-interactor—1 a novel SH3 protein binding to the carboxy-terminal portion of the Abl protein, suppresses v-abl transforming activity, Genes & Dev. 9:2583-2597.
Shi et al. (2001) Gremlin negatively Modulates BMP-4 Induction of Embryonic Mouse Lung Branching Morphogenesis. Am J Physiol Lung Cell Mol Physiol, 280, pp. L1030-L1039.
Shuai, K., Modulation of STAT signaling by STAT interacting proteins, 2000, Oncogene vol. 19, pp. 2638-2644.
siDesign Center for "gene name: src," http://www.dharmacon.com/DesignCenter/DesignCenterPage.aspx, accessed on May 13, 2008.
siRNA Converter, http://web.archive.org/web/20020101-20021231reihttp://www.ambion.com/tech-lib/misc/siRNA.sub.--finder.html. Accessed Mar. 6, 2008. (siRNA Target Finder).
"siRNA Target Finder." results for the entry of the nucleotide sequence of GeneBank Accession No. NM.sub.—021960. http://www.ambion.com/techlib/misc/siRNA.sub.--finder.html, accessed on Mar. 6, 2008 in U.S. Appl. No. 11/633,404.

(56) References Cited

OTHER PUBLICATIONS

Skalecki et al., Arch. Biochem. Biophys. vol. 365, No. 1 pp. 1-9 (1999).
Sorensen, et al. (2003) Gene Silencing by Systemic Delivery of Synthetic siRNAs in Adult Mice, J. Mol. Biol. 327, 761-766.
Stein, T., et al., "Neutralization of transthyretin reverses the neuroprotective effects of secreted amyloid precursor protein (APP) in APP. sub.SW mice resulting in Tau phosphorylation and loss of Hippocampal neurons: support for the amyloid hypothesis." The Journal of Neuroscience, Sep. 1, 2004, vol. 24, No. 35, p. 7707-7717.
Supplementary European Search Report for European Patent Application No. EP 11763336, dated Sep. 13, 2013, 11 Pages.
Tan, et al., (2006) Functional Cooperation Between Fact and MCM Helicase Facilitates Initiation of Chromatin DNA Replication. The EMBO Journal, vol. 25, pp. 3975-3985.
Tasaki, M., et al., "siRNA therapy for TTR-related ocular amyloidosis," Amyloid, 12.sup.th International Symposium on Amyloidosis from Molecular Mechanisms Toward the Cure of Systemic AM, Apr. 18-21, 2010, pp. 52-53, vol. 17, No. Suppl 1.
The State Intellectual Property Office of the People's Republic of China, Notification of the First Office Action, Chinese Patent Application No. 200980141740.4, dated Jun. 5, 2012.
Tijsterman, Dicers at RISC, The Mechanism of RNAi, Cell, Apr. 2004, vol. 117, pp. 1-4.
Truss, M. et al. (2005) HuSiDa—the human siRNA database: an open-access database for published functional siRNA sequences and technical details of efficient transfer into recipient cells. Nucleic Acids Res. 33:D108-D111.
Tsuji, et al. (2006) Essential Role of Phosphoorylation of MCM2 by Cdc7/Dbf4 in the Initiation of DNA Replication in Mammalian Cells. Molecular Biology of the Cell, vol. 17, pp. 4459-4472.
Tsuruga et al., HsMCM6: A new member of the human MCMIP1 family encodes a protein homologous to fission yeast mis5, 1997, Genes to Cells, vol. 2, pp. 381-399.
Tuschl et al. (2003) The siRNA User Guide. 6 pages.
Tuschl et al. The siRNA user guide, Nov. 14, 2001, [online] http://web.archive.org/web/20030501103318/http://www.rockefeller.edu/labh-eads/tuschl/sir . . . Accessed Aug. 2, 2006, 5 pages.
Tuschl T., "RNA Interference and Small Interfering RNAs" Chembiochem, 2001, pp. 239-245, vol. 2.
Tuschl, et al. (2001) The siRNA User Guide. Max Planck Institute for Biophysical Chemistry, pp. 1, 3 and 5, http://www.mpibpc.gwdg.de/abteilungen/100/105/siRNAuserguide.pdf.
Tuschl, Expanding small RNA interference (May 2002), Nature Biotechnology, vol. 20, pp. 446-448.
Tuschl, T., "Functional genomics: RNA sets the standard," Nature, Jan. 16, 2003, vol. 421, No. 6920, pp. 220-221.
Tuschl, T., "Mammalian RNA Interference," RNAi, A Guide to Gene Silencing, Chapter 13, G.J. Hannon (ed,), 2003, pp. 265-295.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., et al., "Targeted mRNA Degradation by Double-Stranded RNA In Vitro," Genes & Development, 1999, pp. 3191-3197, vol. 13.
Tusterman, Dicers at RISC, The Mechanism of RNAi, Cell, Apr. 2004, vol. 117, pp. 1-4.
Ueda, M., et al., "A transgenic rat with the human ATTR V30M: A novel tool for analysis of ATTY metabolisms," Biochemical and Biophysical Research Communications, 2006, pp. 299-304, vol. 352.
Ui-Tei, Guidelines for the selection of highly effective siRNA sequences for mammalian and chick RNA interference, Nucleic Acids Research, Feb. 2004, vol. 32, No. 3 pp. 936-948.
United States Patent and Trademark Office, Final Rejection, U.S. Appl. No. 10/714,333, dated Mar. 16, 2010, 7 Pages.
United States Patent and Trademark Office, Final Rejection, U.S. Appl. No. 10/714,333, dated Mar. 7, 2007, 5 Pages.
United States Patent and Trademark Office, Final Rejection, U.S. Appl. No. 10/714,333, dated May 5, 2006, 9 Pages.
United States Patent and Trademark Office, Final Rejection, U.S. Appl. No. 10/714,333, dated Nov. 8, 2007, 9 Pages.
United States Patent and Trademark Office, Final Rejection, U.S. Appl. No. 10/940,892, dated Jul. 27, 2010, 7 Pages.
United States Patent and Trademark Office, Non-final Rejection, U.S. Appl. No. 10/714,333, dated Apr. 18, 2007, 7 Pages.
United States Patent and Trademark Office, Non-final Rejection, U.S. Appl. No. 10/714,333, dated Aug. 18, 2005, 13 Pages.
United States Patent and Trademark Office, Non-final Rejection, U.S. Appl. No. 10/714,333, dated Aug. 22, 2008, 9 Pages.
United States Patent and Trademark Office, Non-final Rejection, U.S. Appl. No. 10/714,333, dated Aug. 28, 2009, 8 Pages.
United States Patent and Trademark Office, Non-final Rejection, U.S. Appl. No. 10/714,333, dated Dec. 11, 2006, 11 Pages.
United States Patent and Trademark Office, Non-final Rejection, U.S. Appl. No. 10/714,333, dated Dec. 12, 2005, 18 Pages.
United States Patent and Trademark Office, Non-final Rejection, U.S. Appl. No. 10/714,333, dated Dec. 22, 2008, 7 Pages.
United States Patent and Trademark Office, Non-final Rejection, U.S. Appl. No. 10/714,333, dated Jul. 18, 2008, 10 Pages.
United States Patent and Trademark Office, Non-final Rejection, U.S. Appl. No. 10/714,333, dated Jun. 22, 2007, 8 Pages.
United States Patent and Trademark Office, Non-final Rejection, U.S. Appl. No. 10/714,333, dated Oct. 29, 2010, 9 Pages.
United States Patent and Trademark Office, Non-final Rejection, U.S. Appl. No. 10/714,333, dated Sep. 5, 2007, 8 Pages.
United States Patent and Trademark Office, Non-final Rejection, U.S. Appl. No. 10/940,892, dated Apr. 10, 2008, 9 Pages.
United States Patent and Trademark Office, Non-final Rejection, U.S. Appl. No. 10/940,892, dated Feb. 10, 2011, 7 Pages.
United States Patent and Trademark Office, Non-final Rejection, U.S. Appl. No. 10/940,892, dated Jan. 23, 2009, 9 Pages.
United States Patent and Trademark Office, Non-final Rejection, U.S. Appl. No. 10/940,892, dated Jan. 6, 2010, 7 Pages.
United States Patent and Trademark Office, Non-final Rejection, U.S. Appl. No. 10/940,892, dated Jan. 6, 2010, 9 Pages.
United States Patent and Trademark Office, Non-final Rejection, U.S. Appl. No. 10/940,892, dated May 10, 2007, 8 Pages.
United States Patent and Trademark Office, Non-final Rejection, U.S. Appl. No. 10/940,892, dated May 22, 2007, 8 Pages.
United States Patent and Trademark Office, Non-final Rejection, U.S. Appl. No. 10/940,892, dated Nov. 3, 2008, 13 Pages.
United States Patent and Trademark Office, Non-final Rejection, U.S. Appl. No. 10/940,892, dated Oct. 3, 2007, 8 Pages.
United States Office Action, U.S. Appl. No. 14/807,852, dated Jan. 6, 2016, ten pages.
United States Office Action, U.S Appl. No. 14/789,378, dated Jan. 12, 2016, six pages.
Vankayalapati, et al. (2003) Targeting Aurora2 Kinase in Oncogenesis: A Structural Bioinformatics Approach to Target Validation and Rational Drug Design. Molecular Cancer Therapeutics, v.2:283:94.
Vickers, et al., Efficient Reduction of Target RNAs by Small Interfering RNA and RNase H-dependent Antisense Agents, Feb. 2003, The Journal of Biological Chemistry, vol. 278, pp. 7108-7118.
Wacheck, et al., Small Interfering RNA Targeting Bcl-2 Sensitizes Malignant Melanoma, Oligonucleotides 13: 393-400 (2003).
Walton, et al. (1999) (Abstract Only) Prediction of Antisense Oligonucleotide Binding Affinity to a Structured RNA Target. Biotechnol. Bioengineering, v. 65(1):1-9.
Wang et al. Connective Tissue Growth Factor siRNA modulates mRNA levels for a subet of molecules in normaland Tfg-Beta1 stimulated porcine skin fibroblasts, 2004, Wound Rep. Reg.12, pp. 205-206.
Wang, et al., (2006) Dexamethasone Represses Signaling through the Mammalian Target of Rapamycin in Muscle Cells by Enhancing Expression of REDD1. The Journal of Biological Chemistry vol. 281, No. 51, pp. 39128-39134.
Weil, et al (2002) "Targeting the Kinesin Eg5 to Monitor siRNA Transfection in Mammalian Cells," Biotechniques 33(6):1244-1248.
White et al., The nuclear Receptor Co-Repressor Nrip1 (RIP 140) is essential for female fertility. Nature Medicine, 2000, vol. 6, No. 12: 1368-1374.

(56) References Cited

OTHER PUBLICATIONS

Yao et al. (2000) Nature Cell Biology 2:484-491.
Yuan, B. et al. (2004) siRNA Selection Server: an automated siRNA oligonucleotide prediction server. Nucleic Acids Res. 32:W130-W134.
Zender et al., siRNA based strategies for inhibition of apoptotic pathways in vivo—analytical and therapeutic implications, Jan. 2004, vol. 9, pp. 51-54.
Zhang, et al., Physical and Functional Interaction between Myeloid Cell Leukemia 1 Protein (MCL1) and Fortilin, 2002, The Journal of Biological Chemistry, vol. 277, pp. 37340-37438.
Zimmerman, et al. "RNAi-mediated gene silencing in non-human primates," Nature, vol. 441, May 2006: 111-114.
United States Office Action, U.S. Appl. No. 10/940,892, dated May 5, 2016, 8 pages.

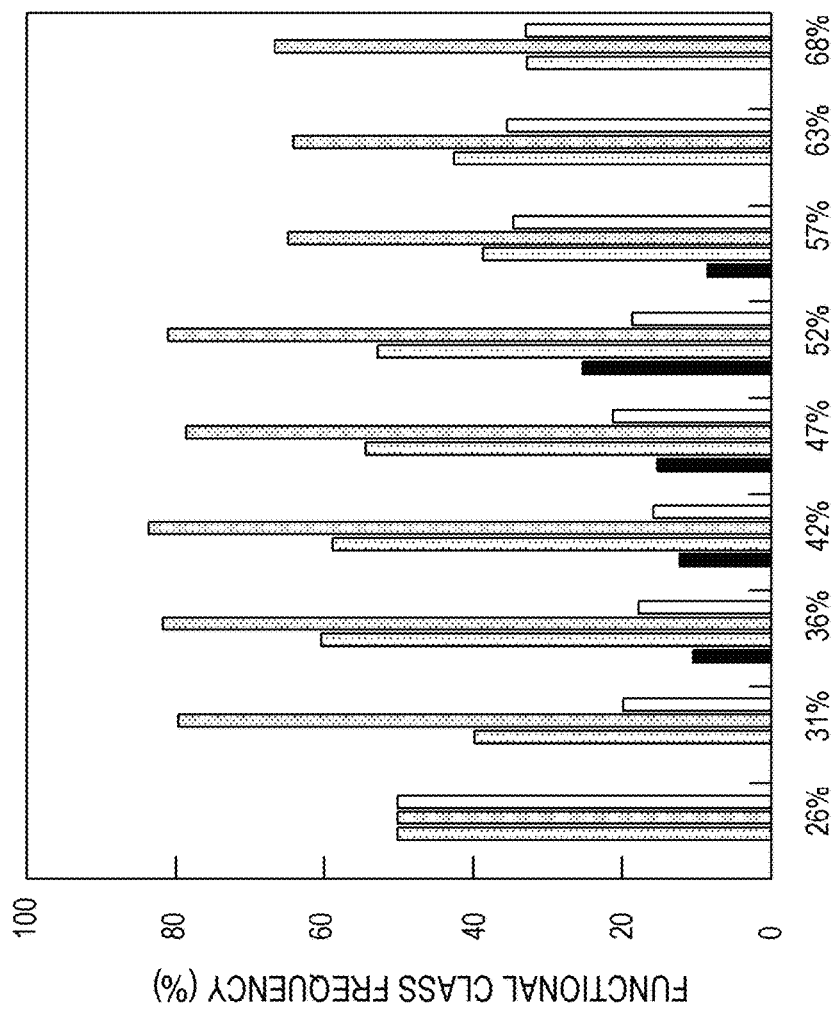

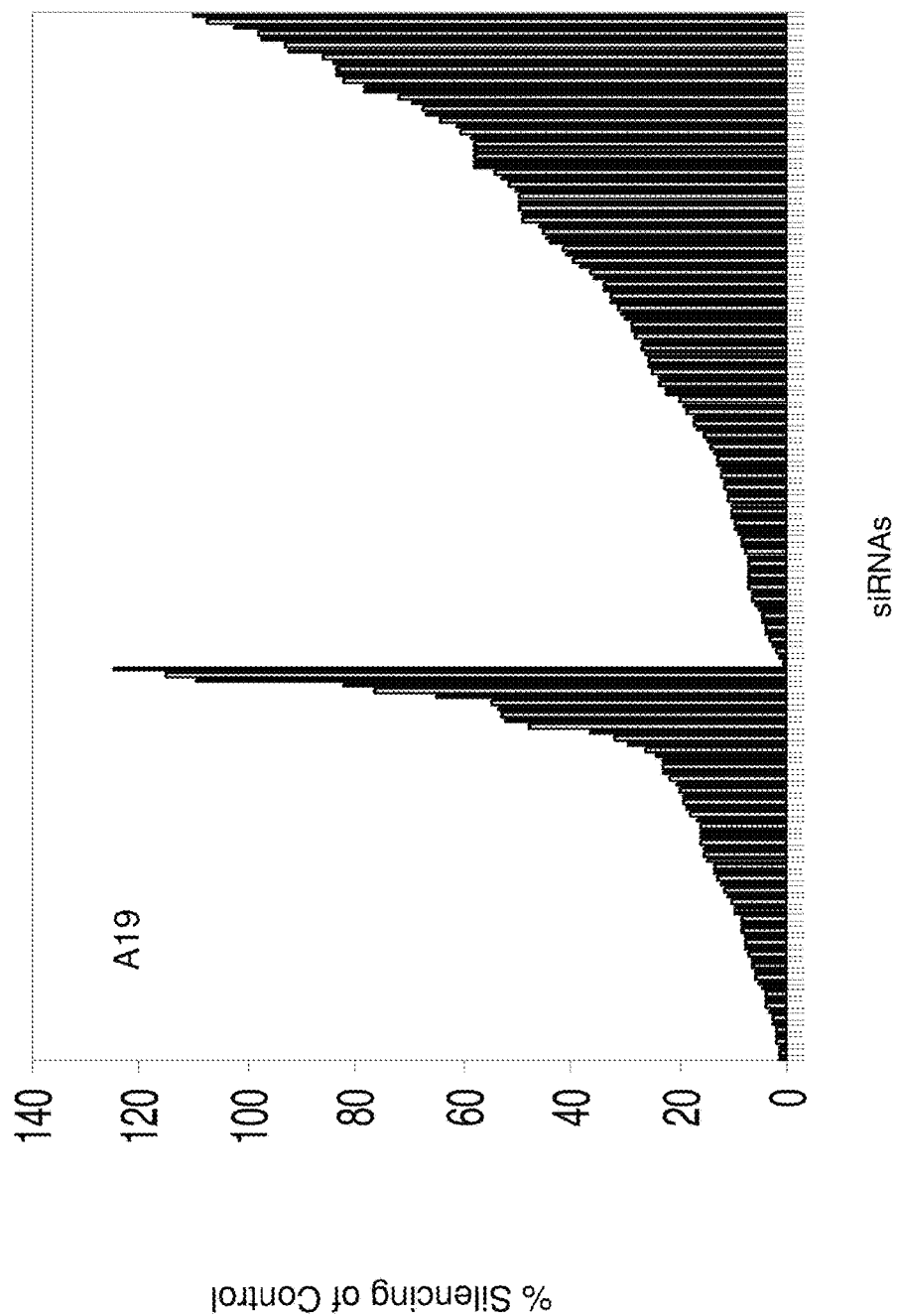

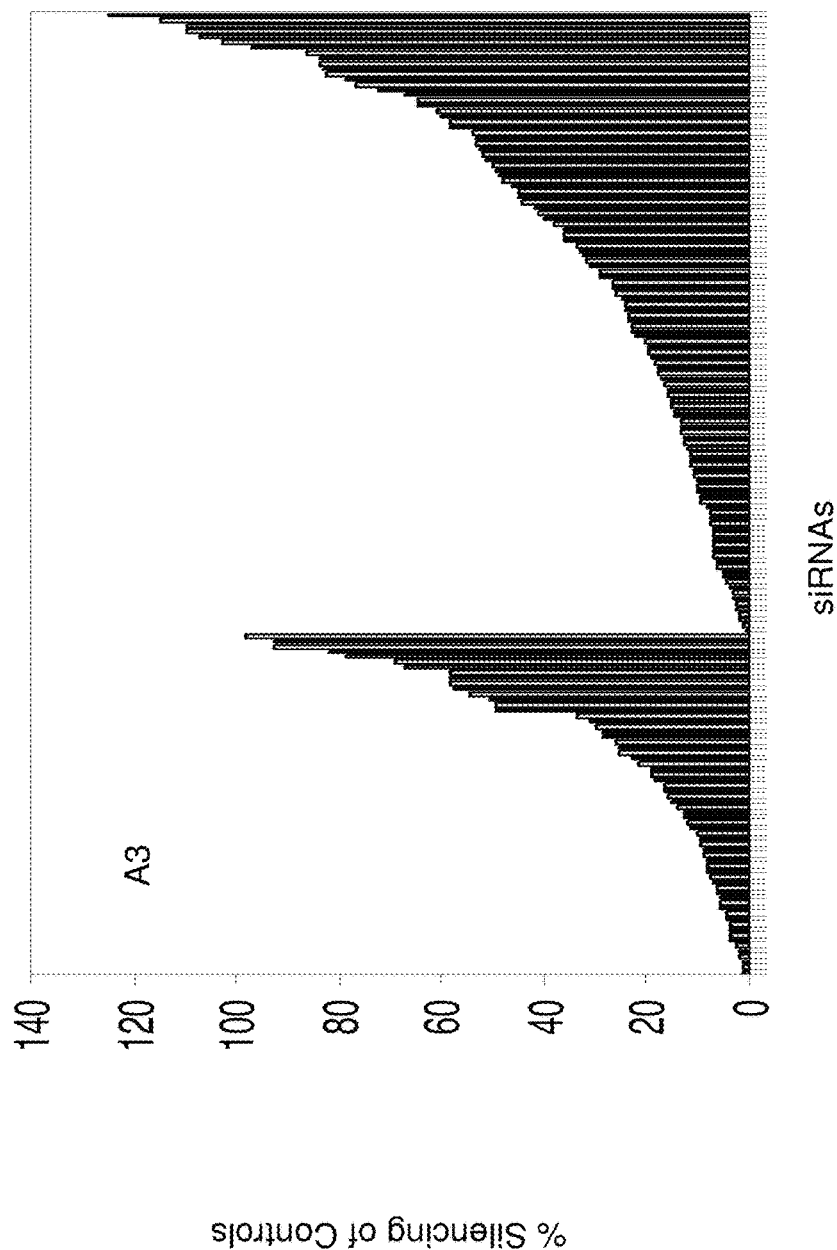

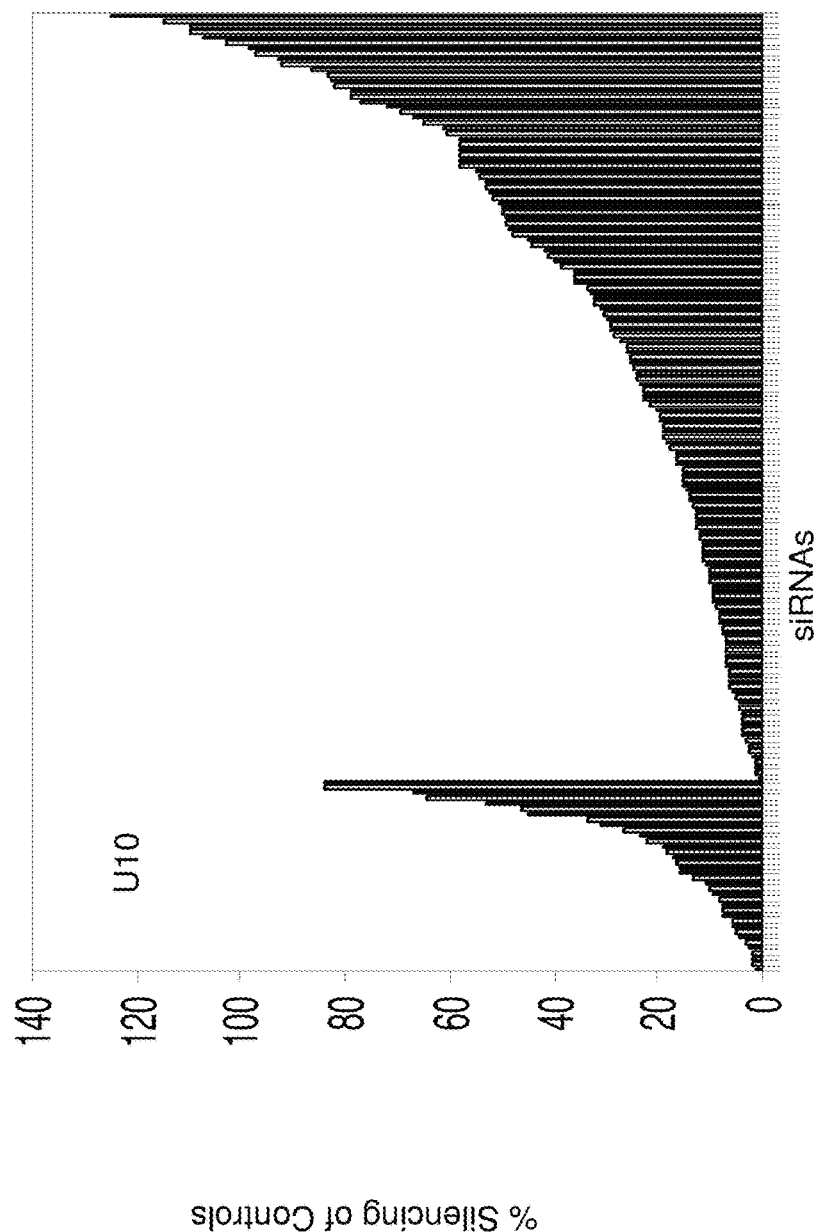

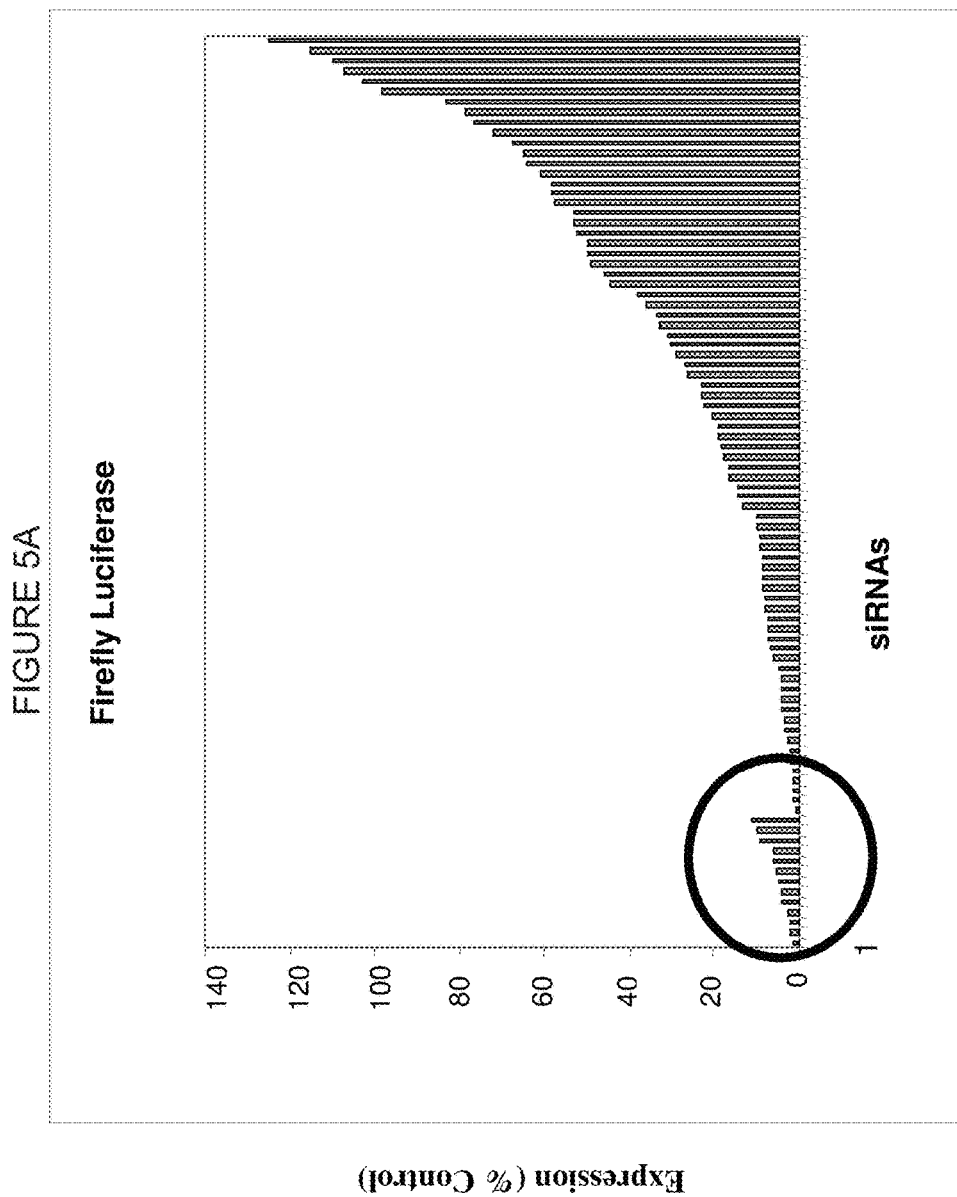

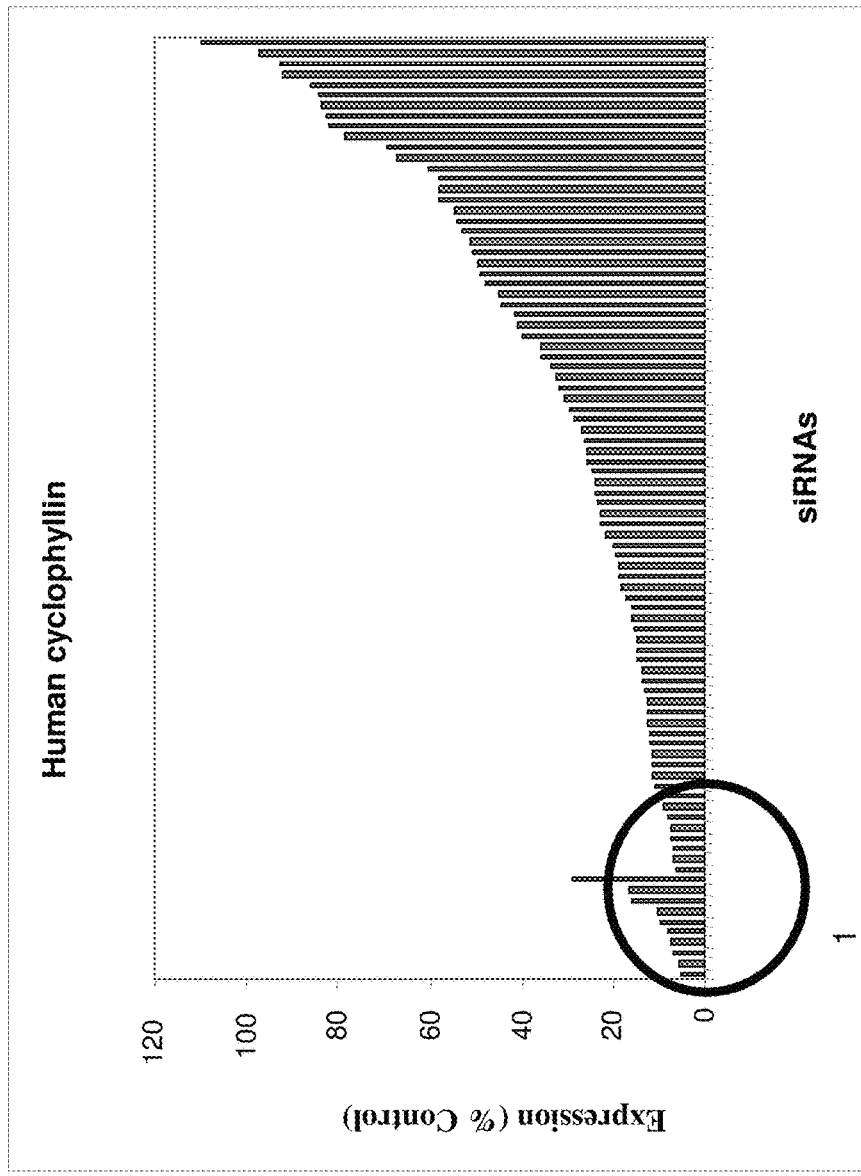

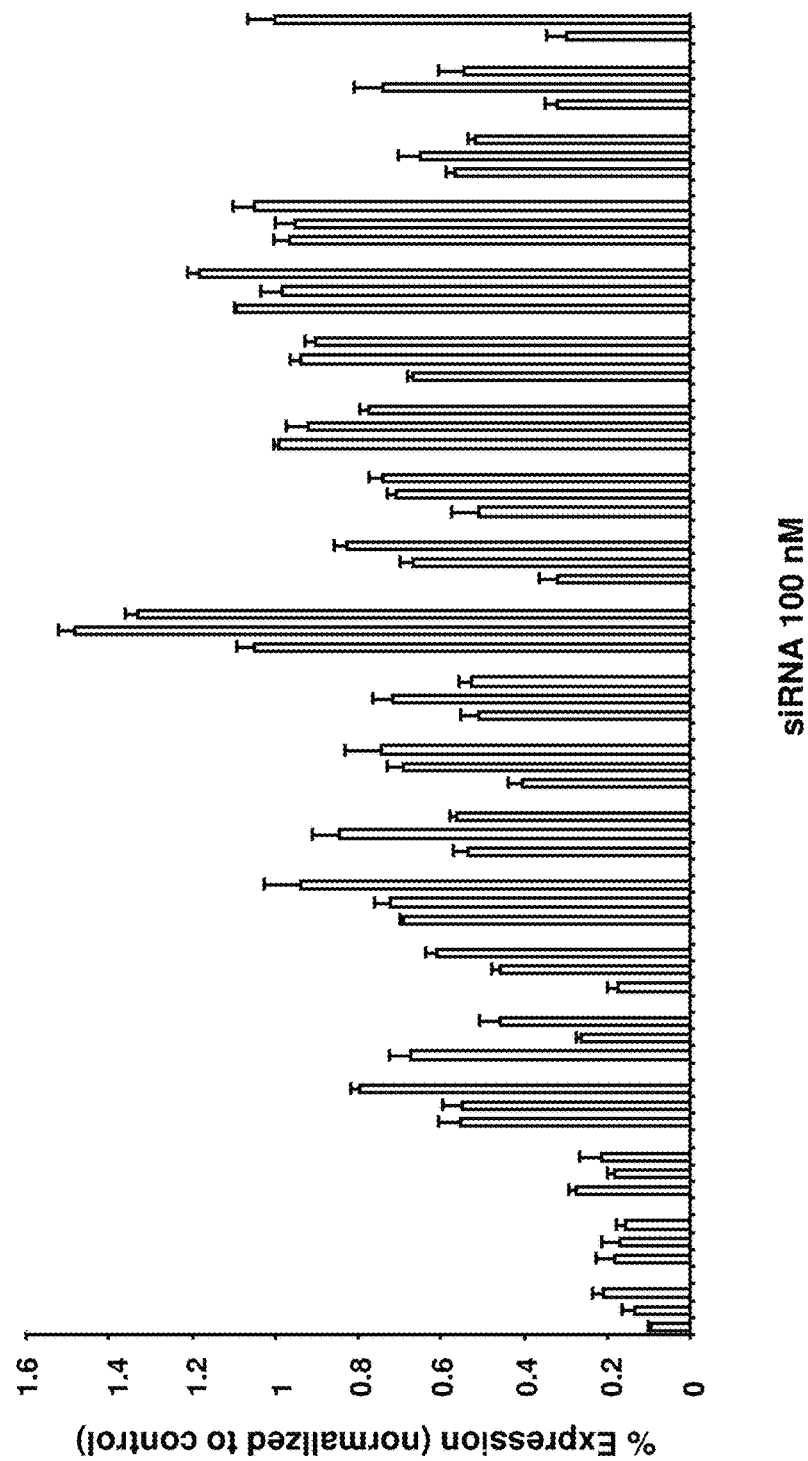

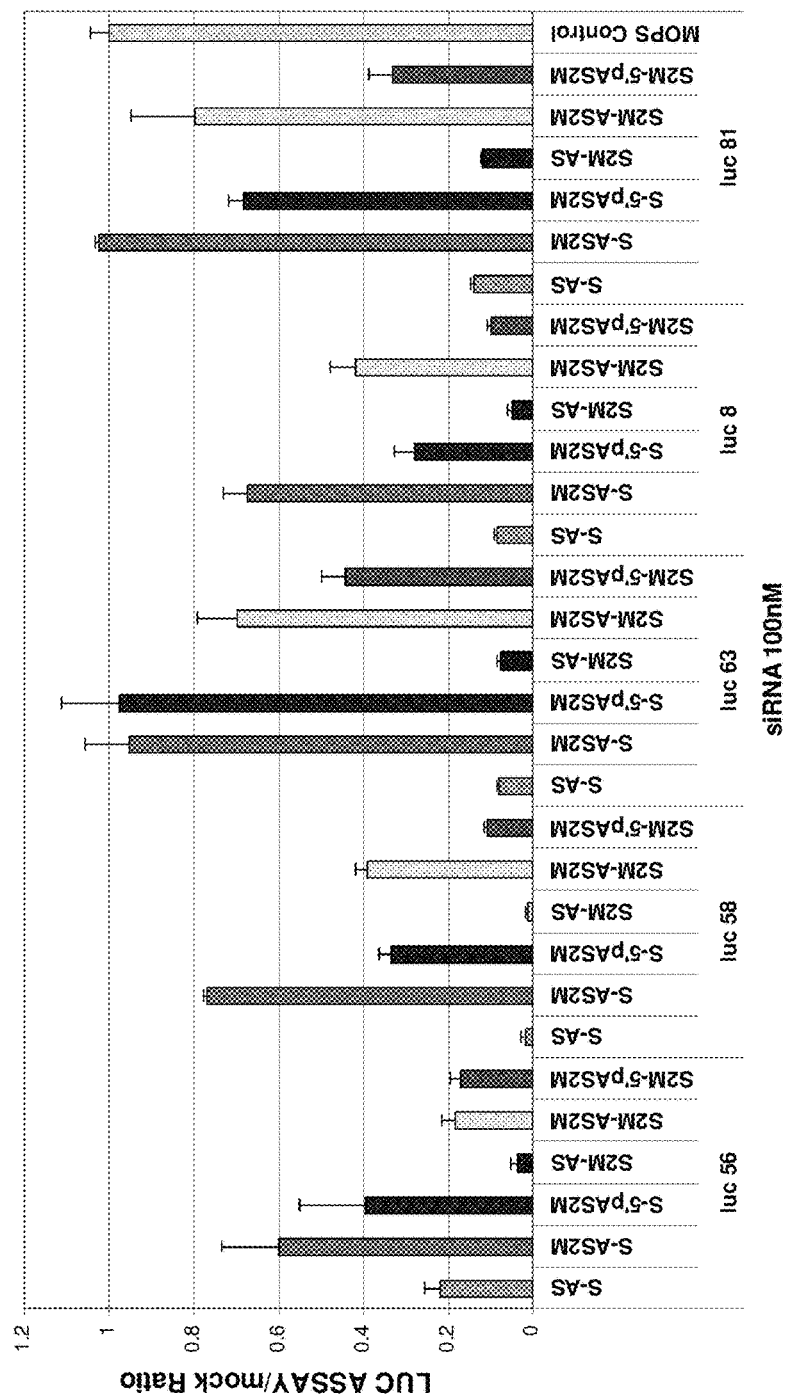

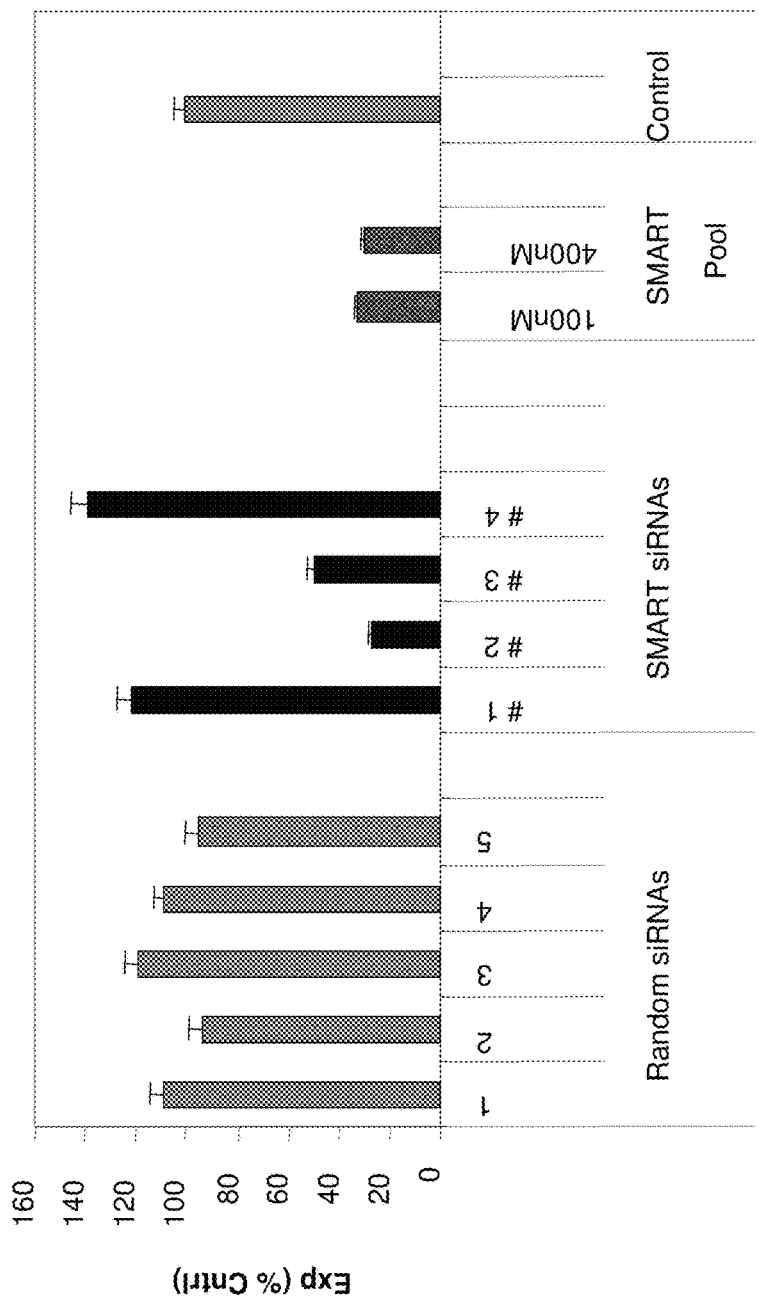

Renila Luciferase

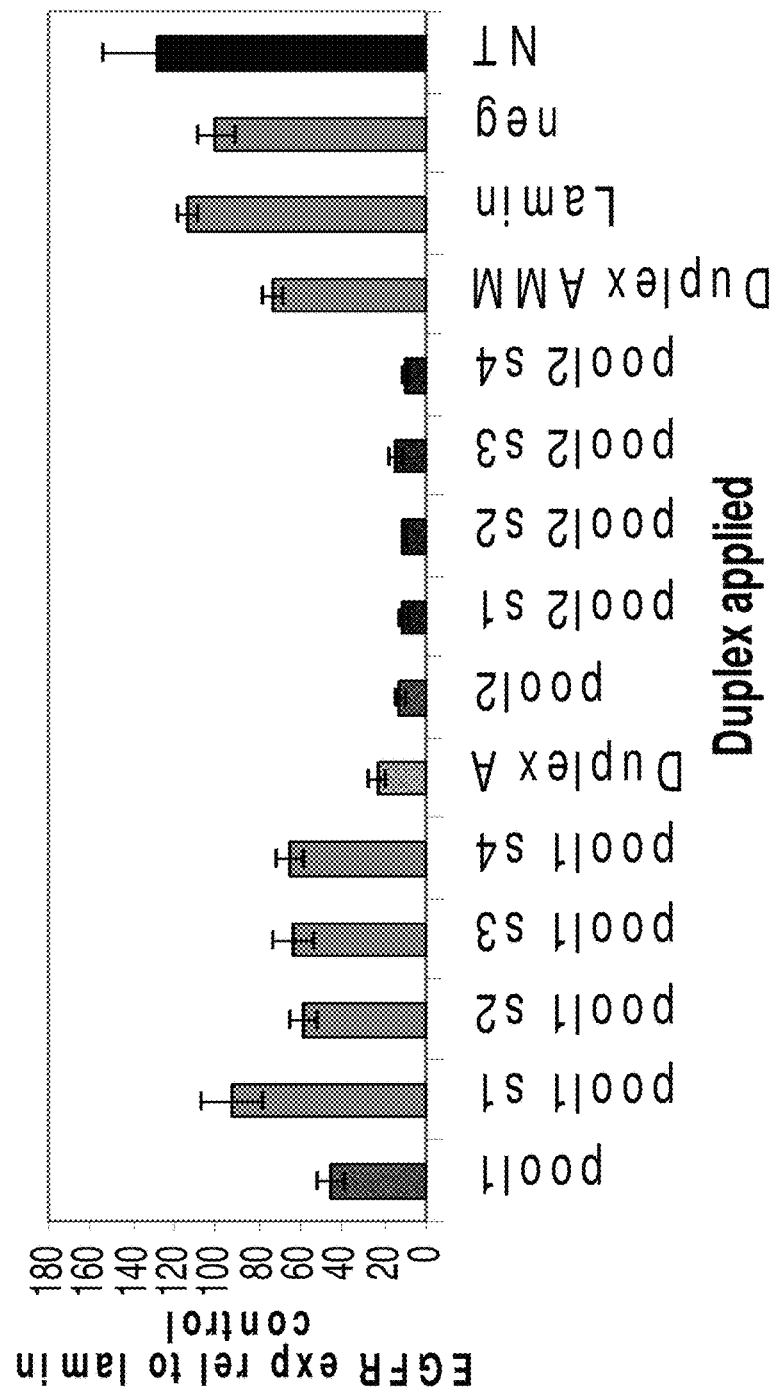

Rational selection validation

FIGURE 13

Sequences of top Bcl2

| | |
|---|---|
| siRNA 1 | GGGAGAUAGUGAUGAAGUA (SEQ. ID No. 302) |
| siRNA 2 | GAAGUACAUCCAUUAUAAG (SEQ. ID No. 303) |
| siRNA 3 | GUACGACAACCGGGAGAUA (SEQ. ID No. 304) |
| siRNA 4 | AGAUAGUGAUGAAGUACAU (SEQ. ID No. 305) |
| siRNA 5 | UGAAGACUCUGCUCAGUUU (SEQ. ID No. 306) |
| siRNA 6 | GCAUGCGGCCUCUGUUUGA (SEQ. ID No. 307) |
| siRNA 7 | UGCGGCCUCUGUUUGAUUU (SEQ. ID No. 308) |
| siRNA 8 | GAGAUAGUGAUGAAGUACA (SEQ. ID No. 309) |
| siRNA 9 | GGGAGAUAGUGAUGAAGUAC (SEQ. ID No. 310) |
| siRNA 10 | GAAGACUCUGCUCAGUUUG (SEQ. ID No. 311) |

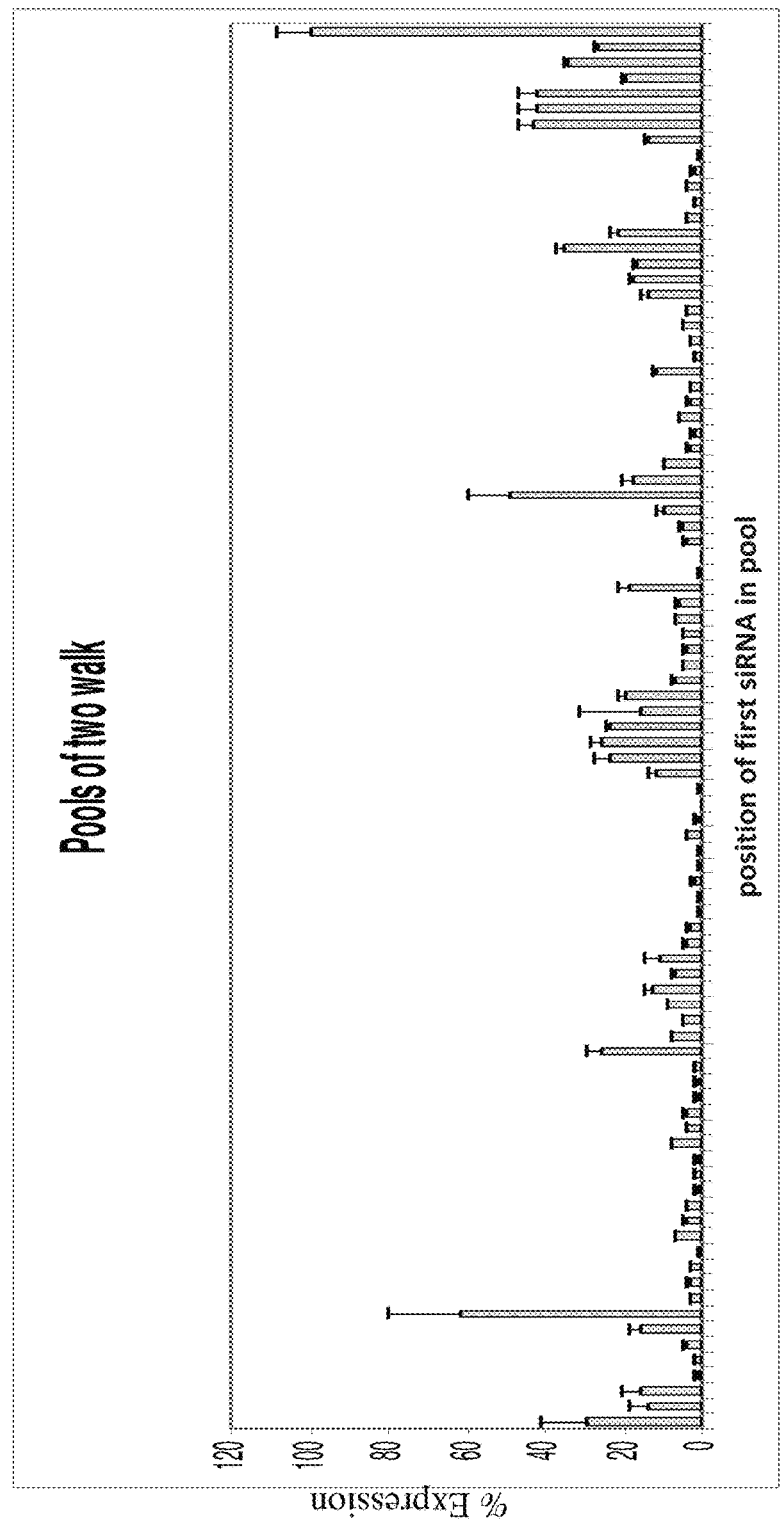

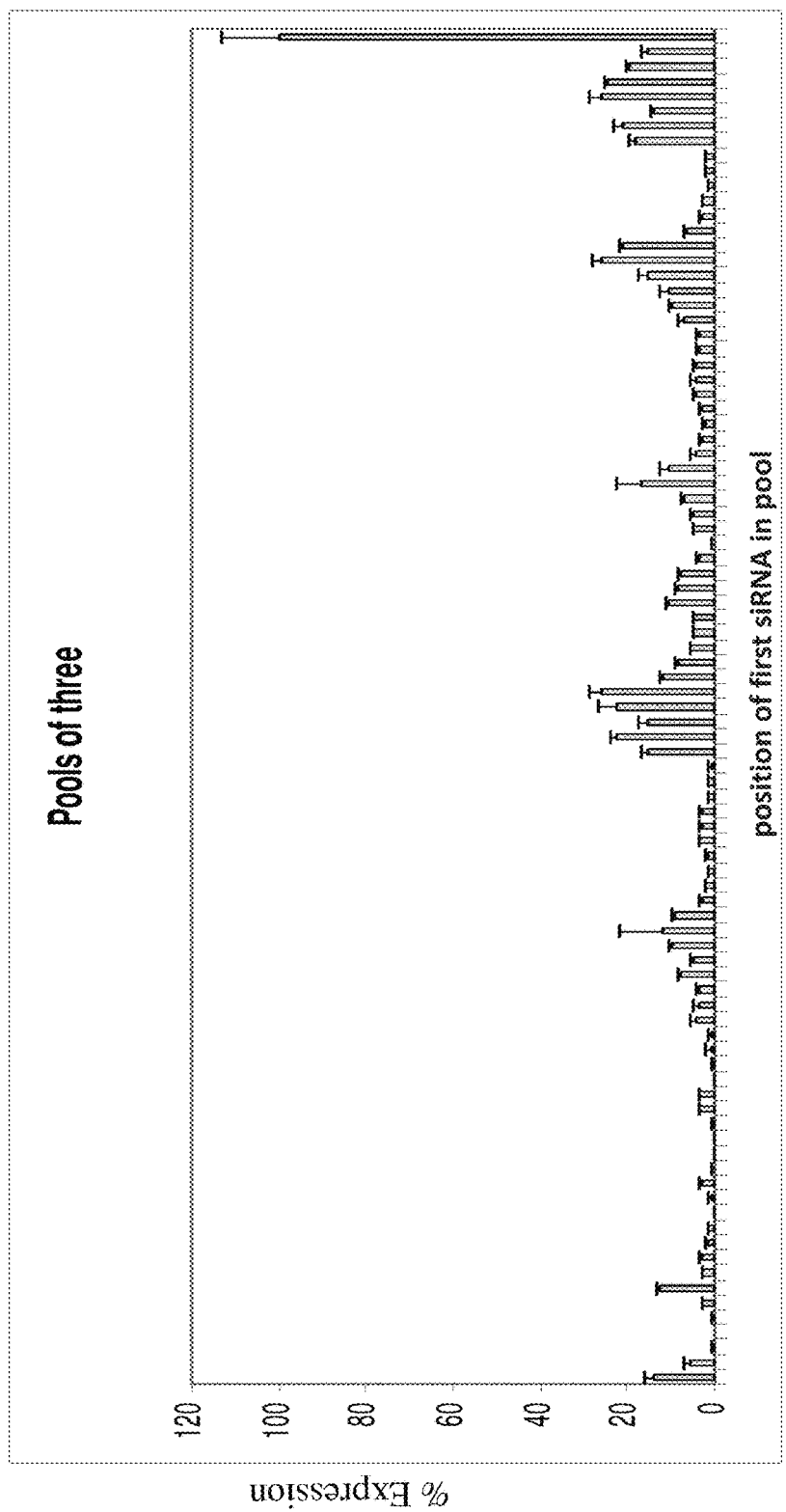

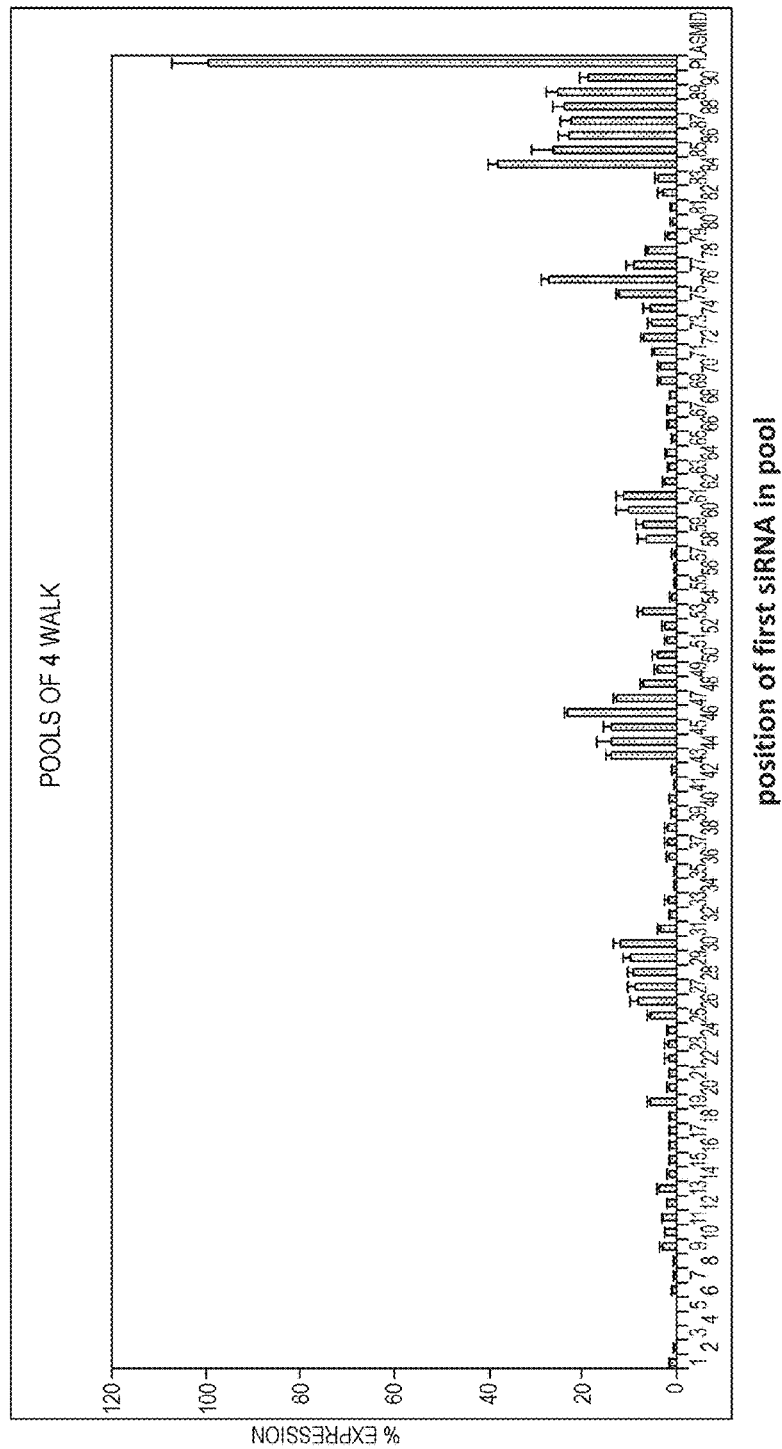

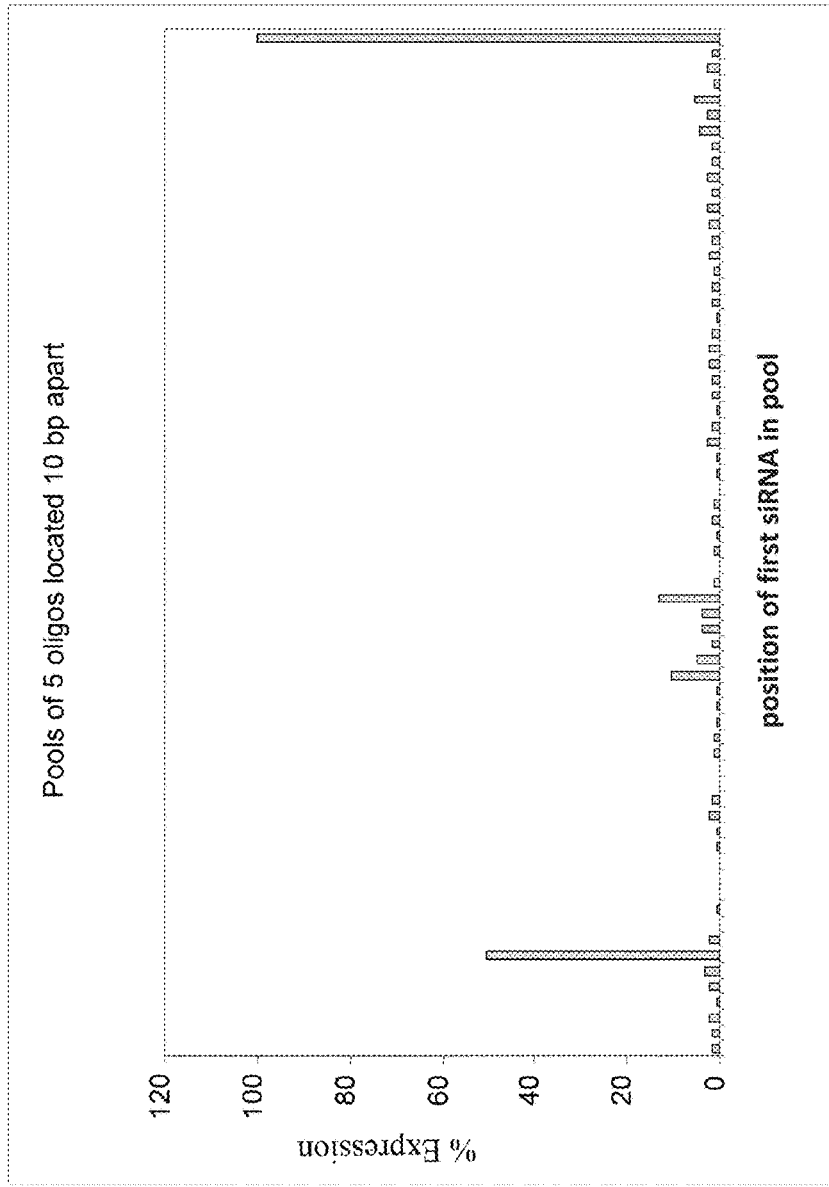

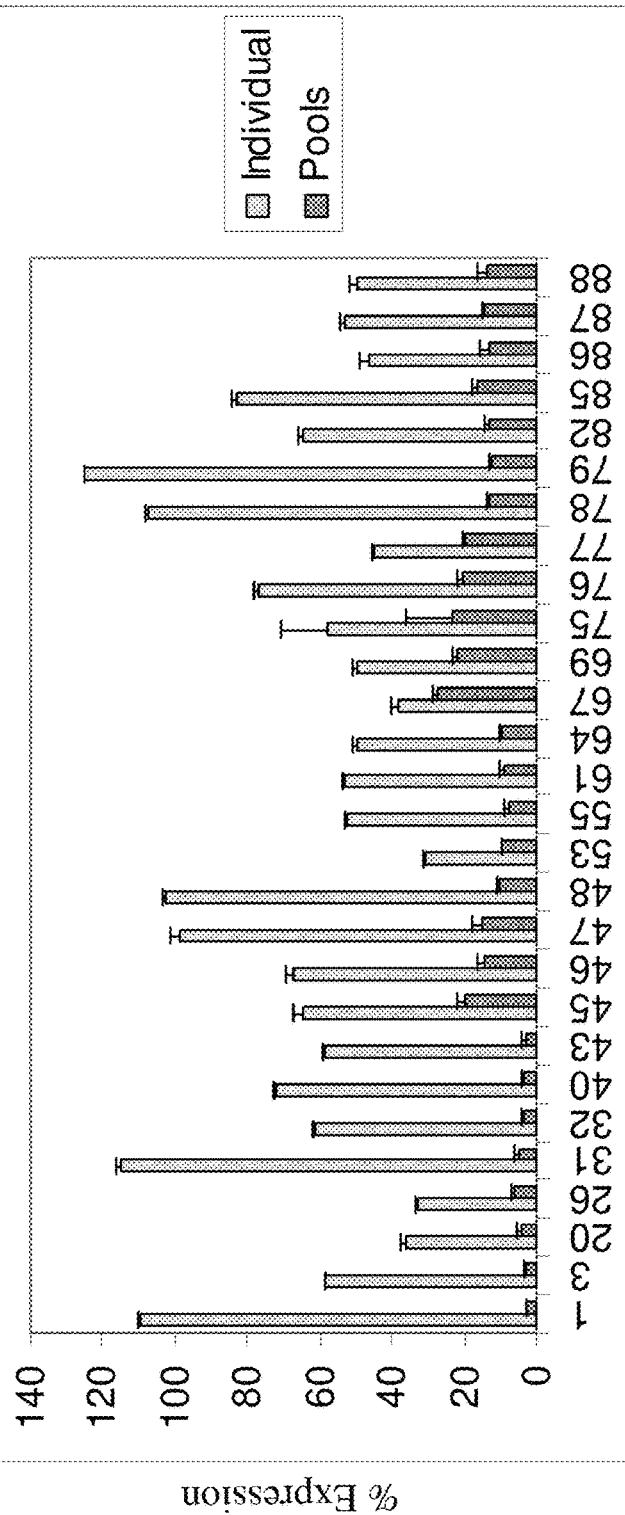

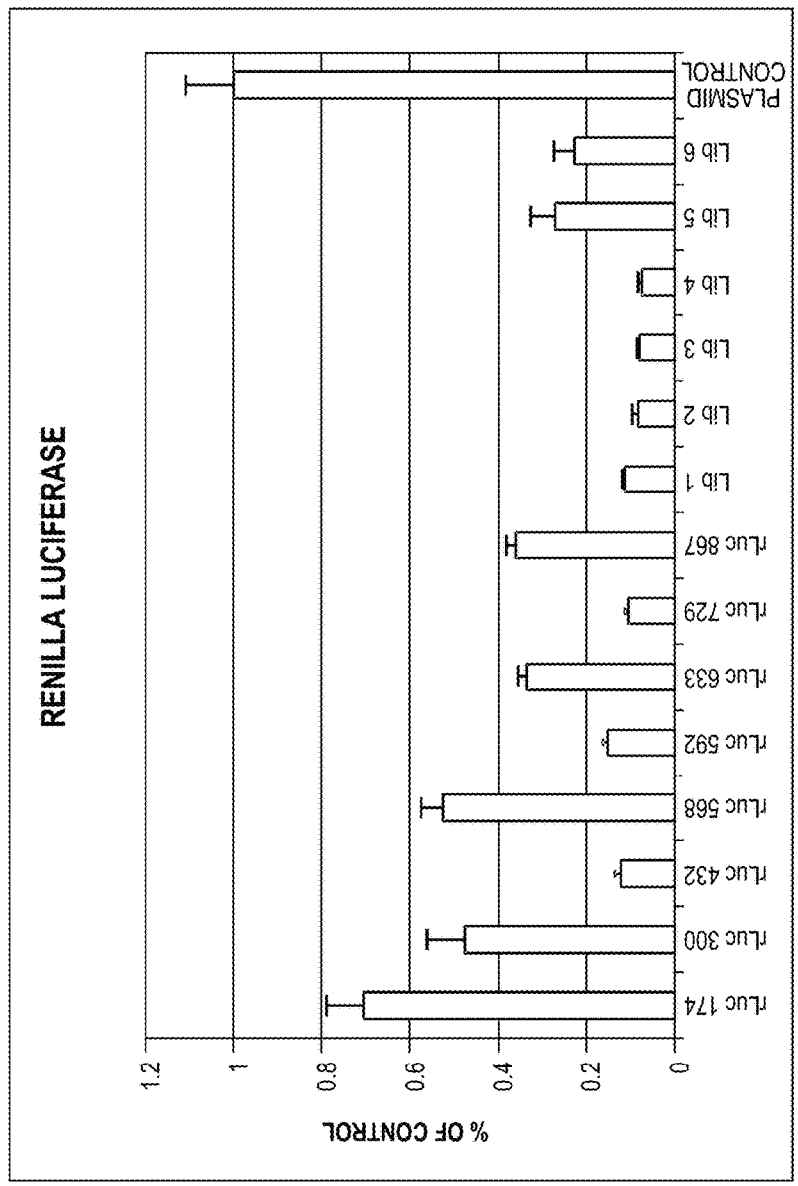

SEQUENCE LISTING

```
<160> NUMBER OF SEQ ID NOS: 481

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 1
nnanannnnu cnaannnna                                                19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 2
nnanannnnu gnaannnna                                                19
```

```
<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 3
nnanannnnu unaannnna                                                19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 4
nnanannnnu cncannnna                                                19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
```

```
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 5
nnanannnnu gncannnna                                                 19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 6
nnanannnnu uncannnna                                                 19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
```

```
<222> LOCATION: (15)..(18)
<223> OTHER INFORMATION: a, c, g, or u

<400> SEQUENCE: 7
nnanannnnu cnuannna                                                19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 8
nnanannnnu gnuannna                                                19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 9
nnanannnnu unuannna                                                19

<210> SEQ ID NO 10
<211> LENGTH: 19
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 10
nnancnnnnu cnaannnna                                                       19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 11
nnancnnnnu gnaannnna                                                       19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
```

```
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 12
nnancnnnnu unaannna                                                  19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 13
nnancnnnnu cncannna                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 14
nnancnnnnu gncannna                                                  19
```

```
<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 15
nnancnnnnu uncannnna                                                  19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 16
nnancnnnnu cnuannnna                                                  19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
```

```
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 17
nnancnnnnu gnuannnna                                                        19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 18
nnancnnnnu unuannnna                                                        19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
```

```
<221> NAME/KEY: modified_base
<222> LOCATION: (15)..(18)
<223> OTHER INFORMATION: a, c, g, or u

<400> SEQUENCE: 19
nnangnnnnu cnaannnna                                                  19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 20
nnangnnnnu gnaannnna                                                  19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 21
nnangnnnnu unaannnna                                                  19

<210> SEQ ID NO 22
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 22
nnangnnnnu cncannnna                                               19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 23
nnangnnnnu gncannnna                                               19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
```

```
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 24
nnangnnnnu uncannnna                                                    19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 25
nnangnnnnu cnuannnna                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(9)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 26
```
nnangnnnnu gnuannnna          19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, or u
<220> FEATURE:
<221> NAME/KEY: modified_base
<222> LOCATION: (4)..(4)
<223> OTHER INFORMATION: a, c, g, or u
<220> FEATURE:
<221> NAME/KEY: modified_base
<222> LOCATION: (6)..(10)
<223> OTHER INFORMATION: a, c, g, or u
<220> FEATURE:
<221> NAME/KEY: modified_base
<222> LOCATION: (12)..(12)
<223> OTHER INFORMATION: a, c, g, or u
<220> FEATURE:
<221> NAME/KEY: modified_base
<222> LOCATION: (15)..(18)
<223> OTHER INFORMATION: a, c, g, or u

<400> SEQUENCE: 27 nnangnnnn unuannnna          19

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, or u
<220> FEATURE:
<221> NAME/KEY: modified_base
<222> LOCATION: (7)..(7)
<223> OTHER INFORMATION: a, c, g, or u
<220> FEATURE:
<221> NAME/KEY: modified_base
<222> LOCATION: (9)..(12)
<223> OTHER INFORMATION: a, c, g, or u
<220> FEATURE:
<221> NAME/KEY: modified_base
<222> LOCATION: (15)..(15)
<223> OTHER INFORMATION: a, c, g, or u
<220> FEATURE:
<221> NAME/KEY: modified_base
<222> LOCATION: (18)..(21)
<223> OTHER INFORMATION: a, c, g, or u

<400> SEQUENCE: 28
gucnnanann nnucnaannn na          22

<210> SEQ ID NO 29
<211> LENGTH: 208
<212> TYPE: DNA
<213> ORGANISM: Homo sapiens

<400> SEQUENCE: 29
gttccaaaaa cagtggataa ttttgtggcc ttagctacag gagagaaagg atttggctac          60
aaaaacagca aattccatcg tgtaatcaag gacttcatga tccagggcgg agacttcacc          120

```
aggggagatg gcacaggagg aaagagcatc tacggtgagc gcttccccga tgagaacttc      180
aaactgaagc actacgggcc tggctggg                                         208

<210> SEQ ID NO 30
<211> LENGTH: 200
<212> TYPE: DNA
<213> ORGANISM: Photinus pyralis

<400> SEQUENCE: 30
tgaacttccc gccgccgttg ttgttttgga gcacggaaag acgatgacgg aaaaagagat      60
cgtggattac gtcgccagtc aagtaacaac cgcgaaaaag ttgcgcggag gagttgtgtt      120
tgtggacgaa gtaccgaaag gtcttaccgg aaaactcgac gcaagaaaaa tcagagagat      180
cctcataaag gccaagaagg                                                  200

<210> SEQ ID NO 31
<211> LENGTH: 108
<212> TYPE: DNA
<213> ORGANISM: Homo sapiens

<400> SEQUENCE: 31
acgggcaagg ccaagtggga tgcctggaat gagctgaaag ggacttccaa ggaagatgcc      60
atgaaagctt acatcaacaa agtagaagag ctaaagaaaa aatacggg                   108

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
guuccaaaaa caguggaua                                                   19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uccaaaaaca guggauaau                                                   19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
caaaaacagu ggauaauuu                                                   19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 35
aaaacagugg auaauuuug                                              19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aacaguggau aauuugug                                               19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
caguggauaa uuuguggc                                               19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
guggauaauu uuguggccu                                              19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ggauaauuuu guggccuua                                              19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
auaauuuugu ggccuuagc                                              19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 41
aauuuugugg ccuuagcua                                                19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uuuuguggcc uuagcuaca                                                19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uuguggccuu agcuacagg                                                19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
guggccuuag cuacaggag                                                19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggccuuagcu acaggagag                                                19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ccuuagcuac aggagagaa                                                19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 47
uuagcuacag gagagaaag                                                19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
agcuacagga gagaaagga                                                19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cuacaggaga gaaaggauu                                                19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
acaggagaga aaggauuug                                                19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aggagagaaa ggauuuggc                                                19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gagagaaagg auuuggcua                                                19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
```
gagaaaggau uuggcuaca                                          19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gaaaggauuu ggcuacaaa                                          19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
aaggauuugg cuacaaaaa                                          19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ggauuuggcu acaaaaaca                                          19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
auuuggcuac aaaacagc                                           19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uuggcuacaa aaacagcaa                                          19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ggcuacaaaa acagcaaau                                              19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cuacaaaaac agcaaauuc                                              19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
acaaaaacag caaauucca                                              19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aaaaacagca aauuccauc                                              19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
aaacagcaaa uuccaucgu                                              19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
acagcaaauu ccaucgugu                                              19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
agcaaauucc aucguguaa                                              19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
caaauuccau cguguaauc                                              19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aauuccaucg uguaaucaa                                              19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uuccaucgug uaaucaagg                                              19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ccaucgugua aucaaggac                                              19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aucguguaau caaggacuu                                              19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cguguaauca aggacuuca                                              19

```
<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uguaaucaag gacuucaug                                                    19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uaaucaagga cuucaugau                                                    19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aucaaggacu ucaugaucc                                                    19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
caaggacuuc augauccag                                                    19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aggacuucau gauccaggg                                                    19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gacuucauga uccagggcg                                                    19
```

```
<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
cuucaugauc cagggcgga                                                    19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ucaugaucca gggcggaga                                                    19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
augauccagg gcggagacu                                                    19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gauccagggc ggagacuuc                                                    19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uccagggcgg agacuucac                                                    19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cagggcggag acuucacca                                                    19

<210> SEQ ID NO 84
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gggcggagac uucaccagg                                                19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gcggagacuu caccagggg                                                19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ggagacuuca ccaggggag                                                19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
agacuucacc agggagau                                                 19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
acuucaccag gggagaugg                                                19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uucaccaggg gagauggca                                                19

<210> SEQ ID NO 90
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
caccagggga gauggcaca                                            19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91 ccagggaga uggcacagg                                             19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
aggggagaug gcacaggag                                            19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
gggagauggc acaggagga                                            19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uggcacagga ggaaagagc                                            19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gauggcacag gaggaaaga                                            19

<210> SEQ ID NO 96
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 96
gcacaggagg aaagagcau                                                19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
acaggaggaa agagcaucu                                                19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
aggaggaaag agcaucuac                                                19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gaggaaagag caucuacgg                                                19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ggaaagagca ucuacggug                                                19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
aaagagcauc uacggugag                                                19

<210> SEQ ID NO 102
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 102
agagcaucua cggugagcg                                                    19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
agcaucuacg gugagcgcu                                                    19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
caucuacggu gagcgcuuc                                                    19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ucuacgguga gcgcuuccc                                                    19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uacggugagc gcuuccccg                                                    19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cggugagcgc uuccccgau                                                    19

<210> SEQ ID NO 108
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 108
gugagcgcuu ccccgauga                                                    19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gagcgcuucc ccgaugaga                                                    19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110 gcgcuuccc cgaugagaac                                                    19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111 gcuucccga ugagaacuu                                                     19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uuccccgaug agaacuuca                                                    19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ccccgaugag aacuucaaa                                                    19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
ccgaugagaa cuucaaacu                                                    19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gaugagaacu ucaaacuga                                                    19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ugagaacuuc aaacugaag                                                    19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
agaacuucaa acugaagca                                                    19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aacuucaaac ugaagcacu                                                    19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cuucaaacug aagcacuac                                                    19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ucaaacugaa gcacuacgg                                              19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
acgggcaagg ccaaguggg                                              19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
cgggcaaggc caaguggga                                              19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gggcaaggcc aagugggau                                              19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ggcaaggcca agugggaug                                              19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gcaaggccaa gugggaugc                                              19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 126
caaggccaag ugggaugcc                                                    19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
aaggccaagu gggaugccu                                                    19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
aggccaagug ggaugccug                                                    19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ggccaagugg gaugccugg                                                    19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gccaaguggg augccugga                                                    19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ccaaguggga ugccuggaa                                                    19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
``` caaguggggau gccuggaau                    19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
aagugggaug ccuggaaug                    19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
agugggaugc cuggaauga                    19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gugggaugcc uggaaugag                    19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ugggaugccu ggaaugagc                    19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gggaugccug gaaugagcu                    19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ggaugccugg aaugagcug					19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gaugccugga augagcuga					19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
augccuggaa ugagcugaa					19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ugccuggaau gagcugaaa					19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gccuggaaug agcugaaag					19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ccuggaauga gcugaaagg					19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cuggaaugag cugaaaggg					19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uggaaugagc ugaaaggga                                                 19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ggaaugagcu gaaagggac                                                 19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gaaugagcug aaagggacu                                                 19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aaugagcuga aagggacuu                                                 19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
augagcugaa agggacuuc                                                 19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ugagcugaaa gggacuucc                                                 19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gagcugaaag ggacuucca                                                    19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
agcugaaagg gacuuccaa                                                    19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gcugaaaggg acuuccaag                                                    19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
cugaaaggga cuuccaagg                                                    19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ugaaagggac uuccaagga                                                    19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gaaagggacu uccaaggaa                                                    19

```
<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aaagggacuu ccaaggaag                                                  19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
aagggacuuc caaggaaga                                                  19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
agggacuucc aaggaagau                                                  19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gggacuucca aggaagaug                                                  19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ggacuuccaa ggaagaugc                                                  19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
gacuuccaag gaagaugcc                                                  19

<210> SEQ ID NO 163
```

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 163 acuccaagg aagaugcca                                                   19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 164
cuuccaagga agaugccau                                                  19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 165
uuccaaggaa gaugccaug                                                  19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 166
uccaaggaag augccauga                                                  19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
ccaaggaaga ugccaugaa                                                  19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
caaggaagau gccaugaaa                                                  19

<210> SEQ ID NO 169
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aaggaagaug ccaugaaag                                                  19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
aggaagaugc caugaaagc                                                  19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ggaagaugcc augaaagcu                                                  19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gaagaugcca ugaaagcuu                                                  19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aagaugccau gaaagcuua                                                  19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
agaugccaug aaagcuuac                                                  19

<210> SEQ ID NO 175
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 175
gaugccauga aagcuuaca                                                       19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
augccaugaa agcuuacau                                                       19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
ugccaugaaa gcuuacauc                                                       19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gccaugaaag cuuacauca                                                       19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
ccaugaaagc uuacaucaa                                                       19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
caugaaagcu uacaucaac                                                       19

<210> SEQ ID NO 181
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 181
augaaagcuu acaucaaca                                                19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ugaaagcuua caucaacaa                                                19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gaaagcuuac aucaacaaa                                                19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
aaagcuuaca ucaacaaag                                                19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aagcuuacau caacaaagu                                                19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
agcuuacauc aacaaagua                                                19

<210> SEQ ID NO 187
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 187
gcuuacauca acaaaguag                                                    19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
cuuacaucaa caaaguaga                                                    19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
uuacaucaac aaaguagaa                                                    19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uacaucaaca aaguagaag                                                    19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
acaucaacaa aguagaaga                                                    19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
caucaacaaa guagaagag                                                    19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 193
aucaacaaag uagaagagc                                          19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ucaacaaagu agaagagcu                                          19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
caacaaagua gaagagcua                                          19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
aacaaaguag aagagcuaa                                          19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
acaaaguaga agagcuaaa                                          19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
caaaguagaa gagcuaaag                                          19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
aaaguagaag agcuaaaga                                              19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
aaguagaaga gcuaaagaa                                              19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
aguagaagag cuaaagaaa                                              19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
guagaagagc uaaagaaaa                                              19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uagaagagcu aaagaaaaa                                              19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
agaagagcua aagaaaaaa                                              19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 205
gaagagcuaa agaaaaaau                                                  19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
aagagcuaaa gaaaaaaua                                                  19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
agagcuaaag aaaaauac                                                   19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gagcuaaaga aaaauacg                                                   19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
agcuaaagaa aaauacgg                                                   19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
gcuaaagaaa aauacggg                                                   19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
```
auccucauaa aggccaaga					19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
agauccucau aaaggccaa					19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
agagauccuc auaaaggcc					19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
agagagaucc ucauaaagg					19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
ucagagagau ccucauaaa					19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
aaucagagag auccucaua					19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
aaaaucagag agauccuca                                          19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218 gaaaaucag agagauccu                                           19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
aagaaaaauc agagagauc                                          19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gcaagaaaaa ucagagaga                                          19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
acgcaagaaa aaucagaga                                          19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
cgacgcaaga aaaaucaga                                          19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cucgacgcaa gaaaaauca                                          19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
aacucgacgc aagaaaaau                                                  19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
aaaacucgac gcaagaaaa                                                  19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ggaaaacucg acgcaagaa                                                  19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ccggaaaacu cgacgcaag                                                  19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
uaccggaaaa cucgacgca                                                  19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
cuuaccggaa aacucgacg                                                  19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
gucuuaccgg aaaacucga                                                19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
aggucuuacc ggaaaacuc                                                19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232 aaagucuua ccggaaaac                                                 19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
cgaaaggucu uaccggaaa                                                19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
accgaaaggu cuuaccgga                                                19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
guaccgaaag gucuuaccg                                                19

-continued

```
<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
aaguaccgaa aggucuuac                                                      19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
cgaaguaccg aaaggucuu                                                      19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
gacgaaguac cgaaagguc                                                      19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
uggacgaagu accgaaagg                                                      19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uguggacgaa guaccgaaa                                                      19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
uuuguggacg aaguaccga                                                      19

<210> SEQ ID NO 242
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uguuugugga cgaaguacc                                                    19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uguguuugug gacgaagua                                                    19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
guuguguuug uggacgaag                                                    19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gaguuguguu uguggacga                                                    19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
aggaguugug uuuguggac                                                    19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ggaggaguug uguuugugg                                                    19

<210> SEQ ID NO 248
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gcggaggagu uguguuugu                                                   19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
gcgcggagga guuguguuu                                                   19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
uugcgcggag gaguugugu                                                   19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
aguugcgcgg aggaguugu                                                   19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
aaaguugcgc ggaggaguu                                                   19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
aaaaaguugc gcggaggag                                                   19

<210> SEQ ID NO 254
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 254
cgaaaaaguu gcgcggagg                                                19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
cgcgaaaaag uugcgcgga                                                19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
accgcgaaaa aguugcgcg                                                19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
caaccgcgaa aaaguugcg                                                19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
aacaaccgcg aaaaaguug                                                19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
guaacaaccg cgaaaaagu                                                19

<210> SEQ ID NO 260
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 260
aaguaacaac cgcgaaaaa                                                19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
ucaaguaaca accgcgaaa                                                19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
agucaaguaa caccgcga                                                 19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ccagucaagu aacaaccgc                                                19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
cgccagucaa guaacaacc                                                19

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gucgccaguc aaguaacaa                                                19

<210> SEQ ID NO 266
<211> LENGTH: 19
<212> TYPE: RNA
<220> FEATURE:
```

```
<223> OTHER INFORMATION: Description of Artificial Sequence: Synthetic
      oligonucleotide

<400> SEQUENCE: 266
acgucgccag ucaaguaac                                                  19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
uuacgucgcc agucaagua                                                  19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
gauuacgucg ccagucaag                                                  19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
uggauuacgu cgccaguca                                                  19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
cguggauuac gucgccagu                                                  19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
aucguggauu acgucgcca                                                  19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 272
agaucgugga uuacgucgc                                           19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
agagaucgug gauuacguc                                           19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
aaagagaucg uggauuacg                                           19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
aaaaagagau cguggauua                                           19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ggaaaaagag aucguggau                                           19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
acggaaaaag agaucgugg                                           19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
ugacggaaaa agagaucgu                                                19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gaugacggaa aaagagauc                                                19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
acgaugacgg aaaaagaga                                                19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
agacgaugac ggaaaaaga                                                19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
aaagacgaug acggaaaaa                                                19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ggaaagacga ugacggaaa                                                19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
acggaaagac gaugacgga                                               19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gcacggaaag acgaugacg                                               19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
gagcacggaa agacgauga                                               19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
uggagcacgg aaagacgau                                               19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uuuggagcac ggaaagacg                                               19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
guuuuggagc acggaaaga                                               19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
uuguuuugga gcacggaaa                                            19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
uguuguuuug gagcacgga                                            19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
guuguuguuu uggagcacg                                            19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ccguuguugu uuuggagca                                            19

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
cgccguuguu guuuuggag                                            19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gccgccguug uuguuuugg                                            19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
ccgccgccgu uguuguuuu                                           19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ucccgccgcc guuguuguu                                           19

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
cuucccgccg ccguuguug                                           19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
aacuucccgc cgccguugu                                           19

<210> SEQ ID NO 300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
ugaacuuccc gccgccguu                                           19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
gaaaugcccu gguaucuca                                           19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
gggagauagu gaugaagua                                           19

```
<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
gaaguacauc cauuauaag                                                19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
guacgacaac cgggagaua                                                19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
agauagugau gaaguacau                                                19

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ugaagacucu gcucaguuu                                                19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gcaugcggcc ucuguuuga                                                19

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308 ugcggcucu guuugauuu                                                 19
```

```
<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gagauaguga ugaaguaca                                                  19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
ggagauagug augaaguac                                                  19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gaagacucug cucaguuug                                                  19

<210> SEQ ID NO 312
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gaaagaatct gtagagaaa                                                  19

<210> SEQ ID NO 313
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gcaatgagct gtttgaaga                                                  19

<210> SEQ ID NO 314
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tgacaaaggt ggataaatt                                                  19
```

<210> SEQ ID NO 315
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 315
ggaaatggat ctctttgaa                                        19

<210> SEQ ID NO 316
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 316
ggaaagtaat ggtccaaca                                        19

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 317
agacagttat gcagctatt                                        19

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 318
ccaattctcg gaagcaaga                                        19

<210> SEQ ID NO 319
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 319
gaaagtaatg gtccaacag                                        19

<210> SEQ ID NO 320
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 320
gcgccagagt gaacaagta                                        19

<210> SEQ ID NO 321

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gaaggtggcc cagctatgt                                                  19

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
ggaaccagcg ccagagtga                                                  19

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gagcgagatt gcaggcata                                                  19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gttagtatct gatgacttg                                                  19

<210> SEQ ID NO 325
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gaaatggaac cactaagaa                                                  19

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ggaaatggaa ccactaaga                                                  19

<210> SEQ ID NO 327
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
caactacact ttccaatgc                                                    19

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ccaccaagat ttcatgata                                                    19

<210> SEQ ID NO 329
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gatcggaact ccaacaaga                                                    19

<210> SEQ ID NO 330
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
aaacggagct acagattat                                                    19

<210> SEQ ID NO 331
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
ccacacagca ttcttgtaa                                                    19

<210> SEQ ID NO 332
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gaagttacct tgagcaatc                                                    19

<210> SEQ ID NO 333
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 333
ggacttggcc gatccagaa                                               19

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
gcacttggat cgagatgag                                               19

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
caaagaccaa ttcgcgtta                                               19

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ccgaatcaat cgcatcttc                                               19

<210> SEQ ID NO 337
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gacatgatcc tgcagttca                                               19

<210> SEQ ID NO 338
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gagcgaatcg tcaccactt                                               19

<210> SEQ ID NO 339
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 339
cctccgagct ggcgtctac                                                19

<210> SEQ ID NO 340
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tcacatggtt aacctctaa                                                19

<210> SEQ ID NO 341
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gatgagggac gccataatc                                                19

<210> SEQ ID NO 342
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
cctctaacta caaatctta                                                19

<210> SEQ ID NO 343
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
ggaaggtgct atccaaaat                                                19

<210> SEQ ID NO 344
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gcaagcaagt cctaacatt                                                19

<210> SEQ ID NO 345
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 345
ggaagaggag tagacctta                                                   19

<210> SEQ ID NO 346
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
aggaatcagt gttgtagta                                                   19

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gaagaggagt agaccttac                                                   19

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gaaagtcaag cctggtatt                                                   19

<210> SEQ ID NO 349
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
aaagtcaagc ctggtatta                                                   19

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gctatgaacg tgaatgatc                                                   19

<210> SEQ ID NO 351
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 351
caagcctggt attacgttt                                                19

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ggaacaagat ctgtcaatt                                                19

<210> SEQ ID NO 353
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
gcaatgaacg tgaacgaaa                                                19

<210> SEQ ID NO 354
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
caatgaacgt gaacgaaat                                                19

<210> SEQ ID NO 355
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ggacaggagc ggtatcaca                                                19

<210> SEQ ID NO 356
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
agacagagct tgagaataa                                                19

<210> SEQ ID NO 357
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gagaagatct ttatgcaaa                                                    19

<210> SEQ ID NO 358
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gaagagaaat cagcagata                                                    19

<210> SEQ ID NO 359
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
gcaagtaact caactaaca                                                    19

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gagctaatct gccacattg                                                    19

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gcagatgagt tactagaaa                                                    19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
caacttaatt gtccagaaa                                                    19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 363
caacacagga ttctgataa                                                    19

<210> SEQ ID NO 364
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
agattgtgcc taagtctct                                                    19

<210> SEQ ID NO 365
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
atgaagatct ggaggtgaa                                                    19

<210> SEQ ID NO 366
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tttgagactt cttgcctaa                                                    19

<210> SEQ ID NO 367
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
agatcaccct ccttaaata                                                    19

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
caacggattt ggtcgtatt                                                    19

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
```
gaaatcccat caccatctt                                                19

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gacctcaact acatggttt                                                19

<210> SEQ ID NO 371
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tggtttacat gttccaata                                                19

<210> SEQ ID NO 372
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gaagaaatcg atgttgttt                                                19

<210> SEQ ID NO 373
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
acacaaactt gaacagcta                                                19

<210> SEQ ID NO 374
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
ggaagaaatc gatgttgtt                                                19

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gaaacgacga gaacagttg                                              19

<210> SEQ ID NO 376
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gcacatggat ggaggttct                                              19

<210> SEQ ID NO 377
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gcagagagag cagatttga                                              19

<210> SEQ ID NO 378
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gaggttctct ggatcaagt                                              19

<210> SEQ ID NO 379
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gagcagattt gaagcaact                                              19

<210> SEQ ID NO 380
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
caaagacgat gacttcgaa                                              19

<210> SEQ ID NO 381
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gatcagcatt tgcatggaa                                              19

<210> SEQ ID NO 382
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
tccaggagtt tgtcaataa                                              19

<210> SEQ ID NO 383
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ggaagctgat ccaccttga                                              19

<210> SEQ ID NO 384
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gcagaaatct aaggatata                                              19

<210> SEQ ID NO 385
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
caacaaggat gaagtctat                                              19

<210> SEQ ID NO 386
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
cagcagaaat ctaaggata                                              19

<210> SEQ ID NO 387
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ctagatggct ttctcagta                                              19

```
<210> SEQ ID NO 388
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
agacaaggtc ccaaagaca                                                  19

<210> SEQ ID NO 389
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
ggaatggcaa gaccagcaa                                                  19

<210> SEQ ID NO 390
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
agaattattc cagggttta                                                  19

<210> SEQ ID NO 391
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gcagacaagg tcccaaaga                                                  19

<210> SEQ ID NO 392
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
agaagcagct tcaggatga                                                  19

<210> SEQ ID NO 393
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
gagcttgact tccagaaga                                                  19
```

```
<210> SEQ ID NO 394
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
ccaccgaagt tcaccctaa                                                    19

<210> SEQ ID NO 395
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gagaagagct cctccatca                                                    19

<210> SEQ ID NO 396
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gaaagagcat ctacggtga                                                    19

<210> SEQ ID NO 397
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gaaaggattt ggctacaaa                                                    19

<210> SEQ ID NO 398
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
acagcaaatt ccatcgtgt                                                    19

<210> SEQ ID NO 399
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
ggaaagactg ttccaaaaa                                                    19

<210> SEQ ID NO 400
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
caacacgcct catcctcta                                              19

<210> SEQ ID NO 401
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
catgaaagct tacatcaac                                              19

<210> SEQ ID NO 402
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
aagatgccat gaaagctta                                              19

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
gcacataccg cctgagtct                                              19

<210> SEQ ID NO 404
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gatcaaatct gaagaagga                                              19

<210> SEQ ID NO 405
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gccaagaagt ttcctaata                                              19

<210> SEQ ID NO 406
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
cagcatatct tgaaccatt                                                19

<210> SEQ ID NO 407
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
gaacaaagga aacggatga                                                19

<210> SEQ ID NO 408
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
cggaaacggt ccaggctat                                                19

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
gcttcgagca gacatgata                                                19

<210> SEQ ID NO 410
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
cctacacggt cctcctata                                                19

<210> SEQ ID NO 411
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
gccaagaacc tcatcatct                                                19

<210> SEQ ID NO 412
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 412
gatatgggct gaatacaaa                                              19

<210> SEQ ID NO 413
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
gcactctgat tgacaaata                                              19

<210> SEQ ID NO 414
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
tgaagtctct gattaagta                                              19

<210> SEQ ID NO 415
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
tcagagagat cctcataaa                                              19

<210> SEQ ID NO 416
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gcaagaagat caccatttc                                              19

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gagagaaatt tgaggatga                                              19

<210> SEQ ID NO 418
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 418
gaaaggattt ggctataag                                                  19

<210> SEQ ID NO 419
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
gaaagaaggc atgaacatt                                                  19

<210> SEQ ID NO 420
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
gggagatagt gatgaagta                                                  19

<210> SEQ ID NO 421
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
gaagtacatc cattataag                                                  19

<210> SEQ ID NO 422
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gtacgacaac cgggagata                                                  19

<210> SEQ ID NO 423
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
agatagtgat gaagtacat                                                  19

<210> SEQ ID NO 424
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 424
tgaagactct gctcagttt                                                       19

<210> SEQ ID NO 425
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gcatgcggcc tctgtttga                                                       19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
gcacacagcu uacuacauc                                                       19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
gagauggcac aggaggaaa                                                       19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gaaggaacgu gaugugauc                                                       19

<210> SEQ ID NO 429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gcacuacucc uguguguga                                                       19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 430
gaacccagcu ggagaacuu                                              19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
gauauacagu gugaucuua                                              19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
guacuacgau ccugauuau                                              19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gugccgaccu uuacaauuu                                              19

<210> SEQ ID NO 434
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
gaaggaaact gaattcaaa                                              19

<210> SEQ ID NO 435
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ggaaatatgt actacgaaa                                              19

<210> SEQ ID NO 436
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 436
ccacaaagca gtgaattta                                                    19

<210> SEQ ID NO 437
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
gtaacaagct cacgcagtt                                                    19

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
gggaugggau uucauguaa                                                    19

<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ggaaauagac accaaaucu                                                    19

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
gaaauagaca ccaaaucuu                                                    19

<210> SEQ ID NO 441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
gaauccaagu guccucuga                                                    19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 442
caacugagga ggaauuugu                                                19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uagaagggau aucaaagu                                                 19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
uaaccaagag uauuccauu                                                19

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ggaauuugua gaagggaua                                                19

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ggucaaaguu cuagaugcu                                                19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
cagaaaggcu gcugaugac                                                19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
```
aaccaagagu auuccauuu                                           19

<210> SEQ ID NO 449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
gacgagggau gggauuuca                                           19

<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ucaccaaucc caaggaaug                                           19

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
gaggaggaau uuguagaag                                           19

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
gugcaugugu ucagaaagg                                           19

<210> SEQ ID NO 453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
gcagagacaa uaaaacauu                                           19

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
ggauauacaa aguggaaau                                                    19

<210> SEQ ID NO 455
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ucacaacuga ggaggaauu                                                    19

<210> SEQ ID NO 456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
guagaaggga uauacaaag                                                    19

<210> SEQ ID NO 457
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
ugaggaggaa uuuguagaa                                                    19

<210> SEQ ID NO 458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
caauaaaaca uuccuguga                                                    19

<210> SEQ ID NO 459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
cgucaccaau cccaaggaa                                                    19

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
cauguaacca agaguauuc                                                    19

<210> SEQ ID NO 461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gaugggauuu cauguaacc                                                19

<210> SEQ ID NO 462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
ggacgaggga ugggauuuc                                                19

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
cugccuugcu ggacuggua                                                19

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
uugcuggacu gguauuugu                                                19

<210> SEQ ID NO 465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
gauuucaugu aaccaagag                                                19

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
ccaagugucc ucugauggu                                                19

<210> SEQ ID NO 467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
cgagggaugg gauuucaug                                                  19

<210> SEQ ID NO 468
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
ccgugcaugu guucagaaa                                                  19

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
gauggucaaa guucuagau                                                  19

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
ggauuucaug uaaccaaga                                                  19

<210> SEQ ID NO 471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
gcaugcagag gugguauuc                                                  19

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ggccgugcau guguucaga                                                  19

```
<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
gacugguauu ugugucuga                                                19

<210> SEQ ID NO 474
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
guccaggcag agacaauaa                                                19

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
ggaugggauu ucauguaac                                                19

<210> SEQ ID NO 476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
gaauuuguag aagggauau                                                19

<210> SEQ ID NO 477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
ccucugaugg ucaaaguuc                                                19

<210> SEQ ID NO 478
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ucaauguggc cgugcaugu                                                19

<210> SEQ ID NO 479
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
uuucauguaa ccaagagua                                                    19

<210> SEQ ID NO 480
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
caauguggcc gugcaugug                                                    19

<210> SEQ ID NO 481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
aaguggaaau agacaccaa                                                    19
```

METHODS AND COMPOSITIONS FOR SELECTING SIRNA OF IMPROVED FUNCTIONALITY

CROSS-REFERENCE TO RELATED APPLICATIONS

This application is a continuation of U.S. application Ser. No. 14/965,816, filed Dec. 10, 2015, allowed, which is a continuation of U.S. application Ser. No. 14/097,551, filed Dec. 5, 2013, now U.S. Pat. No. 9,228,186, issued Jan. 5, 2016, which is a continuation-in-part of U.S. application Ser. No. 10/940,892, filed Sep. 14, 2004, pending. U.S. application Ser. No. 10/940,892 is a continuation of International Application No. PCT/US04/14885, filed May 12, 2004; U.S. application Ser. No. 10/940,892 is also a continuation-in-part of U.S. application Ser. No. 10/714,333, filed Nov. 14, 2003, now U.S. Pat. No. 8,090,542, issued Jan. 3, 2012, which claims the benefit of U.S. Provisional Application No. 60/426,137, filed Nov. 14, 2002, and U.S. Provisional Application No. 60/502,050, filed Sep. 10, 2003. The disclosures of all of these applications, including the sequence listings and tables submitted in electronic form in lieu of paper, are incorporated by reference into the instant specification.

SEQUENCE LISTING

The instant application contains a Sequence Listing with 481 sequences which has been submitted via EFS-Web and is hereby incorporated by reference in its entirety. Said ASCII copy, created on Aug. 2, 2017, is named 38119_US_CRF_sequencelisting.txt, and is 86,016 bytes in size.

FIELD OF INVENTION

The present invention relates to RNA interference ("RNAi").

BACKGROUND OF THE INVENTION

Relatively recently, researchers observed that double stranded RNA ("dsRNA") could be used to inhibit protein expression. This ability to silence a gene has broad potential for treating human diseases, and many researchers and commercial entities are currently investing considerable resources in developing therapies based on this technology.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation.

It is generally considered that the major mechanism of RNA induced silencing (RNA interference, or RNAi) in mammalian cells is mRNA degradation. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) Ribonuclease Activity and RNA Binding of Recombinant Human Dicer, *EMBO J.* 1. 21(21): 5864-5874; Tabara et al. (2002) The dsRNA Binding Protein RDE-4 Interacts with RDE-1, DCR-1 and a DexH-box Helicase to Direct RNAi in *C. elegans, Cell* 109(7):861-71; Ketting et al. (2002) Dicer Functions in RNA Interference and in Synthesis of Small RNA Involved in Developmental Timing *C. elegans;* Martinez et al., Single-Stranded Antisense siRNAs Guide Target RNA Cleavage in RNAi, *Cell* 110(5):563; Hutvagner & Zamore (2002) A microRNA in a multiple-turnover RNAi enzyme complex, *Science* 297:2056.

From a mechanistic perspective, introduction of long double stranded RNA into plants and invertebrate cells is broken down into siRNA by a Type III endonuclease known as Dicer. Sharp, *RNA interference*—2001, Genes Dev. 2001, 15:485. Dicer, a ribonuclease-III-like enzyme, processes the dsRNA into 19-23 base pair short interfering RNAs with characteristic two base 3' overhangs. Bernstein, Caudy, Hammond, & Hannon (2001) Role for a bidentate ribonuclease in the initiation step of RNA interference, *Nature* 409:363. The siRNAs are then incorporated into an RNA-induced silencing complex (RISC) where one or more helicases unwind the siRNA duplex, enabling the complementary antisense strand to guide target recognition. Nykanen, Haley, & Zamore (2001) ATP requirements and small interfering RNA structure in the RNA interference pathway, *Cell* 107:309. Upon binding to the appropriate target mRNA, one or more endonucleases within the RISC cleaves the target to induce silencing. Elbashir, Lendeckel, & Tuschl (2001) RNA interference is mediated by 21- and 22-nucleotide RNAs, *Genes Dev.* 15:188, FIG. 1.

The interference effect can be long lasting and may be detectable after many cell divisions. Moreover, RNAi exhibits sequence specificity. Kisielow, M. et al. (2002) Isoform-specific knockdown and expression of adaptor protein ShcA using small interfering RNA, *J. Biochem.* 363:1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Successful siRNA-dependent gene silencing depends on a number of factors. One of the most contentious issues in RNAi is the question of the necessity of siRNA design, i.e., considering the sequence of the siRNA used. Early work in *C. elegans* and plants circumvented the issue of design by introducing long dsRNA (see, for instance, Fire, A. et al. (1998) *Nature* 391:806-811). In this primitive organism, long dsRNA molecules are cleaved into siRNA by Dicer, thus generating a diverse population of duplexes that can potentially cover the entire transcript. While some fraction of these molecules are non-functional (i.e., induce little or no silencing) one or more have the potential to be highly functional, thereby silencing the gene of interest and alleviating the need for siRNA design. Unfortunately, due to the interferon response, this same approach is unavailable for mammalian systems. While this effect can be circumvented by bypassing the Dicer cleavage step and directly introducing siRNA, this tactic carries with it the risk that the chosen siRNA sequence may be non-functional or semi-functional.

A number of researches have expressed the view that siRNA design is not a crucial element of RNAi. On the other hand, others in the field have begun to explore the possibility that RNAi can be made more efficient by paying attention to the design of the siRNA. Unfortunately, none of the reported methods have provided a satisfactory scheme for reliably selecting siRNA with acceptable levels of functionality. Accordingly, there is a need to develop rational criteria by which to select siRNA with an acceptable level of functionality, and to identify siRNA that have this improved level of functionality, as well as to identify siRNAs that are hyperfunctional.

SUMMARY OF THE INVENTION

The present invention is directed to increasing the efficiency of RNAi, particularly in mammalian systems. Accordingly, the present invention provides kits, siRNAs and methods for increasing siRNA efficacy.

According to a first embodiment, the present invention provides a kit for gene silencing, wherein said kit is comprised of a pool of at least two siRNA duplexes, each of which is comprised of a sequence that is complementary to a portion of the sequence of one or more target messenger RNA, and each of which is selected using non-target specific criteria.

According to a second embodiment, the present invention provides a method for selecting an siRNA, said method comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; and determining the relative functionality of the at least two siRNAs.

According to a third embodiment, the present invention also provides a method for selecting an siRNA wherein said selection criteria are embodied in a formula comprising:

$$(-14)*G_{13}-13*A_1-12*U_7-11*U_2-10*A_{11}-10*U_4-$$
$$10C_3-10*C_5-10*C_6-9*A_{10}-9*U_9-9*C_{18}-$$
$$8*G_{10}-7*U_1-7*U_{16}-7*C_{17}-7*C_{19}+7*U_{17}+$$
$$8*A_2+8*A_4+8*A_5+8*C_4+9*G_8+10*A_7+$$
$$10*U_{18}+11*A_{19}+11*C_9+15*G_1+18*A_3+$$
$$19*U_{10}-Tm-3*(GC_{total})-6*(GC_{15-19})-30*X; \text{ or} \quad \text{Formula VIII}$$

$$(-8)*A1+(-1)*A2+(12)*A3+(7)*A4+(18)*A5+(12)$$
$$*A6+(19)*A7+(6)*A8+(-4)*A9+(-5)*A10+(-2)$$
$$*A11+(5)*A12+(17) *A13+(-3)*A14+(4)$$
$$*A15+(2)*A16+(8)*A17+(11)*A18+(30)*A19+$$
$$(-13)*U1+(-10)*U2+(2)*U3+(-2)*U4+(-5)$$
$$*U5+(5)*U6+(-2)*U7+(-10)*U8+(-5)*U9+(15)$$
$$*U10+(-1)*U11+(0)*U12+(10)*U13+(-9)$$
$$*U14+(-13)*U15+(-10)*U16+(3)*U17+(9)$$
$$*U18+(9)*U19+(7)*C1+(3)*C2+(-21)*C3+(5)$$
$$*C4+(-9)*C5+(-20)*C6+(-18)*C7+(-5)*C8+$$
$$(5)*C9+(1)*C10+(2)*C11+(-5)*C12+(-3)$$
$$*C13+(-6)*C14+(-2)*C15+(-5)*C16+(-3)$$
$$*C17+(-12)*C18+(-18)*C19+(14)*G1+(8)*$$
$$G2+(7)*G3+(-10)*G4+(-4)*G5+(2)*G6+(1)$$
$$*G7+(9)*G8+(5)*G9+(-11)*G10+(1)*G11+(9)$$
$$*G12+(-24)*G13+(18)*G14+(11)* G15+(13)$$
$$*G16+(-7)*G17+(-9)*G18+(-22)*G19+6*$$
$$\text{(number of A+U in position 15-19)} -3*\text{(number}$$
$$\text{of G+C in whole siRNA),} \quad \text{Formula X}$$

wherein position numbering begins at the 5'-most position of a sense strand, and $A_1=1$ if A is the base at position 1 of the sense strand, otherwise its value is 0;

$A_2=1$ if A is the base at position 2 of the sense strand, otherwise its value is 0;

$A_3=1$ if A is the base at position 3 of the sense strand, otherwise its value is 0;

$A_4=1$ if A is the base at position 4 of the sense strand, otherwise its value is 0;

$A_5=1$ if A is the base at position 5 of the sense strand, otherwise its value is 0;

$A_6=1$ if A is the base at position 6 of the sense strand, otherwise its value is 0;

$A_7=1$ if A is the base at position 7 of the sense strand, otherwise its value is 0;

$A_{10}=1$ if A is the base at position 10 of the sense strand, otherwise its value is 0;

$A_{11}=1$ if A is the base at position 11 of the sense strand, otherwise its value is 0;

$A_{13}=1$ if A is the base at position 13 of the sense strand, otherwise its value is 0;

$A_{19}=1$ if A is the base at position 19 of the sense strand, otherwise if another base is present or the sense strand is only 18 base pairs in length, its value is 0;

$C_3=1$ if C is the base at position 3 of the sense strand, otherwise its value is 0;

$C_4=1$ if C is the base at position 4 of the sense strand, otherwise its value is 0;

$C_5=1$ if C is the base at position 5 of the sense strand, otherwise its value is 0;

$C_6=1$ if C is the base at position 6 of the sense strand, otherwise its value is 0;

$C_7=1$ if C is the base at position 7 of the sense strand, otherwise its value is 0;

$C_9=1$ if C is the base at position 9 of the sense strand, otherwise its value is 0;

$C_{17}=1$ if C is the base at position 17 of the sense strand, otherwise its value is 0;

$C_{18}=1$ if C is the base at position 18 of the sense strand, otherwise its value is 0;

$C_{19}=1$ if C is the base at position 19 of the sense strand, otherwise if another base is present or the sense strand is only 18 base pairs in length, its value is 0;

$G_1=1$ if G is the base at position 1 on the sense strand, otherwise its value is 0;

$G_2=1$ if G is the base at position 2 of the sense strand, otherwise its value is 0;

$G_8=1$ if G is the base at position 8 on the sense strand, otherwise its value is 0;

$G_{10}=1$ if G is the base at position 10 on the sense strand, otherwise its value is 0;

$G_{13}=1$ if G is the base at position 13 on the sense strand, otherwise its value is 0:

$G_{19}=1$ if G is the base at position 19 of the sense strand, otherwise if another base is present or the sense strand is only 18 base pairs in length, its value is 0;

$U_1=1$ if U is the base at position 1 on the sense strand, otherwise its value is 0;

$U_2=1$ if U is the base at position 2 on the sense strand, otherwise its value is 0;

$U_3=1$ if U is the base at position 3 on the sense strand, otherwise its value is 0;

$U_4=1$ if U is the base at position 4 on the sense strand, otherwise its value is 0;

$U_7=1$ if U is the base at position 7 on the sense strand, otherwise its value is 0;

$U_9=1$ if U is the base at position 9 on the sense strand, otherwise its value is 0;

$U_{10}=1$ if U is the base at position 10 on the sense strand, otherwise its value is 0;

$U_{15}=1$ if U is the base at position 15 on the sense strand, otherwise its value is 0;

$U_{16}=1$ if U is the base at position 16 on the sense strand, otherwise its value is 0;

$U_{17}=1$ if U is the base at position 17 on the sense strand, otherwise its value is 0;

$U_{18}=1$ if U is the base at position 18 on the sense strand, otherwise its value is 0.

$GC_{15-9}$=the number of G and C bases within positions 15-19 of the sense strand, or within positions 15-18 if the sense strand is only 18 base pairs in length;

$GC_{total}$=the number of G and C bases in the sense strand;

Tm=100 if the siRNA oligo has the internal repeat longer then 4 base pairs, otherwise its value is 0; and X=the number of times that the same nucleotide repeats four or more times in a row.

According to a fourth embodiment, the invention provides a method for developing an algorithm for selecting siRNA, said method comprising: (a) selecting a set of siRNA; (b) measuring gene silencing ability of each siRNA from said set; (c) determining relative functionality of each siRNA; (d) determining improved functionality by the presence or absence of at least one variable selected from the group consisting of the presence or absence of a particular nucleotide at a particular position, the total number of As and Us in positions 15-19, the number of times that the same nucleotide repeats within a given sequence, and the total number of Gs and Cs; and (e) developing an algorithm using the information of step (d).

According to a fifth embodiment, the present invention provides a kit, wherein said kit is comprised of at least two siRNAs, wherein said at least two siRNAs comprise a first optimized siRNA and a second optimized siRNA, wherein said first optimized siRNA and said second optimized siRNA are optimized according a formula comprising Formula X.

The present invention also provides a method for identifying a hyperfunctional siRNA, comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; determining the relative functionality of the at least two siRNAs and assigning each of the at least two siRNAs a functionality score; and selecting siRNAs from the at least two siRNAs that have a functionality score that reflects greater than 80 percent silencing at a concentration in the picomolar range, wherein said greater than 80 percent silencing endures for greater than 120 hours.

According to a sixth embodiment, the present invention provides a hyperfunctional siRNA that is capable of silencing Bcl2.

According to a seventh embodiment, the present invention provides a method for developing an siRNA algorithm for selecting functional and hyperfunctional siRNAs for a given sequence. The method comprises:

(a) selecting a set of siRNAs;

(b) measuring the gene silencing ability of each siRNA from said set;

(c) determining the relative functionality of each siRNA;

(d) determining the amount of improved functionality by the presence or absence of at least one variable selected from the group consisting of the total GC content, melting temperature of the siRNA, GC content at positions 15-19, the presence or absence of a particular nucleotide at a particular position, relative thermodynamic stability at particular positions in a duplex, and the number of times that the same nucleotide repeats within a given sequence; and (e) developing an algorithm using the information of step (d).

According to this embodiment, preferably the set of siRNAs comprises at least 90 siRNAs from at least one gene, more preferably at least 180 siRNAs from at least two different genes, and most preferably at least 270 and 360 siRNAs from at least three and four different genes, respectively. Additionally, in step (d) the determination is made with preferably at least two, more preferably at least three, even more preferably at least four, and most preferably all of the variables. The resulting algorithm is not target sequence specific.

In another embodiment, the present invention provides rationally designed siRNAs identified using the formulas above.

In yet another embodiment, the present invention is directed to hyperfunctional siRNA.

The ability to use the above algorithms, which are not sequence or species specific, allows for the cost-effective selection of optimized siRNAs for specific target sequences. Accordingly, there will be both greater efficiency and reliability in the use of siRNA technologies.

In various embodiments, siRNAs that target nucleotide sequences for transthyretin (TTR, also referred to as TBPA or PALB) are provided. In various embodiments, the siRNAs are rationally designed. In various embodiments, the siRNAs are functional or hyperfunctional.

In various embodiments, an siRNA that targets the nucleotide sequence for TTR is provided, wherein the siRNA is selected from the group consisting of various siRNA sequences targeting the nucleotide sequences for TTR that are disclosed herein. In various embodiments, the siRNA sequence is selected from the group consisting of SEQ ID NO. 438 to SEQ ID NO. 481.

In various embodiments, siRNA comprising a sense region and an antisense region are provided, said sense region and said antisense region together form a duplex region comprising 18-30 base pairs, and said sense region comprises a sequence that is at least 90% similar to a sequence selected from the group consisting of siRNA sequences targeting nucleotide sequences for TTR that are disclosed herein. In various embodiments, the siRNA sequence is selected from the group consisting of SEQ ID NO. 438 to SEQ ID NO. 481.

In various embodiments, an siRNA comprising a sense region and an antisense region is provided, said sense region and said antisense region together form a duplex region comprising 18-30 base pairs, and said sense region comprises a sequence that is identical to a contiguous stretch of at least 18 bases of a sequence selected from the group consisting of SEQ ID NO. 438 to SEQ ID NO. 481. In various embodiments, the duplex region is 19-30 base pairs, and the sense region comprises a sequence that is identical to a sequence selected from the group consisting of SEQ ID NO. 438 to SEQ ID NO. 481.

In various embodiments, a pool of at least two siRNAs is provided, wherein said pool comprises a first siRNA and a second siRNA, said first siRNA comprising a duplex region of length 18-30 base pairs that has a first sense region that is at least 90% similar to 18 bases of a first sequence selected from the group consisting of SEQ ID NO. 438 to SEQ ID NO. 481, and said second siRNA comprises a duplex region of length 18-30 base pairs that has a second sense region that is at least 90% similar to 18 bases of a second sequence selected from the group consisting of SEQ ID NO. 438 to SEQ ID NO. 481, wherein said first sense region and said second sense region are not identical.

In various embodiments, the first sense region comprises a sequence that is identical to at least 18 bases of a sequence selected from the group consisting of SEQ ID NO. 438 to SEQ ID NO. 481, and said second sense region comprises a sequence that is identical to at least 18 bases of a sequence selected from the group consisting of SEQ ID NO. 438 to SEQ ID NO. 481. In various embodiments, the duplex of said first siRNA is 19-30 base pairs, and said first sense region comprises a sequence that is at least 90% similar to a sequence selected from the group consisting of SEQ ID NO. 438 to SEQ ID NO. 481, and said duplex of said second siRNA is 19-30 base pairs and comprises a sequence that is at least 90% similar to a sequence selected from the group consisting of SEQ ID NO. 438 to SEQ ID NO. 481.

In various embodiments, the duplex of said first siRNA is 19-30 base pairs and said first sense region comprises a sequence that is identical to at least 18 bases of a sequence selected from the group consisting of SEQ ID NO. 438 to SEQ ID NO. 481, and said duplex of said second siRNA is 19-30 base pairs and said second region comprises a sequence that is identical to a sequence selected from the group consisting of SEQ ID NO. 438 to SEQ ID NO. 481.

For a better understanding of the present invention together with other and further advantages and embodiments, reference is made to the following description taken, in conjunction with the examples, the scope of which is set forth in the appended claims.

BRIEF DESCRIPTION OF THE FIGURES

FIG. 3B shows the frequency of different functional groups (>95% silencing (black), >80% silencing (gray), >50% silencing (dark gray), and <50% silencing (white)) based on GC content. In cases where a given bar is absent from a particular GC percentage, no siRNA were identified for that particular group.

FIG. 4A, FIG. 4B, FIG. 4C, FIG. 4D, and FIG. 4E are representations of a statistical analysis that revealed correlations between silencing and five sequence-related properties of siRNA: (FIG. 4A) an A at position 19 of the sense strand, (FIG. 4B) an A at position 3 of the sense strand, (FIG. 4C) a U at position 10 of the sense strand, (FIG. 4D) a base other than G at position 13 of the sense strand, and (FIG. 4E) a base other than C at position 19 of the sense strand. All variables were correlated with siRNA silencing of firefly luciferase and human cyclophilin. siRNAs satisfying the criterion are grouped on the left (Selected) while those that do not, are grouped on the right (Eliminated). Y-axis is "% Silencing of Control." Each position on the X-axis represents a unique siRNA.

FIG. 5A and FIG. 5B are representations of firefly luciferase and cyclophilin siRNA panels sorted according to functionality and predicted values using Formula VIII. The siRNA found within the circle represent those that have Formula VIII values (SMARTSCORES™, or siRNA rank) above zero. siRNA outside the indicated area have calculated Formula VIII values that are below zero. Y-axis is "Expression (% Control)." Each position on the X-axis represents a unique siRNA.

FIG. 7 is a histogram showing the differences in duplex functionality upon introduction of base pair mismatches. The X-axis shows the mismatch introduced in the siRNA and the position it is introduced (e.g., 8C >A reveals that position 8 (which normally has a C) has been changed to an A). The Y-axis is "% Silencing (Normalized to Control)." The samples on the X-axis represent siRNAs at 100 nM and are, reading from left to right: 1A to C, 1A to G, 1A to U; 2A to C, 2A to G, 2A to U; 3A to C, 3A to G, 3A to U; 4G to A, 4G to C; 4G to U; 5U to A, 5U to C, 5U to G; 6U to A, 6U to C, 6U to G; 7G to A, 7G to C, 7G to U; 8C to A, 8C to G, 8C to U; 9G to A, 9G to C, 9G to U; 10C to A, 10C to G, 10C to U; 11G to A, 11G to C, 11G to U; 12G to A, 12G to C, 12G to U; 13A to C, 13A to G, 13A to U; 14G to A, 14G to C, 14G to U; 15G to A, 15G to C, 15G to U; 16A to C, 16A to G, 16A to U; 17G to A, 17G to C, 17G to U; 18U to A, 18U to C, 18U to G; 19U to A, 19U to C, 19U to G; 20 wt; Control.

FIG. 8 is histogram that shows the effects of 5' sense and antisense strand modification with 2'-O-methylation on functionality.

FIG. 10A, FIG. 10B, FIG. 10C, FIG. 10D, and FIG. 10E compare the RNAi of five different genes (SEAP, DBI, PLK, Firefly Luciferase, and *Renilla* Luciferase, respectively) by varying numbers of randomly selected siRNA and four rationally designed (SMART-selected) siRNA chosen using the algorithm described in Formula VIII. In addition, RNAi induced by a pool of the four SMART-selected siRNA is reported at two different concentrations (100 and 400 nM). FIG. 10F is a comparison between a pool of randomly selected EGFR siRNA (Pool 1) and a pool of SMART-selected EGFR siRNA (Pool 2). Pool 1, S1-S4 and Pool 2 S1-S4 represent the individual members that made up each respective pool. Note that numbers for random siRNAs represent the position of the 5' end of the sense strand of the duplex. The Y-axis represents the % expression of the control(s). The X-axis is the percent expression of the control.

FIG. 13 is the sequence of the top ten Bcl2 siRNAs as determined by Formula VIII. Sequences are listed 5' to 3'.

FIG. 16A and FIG. 16B are histograms demonstrating the inhibition of target gene expression by pools of 2 (FIG. 16A) and 3 (FIG. 16B) siRNA duplexes taken from the walk described in FIG. 15. The Y-axis in each represents the percent expression relative to control. The X-axis in each represents the position of the first siRNA in paired pools, or trios of siRNAs. For instance, the first paired pool contains siRNAs 1 and 3. The second paired pool contains siRNAs 3 and 5. Pool 3 (of paired pools) contains siRNAs 5 and 7, and so on. For each of FIG. 16A and FIG. 16B, the X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.

FIG. 17A and FIG. 17B are histograms demonstrating the inhibition of target gene expression by pools of 4 (FIG. 17A) and 5 (FIG. 17B) siRNA duplexes. The Y-axis in each represents the percent expression relative to control. The X-axis in each represents the position of the first siRNA in each pool. For each of FIG. 17A and FIG. 17B, the X-axis from left to right is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.

FIG. 18A and FIG. 18B are histograms demonstrating the inhibition of target gene expression by siRNAs that are ten (FIG. 18A) and twenty (FIG. 18B) base pairs apart. The Y-axis represents the percent expression relative to a control. The X-axis represents the position of the first siRNA in each pool. For FIG. 18A, the X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, and Plasmid. For FIG. 18B, the X-axis from left to right designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and Plasmid.

FIG. 20 shows that the combination of several semifunctional siRNAs (dark gray) result in a significant improvement of gene expression inhibition over individual (semifunctional; light gray) siRNA. The X-axis represents the position of the individual siRNAs that were measured for effect on expression. The Y-axis represents the percent expression relative to a control.

FIG. 21A, FIG. 21B and FIG. 21C show both pools (Library, Lib) and individual siRNAs in inhibition of gene expression of Beta-Galactosidase, Renilla Luciferase and SEAP (alkaline phosphatase), respectively. Numbers on the X-axis indicate the position of the 5'-most nucleotide of the sense strand of the duplex. The Y-axis represents the percent expression of each gene relative to a control. Libraries contain 19 nucleotide long siRNAs (not including overhangs) that begin at the following nucleotides: FIG. 21B—SEAP: Lib 1: 206, 766, 812,923, Lib 2: 1117, 1280, 1300, 1487, Lib 3: 206, 766, 812, 923, 1117, 1280, 1300,1487, Lib 4: 206, 812, 1117, 1300, Lib 5: 766, 923, 1280, 1487, Lib 6: 206, 1487; FIG. 21A—Bgal: Lib 1 (denoted as I on the figure): 979, 1339, 2029, 2590, Lib 2 (denoted as II on the figure): 1087,1783,2399,3257, Lib 3 (denoted as III on the figure): 979, 1783, 2590, 3257, Lib 4 (denoted as IV on the figure): 979, 1087, 1339, 1783, 2029, 2399,2590,3257, Lib 5 (denoted as V on the figure): 979, 1087, 1339, 1783, Lib 6 (denoted as VI on the figure): 2029,2399,2590,3257; FIG. 21C—Renilla: Lib 1: 174,300,432,568, Lib 2: 592, 633, 729,867, Lib 3: 174, 300, 432, 568, 592, 633,729,867, Lib 4: 174, 432, 592, 729, Lib 5: 300,568,633,867, Lib 6: 592,568.

DETAILED DESCRIPTION

Definitions

Figure 1:
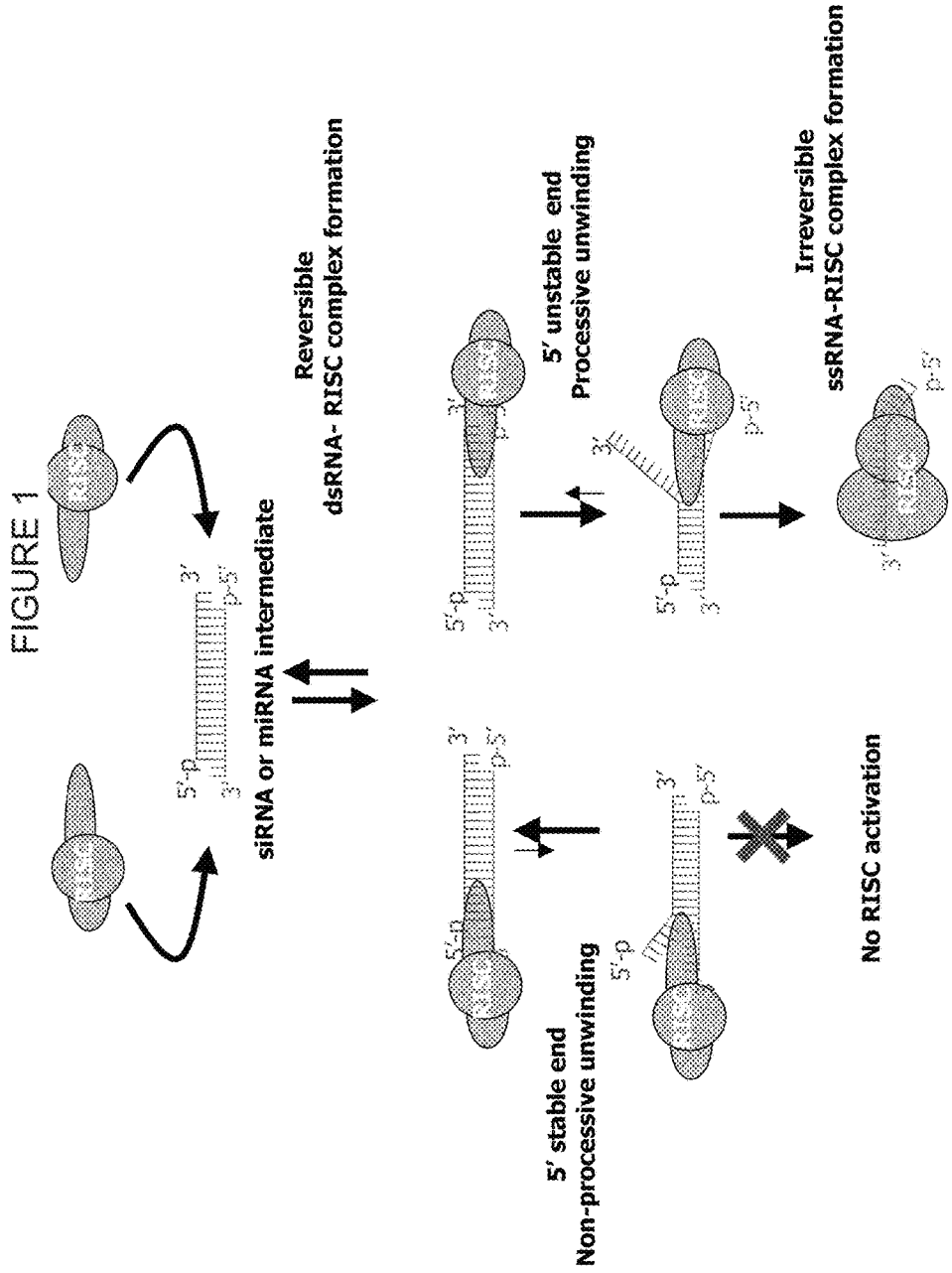
FIG. 1 shows a model for siRNA-RISC interactions. RISC has the ability to interact with either end of the siRNA or miRNA molecule. Following binding, the duplex is unwound, and the relevant target is identified, cleaved, and released.

Unless stated otherwise, the following terms and phrases have the meanings provided below:

Complementary

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity.

Deoxynucleotide

The term "deoxynucleotide" refers to a nucleotide or polynucleotide lacking a hydroxyl group (OH group) at the 2' and/or 3' position of a sugar moiety. Instead, it has a hydrogen bonded to the 2' and/or 3' carbon. Within an RNA molecule that comprises one or more deoxynucleotides, "deoxynucleotide" refers to the lack of an OH group at the 2' position of the sugar moiety, having instead a hydrogen bonded directly to the 2' carbon.

Deoxyribonucleotide

The terms "deoxyribonucleotide" and "DNA" refer to a nucleotide or polynucleotide comprising at least one sugar moiety that has an H, rather than an OH, at its 2' and/or 3' position.

Duplex Region

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" has 19 base pairs. The remaining bases may, for example, exist as 5' and 3' overhangs. Further, within the duplex region, 100% complementarity is not required; substantial complementarity is allowable within a duplex region. Substantial complementarity refers to 79% or greater complementarity. For example, a mismatch in a duplex region consisting of 19 base pairs results in 94.7% complementarity, rendering the duplex region substantially complementary.

Filters

The term "filter" refers to one or more procedures that are performed on sequences that are identified by the algorithm. In some instances, filtering includes in silico procedures where sequences identified by the algorithm can be screened to identify duplexes carrying desirable or undesirable motifs. Sequences carrying such motifs can be selected for, or selected against, to obtain a final set with the preferred properties. In other instances, filtering includes wet lab experiments. For instance, sequences identified by one or more versions of the algorithm can be screened using any one of a number of procedures to identify duplexes that have hyperfunctional traits (e.g., they exhibit a high degree of silencing at subnanomolar concentrations and/or exhibit high degrees of silencing longevity).

Gene Silencing

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

miRNA

The term "miRNA" refers to microRNA.

Nucleotide

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include but are not limited to 3-nitropyrrole, 5-nitroindole, or nebularine. The term " nucleotide" is also meant to include the N3' to P5' phosphoramidate, resulting from the substitution of a ribosyl 3' oxygen with an amine group.

Further, the term nucleotide also includes those species that have a detectable label, such as for example a radioactive or fluorescent moiety, or mass label attached to the nucleotide.

Off-Target Silencing and Off-Target Interference

The phrases "off-target silencing" and "off-target interference" are defined as degradation of mRNA other than the intended target mRNA due to overlapping and/or partial homology with secondary mRNA messages.

Polynucleotide

The term "polynucleotide" refers to polymers of nucleotides, and includes but is not limited to DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

Polyribonucleotide

The term "polyribonucleotide" refers to a polynucleotide comprising two or more modified or unmodified ribonucleotides and/or their analogs. The term "polyribonucleotide" is used interchangeably with the term "oligoribonucleotide."

Ribonucleotide and Ribonucleic Acid

The term "ribonucleotide" and the phrase "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

siRNA

The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

siRNA may be divided into five (5) groups (non-functional, semi-functional, functional, highly functional, and hyper-functional) based on the level or degree of silencing that they induce in cultured cell lines. As used herein, these definitions are based on a set of conditions where the siRNA is transfected into said cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

SMARTSCORE™, or siRNA rank

The term "SMARTSCORE™", or "siRNA rank" refers to a number determined by applying any of the formulas to a given siRNA sequence. The term "SMART-selected" or "rationally selected" or "rational selection" refers to siRNA that have been selected on the basis of their SMART-SCORES™, or siRNA ranking.

Substantially Similar

The phrase "substantially similar" refers to a similarity of at least 90% with respect to the identity of the bases of the sequence.

Target

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

Transfection

The term "transfection" refers to a process by which agents are introduced into a cell. The list of agents that can be transfected is large and includes, but is not limited to, siRNA, sense and/or anti-sense sequences, DNA encoding one or more genes and organized into an expression plasmid, proteins, protein fragments, and more. There are multiple methods for transfecting agents into a cell including, but not limited to, electroporation, calcium phosphate-based transfections, DEAE-dextran-based transfections, lipid-based transfections, molecular conjugate-based transfections (e.g., polylysine-DNA conjugates), microinjection and others.

The present invention is directed to improving the efficiency of gene silencing by siRNA. Through the inclusion of multiple siRNA sequences that are targeted to a particular gene and/or selecting an siRNA sequence based on certain defined criteria, improved efficiency may be achieved.

The present invention will now be described in connection with preferred embodiments. These embodiments are presented in order to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

Furthermore, this disclosure is not a primer on RNA interference. Basic concepts known to persons skilled in the art have not been set forth in detail.

The present invention is directed to increasing the efficiency of RNAi, particularly in mammalian systems. Accordingly, the present invention provides kits, siRNAs and methods for increasing siRNA efficacy.

According to a first embodiment, the present invention provides a kit for gene silencing, wherein said kit is comprised of a pool of at least two siRNA duplexes, each of which is comprised of a sequence that is complementary to a portion of the sequence of one or more target messenger RNA, and each of which is selected using non-target specific criteria. Each of the at least two siRNA duplexes of the kit complementary to a portion of the sequence of one or more target mRNAs is preferably selected using Formula X.

According to a second embodiment, the present invention provides a method for selecting an siRNA, said method comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; and determining the relative functionality of the at least two siRNAs.

In one embodiment, the present invention also provides a method wherein said selection criteria are embodied in a formula comprising:

$$(-14)*G_{13}-13*A_1-12*U_7-11*U_2-10*A_{11}-10*U_4-$$
$$10*C_3-10*C_5-10*C_6-9*A_{10}-9*U_9-9*C_{18}-$$
$$8*G_{10}-7*U_1-7*6U_{16}-7*C_{17}-7*C_{19}+7*U_{17}+$$
$$8*A_2+8*A_4+8*A_5+8*C_4+9*G_8+10*A_7+$$
$$10*U_{18}+11*A_{19}+11*C_9+15*G_1+18*A_3+$$
$$19*U_{10}-Tm-3*(GC_{total})-6*(GC_{15-19})-30*X;\text{ or } \quad \text{Formula VIII}$$

$$(-8)*A1+(-1)*A2+(12)*A3+(7)*A4+(18)*A5+(12)$$
$$*A6+(19)*A7+(6)*A8+(-4)*A9+(-5)*A10+(-2)$$
$$*A11+(-5)*A12+(17)*A13+(-3)*A14+(4)$$
$$*A15+(2)*A16+(8)*A17+(11)*A18+(30)*A19+$$
$$(-13)*U1+(-10)*U2+(2)*U3+(-2)*U4+(-5)$$
$$*U5+(5)*U6+(-2)*U7+(-10)*U8+(-5)*U9+(15)$$
$$*U10+(-1)*U11+(0)*U12+(10)*U13+(-9)$$
$$*U14+(-13)*U15+(-10)*U16+(3)*U17+(9)$$
$$*U18+(9)*U19+(7)*C1+(3)*C2+(-21)*C3+(5)$$
$$*C4+(-9)*C5+(-20)*C6+(-18)*C7+(-5)*C8+$$
$$(5)*C9+(1)*C10+(2)*C11+(-5)*C12+(-3)$$
$$*C13+(-6)*C14+(-2)*C15+(-5)*C16+(-3)$$
$$*C17+(-12)*C18+(-18)*C19+(14)*G1+(8)$$
$$*G2+(7)*G3+(-10)*G4+(-4)*G5+(2)*G6+(1)$$
$$*G7+(9)*G8+(5)*G9+(-11)*G10+(1)*G11+(9)$$
$$*G12+(-24)*G13+(18)*G14+(11)*G15+(13)$$
$$*G16+(-7)*G17+(-9)*G18+(-22)*G19+6*$$
$$\text{(number of A+U in position 15-19)}-3*(\text{number}$$
$$\text{of G+C in whole siRNA)}, \quad \text{Formula X}$$

wherein position numbering begins at the 5'-most position of a sense strand, and $A_1=1$ if A is the base at position 1 of the sense strand, otherwise its value is 0;

$A_2=1$ if A is the base at position 2 of the sense strand, otherwise its value is 0;

$A_3=1$ if A is the base at position 3 of the sense strand, otherwise its value is 0;

$A_4=1$ if A is the base at position 4 of the sense strand, otherwise its value is 0;

$A_5=1$ if A is the base at position 5 of the sense strand, otherwise its value is 0;

$A_6=1$ if A is the base at position 6 of the sense strand, otherwise its value is 0;

$A_7=1$ if A is the base at position 7 of the sense strand, otherwise its value is 0;

$A_{10}=1$ if A is the base at position 10 of the sense strand, otherwise its value is 0;

$A_{11}=1$ if A is the base at position 11 of the sense strand, otherwise its value is 0;

$A_{13}=1$ if A is the base at position 13 of the sense strand, otherwise its value is 0;

$A_{19}=1$ if A is the base at position 19 of the sense strand, otherwise if another base is present or the sense strand is only 18 base pairs in length, its value is 0;

$C_3=1$ if C is the base at position 3 of the sense strand, otherwise its value is 0;

$C_4=1$ if C is the base at position 4 of the sense strand, otherwise its value is 0;

$C_5=1$ if C is the base at position 5 of the sense strand, otherwise its value is 0;

$C_6=1$ if C is the base at position 6 of the sense strand, otherwise its value is 0;

$C_7=1$ if C is the base at position 7 of the sense strand, otherwise its value is 0;

$C_9=1$ if C is the base at position 9 of the sense strand, otherwise its value is 0;

$C_{17}=1$ if C is the base at position 17 of the sense strand, otherwise its value is 0;

$C_{18}=1$ if C is the base at position 18 of the sense strand, otherwise its value is 0;

$C_{19}=1$ if C is the base at position 19 of the sense strand, otherwise if another base is present or the sense strand is only 18 base pairs in length, its value is 0;

$G_1=1$ if G is the base at position 1 on the sense strand, otherwise its value is 0;

$G_2=1$ if G is the base at position 2 of the sense strand, otherwise its value is 0;

$G_8=1$ if G is the base at position 8 on the sense strand, otherwise its value is 0;

$G_{10}=1$ if G is the base at position 10 on the sense strand, otherwise its value is 0;

$G_{13}=1$ if G is the base at position 13 on the sense strand, otherwise its value is 0;

$G_{19}=1$ if G is the base at position 19 of the sense strand, otherwise if another base is present or the sense strand is only 18 base pairs in length, its value is 0;

$U_1=1$ if U is the base at position 1 on the sense strand, otherwise its value is 0;

$U_2=1$ if U is the base at position 2 on the sense strand, otherwise its value is 0;

$U_3=1$ if U is the base at position 3 on the sense strand, otherwise its value is 0;

$U_4=1$ if U is the base at position 4 on the sense strand, otherwise its value is 0;

$U_7=1$ if U is the base at position 7 on the sense strand, otherwise its value is 0;

$U_9=1$ if U is the base at position 9 on the sense strand, otherwise its value is 0;

$U_{10}=1$ if U is the base at position 10 on the sense strand, otherwise its value is 0;

$U_{15}=1$ if U is the base at position 15 on the sense strand, otherwise its value is 0;

$U_{16}=1$ if U is the base at position 16 on the sense strand, otherwise its value is 0;

$U_{17}=1$ if U is the base at position 17 on the sense strand, otherwise its value is 0;

$U_{18}=1$ if U is the base at position 18 on the sense strand, otherwise its value is 0.

$GC_{15-19}$=the number of G and C bases within positions 15-19 of the sense strand, or within positions 15-18 if the sense strand is only 18 base pairs in length;

$GC_{total}$=the number of G and C bases in the sense strand;

Tm=100 if the siRNA oligo has the internal repeat longer then 4 base pairs, otherwise its value is 0; and X=the number of times that the same nucleotide repeats four or more times in a row.

Any of the methods of selecting siRNA in accordance with the invention can further comprise comparing the internal stability profiles of the siRNAs to be selected, and selecting those siRNAs with the most favorable internal stability profiles. Any of the methods of selecting siRNA can further comprise selecting either for or against sequences that contain motifs that induce cellular stress. Such motifs include, for example, toxicity motifs. Any of the methods of selecting siRNA can further comprise either selecting for or selecting against sequences that comprise stability motifs.

In another embodiment, the present invention provides a method of gene silencing, comprising introducing into a cell at least one siRNA selected according to any of the methods of the present invention. The siRNA can be introduced by allowing passive uptake of siRNA, or through the use of a vector.

According to a third embodiment, the invention provides a method for developing an algorithm for selecting siRNA, said method comprising: (a) selecting a set of siRNA; (b) measuring gene silencing ability of each siRNA from said set; (c) determining relative functionality of each siRNA; (d) determining improved functionality by the presence or absence of at least one variable selected from the group consisting of the presence or absence of a particular nucleotide at a particular position, the total number of As and Us in positions 15-19, the number of times that the same nucleotide repeats within a given sequence, and the total number of Gs and Cs; and (e) developing an algorithm using the information of step (d).

In another embodiment, the invention provides a method for selecting an siRNA with improved functionality, comprising using the above-mentioned algorithm to identify an siRNA of improved functionality.

According to a fourth embodiment, the present invention provides a kit, wherein said kit is comprised of at least two siRNAs, wherein said at least two siRNAs comprise a first optimized siRNA and a second optimized siRNA, wherein said first optimized siRNA and said second optimized siRNA are optimized according a formula comprising Formula X.

According to a fifth embodiment, the present invention provides a method for identifying a hyperfunctional siRNA, comprising applying selection criteria to a set of potential siRNA that comprise 18-30 base pairs, wherein said selection criteria are non-target specific criteria, and said set comprises at least two siRNAs and each of said at least two siRNAs contains a sequence that is at least substantially complementary to a target gene; determining the relative functionality of the at least two siRNAs and assigning each of the at least two siRNAs a functionality score; and selecting siRNAs from the at least two siRNAs that have a functionality score that reflects greater than 80 percent silencing at a concentration in the picomolar range, wherein said greater than 80 percent silencing endures for greater than 120 hours.

In other embodiments, the invention provides kits and/or methods wherein the siRNA are comprised of two separate polynucleotide strands; wherein the siRNA are comprised of a single contiguous molecule such as, for example, a unimolecular siRNA (comprising, for example, either a nucleotide or non-nucleotide loop); wherein the siRNA are expressed from one or more vectors; and wherein two or more genes are silenced by a single administration of siRNA.

According to a sixth embodiment, the present invention provides a hyperfunctional siRNA that is capable of silencing Bcl2.

According to a seventh embodiment, the present invention provides a method for developing an siRNA algorithm for selecting functional and hyperfunctional siRNAs for a given sequence. The method comprises:
(a) selecting a set of siRNAs;
(b) measuring the gene silencing ability of each siRNA from said set;
(c) determining the relative functionality of each siRNA;
(d) determining the amount of improved functionality by the presence or absence of at least one variable selected from the group consisting of the total GC content, melting temperature of the siRNA, GC content at positions 15-19, the presence or absence of a particular nucleotide at a particular position, relative thermodynamic stability at particular positions in a duplex, and the number of times that the same nucleotide repeats within a given sequence; and
(e) developing an algorithm using the information of step (d).

According to this embodiment, preferably the set of siRNAs comprises at least 90 siRNAs from at least one gene, more preferably at least 180 siRNAs from at least two different genes, and most preferably at least 270 and 360 siRNAs from at least three and four different genes, respectively. Additionally, in step (d) the determination is made with preferably at least two, more preferably at least three, even more preferably at least four, and most preferably all of the variables. The resulting algorithm is not target sequence specific.

In another embodiment, the present invention provides rationally designed siRNAs identified using the formulas above.

In yet another embodiment, the present invention is directed to hyperfunctional siRNA.

The ability to use the above algorithms, which are not sequence or species specific, allows for the cost-effective selection of optimized siRNAs for specific target sequences. Accordingly, there will be both greater efficiency and reliability in the use of siRNA technologies.

The methods disclosed herein can be used in conjunction with comparing internal stability profiles of selected siRNAs, and designing an siRNA with a desirable internal stability profile; and/or in conjunction with a selection either for or against sequences that contain motifs that induce cellular stress, for example, cellular toxicity.

Any of the methods disclosed herein can be used to silence one or more genes by introducing an siRNA selected, or designed, in accordance with any of the methods disclosed herein. The siRNA(s) can be introduced into the cell by any method known in the art, including passive uptake or through the use of one or more vectors.

Any of the methods and kits disclosed herein can employ either unimolecular siRNAs, siRNAs comprised of two separate polynucleotide strands, or combinations thereof. Any of the methods disclosed herein can be used in gene silencing, where two or more genes are silenced by a single administration of siRNA(s). The siRNA(s) can be directed against two or more target genes, and administered in a single dose or single transfection, as the case may be.

Optimizing siRNA

According to one embodiment, the present invention provides a method for improving the effectiveness of gene silencing for use to silence a particular gene through the selection of an optimal siRNA. An siRNA selected according to this method may be used individually, or in conjunction with the first embodiment, i.e., with one or more other siRNAs, each of which may or may not be selected by this criteria in order to maximize their efficiency.

The degree to which it is possible to select an siRNA for a given mRNA that maximizes these criteria will depend on the sequence of the mRNA itself. However, the selection criteria will be independent of the target sequence. According to this method, an siRNA is selected for a given gene by using a rational design. That said, rational design can be described in a variety of ways. Rational design is, in simplest terms, the application of a proven set of criteria that enhance the probability of identifying a functional or hyperfunctional siRNA. In one method, rationally designed siRNA can be identified by maximizing one or more of the following criteria:

(1) A low GC content, preferably between about 30-52%.
(2) At least 2, preferably at least 3 A or U bases at positions 15-19 of the siRNA on the sense strand.
(3) An A base at position 19 of the sense strand.
(4) An A base at position 3 of the sense strand.
(5) A U base at position 10 of the sense strand.
(6) An A base at position 14 of the sense strand.
(7) A base other than C at position 19 of the sense strand.
(8) A base other than G at position 13 of the sense strand.
(9) A Tm, which refers to the character of the internal repeat that results in inter- or intramolecular structures for one strand of the duplex, that is preferably not stable at greater than 50° C., more preferably not stable at greater than 37° C., even more preferably not stable at greater than 30° C. and most preferably not stable at greater than 20° C.
(10) A base other than U at position 5 of the sense strand.
(11) A base other than A at position 11 of the sense strand.
(12) A base other than an A at position 1 of the sense strand.
(13) A base other than an A at position 2 of the sense strand.
(14) An A base at position 4 of the sense strand.
(15) An A base at position 5 of the sense strand.
(16) An A base at position 6 of the sense strand.
(17) An A base at position 7 of the sense strand.
(18) An A base at position 8 of the sense strand.
(19) A base other than an A at position 9 of the sense strand.
(20) A base other than an A at position 10 of the sense strand.
(21) A base other than an A at position 11 of the sense strand.
(22) A base other than an A at position 12 of the sense strand.
(23) An A base at position 13 of the sense strand.
(24) A base other than an A at position 14 of the sense strand.
(25) An A base at position 15 of the sense strand
(26) An A base at position 16 of the sense strand.
(27) An A base at position 17 of the sense strand.
(28) An A base at position 18 of the sense strand.
(29) A base other than a U at position 1 of the sense strand.
(30) A base other than a U at position 2 of the sense strand.
(31) A U base at position 3 of the sense strand.
(32) A base other than a U at position 4 of the sense strand.
(33) A base other than a U at position 5 of the sense strand.
(34) A U base at position 6 of the sense strand.
(35) A base other than a U at position 7 of the sense strand.
(36) A base other than a U at position 8 of the sense strand.
(37) A base other than a U at position 9 of the sense strand.
(38) A base other than a U at position 11 of the sense strand.
(39) A U base at position 13 of the sense strand.
(40) A base other than a U at position 14 of the sense strand.
(41) A base other than a U at position 15 of the sense strand.
(42) A base other than a U at position 16 of the sense strand.
(43) A U base at position 17 of the sense strand.
(44) A U base at position 18 of the sense strand.
(45) A U base at position 19 of the sense strand.
(46) A C base at position 1 of the sense strand.
(47) A C base at position 2 of the sense strand.
(48) A base other than a C at position 3 of the sense strand.
(49) A C base at position 4 of the sense strand.
(50) A base other than a C at position 5 of the sense strand.
(51) A base other than a C at position 6 of the sense strand.
(52) A base other than a C at position 7 of the sense strand.
(53) A base other than a C at position 8 of the sense strand.
(54) A C base at position 9 of the sense strand.
(55) A C base at position 10 of the sense strand.
(56) A C base at position 11 of the sense strand.
(57) A base other than a C at position 12 of the sense strand.
(58) A base other than a C at position 13 of the sense strand.
(59) A base other than a C at position 14 of the sense strand.
(60) A base other than a C at position 15 of the sense strand.
(61) A base other than a C at position 16 of the sense strand.
(62) A base other than a C at position 17 of the sense strand.
(63) A base other than a C at position 18 of the sense strand.
(64) A G base at position 1 of the sense strand.
(65) A G base at position 2 of the sense strand.
(66) A G base at position 3 of the sense strand.
(67) A base other than a G at position 4 of the sense strand.
(68) A base other than a G at position 5 of the sense strand.
(69) A G base at position 6 of the sense strand.

(70) A G base at position 7 of the sense strand.

(71) A G base at position 8 of the sense strand.

(72) A G base at position 9 of the sense strand.

(73) A base other than a G at position 10 of the sense strand.

(74) A G base at position 11 of the sense strand.

(75) A G base at position 12 of the sense strand.

(76) A G base at position 14 of the sense strand.

(77) A G base at position 15 of the sense strand.

(78) A G base at position 16 of the sense strand.

(79) A base other than a G at position 17 of the sense strand.

(80) A base other than a G at position 18 of the sense strand.

(81) A base other than a G at position 19 of the sense strand.

The importance of various criteria can vary greatly. For instance, a C base at position 10 of the sense strand makes a minor contribution to duplex functionality. In contrast, the absence of a C at position 3 of the sense strand is very important. Accordingly, preferably an siRNA will satisfy as many of the aforementioned criteria as possible.

With respect to the criteria, GC content, as well as a high number of AU in positions 15-19 of the sense strand, may be important for easement of the unwinding of double stranded siRNA duplex. Duplex unwinding has been shown to be crucial for siRNA functionality in vivo.

With respect to criterion 9, the internal structure is measured in terms of the melting temperature of the single strand of siRNA, which is the temperature at which 50% of the molecules will become denatured. With respect to criteria 2-8 and 10-11, the positions refer to sequence positions on the sense strand, which is the strand that is identical to the mRNA.

In one preferred embodiment, at least criteria 1 and 8 are satisfied. In another preferred embodiment, at least criteria 7 and 8 are satisfied. In still another preferred embodiment, at least criteria 1, 8 and 9 are satisfied.

It should be noted that all of the aforementioned criteria regarding sequence position specifics are with respect to the 5' end of the sense strand. Reference is made to the sense strand, because most databases contain information that describes the information of the mRNA. Because according to the present invention a chain can be from 18 to 30 bases in length, and the aforementioned criteria assumes a chain 19 base pairs in length, it is important to keep the aforementioned criteria applicable to the correct bases.

When there are only 18 bases, the base pair that is not present is the base pair that is located at the 3' of the sense strand. When there are twenty to thirty bases present, then additional bases are added at the 5' end of the sense chain and occupy positions $-1$ to $-11$. Accordingly, with respect to SEQ. ID NO. 0001 NNANANNNNUCNAANNNNA and SEQ. ID NO. 0028 GUCNNANANNNNUCNAANNNNA, both would have A at position 3, A at position 5, U at position 10, C at position 11, A and position 13, A and position 14 and A at position 19. However, SEQ. ID NO. 0028 would also have C at position -1, U at position -2 and G at position $-3$.

For a 19 base pair siRNA, an optimal sequence of one of the strands may be represented below, where N is any base, A, C, G, or U:

SEQ. ID NO. 0001.   NNANANNNNUCNAANNNNA

SEQ. ID NO. 0002.   NNANANNNNUGNAANNNNA

SEQ. ID NO. 0003.   NNANANNNNUUNAANNNNA

SEQ. ID NO. 0004.   NNANANNNNUCNCANNNNA

SEQ. ID NO. 0005.   NNANANNNNUGNCANNNNA

SEQ. ID NO. 0006.   NNANANNNNUUNCANNNNA

SEQ. ID NO. 0007.   NNANANNNNUCNUANNNNA

SEQ. ID NO. 0008.   NNANANNNNUGNUANNNNA

SEQ. ID NO. 0009.   NNANANNNNUUNUANNNNA

SEQ. ID NO. 0010.   NNANCNNNNUCNAANNNNA

SEQ. ID NO. 0011.   NNANCNNNNUGNAANNNNA

SEQ. ID NO. 0012.   NNANCNNNNUUNAANNNNA

SEQ. ID NO. 0013.   NNANCNNNNUCNANNNNA

SEQ. ID NO. 0014.   NNANCNNNNUGNCANNNNA

SEQ. ID NO. 0015.   NNANCNNNNUUNCANNNNA

SEQ. ID NO. 0016.   NNANCNNNNUCNUANNNNA

SEQ. ID NO. 0017.   NNANCNNNNUGNUANNNNA

SEQ. ID NO. 0018.   NNANCNNNNUUNUANNNNA

SEQ. ID NO. 0019.   NNANGNNNNUCNAANNNNA

SEQ. ID NO. 0020.   NNANGNNNNUGNAANNNNA

SEQ. ID NO. 0021.   NNANGNNNNUUNAANNNNA

SEQ. ID NO. 0022.   NNANGNNNNUCNCANNNNA

SEQ. ID NO. 0023.   NNANGNNNNUGNCANNNNA

SEQ. ID NO. 0024.   NNANGNNNNUUNCANNNNA

SEQ. ID NO. 0025.   NNANGNNNNUCNUANNNNA

SEQ. ID NO. 0026.   NNANGNNNNUGNUANNNNA

SEQ. ID NO. 0027.   NNANGNNNNNUNUANNNNA

In one embodiment, the sequence used as an siRNA is selected by choosing the siRNA that score highest according to one of the following seven algorithms that are represented by Formulas I-VII:

$$\text{Relative functionality of siRNA} = -(GC/3) + (AU_{15-19}) - (Tm_{20°C})*3 - (G13)*3 - (C_{19}) + (A_{19})*2 + (A_3) + (U_{10}) + (A_{14}) - (U_5) - (A_{11}) \quad \text{Formula I}$$

$$\text{Relative functionality of siRNA} = -(GC/3) - (AU_{15-19})*3 - (G_{13})*3 - (C_{19}) + (A_{19})*2 + (A_3) \quad \text{Formula II}$$

$$\text{Relative functionality of siRNA} = -(GC/3) + (AU_{15-19}) - (Tm_{20°C})*3 \quad \text{Formula III}$$

$$\text{Relative functionality of siRNA} = -GC/2 + (AU_{15-19})/2 - (Tm_{20°C})*2 - (G_{13})*3 - (C_{19}) + (A_{19})*2 + (A_3) + (U_{10}) + (A_{14}) - (U_5) - (A_{11}) \quad \text{Formula IV}$$

$$\text{Relative functionality of siRNA} = -(G_{13})*3 - (C_{19}) + (A_{19})*2 + (A_3) + (U_{10}) + (A_{14}) - (U_5) - (A_{11}) \quad \text{Formula V}$$

$$\text{Relative functionality of siRNA} = -(G_{13})*3 - (C_{19}) + (A_{19})*2 + (A_3) \quad \text{Formula VI}$$

Relative functionality of siRNA=−(GC/2)+(AU$_{15-19}$)/
2−(Tm$_{20°\ C.}$)*1−(G$_{13}$)*3−(C$_{19}$)+(A$_{19}$)*3+(A$_{3}$)*3+
(U$_{10}$)/2+(A$_{14}$)/2−(U$_{5}$)/2−(A$_{11}$)/2               Formula VII In Formulas I-VII:
wherein A$_{15-19}$=1 if A is the base at position 19 on the sense strand, otherwise its value is 0, AU$_{15-19}$=0-5 depending on the number of A or U bases on the sense strand at positions 15-19;

G$_{13}$=1 if G is the base at position 13 on the sense strand, otherwise its value is 0;

C$_{19}$=1 if C is the base at position 19 of the sense strand, otherwise its value is 0;

GC=the number of G and C bases in the entire sense strand;

Tm$_{20°\ C.}$=1 if the T m is greater than 20° C.;

A$_{3}$=1 if A is the base at position 3 on the sense strand, otherwise its value is 0;

U$_{10}$=1 if U is the base at position 10 on the sense strand, otherwise its value is 0;

A$_{14}$=1 if A is the base at position 14 on the sense strand, otherwise its value is 0;

U$_{5}$=1 if U is the base at position 5 on the sense strand, otherwise its value is 0; and A$_{11}$=1 if A is the base at position 11 of the sense strand, otherwise its value is 0.

Formulas I-VII provide relative information regarding functionality. When the values for two sequences are compared for a given formula, the relative functionality is ascertained; a higher positive number indicates a greater functionality. For example, in many applications a value of 5 or greater is beneficial.

Additionally, in many applications, more than one of these formulas would provide useful information as to the relative functionality of potential siRNA sequences. However, it is beneficial to have more than one type of formula, because not every formula will be able to help to differentiate among potential siRNA sequences. For example, in particularly high GC mRNAs, formulas that take that parameter into account would not be useful and application of formulas that lack GC elements (e.g., formulas V and VI) might provide greater insights into duplex functionality. Similarly, formula II might by used in situations where hairpin structures are not observed in duplexes, and formula IV might be applicable for sequences that have higher AU content. Thus, one may consider a particular sequence in light of more than one or even all of these algorithms to obtain the best differentiation among sequences. In some instances, application of a given algorithm may identify an unusually large number of potential siRNA sequences, and in those cases, it may be appropriate to re-analyze that sequence with a second algorithm that is, for instance, more stringent. Alternatively, it is conceivable that analysis of a sequence with a given formula yields no acceptable siRNA sequences (i.e. low SMARTSCORES™, or siRNA ranking).

In this instance, it may be appropriate to re-analyze that sequences with a second algorithm that is, for instance, less stringent. In still other instances, analysis of a single sequence with two separate formulas may give rise to conflicting results (i.e. one formula generates a set of siRNA with high SMARTSCORES™, or siRNA ranking, while the other formula identifies a set of siRNA with low SMART-SCORES™, or siRNA ranking). In these instances, it may be necessary to determine which weighted factor(s) (e.g. GC content) are contributing to the discrepancy and assessing the sequence to decide whether these factors should or should not be included. Alternatively, the sequence could be analyzed by a third, fourth, or fifth algorithm to identify a set of rationally designed siRNA.

The above-referenced criteria are particularly advantageous when used in combination with pooling techniques as depicted in Table I:

TABLE I

| | FUNCTIONAL PROBABILITY | | | | | |
|---|---|---|---|---|---|---|
| | OLIGOS | | | POOLS | | |
| CRITERIA | >95% | >80% | <70% | >95% | >80% | <70% |
| CURRENT | 33.0 | 50.0 | 23.0 | 79.5 | 97.3 | 0.3 |
| NEW | 50.0 | 88.5 | 8.0 | 93.8 | 99.98 | 0.005 |
| (GC) | 28.0 | 58.9 | 36.0 | 72.8 | 97.1 | 1.6 |

The term "current" used in Table I refers to Tuschl's conventional siRNA parameters (Elbashir, S. M. et al. (2002) "Analysis of gene function in somatic mammalian cells using small interfering RNAs" Methods 26: 199-213). "New" refers to the design parameters described in Formulas I-VII. "GC" refers to criteria that select siRNA solely on the basis of GC content.

As Table I indicates, when more functional siRNA duplexes are chosen, siRNAs that produce <70% silencing drops from 23% to 8% and the number of siRNA duplexes that produce >80% silencing rises from 50% to 88.5%. Further, of the siRNA duplexes with >80% silencing, a larger portion of these siRNAs actually silence >95% of the target expression (the new criteria increases the portion from 33% to 50%). Using this new criteria in pooled siRNAs, shows that, with pooling, the amount of silencing >95% increases from 79.5% to 93.8% and essentially eliminates any siRNA pool from silencing less than 70%.

Table II similarly shows the particularly beneficial results of pooling in combination with the aforementioned criteria. However, Table II, which takes into account each of the aforementioned variables, demonstrates even a greater degree of improvement in functionality.

TABLE II

| | FUNCTIONAL PROBABILITY | | | | | |
|---|---|---|---|---|---|---|
| | OLIGOS | | | POOLS | | |
| | FUNCTIONAL | AVERAGE | NON-FUNCTIONAL | FUNCTIONAL | AVERAGE | NON-FUNCTIONAL |
| RANDOM | 20 | 40 | 50 | 67 | 97 | 3 |
| CRITERIA 1 | 52 | 99 | 0.1 | 97 | 93 | 0.0040 |
| CRITERIA 4 | 89 | 99 | 0.1 | 99 | 99 | 0.0000 |

The terms "functional," "Average," and "Non-functional" used in Table II, refer to siRNA that exhibit >80%, >50%, and <50% functionality, respectively. Criteria 1 and 4 refer to specific criteria described above.

The above-described algorithms may be used with or without a computer program that allows for the inputting of the sequence of the mRNA and automatically outputs the optimal siRNA. The computer program may, for example, be accessible from a local terminal or personal computer, over an internal network or over the Internet.

In addition to the formulas above, more detailed algorithms may be used for selecting siRNA. Preferably, at least one RNA duplex of 18-30 base pairs is selected such that it is optimized according a formula selected from:

$(-14)*G_{13}-13*A_1-12*U_7-11*U_2-10*A_{11}-10*U_4-10*C_3-10*C_5-10*C_6-9*A_{10}-9*U_9-9*C_{18}-8*G_{10}-7*U_1-7*U_{16}-7*C_{17}-7*C_{19}+7*U_{17}+8*A_2+8*A_4+8*A_5+8*C_4+9*G_8+10*A_7+10*U_{18}+11*A_{19}+11*C_9+15*G_1+18*A_3+19*U_{10}-Tm-3*(GC_{total})-6*(GC_{15\text{-}19})-30*X;$ and    Formula VIII $(14.1)*A_3+(14.9)*A_6+(17.6)*A_{13}+(24.7)*A_{19}+(14.2)*U_{10}+(10.5)*C_9+(23.9)*G_1+(16.3)*G_2+(-12.3)*A_{11}+(-19.3)*U_1+(-12.1)*U_2+(-11)*U_3+(-15.2)*U_{15}+(-11.3)*U_{16}+(-11.8)*C_3+(-17.4)*C_6+(-10.5)*C_7+(-13.7)*G_{13}+(-25.9)*G_{19}-Tm-3*(GC_{total})-6*(GC_{15\text{-}19})-19)-30*X;$ and    Formula IX $(-8)*A1+(-1)*A2+(12)*A3+(7)*A4+(18)*A5+(12)*A6+(19)*A7+(6)*A8+(-4)*A9+(-5)*A10+(-2)*A11+(-5)*A12+(17)*A13+(-3)*A14+(4)*A15+(2)*A16+(8)*A17+(11)*A18+(30)*A19+(-13)*U1+(-10)*U2+(2)*U3+(-2)*U4+(-5)*U5+(5)*U6+(-2)*U7+(-10)*U8+(-5)*U9+(15)*U10+(-1)*U11+(0)*U12+(10)*U13+(-9)*U14+(-13)*U15+(-10)*U16+(3)*U17+(9)*U18+(9)*U19+(7)*C1+(3)*C2+(-21)*C3+(5)*C4+(-9)*C5+(-20)*C6+(-18)*C7+(-5)*C8+(5)*C9+(1)*C10+(2)*C11+(-5)*C12+(-3)*C13+(-6)*C14+(-2)*C15+(-5)*C16+(-3)*C17+(-12)*C18+(-18)*C19+(14)*G1+(8)*G2+(7)*G3+(-10)*G4+(-4)*G5+(2)*G6+(1)*G7+(9)*G8+(5)*G9+(-11)*G10+(1)*G11+(9)*G12+(-24)*G13+(18)*G14+(11)*G15+(13)*G16+(-7)*G17+(-9)*G18+(-22)*G19+6*$ (number of A+U in position 15-19)-3*(number of G+C in whole siRNA).    Formula X wherein $A_1=1$ if A is the base at position 1 of the sense strand, otherwise its value is 0;

$A_2=1$ if A is the base at position 2 of the sense strand, otherwise its value is 0;

$A_3=1$ if A is the base at position 3 of the sense strand, otherwise its value is 0;

$A_4=1$ if A is the base at position 4 of the sense strand, otherwise its value is 0;

$A_5=1$ if A is the base at position 5 of the sense strand, otherwise its value is 0;

$A_6=1$ if A is the base at position 6 of the sense strand, otherwise its value is 0;

$A_7=1$ if A is the base at position 7 of the sense strand, otherwise its value is 0;

$A_{10}=1$ if A is the base at position 10 of the sense strand, otherwise its value is 0;

$A_{11}=1$ if A is the base at position 11 of the sense strand, otherwise its value is 0;

$A_{13}=1$ if A is the base at position 13 of the sense strand, otherwise its value is 0;

$A_{19}=1$ if A is the base at position 19 of the sense strand, otherwise if another base is present or the sense strand is only 18 base pairs in length, its value is 0;

$C_3=1$ if C is the base at position 3 of the sense strand, otherwise its value is 0;

$C_4=1$ if C is the base at position 4 of the sense strand, otherwise its value is. 0;

$C_5=1$ if C is the base at position 5 of the sense strand, otherwise its value is 0;

$C_6=1$ if C is the base at position 6 of the sense strand, otherwise its value is 0;

$C_7=1$ if C is the base at position 7 of the sense strand, otherwise its value is 0;

$C_9=1$ if C is the base at position 9 of the sense strand, otherwise its value is 0;

$C_{17}=1$ if C is the base at position 17 of the sense strand, otherwise its value is 0;

$C_{18}=1$ if C is the base at position 18 of the sense strand, otherwise its value is 0;

$C_{19}=1$ if C is the base at position 19 of the sense strand, otherwise if another base is present or the sense strand is only 18 base pairs in length, its value is 0;

$G_1=1$ if G is the base at position 1 on the sense strand, otherwise its value is 0;

$G_2=1$ if G is the base at position 2 of the sense strand, otherwise its value is 0;

$G_8=1$ if G is the base at position 8 on the sense strand, otherwise its value is 0;

$G_{10}=1$ if G is the base at position 10 on the sense strand, otherwise its value is 0;

$G_{13}=1$ if G is the base at position 13 on the sense strand, otherwise its value is 0;

$G_{19}=1$ if G is the base a t position 19 of the sense strand, otherwise if another base is present or the sense strand is only 18 base pairs in length, its value is 0;

$U_1=1$ if U is the base at position 1 on the sense strand, otherwise its value is 0;

$U_2=1$ if U is the base at position 2 on the sense strand, otherwise its value is 0;

$U_3=1$ if U is the base at position 3 on the sense strand, otherwise its value is 0;

$U_4=1$ if U is the base at position 4 on the sense strand, otherwise its value is 0;

$U_7=1$ if U is the base at position 7 on the sense strand, otherwise its value is 0;

$U_9=1$ if U is the base at position 9 on the sense strand, otherwise its value is 0;

$U_{10}=1$ if U is the base at position 10 on the sense strand, otherwise its value is 0;

$U_{15}=1$ if U is the base at position 15 on the sense strand, otherwise its value is 0;

$U_{16}=1$ if U is the base at position 16 on the sense strand, otherwise its value is 0;

$U_{17}=1$ if U is the base at position 17 on the sense strand, otherwise its value is 0;

$U_{18}=1$ if U is the base at position 18 on the sense strand, otherwise its value is 0;

$GC_{15\text{-}19}$=the number of G and C bases within positions 15-19 of the sense strand, or within positions 15-18 if the sense strand is only 18 base pairs in length;

$GC_{total}$ the number of G and C bases in the sense strand;

Tm=100 if the siRNA oligo has the internal repeat longer then 4 base pairs, otherwise its value is 0; and X=the number of times that the same nucleotide repeats four or more times in a row.

The above formulas VIII, IX, and X, as well as formulas I-VII, provide methods for selecting siRNA in order to increase the efficiency of gene silencing. A subset of variables of any of the formulas may be used, though when fewer variables are used, the optimization hierarchy becomes less reliable.

With respect to the variables of the above-referenced formulas, a single letter of A or C or G or U followed by a subscript refers to a binary condition. The binary condition is that either the particular base is present at that particular position (wherein the value is "1") or the base is not present (wherein the value is "0"). Because position 19 is optional, i.e., there might be only 18 base pairs, when there are only 18 base pairs, any base with a subscript of 19 in the formulas above would have a zero value for that parameter. Before or after each variable is a number followed by *, which indicates that the value of the variable is to be multiplied or weighed by that number.

The numbers preceding the variables A, or G, or C, or U in Formulas VIII, IX, and X (or after the variables in Formula I-VII) were determined by comparing the difference in the frequency of individual bases at different positions in functional siRNA and total siRNA. Specifically, the frequency in which a given base was observed at a particular position in functional groups was compared with the frequency that that same base was observed in the total, randomly selected siRNA set. If the absolute value of the difference between the functional and total values was found to be greater than 6%, that parameter was included in the equation. Thus, for instance, if the frequency of finding a "G" at position 13 ($G_{13}$) is found to be 6% in a given functional group, and the frequency of $G_{13}$ in the total population of siRNAs is 20%, the difference between the two values is 6%-20%=-14%. As the absolute value is greater than six (6), this factor (-14) is included in the equation. Thus, in Formula VIII, in cases where the siRNA under study has a G in position 13, the accrued value is (-14)*(1)=-14. In contrast, when a base other than G is found at position 13, the accrued value is (-14)*(0)=0.

When developing a means to optimize siRNAs, the inventors observed that a bias toward low internal thermodynamic stability of the duplex at the 5'-antisense (AS) end is characteristic of naturally occurring miRNA precursors. The inventors extended this observation to siRNAs for which functionality had been assessed in tissue culture.

With respect to the parameter $GC_{15-19}$, a value of 0-5 will be ascribed depending on the number of G or C bases at positions 15 to 19. If there are only 18 base pairs, the value is between 0 and 4.

With respect to the criterion $GC_{total}$ content, a number from 0-30 will be ascribed, which correlates to the total number of G and C nucleotides on the sense strand, excluding overhangs. Without wishing to be bound by any one theory, it is postulated that the significance of the GC content (as well as AU content at positions 15-19, which is a parameter for formulas III-VII) relates to the easement of the unwinding of a double-stranded siRNA duplex. Duplex unwinding is believed to be crucial for siRNA functionality in vivo and overall low internal stability, especially low internal stability of the first unwound base pair is believed to be important to maintain sufficient processivity of RISC complex-induced duplex unwinding. If the duplex has 19 base pairs, those at positions 15-19 on the sense strand will unwind first if the molecule exhibits a sufficiently low internal stability at that position. As persons skilled in the art are aware, RISC is a complex of approximately twelve proteins; Dicer is one, but not the only, helicase within this complex. Accordingly, although the GC parameters are believed to relate to activity with Dicer, they are also important for activity with other RISC proteins.

The value of the parameter Tm is 0 when there are no internal repeats longer than (or equal to) four base pairs present in the siRNA duplex; otherwise the value is 1. Thus for example, if the sequence ACGUACGU, or any other four nucleotide (or more) palindrome exists within the structure, the value will be one (1). Alternatively if the structure ACGGACG, or any other 3 nucleotide (or less) palindrome exists, the value will be zero (0).

The variable "X" refers to the number of times that the same nucleotide occurs contiguously in a stretch of four or more units. If there are, for example, four contiguous As in one part of the sequence and elsewhere in the sequence four contiguous Cs, X=2. Further, if there are two separate contiguous stretches of four of the same nucleotides or eight or more of the same nucleotides in a row, then X=2. However, X does not increase for five, six or seven contiguous nucleotides.

Again, when applying Formula VIII, Formula IX, or Formula X, to a given mRNA, (the "target RNA" or "target molecule"), one may use a computer program to evaluate the criteria for every sequence of 18-30 base pairs or only sequences of a fixed length, e.g., 19 base pairs. Preferably the computer program is designed such that it provides a report ranking of all of the potential siRNAs 18-30 base pairs, ranked according to which sequences generate the highest value. A higher value refers to a more efficient siRNA for a particular target gene. The computer program that may be used may be developed in any computer language that is known to be useful for scoring nucleotide sequences, or it may be developed with the assistance of commercially available product such as Microsoft's PRODUCT.NET. Additionally, rather than run every sequence through one and/or another formula, one may compare a subset of the sequences, which may be desirable if for example only a subset are available. For instance, it may be desirable to first perform a BLAST (Basis Local Alignment Search Tool) search and to identify sequences that have no homology to other targets. Alternatively, it may be desirable to scan the sequence and to identify regions of moderate GC context, then perform relevant calculations using one of the above-described formulas on these regions. These calculations can be done manually or with the aid of a computer.

As with Formulas I-VII, either Formula VIII, Formula IX, or Formula X may be used for a given mRNA target sequence. However, it is possible that according to one or the other formula more than one siRNA will have the same value. Accordingly, it is beneficial to have a second formula by which to differentiate sequences. Formulas IX and X were derived in a similar fashion as Formula VIII, yet used a larger data set and thus yields sequences with higher statistical correlations to highly functional duplexes. The sequence that has the highest value ascribed to it may be referred to as a "first optimized duplex." The sequence that has the second highest value ascribed to it may be referred to as a "second optimized duplex." Similarly, the sequences that have the third and fourth highest values ascribed to them may be referred to as a third optimized duplex and a fourth optimized duplex, respectively. When more than one sequence has the same value, each of them may, for example, be referred to as first optimized duplex sequences or co-first optimized duplexes. Formula X is similar to Formula IX, yet uses a greater numbers of variables and for that reason, identifies sequences on the basis of slightly different criteria.

It should also be noted that the output of a particular algorithm will depend on several of variables including: (1) the size of the data base(s) being analyzed by the algorithm, and (2) the number and stringency of the parameters being applied to screen each sequence. Thus, for example, in U.S. patent application Ser. No. 10/714,333, entitled " Functional and Hyperfunctional siRNA," filed Nov. 14, 2003, Formula VIII was applied to the known human genome (NCBI REFSEQ database) through ENTREZ (EFETCH). As a result of these procedures, roughly 1.6 million siRNA sequences were identified. Application of Formula VIII to the same database in March of 2004 yielded roughly 2.2 million sequences, a difference of approximately 600,000 sequences resulting from the growth of the database over the course of the months that span this period of time. Application of other formulas (e.g., Formula X) that change the emphasis of, include, or eliminate different variables can yield unequal numbers of siRNAs. Alternatively, in cases where application of one formula to one or more genes fails to yield sufficient numbers of siRNAs with scores that would be indicative of strong silencing, said genes can be reassessed with a second algorithm that is, for instance, less stringent.

siRNA sequences identified using Formula VIII and Formula X (minus sequences generated by Formula VIII) are contained within the sequence listing. The data included in the sequence listing is described more fully below. The sequences identified by Formula VIII and Formula X that are disclosed in the sequence listing may be used in gene silencing applications.

It should be noted that for Formulas VIII, IX, and X all of the aforementioned criteria are identified as positions on the sense strand when oriented in the 5' to 3' direction as they are identified in connection with Formulas I-VII unless otherwise specified.

Formulas I-X, may be used to select or to evaluate one, or more than one, siRNA in order to optimize silencing. Preferably, at least two optimized siRNAs that have been selected according to at least one of these formulas are used to silence a gene, more preferably at least three and most preferably at least four. The siRNAs may be used individually or together in a pool or kit. Further, they may be applied to a cell simultaneously or separately. Preferably, the at least two siRNAs are applied simultaneously. Pools are particularly beneficial for many research applications. However, for therapeutics, it may be more desirable to employ a single hyperfunctional siRNA as described elsewhere in this application.

When planning to conduct gene silencing, and it is necessary to choose between two or more siRNAs, one should do so by comparing the relative values when the siRNA are subjected to one of the formulas above. In general a higher scored siRNA should be used.

Useful applications include, but are not limited to, target validation, gene functional analysis, research and drug discovery, gene therapy and therapeutics. Methods for using siRNA in these applications are well known to persons of skill in the art.

Because the ability of siRNA to function is dependent on the sequence of the RNA and not the species into which it is introduced, the present invention is applicable across a broad range of species, including but not limited to all mammalian species, such as humans, dogs, horses, cats, cows, mice, hamsters, chimpanzees and gorillas, as well as other species and organisms such as bacteria, viruses, insects, plants and *C. elegans*.

The present invention is also applicable for use for silencing a broad range of genes, including but not limited to the roughly 45,000 genes of a human genome, and has particular relevance in cases where those genes are associated with diseases such as diabetes, Alzheimer's, cancer; as well as all genes in the genomes of the aforementioned organisms.

The siRNA selected according to the aforementioned criteria or one of the aforementioned algorithms are also, for example, useful in the simultaneous screening and functional analysis of multiple genes and gene families using high throughput strategies, as well as in direct gene suppression or silencing.

Development of the Algorithms

To identify siRNA sequence features that promote functionality and to quantify the importance of certain currently accepted conventional factors—such as G/C content and target site accessibility—the inventors synthesized an siRNA panel consisting of 270 siRNAs targeting three genes, Human Cyclophilin, Firefly Luciferase, and Human DBI. In all three cases, siRNAs were directed against specific regions of each gene. For Human Cyclophilin and Firefly Luciferase, ninety siRNAs were directed against a 199 bp segment of each respective mRNA. For DBI, 90 siRNAs were directed against a smaller, 109 base pair region of the mRNA. The sequences to which the siRNAs were directed are provided below.

It should be noted that in certain sequences, "t" is present. This is because many databases contain information in this manner. However, the t denotes a uracil residue in mRNA and siRNA. Any algorithm will, unless otherwise specified, process a t in a sequence as a u.

```
Human cyclophilin: 193-390, M60857
SEQ. ID NO. 29:
gttccaaaaa cagtggataa ttttgtggcc ttagctacag gagagaaagg atttggctac aaaaacagca aattccatcg tgtaatcaag gacttcatga tccagggcgg agacttcacc aggggagatg gcacaggagg aaagagcatc tacggtgagc gcttccccga tgagaacttc aaactgaagc actacgggcc tggctggg Firefly luciferase: 1434-1631, U47298 (pGL3,
Promega) SEQ. ID NO. 30:
tgaacttccc gccgccgttg ttgttttgga gcacggaaag acgatgacgg aaaaagagat cgtggattac gtcgccagtc aagtaacaac cgcgaaaaag ttgcgcggag gagttgtgtt tgtggacgaa gtaccgaaag gtcttaccgg aaaactcgac gcaagaaaaa tcagagagat cctcataaag gccaagaagg DBI, NM_020548 (202-310) (every position)
SEQ. ID NO. 0031:
acgggcaagg ccaagtggga tgcctggaat gagctgaaag ggacttccaa ggaagatgcc atgaaagctt acatcaacaa agtagaagag ctaaagaaaa aatacggg
```

A list of the siRNAs appears in Table IV (see Examples Section, Example II)

The set of duplexes was analyzed to identify correlations between siRNA functionality and other biophysical or thermodynamic properties. When the siRNA panel was analyzed in functional and non-functional subgroups, certain nucleotides were much more abundant at certain positions in functional or non-functional groups. More specifically, the frequency of each nucleotide at each position in highly functional siRNA duplexes was compared with that of nonfunctional duplexes in order to assess the preference for or against any given nucleotide at every position. These analyses were used to determine important criteria to be included in the siRNA algorithms (Formulas VIII, IX, and X).

The data set was also analyzed for distinguishing biophysical properties of siRNAs in the functional group, such as optimal percent of GC content, propensity for internal structures and regional thermodynamic stability. Of the presented criteria, several are involved in duplex recognition, RISC activation/duplex unwinding, and target cleavage catalysis.

Figure 2:
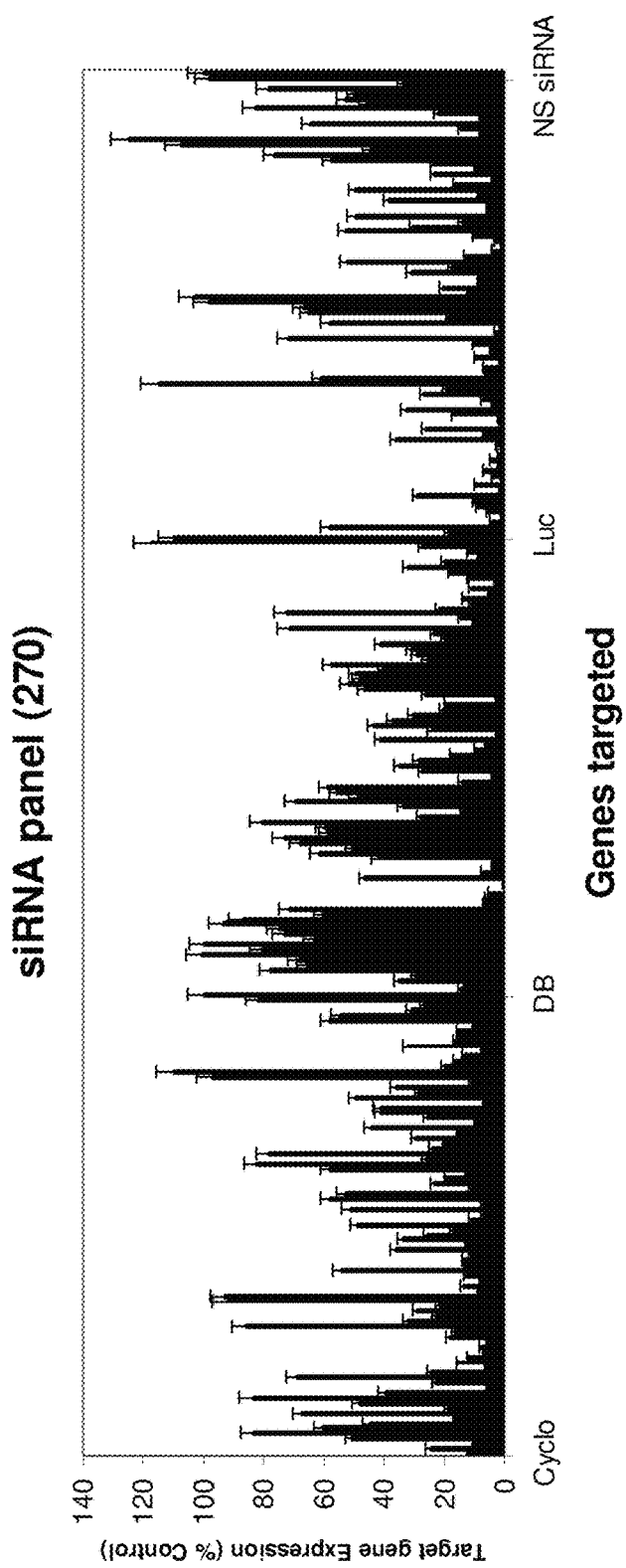
FIG. 2 is a representation of the functionality of two hundred and seventy siRNA duplexes that were generated to target human cyclophilin, human diazepam-binding inhibitor (DB), and firefly luciferase.
Figure 3A:
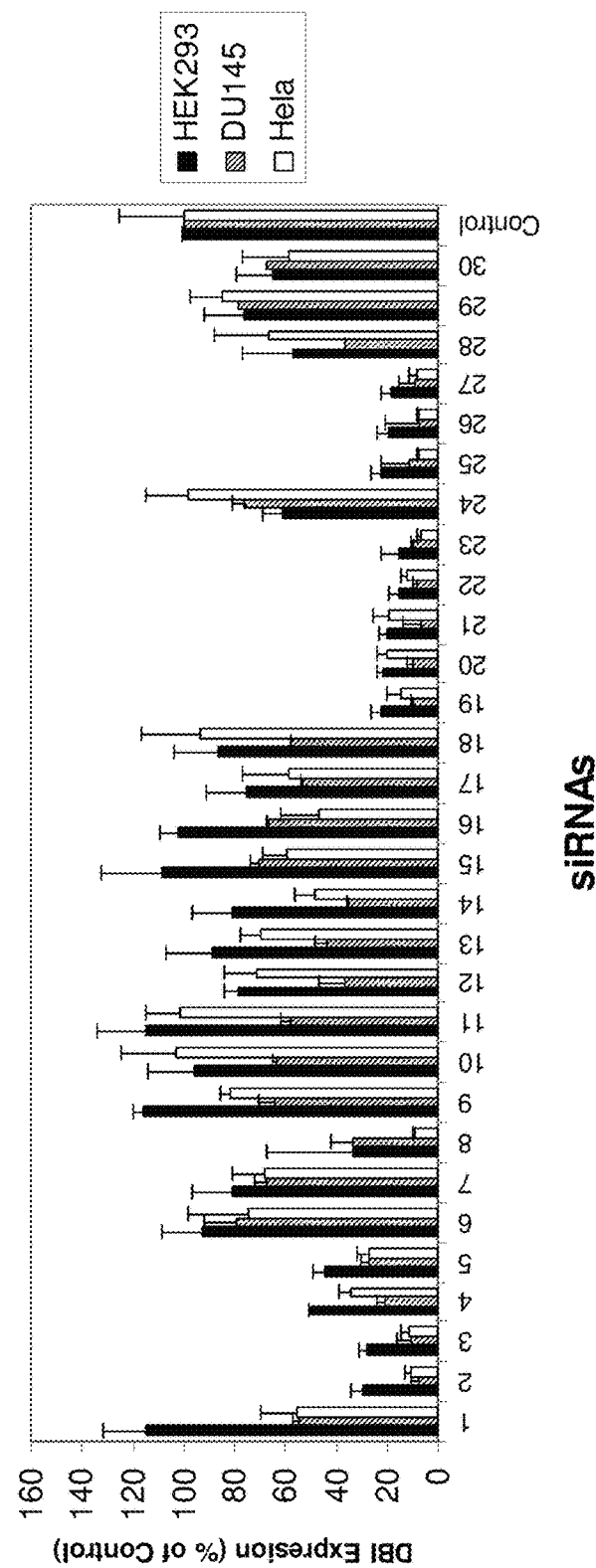
FIG. 3A is a representation of the silencing effect of 30 siRNAs in three different cells lines, HEK293, DU145, and Hela.

The original data set that was the source of the statistically derived criteria is shown in FIG. 2. Additionally, this figure shows that random selection yields siRNA duplexes with unpredictable and widely varying silencing potencies as measured in tissue culture using HEK293 cells. In the figure, duplexes are plotted such that each x-axis tick-mark represents an individual siRNA, with each subsequent siRNA differing in target position by two nucleotides for Human Cyclophilin B and Firefly Luciferase, and by one nucleotide for Human DBI. Furthermore, the y-axis denotes the level of target expression remaining after transfection of the duplex into cells and subsequent silencing of the target.

siRNA identified and optimized in this document work equally well in a wide range of cell types. FIG. 3a shows the evaluation of thirty siRNAs targeting the DBI gene in three cell lines derived from different tissues. Each DBI siRNA displays very similar functionality in HEK293 (ATCC, CRL-1573, human embryonic kidney), HeLa (ATCC, CCL-2, cervical epithelial adenocarcinoma) and DUI 45 (HTB-81, prostate) cells as determined by the B-DNA assay. Thus, siRNA functionality is determined by the primary sequence of the siRNA and not by the intracellular environment. Additionally, it should be noted that although the present invention provides for a determination of the functionality of siRNA for a given target, the same siRNA may silence more than one gene. For example, the complementary sequence of the silencing siRNA may be present in more than one gene. Accordingly, in these circumstances, it may be desirable not to use the siRNA with highest SMARTSCORE™, or siRNA ranking. In such circumstances, it may be desirable to use the siRNA with the next highest SMARTSCORE™, or siRNA ranking.

To determine the relevance of G/C content in siRNA function, the G/C content of each duplex in the panel was calculated and the functional classes of siRNAs (<F50, ≥F50, ≥F80, ≥F95 where F refers to the percent gene silencing) were sorted accordingly. The majority of the highly-functional siRNAs (≥F95) fell within the G/C content range of 36%-52% (FIG. 3B). Twice as many non-functional (<F50) duplexes fell within the high G/C content groups (>57% GC content) compared to the 36%-52% group. The group with extremely low GC content (26% or less) contained a higher proportion of non-functional siRNAs and no highly-functional siRNAs. The G/C content range of 30%-52% was therefore selected as Criterion I for siRNA functionality, consistent with the observation that a G/C range 30%-70% promotes efficient RNAi targeting. Application of this criterion alone provided only a marginal increase in the probability of selecting functional siRNAs from the panel: selection of F50 and F95 siRNAs was improved by 3.6% and 2.2%, respectively. The siRNA panel presented here permitted a more systematic analysis and quantification of the importance of this criterion than that used previously.

A relative measure of local internal stability is the A/U base pair (bp) content; therefore, the frequency of A/U bp was determined for each of the five terminal positions of the duplex (5' sense (S)/5' antisense (AS)) of all siRNAs in the panel. Duplexes were then categorized by the number of A/U bp in positions 1-5 and 15-19 of the sense strand. The thermodynamic flexibility of the duplex 5'-end (positions 1-5; S) did not appear to correlate appreciably with silencing potency, while that of the 3'-end (positions 15-19; S) correlated with efficient silencing. No duplexes lacking A/U bp in positions 15-19 were functional. The presence of one A/U bp in this region conferred some degree of functionality, but the presence of three or more A/Us was preferable and therefore defined as Criterion II. When applied to the test panel, only a marginal increase in the probability of functional siRNA selection was achieved: a 1.8% and 2.3% increase for F50 and F95 duplexes, respectively (Table III).

Figure 3C:
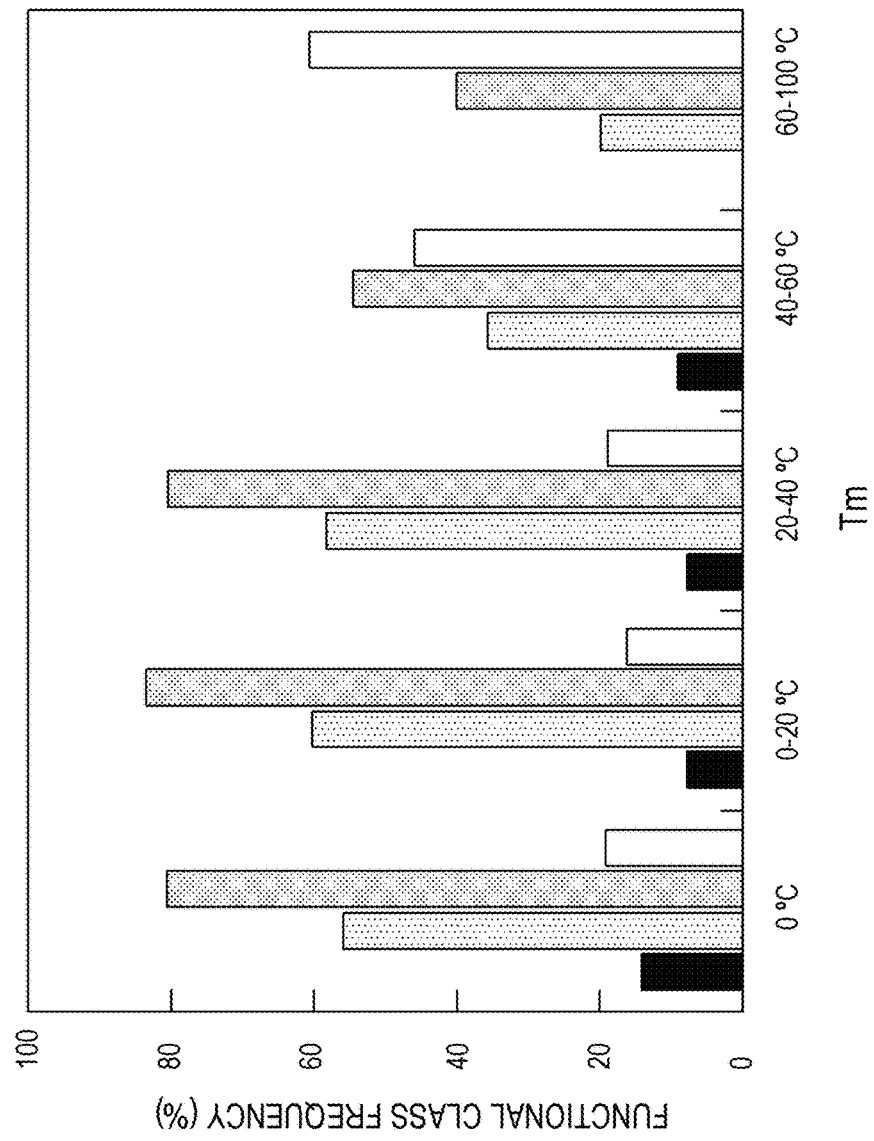
FIG. 3C shows the frequency of different functional groups based on melting temperature (Tm).

The complementary strands of siRNAs that contain internal repeats or palindromes may form internal fold-back structures. These hairpin-like structures exist in equilibrium with the duplexed form effectively reducing the concentration of functional duplexes. The propensity to form internal hairpins and their relative stability can be estimated by predicted melting temperatures. High Tm reflects a tendency to form hairpin structures. Lower Tm values indicate a lesser tendency to form hairpins. When the functional classes of siRNAs were sorted by $T_m$ (FIG. 3c), the following trends were identified: duplexes lacking stable internal repeats were the most potent silencers (no F95 duplex with predicted hairpin structure $T_m>60°$ C.). In contrast, about 60% of the duplexes in the groups having internal hairpins with calculated $T_m$ values less than 20° C. were F80. Thus, the stability of internal repeats is inversely proportional to the silencing effect and defines Criterion III (predicted hairpin structure $T_m \leq 20°$ C.).

Sequence-Based Determinants of siRNA Functionality

Figure 4D:
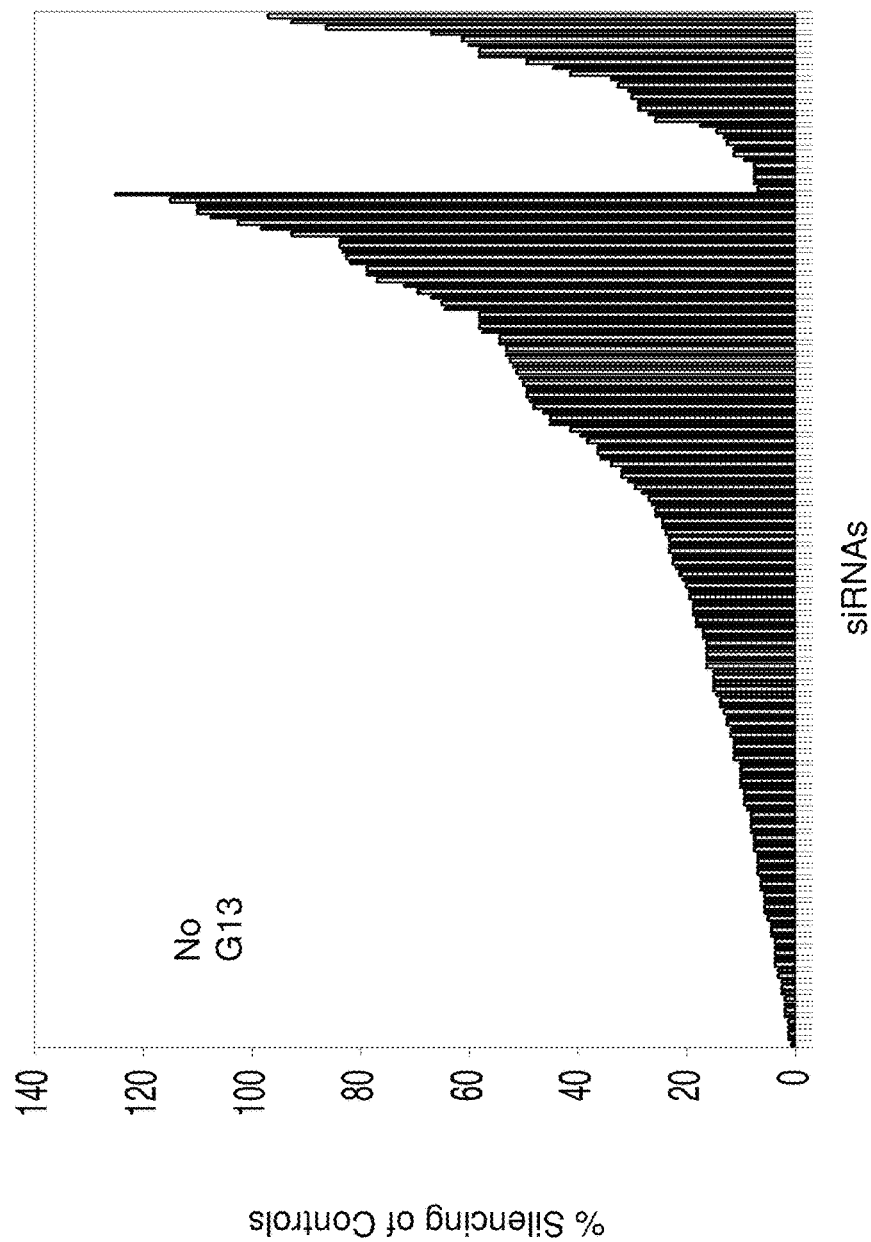
Figure 4E:
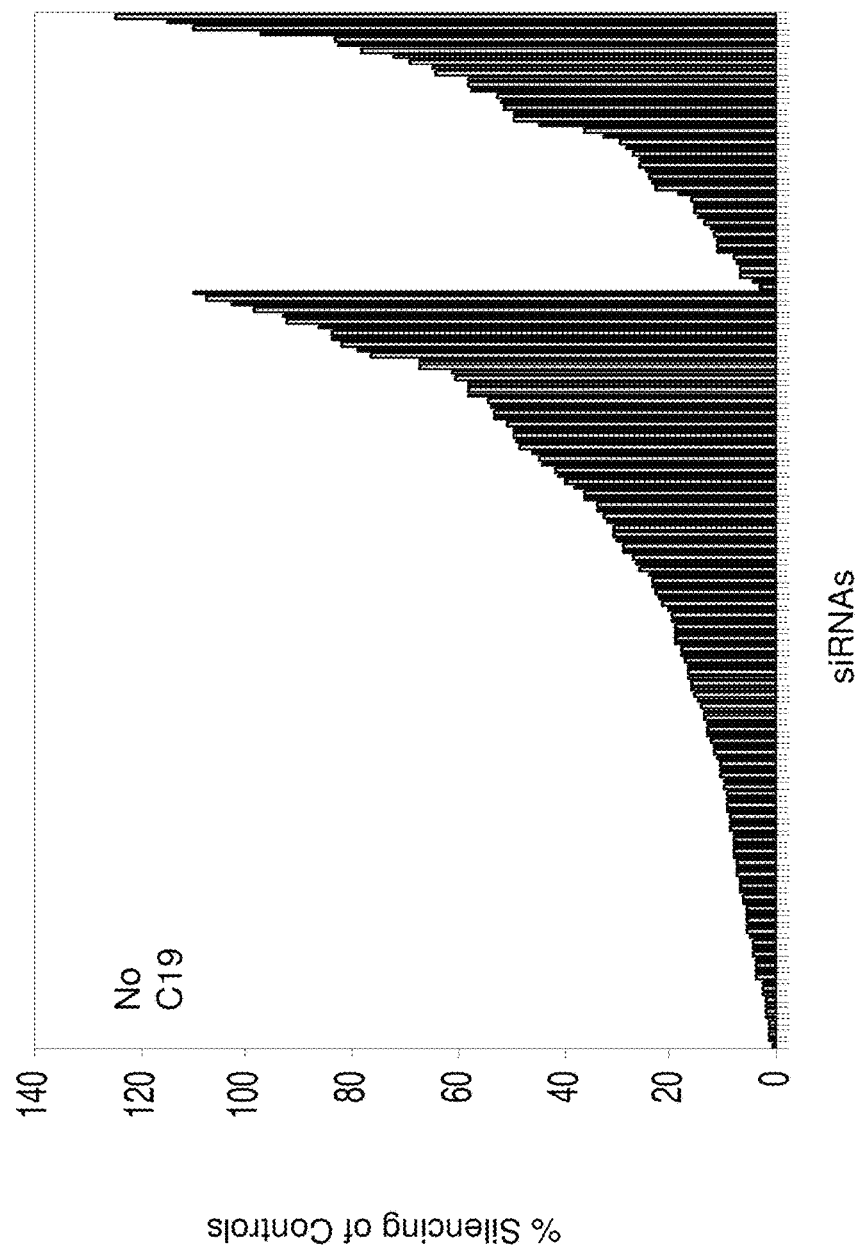

When the siRNA panel was sorted into functional and non-functional groups, the frequency of a specific nucleotide at each position in a functional siRNA duplex was compared with that of a nonfunctional duplex in order to assess the preference for or against a certain nucleotide. FIG. 4 shows the results of these queries and the subsequent resorting of the data set (from FIG. 2). The data is separated into two sets: those duplexes that meet the criteria, a specific nucleotide in a certain position—grouped on the left (Selected) and those that do not—grouped on the right (Eliminated). The duplexes are further sorted from most functional to least functional with the y-axis of FIG. 4a-e representing the % expression i.e., the amount of silencing that is elicited by the duplex (Note: each position on the X-axis represents a different duplex). Statistical analysis revealed correlations between silencing and several sequence-related properties of siRNAs. FIG. 4 and Table III show quantitative analysis for the following five sequence-related properties of siRNA: (A) an A at position 19 of the sense strand; (B) an A at position 3 of the sense strand; (C) a U at position 10 of the sense strand; (D) a base other than G at position 13 of the sense strand; and (E) a base other than C at position 19 of the sense strand.

When the siRNAs in the panel were evaluated for the presence of an A at position 19 of the sense strand, the percentage of non-functional duplexes decreased from 20% to 11.8%, and the percentage of F95 duplexes increased from 21.7% to 29.4% (Table III). Thus, the presence of an A in this position defined Criterion IV.

Another sequence-related property correlated with silencing was the presence of an A in position 3 of the sense strand (FIG. 4b). Of the siRNAs with A3, 34.4% were F95, compared with 21.7% randomly selected siRNAs. The presence of a U base in position 10 of the sense strand exhibited an even greater impact (FIG. 4c). Of the duplexes in this group, 41.7% were F95. These properties became criteria V and VI, respectively.

Two negative sequence-related criteria that were identified also appear on FIG. 4. The absence of a G at position 13 of the sense strand, conferred a marginal increase in selecting functional duplexes (FIG. 4d). Similarly, lack of a C at position 19 of the sense strand also correlated with functionality (FIG. 4e). Thus, among functional duplexes, position 19 was most likely occupied by A, and rarely occupied by C. These rules were defined as criteria VII and VIII, respectively.

Application of each criterion individually provided marginal but statistically significant increases in the probability of selecting a potent siRNA. Although the results were informative, the inventors sought to maximize potency and therefore consider multiple criteria or parameters. Optimization is particularly important when developing therapeutics. Interestingly, the probability of selecting a functional siRNA based on each thermodynamic criteria was 2%-4% higher than random, but 4%-8% higher for the sequence-related determinates. Presumably, these sequence-related increases reflect the complexity of the RNAi mechanism and the multitude of protein-RNA interactions that are involved in RNAi-mediated silencing.

TABLE III

| CRITERION | | PERCENT FUNCTIONAL | IMPROVEMENT OVER RANDOM (%) |
|---|---|---|---|
| I. 30%-52% G/C Content | <F50 | 16.4 | −3.6 |
| | ≥F50 | 83.6 | 3.6 |
| | ≥F80 | 60.4 | 4.3 |
| | ≥F95 | 23.9 | 2.2 |
| II. At least 3 A/U bases at positions 15-19 of the sense strand | <F50 | 18.2 | −1.8 |
| | ≥F50 | 81.8 | 1.8 |
| | ≥F80 | 59.7 | 3.6 |
| | ≥F95 | 24.0 | 2.3 |
| III. Absence of internal repeats, as measured by Tm of secondary structure ≤20° C. | <F50 | 16.7 | −3.3 |
| | ≥F50 | 83.3 | 3.3 |
| | ≥F80 | 61.1 | 5.0 |
| | ≥F95 | 24.6 | 2.9 |
| IV. An A base at position 19 of the sense strand | <F50 | 11.8 | −8.2 |
| | ≥F50 | 88.2 | 8.2 |
| | ≥F80 | 75.0 | 18.9 |
| | ≥F95 | 29.4 | 7.7 |
| V. An A base at position 3 of the sense strand | <F50 | 17.2 | −2.8 |
| | ≥F50 | 82.8 | 2.8 |
| | ≥F80 | 62.5 | 6.4 |
| | ≥F95 | 34.4 | 12.7 |
| VI. A U base at position 10 of the sense strand | <F50 | 13.9 | −6.1 |
| | ≥F50 | 86.1 | 6.1 |
| | ≥F80 | 69.4 | 13.3 |
| | ≥F95 | 41.7 | 20 |
| VII. A base other than C at position 19 of the sense strand | <F50 | 18.8 | −1.2 |
| | ≥F50 | 81.2 | 1.2 |
| | ≥F80 | 59.7 | 3.6 |
| | ≥F95 | 24.2 | 2.5 |
| VIII. A base other than G at position 13 of the sense strand | <F50 | 15.2 | −4.8 |
| | ≥F50 | 84.8 | 4.8 |
| | ≥F80 | 61.4 | 5.3 |
| | ≥F95 | 26.5 | 4.8 |

The siRNA Selection Algorithm

In an effort to improve selection further, all identified criteria, including but not limited to those listed in Table III were combined into the algorithms embodied in Formula VIII, Formula IX, and Formula X. Each siRNA was then assigned a score (referred to as a SMARTSCORE™, or siRNA ranking) according to the values derived from the formulas. Duplexes that scored higher than 0 or − (unadjusted), for Formulas VIII and IX, respectively, effectively selected a set of functional siRNAs and excluded all non-functional siRNAs. Conversely, all duplexes scoring lower than 0 and −20 (minus 20) according to formulas VIII and IX, respectively, contained some functional siRNAs but included all non-functional siRNAs. A graphical representation of this selection is shown in FIG. 5. It should be noted that the scores derived from the algorithm can also be provided as "adjusted" scores. To convert Formula VIII unadjusted scores into adjusted scores it is necessary to use the following equation:

(160+unadjusted score)/2.25

When this takes place, an unadjusted score of "0" (zero) is converted to 75. Similarly, unadjusted scores for Formula X can be converted to adjusted scores. In this instance, the following equation is applied:

(228+unadjusted score)/3.56

When these manipulations take place, an unadjusted score of 38 is converted to an adjusted score of 75.

The methods for obtaining the seven criteria embodied in Table III are illustrative of the results of the process used to develop the information for Formulas VIII, IX, and X. Thus similar techniques were used to establish the other variables and their multipliers. As described above, basic statistical methods were use to determine the relative values for these multipliers.

To determine the value for "Improvement over Random" the difference in the frequency of a given attribute (e.g., GC content, base preference) at a particular position is determined between individual functional groups (e.g., <F50) and the total siRNA population studied (e.g., 270 siRNA molecules selected randomly). Thus, for instance, in Criterion I (30%-52% GC content) members of the <F50 group were observed to have GC contents between 30-52% in 16.4% of the cases. In contrast, the total group of 270 siRNAs had GC contents in this range, 20% of the time. Thus for this particular attribute, there is a small negative correlation between 30%-52% GC content and this functional group (i.e., 16.4%-20% = −3.6%). Similarly, for Criterion VI, (a "U" at position 10 of the sense strand), the >F95 group contained a "U" at this position 41.7% of the time. In contrast, the total group of 270 siRNAs had a "U" at this position 21.7% of the time, thus the improvement over random is calculated to be 20% (or 41.7%-21.7%).

Identifying The Average Internal Stability Profile of Strong siRNA

In order to identify an internal stability profile that is characteristic of strong siRNA, 270 different siRNAs derived from the cyclophilin B, the diazepam binding inhibitor (DBI), and the luciferase gene were individually transfected into HEK293 cells and tested for their ability to induce RNAi of the respective gene. Based on their performance in the in vivo assay, the sequences were then subdivided into three groups, (i) >95% silencing; (ii) 80-95% silencing; and (iii) less than 50% silencing. Sequences exhibiting 51-84% silencing were eliminated from further consideration to reduce the difficulties in identifying relevant thermodynamic patterns.

Following the division of siRNA into three groups, a statistical analysis was performed on each member of each group to determine the average internal stability profile (AISP) of the siRNA. To accomplish this the Oligo 5.0 Primer Analysis Software and other related statistical packages (e.g., Excel) were exploited to determine the internal stability of pentamers using the nearest neighbor method described by Freier et al., (1986) Improved free-energy parameters for predictions of RNA duplex stability, *Proc Natl. Acad. Sci. USA* 83(24): 9373-7. Values for each group at each position were then averaged, and the resulting data were graphed on a linear coordinate system with the Y-axis expressing the G (free energy) values in kcal/mole and the X-axis identifying the position of the base relative to the 5' end.

Figure 6A:
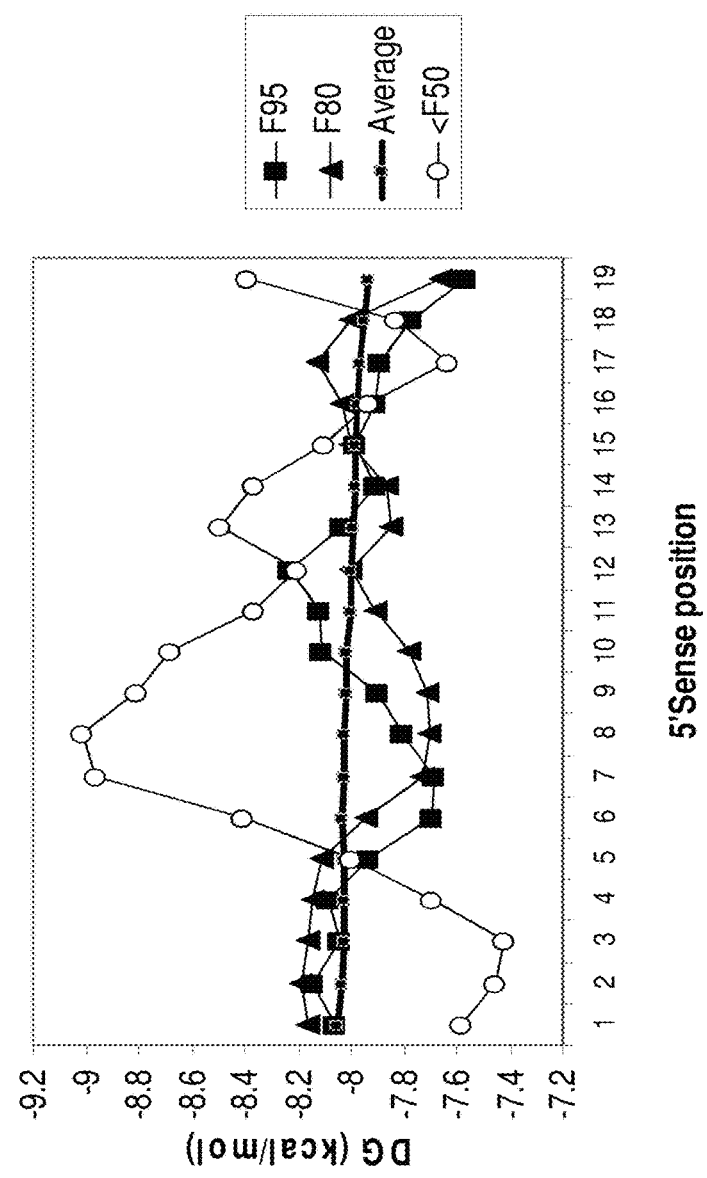
FIG. 6A is a representation of the average internal stability profile (AISP) derived from 270 siRNAs taken from three separate genes (cyclophilin B, DBI and firefly luciferase). Graphs represent AISP values of highly functional, functional, and non-functional siRNA.

The results of the analysis identified multiple key regions in siRNA molecules that were critical for successful gene silencing. At the 3'-most end of the sense strand (5' antisense), highly functional siRNA (>95% gene silencing, see FIG. 6a, >F95) have a low internal stability (AISP of position 19=~−7.6 kcal/mol). In contrast low-efficiency siRNA (i.e., those exhibiting less than 50% silencing, <F50) display a distinctly different profile, having high G values (~−8.4 kcal/mol) for the same position. Moving in a 5' (sense strand) direction, the internal stability of highly efficient siRNA rises (position 12=~−8.3 kcal/mole) and then drops again (position 7=~−7.7 kcal/mol) before leveling off at a value of approximately −8.1 kcal/mol for the 5' terminus. siRNA with poor silencing capabilities show a distinctly different profile. While the AISP value at position 12 is nearly identical with that of strong siRNAs, the values at positions 7 and 8 rise considerably, peaking at a high of ~−9.0 kcal/mol. In addition, at the 5' end of the molecule the AISP profile of strong and weak siRNA differ dramatically. Unlike the relatively strong values exhibited by siRNA in the >95% silencing group, siRNAs that exhibit poor silencing activity have weak AISP values (−7.6, −7.5, and −7.5 kcal/mol for positions 1, 2 and 3 respectively).

Overall the profiles of both strong and weak siRNAs form distinct sinusoidal shapes that are roughly 180° out-of-phase with each other. While these thermodynamic descriptions define the archetypal profile of a strong siRNA, it will likely be the case that neither the G values given for key positions in the profile or the absolute position of the profile along the Y-axis (i.e., the G -axis) are absolutes. Profiles that are shifted upward or downward (i.e., having on an average, higher or lower values at every position) but retain the relative shape and position of the profile along the X-axis can be foreseen as being equally effective as the model profile described here. Moreover, it is likely that siRNA that have strong or even stronger gene-specific silencing effects might have exaggerated G values (either higher or lower) at key positions. Thus, for instance, it is possible that the 5'-most position of the sense strand (position 19) could have G values of 7.4 kcal/mol or lower and still be a strong siRNA if, for instance, a G-C G-T/U mismatch were substituted at position 19 and altered duplex stability. Similarly, position 12 and position 7 could have values above 8.3 kcal/mol and below 7.7 kcal/mole, respectively, without abating the silencing effectiveness of the molecule. Thus, for instance, at position 12, a stabilizing chemical modification (e.g., a chemical modification of the 2' position of the sugar backbone) could be added that increases the average internal stability at that position. Similarly, at position 7, mismatches similar to those described previously could be introduced that would lower the G values at that position.

Lastly, it is important to note that while functional and non-functional siRNA were originally defined as those molecules having specific silencing properties, both broader or more limiting parameters can be used to define these molecules. As used herein, unless otherwise specified, "non-functional siRNA" are defined as those siRNA that induce less than 50% (<50%) target silencing, "semi-functional siRNA" induce 50-79% target silencing, "functional siRNA" are molecules that induce 80-95% gene silencing, and "highly-functional siRNA" are molecules that induce great than 95% gene silencing. These definitions are not intended to be rigid and can vary depending upon the design and needs of the application. For instance, it is possible that a researcher attempting to map a gene to a chromosome using a functional assay, may identify an siRNA that reduces gene activity by only 30%. While this level of gene silencing may be "non-functional" for, e.g., therapeutic needs, it is sufficient for gene mapping purposes and is, under these uses and conditions, "functional." For these reasons, functional siRNA can be defined as those molecules having greater than 10%, 20%, 30%, 40%, 50%, 60%, 70%, 80%, or 90% silencing capabilities at 100 nM transfection conditions. Similarly, depending upon the needs of the study and/or application, non-functional and semi-functional siRNA can be defined as having different parameters. For instance, semi-functional siRNA can be defined as being those molecules that induce 20%, 30%, 40%, 50%, 60%, or 70% silencing at 100 nM transfection conditions. Similarly, non-functional siRNA can be defined as being those molecules that silence gene expression by less than 70%, 60%, 50%, 40%, 30%, or less. Nonetheless, unless otherwise stated, the descriptions stated in the "Definitions" section of this text should be applied.

Functional attributes can be assigned to each of the key positions in the AISP of strong siRNA. The low 5' (sense strand) AISP values of strong siRNAs may be necessary for determining which end of the molecule enters the RISC complex. In contrast, the high and low AISP values observed in the central regions of the molecule may be critical for siRNA-target mRNA interactions and product release, respectively.

Figure 6B:
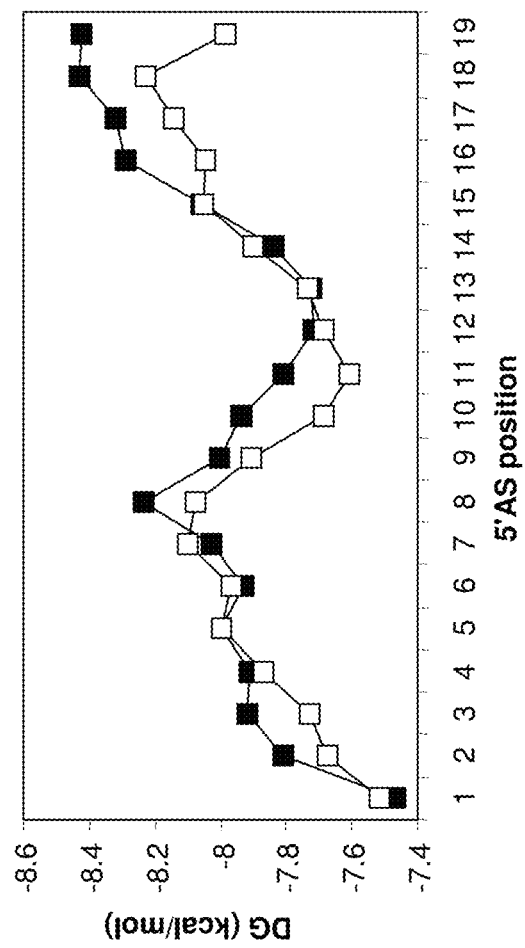
FIG. 6B is a comparison between the AISP of naturally derived GFP siRNA (filled squares) and the AISP of siRNA from cyclophilin B, DBI, and luciferase having >90% silencing properties (no fill) for the antisense strand. "DG" is the symbol for G, free energy.

If the AISP values described above accurately define the thermodynamic parameters of strong siRNA, it would be expected that similar patterns would be observed in strong siRNA isolated from nature. Natural siRNAs exist in a harsh, RNase-rich environment and it can be hypothesized that only those siRNA that exhibit heightened affinity for RISC (i.e., siRNA that exhibit an average internal stability profile similar to those observed in strong siRNA) would survive in an intracellular environment. This hypothesis was tested using GFP-specific siRNA isolated from N benthamiana. Llave et al. (2002) Endogenous and Silencing-Associated Small RNAs in Plants, *The Plant Cell* 14, 1605-1619, introduced long double-stranded GFP-encoding RNA into plants and subsequently re-isolated GFP-specific siRNA from the tissues. The AISP of fifty-nine of these GFP-siRNA were determined, averaged, and subsequently plotted alongside the AISP profile obtained from the cyclophilin B/DBI/luciferase siRNA having >90% silencing properties (FIG. 6b). Comparison of the two groups show that profiles are nearly identical. This finding validates the information provided by the internal stability profiles and demonstrates that: (I) the profile identified by analysis of the cyclophilin B/DBI/luciferase siRNAs are not gene specific; and (2) AISP values can be used to search for strong siRNAs in a variety of species.

Both chemical modifications and base-pair mismatches can be incorporated into siRNA to alter the duplex's AISP and functionality. For instance, introduction of mismatches at positions 1 or 2 of the sense strand destabilized the 5' end of the sense strand and increases the functionality of the molecule (see Luc, FIG. 7). Similarly, addition of 2-O-methyl groups to positions 1 and 2 of the sense strand can also alter the AISP and (as a result) increase both the functionality of the molecule and eliminate off-target effects that results from sense strand homology with the unrelated targets (FIG. 8).

Rationale for Criteria in a Biological Context

The fate of siRNA in the RNAi pathway may be described in 5 major steps: (1) duplex recognition and pre-RISC complex formation; (2) ATP-dependent duplex unwinding/strand selection and RISC activation; (3) mRNA target identification; (4) mRNA cleavage, and (5) product release (FIG. 1). Given the level of nucleic acid-protein interactions at each step, siRNA functionality is likely influenced by specific biophysical and molecular properties that promote efficient interactions within the context of the multi-component complexes. Indeed, the systematic analysis of the siRNA test set identified multiple factors that correlate well with functionality. When combined into a single algorithm, they proved to be very effective in selecting active siRNAs.

The factors described here may also be predictive of key functional associations important for each step in RNAi. For example, the potential formation of internal hairpin structures correlated negatively with siRNA functionality. Complementary strands with stable internal repeats are more likely to exist as stable hairpins thus decreasing the effective concentration of the functional duplex form. This suggests that the duplex is the preferred conformation for initial pre-RISC association. Indeed, although single complementary strands can induce gene silencing, the effective concentration required is at least two orders of magnitude higher than that of the duplex form.

siRNA-pre-RISC complex formation is followed by an ATP-dependent duplex unwinding step and "activation" of the RISC. The siRNA functionality was shown to correlate with overall low internal stability of the duplex and low internal stability of the 3' sense end (or differential internal stability of the 3' sense compare to the 5' sense strand), which may reflect strand selection and entry into the RISC. Overall duplex stability and low internal stability at the 3' end of the sense strand were also correlated with siRNA functionality. Interestingly, siRNAs with very high and very low overall stability profiles correlate strongly with non-functional duplexes. One interpretation is that high internal stability prevents efficient unwinding while very low stability reduces siRNA target affinity and subsequent mRNA cleavage by the RISC.

Several criteria describe base preferences at specific positions of the sense strand and are even more intriguing when considering their potential mechanistic roles in target recognition and mRNA cleavage. Base preferences for A at position 19 of the sense strand but not C, are particularly interesting because they reflect the same base preferences observed for naturally occurring miRNA precursors. That is, among the reported miRNA precursor sequences 75% contain a U at position 1 which corresponds to an A in position 19 of the sense strand of siRNAs, while G was under-represented in this same position for miRNA precursors. These observations support the hypothesis that both miRNA precursors and siRNA duplexes are processed by very similar if not identical protein machinery. The functional interpretation of the predominance of a U/A base pair is that it promotes flexibility at the 5' antisense ends of both siRNA duplexes and miRNA precursors and facilitates efficient unwinding and selective strand entrance into an activated RISC.

Among the criteria associated with base preferences that are likely to influence mRNA cleavage or possibly product release, the preference for U at position 10 of the sense strand exhibited the greatest impact, enhancing the probability of selecting an F80 sequence by 13.3%. Activated RISC preferentially cleaves target mRNA between nucleotides 10 and 11 relative to the 5' end of the complementary targeting strand. Therefore, it may be that U, the preferred base for most endoribonucleases, at this position supports more efficient cleavage. Alternatively, a U/A bp between the targeting siRNA strand and its cognate target mRNA may create an optimal conformation for the RISC-associated "slicing" activity.

Post Algorithm Filters

According to another embodiment, the output of any one of the formulas previously listed can be filtered to remove or select for siRNAs containing undesirable or desirable motifs or properties, respectively. In one example, sequences identified by any of the formulas can be filtered to remove any and all sequences that induce toxicity or cellular stress. Introduction of an siRNA containing a toxic motif into a cell can induce cellular stress and/or cell death (apoptosis) which in turn can mislead researchers into associating a particular (e.g., nonessential) gene with, e.g., an essential function. Alternatively, sequences generated by any of the before mentioned formulas can be filtered to identify and retain duplexes that contain toxic motifs. Such duplexes may be valuable from a variety of perspectives including, for instance, uses as therapeutic molecules. A variety of toxic motifs exist and can exert their influence on the cell through RNAi and non-RNAi pathways. Examples of toxic motifs are explained more fully in commonly assigned U.S. Provisional Patent Application Serial No. 60/538,874, entitled "Identification of Toxic Sequences," filed Jan. 23, 2004. Briefly, toxic motifs include A/G UUU A/G/U, G/C AAA G/C, and GCCA, or a complement of any of the foregoing.

In another instance, sequences identified by any of the before mentioned formulas can be filtered to identify duplexes that contain motifs (or general properties) that provide serum stability or induce serum instability. In one envisioned application of siRNA as therapeutic molecules, duplexes targeting disease-associated genes will be introduced into patients intravenously. As the half-life of single and double stranded RNA in serum is short, post-algorithm filters designed to select molecules that contain motifs that enhance duplex stability in the presence of serum and/or (conversely) eliminate duplexes that contain motifs that destabilize siRNA in the presence of serum, would be beneficial.

In another instance, sequences identified by any of the before mentioned formulas can be filtered to identify duplexes that are hyperfunctional. Hyperfunctional sequences are defined as those sequences that (1) induce greater than 95% silencing of a specific target when they are transfected at subnanomolar concentrations (i.e., less than one nanomolar); and/or (2) induce functional (or better) levels of silencing for greater than 96 hours. Filters that identify hyperfunctional molecules can vary widely. In one example, the top ten, twenty, thirty, or forty siRNA can be assessed for the ability to silence a given target at, e.g., concentrations of 1 nM and 0.5 nM to identify hyperfunctional molecules.

Pooling

According to another embodiment, the present invention provides a pool of at least two siRNAs, preferably in the form of a kit or therapeutic reagent, wherein one strand of each of the siRNAs, the sense strand comprises a sequence that is substantially similar to a sequence within a target mRNA. The opposite strand, the antisense strand, will preferably comprise a sequence that is substantially complementary to that of the target mRNA. More preferably, one strand of each siRNA will comprise a sequence that is identical to a sequence that is contained in the target mRNA. Most preferably, each siRNA will be 19 base pairs in length, and one strand of each of the siRNAs will be 100% complementary to a portion of the target mRNA.

By increasing the number of siRNAs directed to a particular target using a pool or kit, one is able both to increase the likelihood that at least one siRNA with satisfactory functionality will be included, as well as to benefit from additive or synergistic effects. Further, when two or more siRNAs directed against a single gene do not have satisfactory levels of functionality alone, if combined, they may satisfactorily promote degradation of the target messenger RNA and successfully inhibit translation. By including multiple siRNAs in the system, not only is the probability of silencing increased, but the economics of operation are also improved when compared to adding different siRNAs sequentially. This effect is contrary to the conventional wisdom that the concurrent use of multiple siRNA will negatively impact gene silencing (e.g., Holen, T. et al. (2003) Similar behavior of single strand and double strand siRNAs suggests they act through a common RNAi pathway. *NAR* 31: 2401-21407).

In fact, when two siRNAs were pooled together, 54% of the pools of two siRNAs induced more than 95% gene silencing. Thus, a 2.5-fold increase in the percentage of functionality was achieved by randomly combining two siRNAs. Further, over 84% of pools containing two siRNAs induced more than 80% gene silencing.

More preferably, the kit is comprised of at least three siRNAs, wherein one strand of each siRNA comprises a sequence that is substantially similar to a sequence of the target mRNA and the other strand comprises a sequence that is substantially complementary to the region of the target mRNA. As with the kit that comprises at least two siRNAs, more preferably one strand will comprise a sequence that is identical to a sequence that is contained in the mRNA and another strand that is 100% complementary to a sequence that is contained in the mRNA. During experiments, when three siRNAs were combined together, 60% of the pools induced more than 95% gene silencing and 92% of the pools induced more than 80% gene silencing.

Further, even more preferably, the kit is comprised of at least four siRNAs, wherein one strand of each siRNA comprises a sequence that is substantially similar to a region of the sequence of the target mRNA, and the other strand comprises a sequence that is substantially complementary to the region of the target mRNA. As with the kit or pool that comprises at least two siRNAs, more preferably one strand of each of the siRNA duplexes will comprise a sequence that is identical to a sequence that is contained in the mRNA, and another strand that is 100% complementary to a sequence that is contained in the mRNA.

Additionally, kits and pools with at least five, at least six, and at least seven siRNAs may also be useful with the present invention. For example, pools of five siRNA induced 95% gene silencing with 77% probability and 80% silencing with 98.8% probability. Thus, pooling of siRNAs together can result in the creation of a target-specific silencing reagent with almost a 99% probability of being functional. The fact that such high levels of success are achievable using such pools of siRNA, enables one to dispense with costly and time-consuming target-specific validation procedures.

For this embodiment, as well as the other aforementioned embodiments, each of the siRNAs within a pool will preferably comprise 18-30 base pairs, more preferably 18-25 base pairs, and most preferably 19 base pairs. Within each siRNA, preferably at least 18 contiguous bases of the antisense strand will be 100% complementary to the target mRNA. More preferably, at least 19 contiguous bases of the antisense strand will be 100% complementary to the target mRNA. Additionally, there may be overhangs on either the sense strand or the antisense strand, and these overhangs may be at either the 5' end or the 3' end of either of the strands, for example there may be one or more overhangs of 1-6 bases. When overhangs are present, they are not included in the calculation of the number of base pairs. The two nucleotide 3' overhangs mimic natural siRNAs and are commonly used but are not essential. Preferably, the overhangs should consist of two nucleotides, most often dTdT or UU at the 3' end of the sense and antisense strand that are not complementary to the target sequence. The siRNAs may be produced by any method that is now known or that comes to be known for synthesizing double stranded RNA that one skilled in the art would appreciate would be useful in the present invention. Preferably, the siRNAs will be produced by Dharmacon's proprietary ACE® technology. However, other methods for synthesizing siRNAs are well known to persons skilled in the art and include, but are not limited to, any chemical synthesis of RNA oligonucleotides, ligation of shorter oligonucleotides, in vitro transcription of RNA oligonucleotides, the use of vectors for expression within cells, recombinant Dicer products and PCR products.

The siRNA duplexes within the aforementioned pools of siRNAs may correspond to overlapping sequences within a particular mRNA, or non-overlapping sequences of the mRNA. However, preferably they correspond to non-overlapping sequences. Further, each siRNA may be selected randomly, or one or more of the siRNA may be selected according to the criteria discussed above for maximizing the effectiveness of siRNA.

Included in the definition of siRNAs are siRNAs that contain substituted and/or labeled nucleotides that may, for example, be labeled by radioactivity, fluorescence or mass. The most common substitutions are at the 2' position of the ribose sugar, where moieties such as H (hydrogen) F, $NH_3$, $OCH_3$ and other O— alkyl, alkenyl, alkynyl, and orthoesters, may be substituted, or in the phosphorous backbone, where sulfur, amines or hydrocarbons may be substituted for the bridging of non-bridging atoms in the phosphodiester bond. Examples of modified siRNAs are explained more fully in commonly assigned U.S. patent application Ser. No. 10/613,077, filed Jul. 1, 2003.

Additionally, as noted above, the cell type into which the siRNA is introduced may affect the ability of the siRNA to enter the cell; however, it does not appear to affect the ability of the siRNA to function once it enters the cell. Methods for introducing double-stranded RNA into various cell types are well known to persons skilled in the art.

As persons skilled in the art are aware, in certain species, the presence of proteins such as RdRP, the RNA-dependent RNA polymerase, may catalytically enhance the activity of the siRNA. For example, RdRP propagates the RNAi effect in *C. elegans* and other non-mammalian organisms. In fact, in organisms that contain these proteins, the siRNA may be inherited. Two other proteins that are well studied and known to be a part of the machinery are members of the Argonaute family and Dicer, as well as their homologues. There is also initial evidence that the RISC complex might be associated with the ribosome so the more efficiently translated mRNAs will be more susceptible to silencing than others.

Another very important factor in the efficacy of siRNA is mRNA localization. In general, only cytoplasmic mRNAs are considered to be accessible to RNAi to any appreciable degree. However, appropriately designed siRNAs, for example, siRNAs modified with internucleotide linkages or 2'-O-methyl groups, may be able to cause silencing by acting in the nucleus. Examples of these types of modifications are described in commonly assigned U.S. patent application Ser. Nos. 10/431,027 and 10/613,077.

As described above, even when one selects at least two siRNAs at random, the effectiveness of the two may be greater than one would predict based on the effectiveness of two individual siRNAs. This additive or synergistic effect is particularly noticeable as one increases to at least three siRNAs, and even more noticeable as one moves to at least four siRNAs. Surprisingly, the pooling of the non-functional and semi-functional siRNAs, particularly more than five siRNAs, can lead to a silencing mixture that is as effective if not more effective than any one particular functional siRNA.

Within the kits of the present invention, preferably each siRNA will be present in a concentration of between 0.001 and 200 M, more preferably between 0.01 and 200 nM, and most preferably between 0.1 and 10 nM.

In addition to preferably comprising at least four or five siRNAs, the kits of the present invention will also preferably comprise a buffer to keep the siRNA duplex stable. Persons skilled in the art are aware of buffers suitable for keeping siRNA stable. For example, the buffer may be comprised of 100 mM KCl, 30 mM HEPES-pH 7.5, and 1 mM $MgCl_2$. Alternatively, kits might contain complementary strands that contain any one of a number of chemical modifications (e.g., a 2'-O-ACE) that protect the agents from degradation by nucleases. In this instance, the user may (or may not) remove the modifying protective group (e.g., deprotect) before annealing the two complementary strands together.

By way of example, the kits may be organized such that pools of siRNA duplexes are provided on an array or microarray of wells or drops for a particular gene set or for unrelated genes. The array may, for example, be in 96 wells, 384 wells or 1284 wells arrayed in a plastic plate or on a glass slide using techniques now known or that come to be known to persons skilled in the art. Within an array, preferably there will be controls such as functional anti-lamin A/C, cyclophilin and two siRNA duplexes that are not specific to the gene of interest.

In order to ensure stability of the siRNA pools prior to usage, they may be retained in lyophilized form at minus twenty degrees (−20° C.) until they are ready for use. Prior to usage, they should be resuspended; however, even once resuspended, for example, in the aforementioned buffer, they should be kept at minus twenty degrees, (−20° C.) until used. The aforementioned buffer, prior to use, may be stored at approximately 4° C. or room temperature. Effective temperatures at which to conduct transfections are well known to persons skilled in the art and include for example, room temperature.

The kits may be applied either in vivo or in vitro. Preferably, the siRNA of the pools or kits is applied to a cell through transfection, employing standard transfection protocols. These methods are well known to persons skilled in the art and include the use of lipid-based carriers, electroporation, cationic carriers, and microinjection. Further, one could apply the present invention by synthesizing equivalent DNA sequences (either as two separate, complementary strands, or as hairpin molecules) instead of siRNA sequences and introducing them into cells through vectors. Once in the cells, the cloned DNA could be transcribed, thereby forcing the cells to generate the siRNA. Examples of vectors suitable for use with the present application include but are not limited to the standard transient expression vectors, adenoviruses, retroviruses, lentivirus-based vectors, as well as other traditional expression vectors. Any vector that has an adequate siRNA expression and procession module may be used. Furthermore, certain chemical modifications to siRNAs, including but not limited to conjugations to other molecules, may be used to facilitate delivery. For certain applications it may be preferable to deliver molecules without transfection by simply formulating in a physiological acceptable solution.

This embodiment may be used in connection with any of the aforementioned embodiments. Accordingly, the sequences within any pool may be selected by rational design.

Multigene Silencing

In addition to developing kits that contain multiple siRNA directed against a single gene, another embodiment includes the use of multiple siRNA targeting multiple genes. Multiple genes may be targeted through the use of high- or hyperfunctional siRNA. High- or hyper- functional siRNA that exhibit increased potency, require lower concentrations to induce desired phenotypic (and thus therapeutic) effects. This circumvents RISC saturation. It therefore reasons that if lower concentrations of a single siRNA are needed for knockout or knockdown expression of one gene, then the remaining (uncomplexed) RISC will be free and available to interact with siRNA directed against two, three, four, or more, genes. Thus in this embodiment, the authors describe the use of highly functional or hyper-functional siRNA to knock out three separate genes. More preferably, such reagents could be combined to knockout four distinct genes. Even more preferably, highly functional or hyperfunctional siRNA could be used to knock out five distinct genes. Most preferably, siRNA of this type could be used to knockout or knockdown the expression of six or more genes.

Hyperfunctional siRNA

The term hyperfunctional siRNA (hf-siRNA) describes a subset of the siRNA population that induces RNAi in cells at low- or sub-nanomolar concentrations for extended periods of time. These traits, heightened potency and extended longevity of the RNAi phenotype, are highly attractive from a therapeutic standpoint. Agents having higher potency require lesser amounts of the molecule to achieve the desired physiological response, thus reducing the probability of side effects due to "off-target" interference. In addition to the potential therapeutic benefits associated with hyperfunctional siRNA, hf-siRNA are also desirable from an economic perspective. Hyperfunctional siRNA may cost less on a per-treatment basis, thus reducing overall expenditures to both the manufacturer and the consumer.

Figure 9:
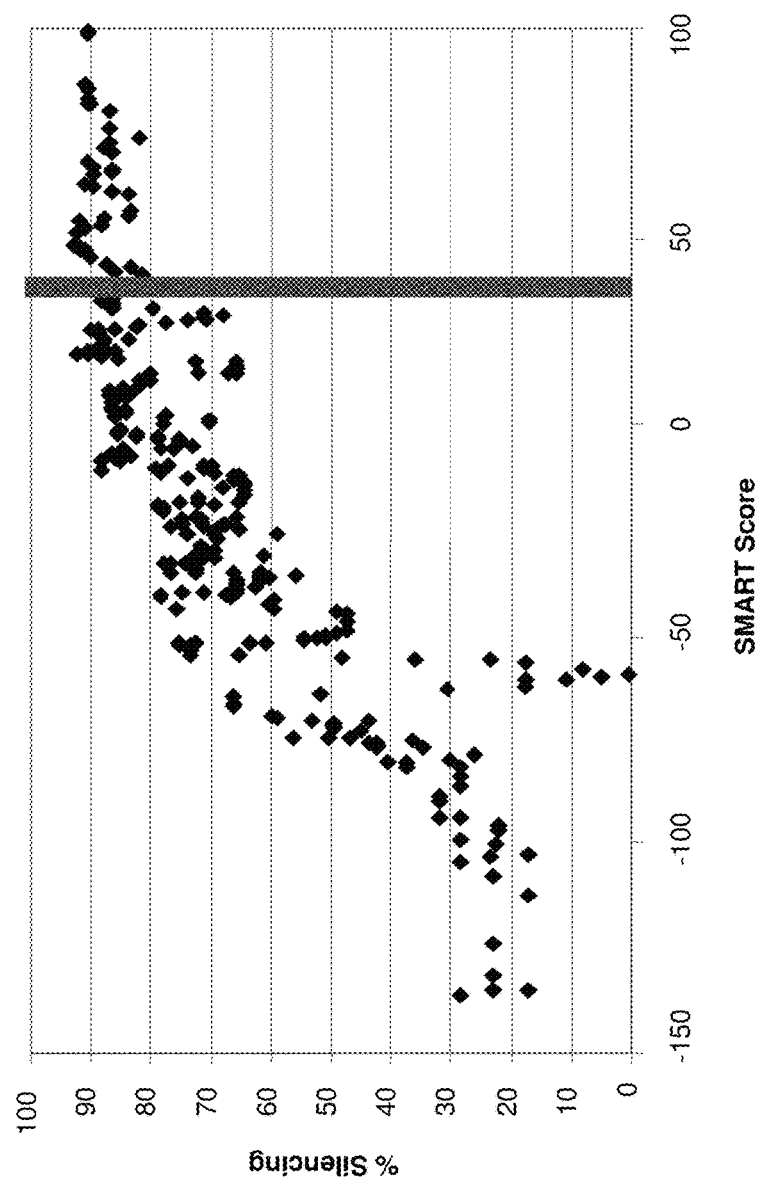
FIG. 9 shows a graph of SMARTSCORE™, or siRNA rank, versus RNAi silencing values for more than 360 siRNA directed against 30 different genes. SiRNA to the right of the vertical bar represent those siRNA that have desirable SMARTSCORES™, or siRNA rank.
Figure 10A:
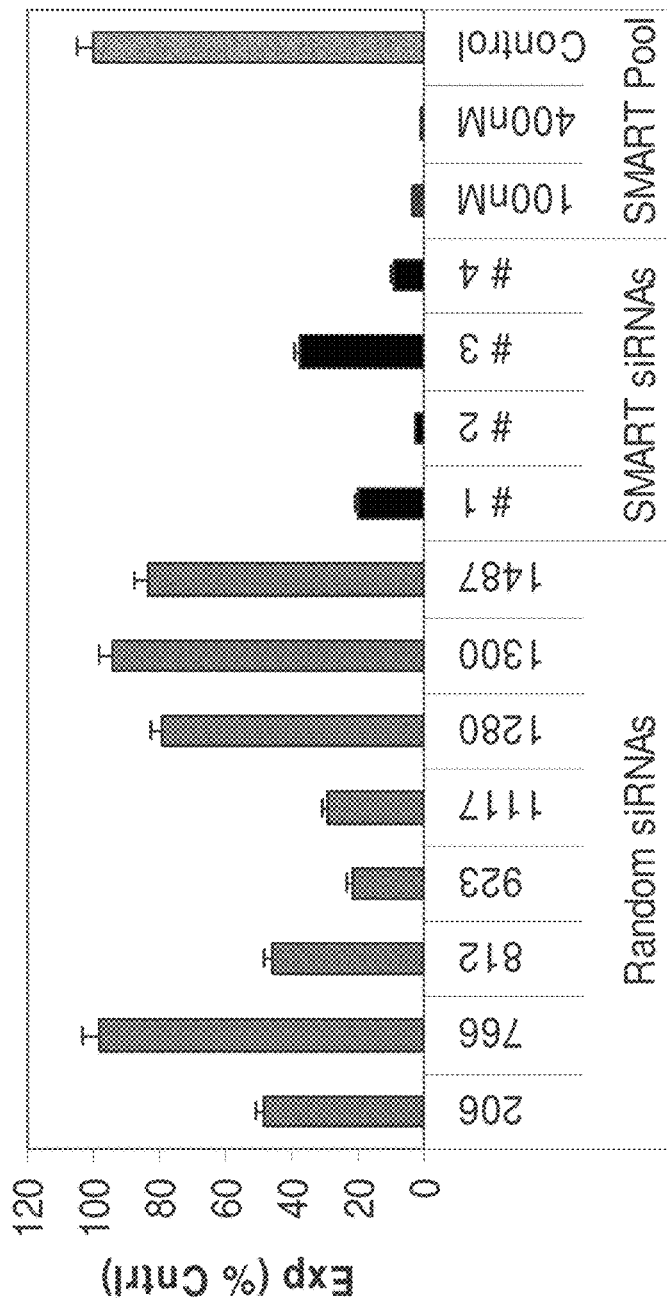
Figure 10C:
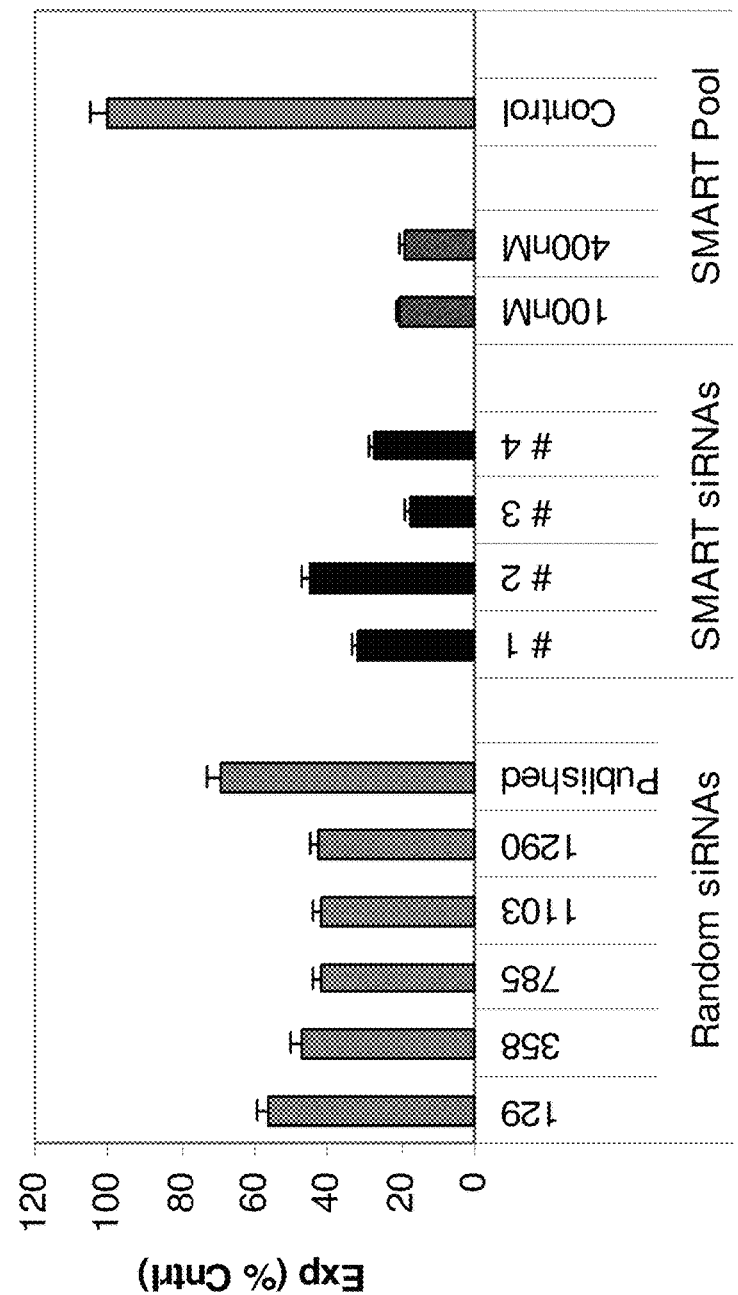
Figure 10D:
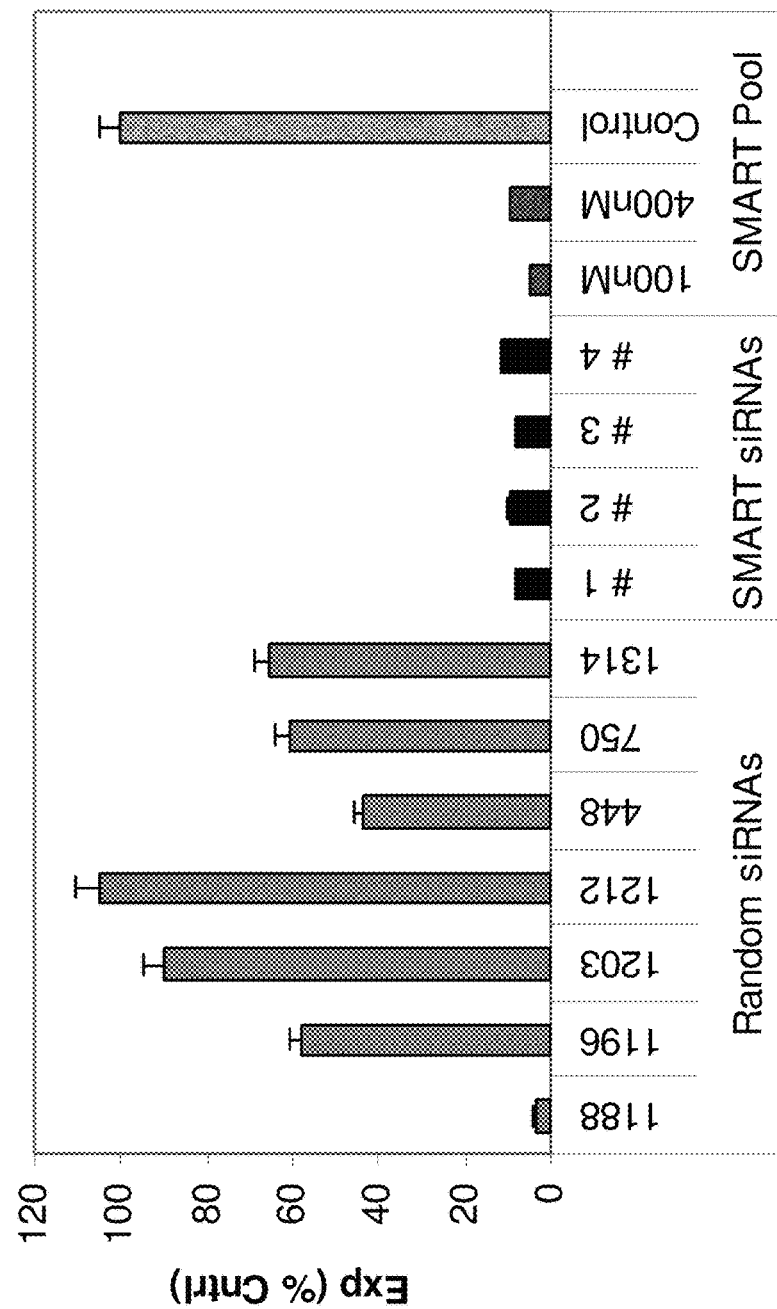
Figure 10E:
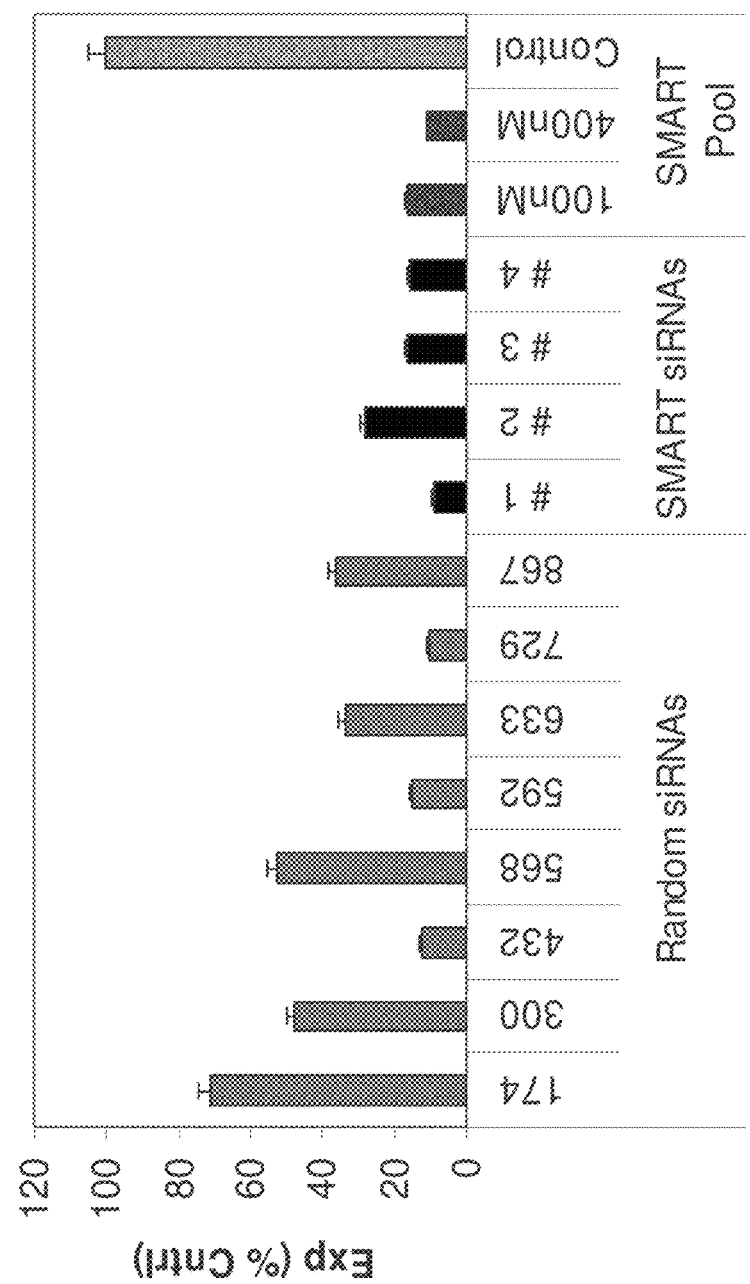

Identification of hyperfunctional siRNA involves multiple steps that are designed to examine an individual siRNA agent's concentration- and/or longevity-profiles. In one non-limiting example, a population of siRNA directed against a single gene are first analyzed using the previously described algorithm (Formula VIII). Individual siRNA are then introduced into a test cell line and assessed for the ability to degrade the target mRNA. It is important to note that when performing this step it is not necessary to test all of the siRNA. Instead, it is sufficient to test only those siRNA having the highest SMARTSCORES™, or siRNA ranking (i.e., SMARTSCORES™, or siRNA ranking >−10). Subsequently, the gene silencing data is plotted against the SMARTSCORES™, or siRNA rankings (see FIG. 9). siRNA that (1) induce a high degree of gene silencing (i.e., they induce greater than 80% gene knockdown) and (2) have superior SMARTSCORES™ (i.e., a SMARTSCORE™, or siRNA ranking, of >−10, suggesting a desirable average internal stability profile) are selected for further investigations designed to better understand the molecule's potency and longevity. In one, non-limiting study dedicated to understanding a molecule's potency, an siRNA is introduced into one (or more) cell types in increasingly diminishing concentrations (e.g., 3.0 0.3 nM). Subsequently, the level of gene silencing induced by each concentration is examined and siRNA that exhibit hyperfunctional potency (i.e., those that induce 80% silencing or greater at, e.g., picomolar concentrations) are identified. In a second study, the longevity profiles of siRNA having high (>−10) SMARTSCORES™, or siRNA rankings and greater than 80% silencing are examined. In one non-limiting example of how this is achieved, siRNA are introduced into a test cell line and the levels of RNAi are measured over an extended period of time (e.g., 24-168 hrs). siRNAs that exhibit strong RNA interference patterns (i.e., >80% interference) for periods of time greater than, e.g., 120 hours, are thus identified. Studies similar to those described above can be performed on any and all of the >$10^6$ siRNA included in this document to further define the most functional molecule for any given gene. Molecules possessing one or both properties (extended longevity and heightened potency) are labeled "hyperfunctional siRNA," and earmarked as candidates for future therapeutic studies.

While the example(s) given above describe one means by which hyperfunctional siRNA can be isolated, neither the assays themselves nor the selection parameters used are rigid and can vary with each family of siRNA. Families of siRNA include siRNAs directed against a single gene, or directed against a related family of genes.

The highest quality siRNA achievable for any given gene may vary considerably. Thus, for example, in the case of one gene (gene X), rigorous studies such as those described above may enable the identification of an siRNA that, at picomolar concentrations, induces 99$^+$% silencing for a period of 10 days. Yet identical studies of a second gene (gene Y) may yield an siRNA that at high nanomolar concentrations (e.g., 100 nM) induces only 75% silencing for a period of 2 days. Both molecules represent the very optimum siRNA for their respective gene targets and therefore are designated "hyperfunctional." Yet due to a variety of factors including but not limited to target concentration, siRNA stability, cell type, off-target interference, and others, equivalent levels of potency and longevity are not achievable. Thus, for these reasons, the parameters described in the before mentioned assays can vary. While the initial screen selected siRNA that had SMARTSCORES™ above—and a gene silencing capability of greater than 80%, selections that have stronger (or weaker) parameters can be implemented. Similarly, in the subsequent studies designed to identify molecules with high potency and longevity, the desired cutoff criteria (i.e., the lowest concentration that induces a desirable level of interference, or the longest period of time that interference can be observed) can vary. The experimentation subsequent to application of the rational criteria of this application is significantly reduced where one is trying to obtain a suitable hyperfunctional siRNA for, for example, therapeutic use. When, for example, the additional experimentation of the type described herein is applied by one skilled in the art with this disclosure in hand, a hyperfunctional siRNA is readily identified.

The siRNA may be introduced into a cell by any method that is now known or that comes to be known and that from reading this disclosure, persons skilled in the art would determine would be useful in connection with the present invention in enabling siRNA to cross the cellular membrane. These methods include, but are not limited to, any manner of transfection, such as, for example, transfection employing DEAE-Dextran, calcium phosphate, cationic lipids/liposomes, micelles, manipulation of pressure, microinjection, electroporation, immunoporation, use of vectors such as viruses, plasmids, cosmids, bacteriophages, cell fusions, and coupling of the polynucleotides to specific conjugates or ligands such as antibodies, antigens, or receptors, passive introduction, adding moieties to the siRNA that facilitate its uptake, and the like.

Having described the invention with a degree of particularity, examples will now be provided. These examples are not intended to and should not be construed to limit the scope of the claims in any way.

EXAMPLES

General Techniques and Nomenclatures siRNA nomenclature. All siRNA duplexes are referred to by sense strand. The first nucleotide of the 5'-end of the sense strand is position 1, which corresponds to position 19 of the antisense strand for a 19-mer. In most cases, to compare results from different experiments, silencing was determined by measuring specific transcript mRNA levels or enzymatic activity associated with specific transcript levels, 24 hours post-transfection, with siRNA concentrations held constant at 100 nM. For all experiments, unless otherwise specified, transfection efficiency was ensured to be over 95%, and no detectable cellular toxicity was observed. The following system of nomenclature was used to compare and report siRNA-silencing functionality: "F" followed by the degree of minimal knockdown. For example, F50 signifies at least 50% knockdown, F80 means at least 80%, and so forth. For this study, all sub-F50 siRNAs were considered non-functional.

Cell culture and transfection. 96-well plates are coated with 50 1 of 50 mg/ml poly-L-lysine (Sigma) for 1 hr, and then washed 3× with distilled water before being dried for 20 min. HEK293 cells or HEK293Lucs or any other cell type of interest are released from their solid support by trypsinization, diluted to 3.5×$10^5$ cells/ml, followed by the addition of 100 L of cells/well. Plates are then incubated overnight at 37° C., 5% $CO_2$. Transfection procedures can vary widely depending on the cell type and transfection reagents. In one non-limiting example, a transfection mixture consisting of 2 mL Opti-MEM I (Gibco-BRL), 80 1 Lipofectamine 2000 (Invitrogen), 15 L SUPERNasin at 20 U/1 (Ambion), and 1.5 1 of reporter gene plasmid at 1 g/1 is prepared in 5-ml polystyrene round bottom tubes. One hundred 1 of transfection reagent is then combined with 100 1 of siRNAs in polystyrene deep-well titer plates (Beckman) and incubated for 20 to 30 min at room temperature. Five hundred and fifty microliters of Opti-MEM is then added to each well to bring the final siRNA concentration to 100 nM. Plates are then sealed with parafilm and mixed. Media is removed from HEK293 cells and replaced with 95 1 of transfection mixture. Cells are incubated overnight at 37° C., 5% $CO_2$.

Quantification of gene knockdown. A variety of quantification procedures can be used to measure the level of silencing induced by siRNA or siRNA pools. In one non-limiting example: to measure mRNA levels 24 hrs post-transfection, QuantiGene branched-DNA (bDNA) kits (Bayer) (Wang, et al, *Regulation of insulin preRNA splicing by glucose*. Proc. Natl. Acad. Sci. USA 1997, 94:4360.) are used according to manufacturer instructions. To measure luciferase activity, media is removed from HEK293 cells 24 hrs post-transfection, and 50 1 of Steady-GLO reagent (Promega) is added. After 5 minutes, plates are analyzed on a plate reader.

Example I

Sequences Used to Develop the Algorithm

Anti-Firefly and anti-Cyclophilin siRNAs panels (FIG. 5a, b) sorted according to using Formula VIII predicted values. All siRNAs scoring more than 0 (formula VIII) and more then 20 (formula IX) are fully functional. All ninety sequences for each gene (and DBI) appear below in Table IV.

TABLE IV

| | | | | |
|---|---|---|---|---|
| Cyclo | 1 | SEQ. ID NO: | 0032 | GUUCCAAAAACAGUGGAUA |
| Cyclo | 2 | SEQ. ID NO: | 0033 | UCCAAAAACAGUGGAUAAU |
| Cyclo | 3 | SEQ. ID NO: | 0034 | CAAAAACAGUGGAUAAUUU |
| Cyclo | 4 | SEQ. ID NO: | 0035 | AAAACAGUGGAUAAUUUUG |
| Cyclo | 5 | SEQ. ID NO: | 0036 | AACAGUGGAUAAUUUUGUG |
| Cyclo | 6 | SEQ. ID NO: | 0037 | CAGUGGAUAAUUUUGUGGC |
| Cyclo | 7 | SEQ. ID NO: | 0038 | GUGGAUAAUUUUGUGGCCU |
| Cyclo | 8 | SEQ. ID NO: | 0039 | GGAUAAUUUUGUGGCCUUA |
| Cyclo | 9 | SEQ. ID NO: | 0040 | AUAAUUUUGUGGCCUUAGC |
| Cyclo | 10 | SEQ. ID NO: | 0041 | AAUUUUGUGGCCUUAGCUA |
| Cyclo | 11 | SEQ. ID NO: | 0042 | UUUUGUGGCCUUAGCUACA |
| Cyclo | 12 | SEQ. ID NO: | 0043 | UUGUGGCCUUAGCUACAGG |
| Cyclo | 13 | SEQ. ID NO: | 0044 | GUGGCCUUAGCUACAGGAG |
| Cyclo | 14 | SEQ. ID NO: | 0045 | GGCCUUAGCUACAGGAGAG |
| Cyclo | 15 | SEQ. ID NO: | 0046 | CCUUAGCUACAGGAGAGAA |
| Cyclo | 16 | SEQ. ID NO: | 0047 | UUAGCUACAGGAGAGAAAG |
| Cyclo | 17 | SEQ. ID NO: | 0048 | AGCUACAGGAGAGAAAGGA |
| Cyclo | 18 | SEQ. ID NO: | 0049 | CUACAGGAGAGAAAGGAUU |
| Cyclo | 19 | SEQ. ID NO: | 0050 | ACAGGAGAGAAAGGAUUUG |
| Cyclo | 20 | SEQ. ID NO: | 0051 | AGGAGAGAAAGGAUUUGGC |
| Cyclo | 21 | SEQ. ID NO: | 0052 | GAGAGAAAGGAUUUGGCUA |
| Cyclo | 22 | SEQ. ID NO: | 0053 | GAGAAAGGAUUUGGCUACA |
| Cyclo | 23 | SEQ. ID NO: | 0054 | GAAAGGAUUUGGCUACAAA |
| Cyclo | 24 | SEQ. ID NO: | 0055 | AAGGAUUUGGCUACAAAAA |
| Cyclo | 25 | SEQ. ID NO: | 0056 | GGAUUUGGCUACAAAAACA |
| Cyclo | 26 | SEQ. ID NO: | 0057 | AUUUGGCUACAAAAACAGC |
| Cyclo | 27 | SEQ. ID NO: | 0058 | UUGGCUACAAAAACAGCAA |
| Cyclo | 28 | SEQ. ID NO: | 0059 | GGCUACAAAAACAGCAAAU |
| Cyclo | 29 | SEQ. ID NO: | 0060 | CUACAAAAACAGCAAAUUC |
| Cyclo | 30 | SEQ. ID NO: | 0061 | ACAAAAACAGCAAAUUCCA |

TABLE IV-continued

| | | | | |
|---|---|---|---|---|
| Cyclo | 31 | SEQ. ID NO: | 0062 | AAAAACAGCAAAUUCCAUC |
| Cyclo | 32 | SEQ. ID NO: | 0063 | AAACAGCAAAUUCCAUCGU |
| Cyclo | 33 | SEQ. ID NO: | 0064 | ACAGCAAAUUCCAUCGUGU |
| Cyclo | 34 | SEQ. ID NO: | 0065 | AGCAAAUUCCAUCGUGUAA |
| Cyclo | 35 | SEQ. ID NO: | 0066 | CAAAUUCCAUCGUGUAAUC |
| Cyclo | 36 | SEQ. ID NO: | 0067 | AAUUCCAUCGUGUAAUCAA |
| Cyclo | 37 | SEQ. ID NO: | 0068 | UUCCAUCGUGUAAUCAAGG |
| Cyclo | 38 | SEQ. ID NO: | 0069 | CCAUCGUGUAAUCAAGGAC |
| Cyclo | 39 | SEQ. ID NO: | 0070 | AUCGUGUAAUCAAGGACUU |
| Cyclo | 40 | SEQ. ID NO: | 0071 | CGUGUAAUCAAGGACUUCA |
| Cyclo | 41 | SEQ. ID NO: | 0072 | UGUAAUCAAGGACUUCAUG |
| Cyclo | 42 | SEQ. ID NO: | 0073 | UAAUCAAGGACUUCAUGAU |
| Cyclo | 43 | SEQ. ID NO: | 0074 | AUCAAGGACUUCAUGAUCC |
| Cyclo | 44 | SEQ. ID NO: | 0075 | CAAGGACUUCAUGAUCCAG |
| Cyclo | 45 | SEQ. ID NO: | 0076 | AGGACUUCAUGAUCCAGGG |
| Cyclo | 46 | SEQ. ID NO: | 0077 | GACUUCAUGAUCCAGGGCG |
| Cyclo | 47 | SEQ. ID NO: | 0078 | CUUCAUGAUCCAGGGCGGA |
| Cyclo | 48 | SEQ. ID NO: | 0079 | UCAUGAUCCAGGGCGGAGA |
| Cyclo | 49 | SEQ. ID NO: | 0080 | AUGAUCCAGGGCGGAGACU |
| Cyclo | 50 | SEQ. ID NO: | 0081 | GAUCCAGGGCGGAGACUUC |
| Cyclo | 51 | SEQ. ID NO: | 0082 | UCCAGGGCGGAGACUUCAC |
| Cyclo | 52 | SEQ. ID NO: | 0083 | CAGGGCGGAGACUUCACCA |
| Cyclo | 53 | SEQ. ID NO: | 0084 | GGGCGGAGACUUCACCAGG |
| Cyclo | 54 | SEQ. ID NO: | 0085 | GCGGAGACUUCACCAGGGG |
| Cyclo | 55 | SEQ. ID NO: | 0086 | GGAGACUUCACCAGGGGAG |
| Cyclo | 56 | SEQ. ID NO: | 0087 | AGACUUCACCAGGGGAGAU |
| Cyclo | 57 | SEQ. ID NO: | 0088 | ACUUCACCAGGGGAGAUGG |
| Cyclo | 58 | SEQ. ID NO: | 0089 | UUCACCAGGGGAGAUGGCA |
| Cyclo | 59 | SEQ. ID NO: | 0090 | CACCAGGGGAGAUGGCACA |
| Cyclo | 60 | SEQ. ID NO: | 0091 | CCAGGGGAGAUGGCACAGG |
| Cyclo | 61 | SEQ. ID NO: | 0092 | AGGGGAGAUGGCACAGGAG |
| Cyclo | 62 | SEQ. ID NO: | 0093 | GGGAGAUGGCACAGGAGGA |
| Cyclo | 63 | SEQ. ID NO: | 0427 | GAGAUGGCACAGGAGGAAA |
| Cyclo | 64 | SEQ. ID NO: | 0095 | GAUGGCACAGGAGGAAAGA |
| Cyclo | 65 | SEQ. ID NO: | 0094 | UGGCACAGGAGGAAAGAGC |
| Cyclo | 66 | SEQ. ID NO: | 0096 | GCACAGGAGGAAAGAGCAU |
| Cyclo | 67 | SEQ. ID NO: | 0097 | ACAGGAGGAAAGAGCAUCU |
| Cyclo | 68 | SEQ. ID NO: | 0098 | AGGAGGAAAGAGCAUCUAC |
| Cyclo | 69 | SEQ. ID NO: | 0099 | GAGGAAAGAGCAUCUACGG |
| Cyclo | 70 | SEQ. ID NO: | 0100 | GGAAAGAGCAUCUACGGUG |

TABLE IV-continued

| | | | |
|---|---|---|---|
| Cyclo | 71 | SEQ. ID NO: 0101 | AAAGAGCAUCUACGGUGAG |
| Cyclo | 72 | SEQ. ID NO: 0102 | AGAGCAUCUACGGUGAGCG |
| Cyclo | 73 | SEQ. ID NO: 0103 | AGCAUCUACGGUGAGCGCU |
| Cyclo | 74 | SEQ. ID NO: 0104 | CAUCUACGGUGAGCGCUUC |
| Cyclo | 75 | SEQ. ID NO: 0105 | UCUACGGUGAGCGCUUCCC |
| Cyclo | 76 | SEQ. ID NO: 0106 | UACGGUGAGCGCUUCCCCG |
| Cyclo | 77 | SEQ. ID NO: 0107 | CGGUGAGCGCUUCCCCGAU |
| Cyclo | 78 | SEQ. ID NO: 0108 | GUGAGCGCUUCCCCGAUGA |
| Cyclo | 79 | SEQ. ID NO: 0109 | GAGCGCUUCCCCGAUGAGA |
| Cyclo | 80 | SEQ. ID NO: 0110 | GCGCUUCCCCGAUGAGAAC |
| Cyclo | 81 | SEQ. ID NO: 0111 | GCUUCCCCGAUGAGAACUU |
| Cyclo | 82 | SEQ. ID NO: 0112 | UUCCCCGAUGAGAACUUCA |
| Cyclo | 83 | SEQ. ID NO: 0113 | CCCCGAUGAGAACUUCAAA |
| Cyclo | 84 | SEQ. ID NO: 0114 | CCGAUGAGAACUUCAAACU |
| Cyclo | 85 | SEQ. ID NO: 0115 | GAUGAGAACUUCAAACUGA |
| Cyclo | 86 | SEQ. ID NO: 0116 | UGAGAACUUCAAACUGAAG |
| Cyclo | 87 | SEQ. ID NO: 0117 | AGAACUUCAAACUGAAGCA |
| Cyclo | 88 | SEQ. ID NO: 0118 | AACUUCAAACUGAAGCACU |
| Cyclo | 89 | SEQ. ID NO: 0119 | CUUCAAACUGAAGCACUAC |
| Cyclo | 90 | SEQ. ID NO: 0120 | UCAAACUGAAGCACUACGG |
| DB | 1 | SEQ. ID NO: 0121 | ACGGGCAAGGCCAAGUGGG |
| DB | 2 | SEQ. ID NO: 0122 | CGGGCAAGGCCAAGUGGGA |
| DB | 3 | SEQ. ID NO: 0123 | GGGCAAGGCCAAGUGGGAU |
| DB | 9 | SEQ. ID NO: 0124 | GGCAAGGCCAAGUGGGAUG |
| DB | 5 | SEQ. ID NO: 0125 | GCAAGGCCAAGUGGGAUGC |
| DB | 6 | SEQ. ID NO: 0126 | CAAGGCCAAGUGGGAUGCC |
| DB | 7 | SEQ. ID NO: 0127 | AAGGCCAAGUGGGAUGCCU |
| DB | 8 | SEQ. ID NO: 0128 | AGGCCAAGUGGGAUGCCUG |
| DB | 9 | SEQ. ID NO: 0129 | GGCCAAGUGGGAUGCCUGG |
| DB | 10 | SEQ. ID NO: 0130 | GCCAAGUGGGAUGCCUGGA |
| DB | 11 | SEQ. ID NO: 0131 | CCAAGUGGGAUGCCUGGAA |
| DB | 12 | SEQ. ID NO: 0132 | CAAGUGGGAUGCCUGGAAU |
| DB | 13 | SEQ. ID NO: 0133 | AAGUGGGAUGCCUGGAAUG |
| DB | 14 | SEQ. ID NO: 0134 | AGUGGGAUGCCUGGAAUGA |
| DB | 15 | SEQ. ID NO: 0135 | GUGGGAUGCCUGGAAUGAG |
| DB | 16 | SEQ. ID NO: 0136 | UGGGAUGCCUGGAAUGAGC |
| DB | 17 | SEQ. ID NO: 0137 | GGGAUGCCUGGAAUGAGCU |
| DB | 18 | SEQ. ID NO: 0138 | GGAUGCCUGGAAUGAGCUG |
| DB | 19 | SEQ. ID NO: 0139 | GAUGCCUGGAAUGAGCUGA |
| DB | 20 | SEQ. ID NO: 0140 | AUGCCUGGAAUGAGCUGAA |
| DB | 21 | SEQ. ID NO: 0141 | UGCCUGGAAUGAGCUGAAA |
| DB | 22 | SEQ. ID NO: 0142 | GCCUGGAAUGAGCUGAAAG |
| DB | 23 | SEQ. ID NO: 0143 | CCUGGAAUGAGCUGAAAGG |
| DB | 24 | SEQ. ID NO: 0144 | CUGGAAUGAGCUGAAAGGG |
| DB | 25 | SEQ. ID NO: 0145 | UGGAAUGAGCUGAAAGGGA |
| DB | 26 | SEQ. ID NO: 0146 | GGAAUGAGCUGAAAGGGAC |
| DB | 27 | SEQ. ID NO: 0147 | GAAUGAGCUGAAAGGGACU |
| DB | 28 | SEQ. ID NO: 0148 | AAUGAGCUGAAAGGGACUU |
| DB | 29 | SEQ. ID NO: 0149 | AUGAGCUGAAAGGGACUUC |
| DB | 30 | SEQ. ID NO: 0150 | UGAGCUGAAAGGGACUUCC |
| DB | 31 | SEQ. ID NO: 0151 | GAGCUGAAAGGGACUUCCA |
| DB | 32 | SEQ. ID NO: 0152 | AGCUGAAAGGGACUUCCAA |
| DB | 33 | SEQ. ID NO: 0153 | GCUGAAAGGGACUUCCAAG |
| DB | 34 | SEQ. ID NO: 0154 | CUGAAAGGGACUUCCAAGG |
| DB | 35 | SEQ. ID NO: 0155 | UGAAAGGGACUUCCAAGGA |
| DB | 36 | SEQ. ID NO: 0156 | GAAAGGGACUUCCAAGGAA |
| DB | 37 | SEQ. ID NO: 0157 | AAAGGGACUUCCAAGGAAG |
| DB | 38 | SEQ. ID NO: 0158 | AAGGGACUUCCAAGGAAGA |
| DB | 39 | SEQ. ID NO: 0159 | AGGGACUUCCAAGGAAGAU |
| DB | 40 | SEQ. ID NO: 0160 | GGGACUUCCAAGGAAGAUG |
| DB | 41 | SEQ. ID NO: 0161 | GGACUUCCAAGGAAGAUGC |
| DB | 42 | SEQ. ID NO: 0162 | GACUUCCAAGGAAGAUGCC |
| DB | 43 | SEQ. ID NO: 0163 | ACUUCCAAGGAAGAUGCCA |
| DB | 44 | SEQ. ID NO: 0164 | CUUCCAAGGAAGAUGCCAU |
| DB | 45 | SEQ. ID NO: 0165 | UUCCAAGGAAGAUGCCAUG |
| DB | 46 | SEQ. ID NO: 0166 | UCCAAGGAAGAUGCCAUGA |
| DB | 47 | SEQ. ID NO: 0167 | CCAAGGAAGAUGCCAUGAA |
| DB | 48 | SEQ. ID NO: 0168 | CAAGGAAGAUGCCAUGAAA |
| DB | 49 | SEQ. ID NO: 0169 | AAGGAAGAUGCCAUGAAAG |
| DB | 50 | SEQ. ID NO: 0170 | AGGAAGAUGCCAUGAAAGC |
| DB | 51 | SEQ. ID NO: 0171 | GGAAGAUGCCAUGAAAGCU |
| DB | 52 | SEQ. ID NO: 0172 | GAAGAUGCCAUGAAAGCUU |
| DB | 53 | SEQ. ID NO: 0173 | AAGAUGCCAUGAAAGCUUA |
| DB | 54 | SEQ. ID NO: 0174 | AGAUGCCAUGAAAGCUUAC |
| DB | 55 | SEQ. ID NO: 0175 | GAUGCCAUGAAAGCUUACA |
| DB | 56 | SEQ. ID NO: 0176 | AUGCCAUGAAAGCUUACAU |
| DB | 57 | SEQ. ID NO: 0177 | UGCCAUGAAAGCUUACAUC |
| DB | 58 | SEQ. ID NO: 0178 | GCCAUGAAAGCUUACAUCA |
| DB | 59 | SEQ. ID NO: 0179 | CCAUGAAAGCUUACAUCAA |
| DB | 60 | SEQ. ID NO: 0180 | CAUGAAAGCUUACAUCAAC |

TABLE IV-continued

| | | | |
|---|---|---|---|
| DB | 61 | SEQ. ID NO: 0181 | AUGAAAGCUUACAUCAACA |
| DB | 62 | SEQ. ID NO: 0182 | UGAAAGCUUACAUCAACAA |
| DB | 63 | SEQ. ID NO: 0183 | GAAAGCUUACAUCAACAAA |
| DB | 64 | SEQ. ID NO: 0184 | AAAGCUUACAUCAACAAAG |
| DB | 65 | SEQ. ID NO: 0185 | AAGCUUACAUCAACAAAGU |
| DB | 66 | SEQ. ID NO: 0186 | AGCUUACAUCAACAAAGUA |
| DB | 67 | SEQ. ID NO: 0187 | GCUUACAUCAACAAAGUAG |
| DB | 68 | SEQ. ID NO: 0188 | CUUACAUCAACAAAGUAGA |
| DB | 69 | SEQ. ID NO: 0189 | UUACAUCAACAAAGUAGAA |
| DB | 70 | SEQ. ID NO: 0190 | UACAUCAACAAAGUAGAAG |
| DB | 71 | SEQ. ID NO: 0191 | ACAUCAACAAAGUAGAAGA |
| DB | 72 | SEQ. ID NO: 0192 | CAUCAACAAAGUAGAAGAG |
| DB | 73 | SEQ. ID NO: 0193 | AUCAACAAAGUAGAAGAGC |
| DB | 74 | SEQ. ID NO: 0194 | UCAACAAAGUAGAAGAGCU |
| DB | 75 | SEQ. ID NO: 0195 | CAACAAAGUAGAAGAGCUA |
| DB | 76 | SEQ. ID NO: 0196 | AACAAAGUAGAAGAGCUAA |
| DB | 77 | SEQ. ID NO: 0197 | ACAAAGUAGAAGAGCUAAA |
| DB | 78 | SEQ. ID NO: 0198 | CAAAGUAGAAGAGCUAAAG |
| DB | 79 | SEQ. ID NO: 0199 | AAAGUAGAAGAGCUAAAGA |
| DB | 80 | SEQ. ID NO: 0200 | AAGUAGAAGAGCUAAAGAA |
| DB | 81 | SEQ. ID NO: 0201 | AGUAGAAGAGCUAAAGAAA |
| DB | 82 | SEQ. ID NO: 0202 | GUAGAAGAGCUAAAGAAAA |
| DB | 83 | SEQ. ID NO: 0203 | UAGAAGAGCUAAAGAAAAA |
| DB | 84 | SEQ. ID NO: 0204 | AGAAGAGCUAAAGAAAAAA |
| DB | 85 | SEQ. ID NO: 0205 | GAAGAGCUAAAGAAAAAU |
| DB | 86 | SEQ. ID NO: 0206 | AAGAGCUAAAGAAAAAUA |
| DB | 87 | SEQ. ID NO: 0207 | AGAGCUAAAGAAAAAUAC |
| DB | 88 | SEQ. ID NO: 0208 | GAGCUAAAGAAAAAUACG |
| DB | 89 | SEQ. ID NO: 0209 | AGCUAAAGAAAAAUACGG |
| DB | 90 | SEQ. ID NO: 0210 | GCUAAAGAAAAAUACGGG |
| Luc | 1 | SEQ. ID NO: 0211 | AUCCUCAUAAAGGCCAAGA |
| Luc | 2 | SEQ. ID NO: 0212 | AGAUCCUCAUAAAGGCCAA |
| Luc | 3 | SEQ. ID NO: 0213 | AGAGAUCCUCAUAAAGGCC |
| Luc | 4 | SEQ. ID NO: 0214 | AGAGAGAUCCUCAUAAAGG |
| Luc | 5 | SEQ. ID NO: 0215 | UCAGAGAGAUCCUCAUAAA |
| Luc | 6 | SEQ. ID NO: 0216 | AAUCAGAGAGAUCCUCAUA |
| Luc | 7 | SEQ. ID NO: 0217 | AAAAUCAGAGAGAUCCUCA |
| Luc | 8 | SEQ. ID NO: 0218 | GAAAAAUCAGAGAGAUCCU |
| Luc | 9 | SEQ. ID NO: 0219 | AAGAAAAAUCAGAGAGAUC |
| Luc | 10 | SEQ. ID NO: 0220 | GCAAGAAAAAUCAGAGAGA |
| Luc | 11 | SEQ. ID NO: 0221 | ACGCAAGAAAAAUCAGAGA |
| Luc | 12 | SEQ. ID NO: 0222 | CGACGCAAGAAAAAUCAGA |
| Luc | 13 | SEQ. ID NO: 0223 | CUCGACGCAAGAAAAAUCA |
| Luc | 14 | SEQ. ID NO: 0224 | AACUCGACGCAAGAAAAAU |
| Luc | 15 | SEQ. ID NO: 0225 | AAAACUCGACGCAAGAAAA |
| Luc | 16 | SEQ. ID NO: 0226 | GGAAAACUCGACGCAAGAA |
| Luc | 17 | SEQ. ID NO: 0227 | CCGGAAAACUCGACGCAAG |
| Luc | 18 | SEQ. ID NO: 0228 | UACCGGAAAACUCGACGCA |
| Luc | 19 | SEQ. ID NO: 0229 | CUUACCGGAAAACUCGACG |
| Luc | 20 | SEQ. ID NO: 0230 | GUCUUACCGGAAAACUCGA |
| Luc | 21 | SEQ. ID NO: 0231 | AGGUCUUACCGGAAAACUC |
| Luc | 22 | SEQ. ID NO: 0232 | AAAGGUCUUACCGGAAAAC |
| Luc | 23 | SEQ. ID NO: 0233 | CGAAAGGUCUUACCGGAAA |
| Luc | 24 | SEQ. ID NO: 0234 | ACCGAAAGGUCUUACCGGA |
| Luc | 25 | SEQ. ID NO: 0235 | GUACCGAAAGGUCUUACCG |
| Luc | 26 | SEQ. ID NO: 0236 | AAGUACCGAAAGGUCUUAC |
| Luc | 27 | SEQ. ID NO: 0237 | CGAAGUACCGAAAGGUCUU |
| Luc | 28 | SEQ. ID NO: 0238 | GACGAAGUACCGAAAGGUC |
| Luc | 29 | SEQ. ID NO: 0239 | UGGACGAAGUACCGAAAGG |
| Luc | 30 | SEQ. ID NO: 0240 | UGUGGACGAAGUACCGAAA |
| Luc | 31 | SEQ. ID NO: 0241 | UUUGUGGACGAAGUACCGA |
| Luc | 32 | SEQ. ID NO: 0242 | UGUUUGUGGACGAAGUACC |
| Luc | 33 | SEQ. ID NO: 0243 | UGUGUUUGUGGACGAAGUA |
| Luc | 34 | SEQ. ID NO: 0244 | GUUGUGUUUGUGGACGAAG |
| Luc | 35 | SEQ. ID NO: 0245 | GAGUUGUGUUUGUGGACGA |
| Luc | 36 | SEQ. ID NO: 0246 | AGGAGUUGUGUUUGUGGAC |
| Luc | 37 | SEQ. ID NO: 0247 | GGAGGAGUUGUGUUUGUGG |
| Luc | 38 | SEQ. ID NO: 0248 | GCGGAGGAGUUGUGUUUGU |
| Luc | 39 | SEQ. ID NO: 0249 | GCGCGGAGGAGUUGUGUUU |
| Luc | 40 | SEQ. ID NO: 0250 | UUGCGCGGAGGAGUUGUGU |
| Luc | 41 | SEQ. ID NO: 0251 | AGUUGCGCGGAGGAGUUGU |
| Luc | 42 | SEQ. ID NO: 0252 | AAAGUUGCGCGGAGGAGUU |
| Luc | 43 | SEQ. ID NO: 0253 | AAAAGUUGCGCGGAGGAG |
| Luc | 44 | SEQ. ID NO: 0254 | CGAAAAGUUGCGCGGAGG |
| Luc | 45 | SEQ. ID NO: 0255 | CGCGAAAAGUUGCGCGGA |
| Luc | 46 | SEQ. ID NO: 0256 | ACCGCGAAAAGUUGCGCG |
| Luc | 47 | SEQ. ID NO: 0257 | CAACCGCGAAAAGUUGCG |
| Luc | 48 | SEQ. ID NO: 0258 | AACAACCGCGAAAAGUUG |
| Luc | 49 | SEQ. ID NO: 0259 | GUAACAACCGCGAAAAGU |
| Luc | 50 | SEQ. ID NO: 0260 | AAGUAACAACCGCGAAAAA |

TABLE IV-continued

| | | | | |
|---|---|---|---|---|
| Luc | 51 | SEQ. ID NO: 0261 | UCAAGUAACAACCGCGAAA |
| Luc | 52 | SEQ. ID NO: 0262 | AGUCAAGUAACAACCGCGA |
| Luc | 53 | SEQ. ID NO: 0263 | CCAGUCAAGUAACAACCGC |
| Luc | 54 | SEQ. ID NO: 0264 | CGCCAGUCAAGUAACAACC |
| Luc | 55 | SEQ. ID NO: 0265 | GUCGCCAGUCAAGUAACAA |
| Luc | 56 | SEQ. ID NO: 0266 | ACGUCGCCAGUCAAGUAAC |
| Luc | 57 | SEQ. ID NO: 0267 | UUACGUCGCCAGUCAAGUA |
| Luc | 58 | SEQ. ID NO: 0268 | GAUUACGUCGCCAGUCAAG |
| Luc | 59 | SEQ. ID NO: 0269 | UGGAUUACGUCGCCAGUCA |
| Luc | 60 | SEQ. ID NO: 0270 | CGUGGAUUACGUCGCCAGU |
| Luc | 61 | SEQ. ID NO: 0271 | AUCGUGGAUUACGUCGCCA |
| Luc | 62 | SEQ. ID NO: 0272 | AGAUCGUGGAUUACGUCGC |
| Luc | 63 | SEQ. ID NO: 0273 | AGAGAUCGUGGAUUACGUC |
| Luc | 64 | SEQ. ID NO: 0274 | AAAGAGAUCGUGGAUUACG |
| Luc | 65 | SEQ. ID NO: 0275 | AAAAAGAGAUCGUGGAUUA |
| Luc | 66 | SEQ. ID NO: 0276 | GGAAAAGAGAUCGUGGAU |
| Luc | 67 | SEQ. ID NO: 0277 | ACGGAAAAGAGAUCGUGG |
| Luc | 68 | SEQ. ID NO: 0278 | UGACGGAAAAGAGAUCGU |
| Luc | 69 | SEQ. ID NO: 0279 | GAUGACGGAAAAGAGAUC |
| Luc | 70 | SEQ. ID NO: 0280 | ACGAUGACGGAAAAGAGA |
| Luc | 71 | SEQ. ID NO: 0281 | AGACGAUGACGGAAAAGA |
| Luc | 72 | SEQ. ID NO: 0282 | AAAGACGAUGACGGAAAAA |
| Luc | 73 | SEQ. ID NO: 0283 | GGAAAGACGAUGACGGAAA |
| Luc | 74 | SEQ. ID NO: 0284 | ACGGAAAGACGAUGACGGA |
| Luc | 75 | SEQ. ID NO: 0285 | GCACGGAAAGACGAUGACG |
| Luc | 76 | SEQ. ID NO: 0286 | GAGCACGGAAAGACGAUGA |
| Luc | 77 | SEQ. ID NO: 0287 | UGGAGCACGGAAAGACGAU |
| Luc | 78 | SEQ. ID NO: 0288 | UUUGGAGCACGGAAAGACG |
| Luc | 79 | SEQ. ID NO: 0289 | GUUUGGAGCACGGAAAGA |
| Luc | 80 | SEQ. ID NO: 0290 | UUGUUUGGAGCACGGAAA |
| Luc | 81 | SEQ. ID NO: 0291 | UGUUGUUUGGAGCACGGA |
| Luc | 82 | SEQ. ID NO: 0292 | GUUGUUGUUUGGAGCACG |
| Luc | 83 | SEQ. ID NO: 0293 | CCGUUGUUGUUUGGAGCA |
| Luc | 84 | SEQ. ID NO: 0294 | CGCCGUUGUUGUUUGGAG |
| Luc | 85 | SEQ. ID NO: 0295 | GCCGCCGUUGUUGUUUGG |
| Luc | 86 | SEQ. ID NO: 0296 | CCGCCGCCGUUGUUGUUU |
| Luc | 87 | SEQ. ID NO: 0297 | UCCCGCCGCCGUUGUUGUU |
| Luc | 88 | SEQ. ID NO: 0298 | CUUCCCGCCGCCGUUGUUG |
| Luc | 89 | SEQ. ID NO: 0299 | AACUUCCCGCCGCCGUUGU |
| Luc | 90 | SEQ. ID NO: 0300 | UGAACUUCCCGCCGCCGUU |

Example II

Validation of the Algorithm Using DBI, Luciferase, PLK, EGRS, and SEAP

The algorithm (Formula VIII) identified siRNAs for five genes, human DBI, firefly luciferase (fLuc), *renilla* luciferase (rLuc), human PLK, and human secreted alkaline phosphatase (SEAP). Four individual siRNAs were selected on the basis of their SMARTSCORES™ derived by analysis of their sequence using Formula VIII (all of the siRNAs would be selected with Formula IX as well) and analyzed for their ability to silence their targets' expression. In addition to the scoring, a BLAST search was conducted for each siRNA. To minimize the potential for off-target silencing effects, only those target sequences with more than three mismatches against un-related sequences were selected. Semizarov, et al. (2003) Specificity of short interfering RNA determined through gene expression signatures, *Proc. Natl. Acad. Sci. USA,* 100:6347. These duplexes were analyzed individually and in pools of 4 and compared with several siRNAs that were randomly selected. The functionality was measured as a percentage of targeted gene knockdown as compared to controls. All siRNAs were transfected as described by the methods above at 100 nM concentration into HEK293 using Lipofectamine 2000. The level of the targeted gene expression was evaluated by B-DNA as described above and normalized to the non-specific control. FIG. 10 shows that the siRNAs selected by the algorithm disclosed herein were significantly more potent than randomly selected siRNAs. The algorithm increased the chances of identifying an F50 siRNA from 48% to 91%, and an F80 siRNA from 13% to 57%. In addition, pools of SMART siRNA silence the selected target better than randomly selected pools (see FIG. 10F).

Example III

Validation of the Algorithm Using Genes Involved in Clathrin-Dependent Endocytosis Components of clathrin-mediated endocytosis pathway are key to modulating intracellular signaling and play important roles in disease. Chromosomal rearrangements that result in fusion transcripts between the Mixed-Lineage Leukemia gene (MLL) and CALM (clathrin assembly lymphoid myeloid leukemia gene) are believed to play a role in leukemogenesis. Similarly, disruptions in Rab7 and Rab9, as well as HIP1 (Huntingtin-interacting protein), genes that are believed to be involved in endocytosis, are potentially responsible for ailments resulting in lipid storage, and neuronal diseases, respectively. For these reasons, siRNA directed against clathrin and other genes involved in the clathrin-mediated endocytotic pathway are potentially important research and therapeutic tools.

siRNAs directed against genes involved in the clathrin-mediated endocytosis pathways were selected using Formula VIII. The targeted genes were clathrin heavy chain (CHC, accession # NM_004859), clathrin light chain A (CLCa, NM_001833), clathrin light chain B (CLCb, NM_001834), CALM (U45976), 2 subunit of AP-2 (β2, NM_001282), Eps15 (NM_001981), Eps15R (NM_021235), dynamin II (DYNII, NM_004945), Rab5a (BC001267), Rab5b (NM_002868), Rab5c (AF141304), and EEA.1 (XM_018197).

For each gene, four siRNAs duplexes with the highest scores were selected and a BLAST search was conducted for each of them using the Human EST database. In order to minimize the potential for off-target silencing effects, only those sequences with more than three mismatches against un-related sequences were used. All duplexes were synthesized at Dharmacon, Inc. as 21-mers with 3'-UU overhangs using a modified method of 2'-ACE chemistry, Scaringe (2000) Advanced 5'-silyl-2'-orthoester approach to RNA oligonucleotide synthesis, *Methods Enzymol.* 317:3, and the antisense strand was chemically phosphorylated to insure maximized activity.

HeLa cells were grown in Dulbecco's modified Eagle's medium (DMEM) containing 10% fetal bovine serum, antibiotics and glutamine. siRNA duplexes were resuspended in 1× siRNA Universal buffer (Dharmacon, Inc.) to 20 M prior to transfection. HeLa cells in 12-well plates were transfected twice with 41 of 20 M siRNA duplex in 3 1 Lipofectamine 2000 reagent (Invitrogen, Carlsbad, Calif., USA) at 24-hour intervals. For the transfections in which 2 or 3 siRNA duplexes were included, the amount of each duplex was decreased, so that the total amount was the same as in transfections with single siRNAs. Cells were plated into normal culture medium 12 hours prior to experiments, and protein levels were measured 2 or 4 days after the first transfection.

Equal amounts of lysates were resolved by electrophoresis, blotted, and stained with the antibody specific to targeted protein, as well as antibodies specific to unrelated proteins, PPI phosphatase and Tsg101 (not shown). The cells were lysed in Triton X-100/glycerol solubilization buffer as described previously. Tebar, Bohlander, & Sorkin (1999) Clathrin Assembly Lymphoid Myeloid Leukemia (CALM) Protein: Localization in Endocytic-coated Pits, Interactions with Clathrin, and the Impact of Overexpression on Clathrin-mediated Traffic, *Mol. Biol. Cell,* 10:2687. Cell lysates were electrophoresed, transferred to nitrocellulose membranes, and Western blotting was performed with several antibodies followed by detection using enhanced chemiluminescence system (Pierce, Inc). Several x-ray films were analyzed to determine the linear range of the chemiluminescence signals, and the quantifications were performed using densitometry and AlphaImager v5.5 software (Alpha Innotech Corporation). In experiments with Eps15R-targeted siRNAs, cell lysates were subjected to immunoprecipitation with Ab860, and Eps15R was detected in immunoprecipitates by Western blotting as described above.

The antibodies to assess the levels of each protein by Western blot were obtained from the following sources: monoclonal antibody to clathrin heavy chain (TD.1) was obtained from American Type Culture Collection (Rockville, Md., USA); polyclonal antibody to dynamin II was obtained from Affinity Bioreagents, Inc. (Golden, Colo., USA); monoclonal antibodies to EEA.1 and Rab5a were purchased from BD Transduction Laboratories (Los Angeles, Calif., USA); the monoclonal antibody to Tsg101 was purchased from Santa Cruz Biotechnology, Inc. (Santa Cruz, Calif., USA); the monoclonal antibody to GFP was from ZYMED Laboratories Inc. (South San Francisco, Calif., USA); the rabbit polyclonal antibodies Ab32 specific to a-adaptins and Ab20 to CALM were described previously (Sorkin et aL (1995) Stoichiometric Interaction of the Epidermal Growth Factor Receptor with the Clathrin-associated Protein Complex AP-2, *J. Biol. Chem.,* 270:619), the polyclonal antibodies to clathrin light chains A and B were kindly provided by Dr. F. Brodsky (UCSF); monoclonal antibodies to PPI (BD Transduction Laboratories) and α-Actinin (Chemicon) were kindly provided by Dr. M. Dell'Acqua (University of Colorado); Eps15 Ab577 and Eps15R Ab860 were kindly provided by Dr. P.P. Di Fiore (European Cancer Institute).

Figure 11:
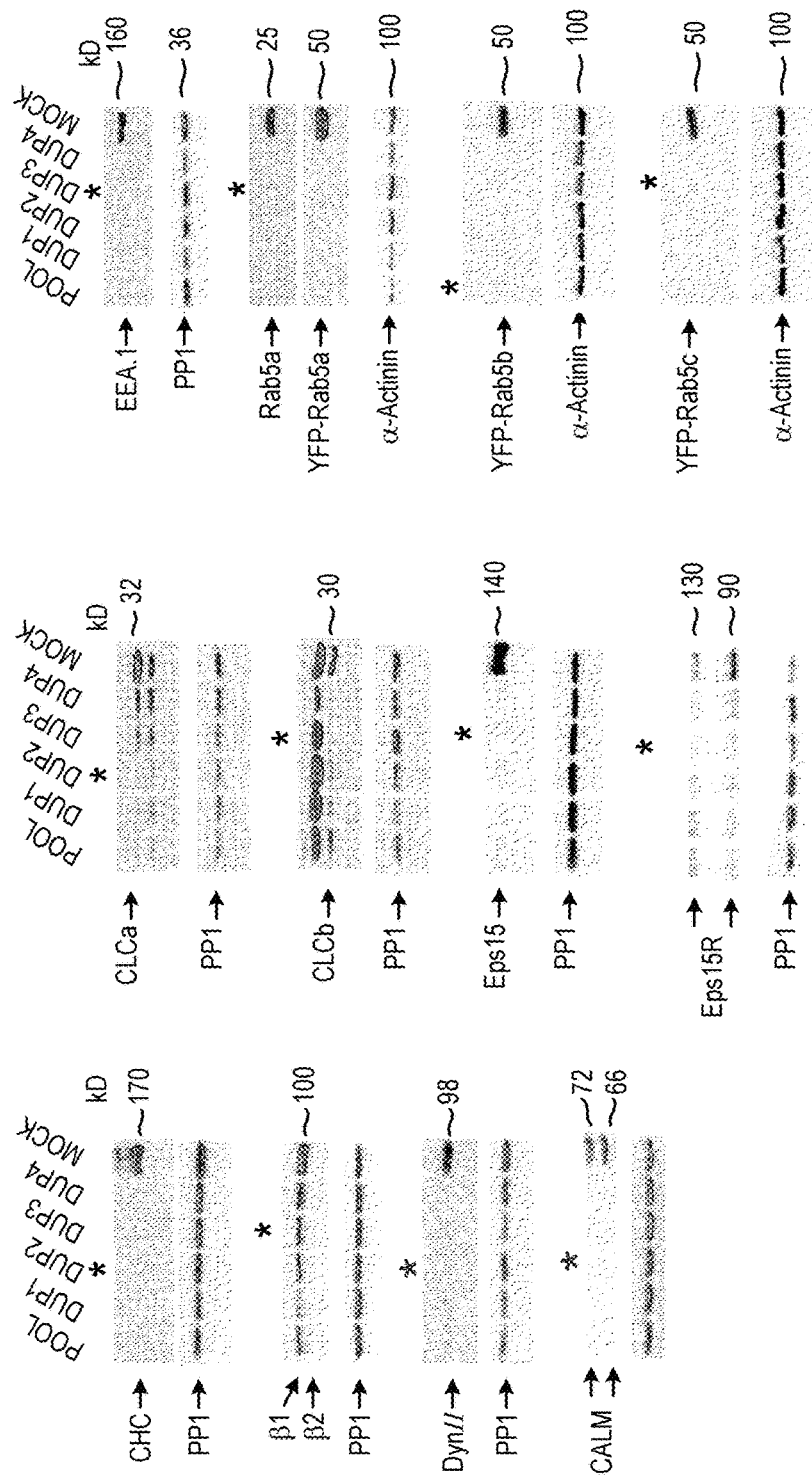
FIG. 11 shows the Western blot results from cells treated with siRNA directed against twelve different genes involved in the clathrin-dependent endocytosis pathway (CHC, DynII, CALM, CLCa, CLCb, Eps15, Eps15R, Rab5a, Rab5b, Rab5c, 2 subunit of AP-2 and EEA.1). siRNA were selected using Formula VIII. "Pool" represents a mixture of duplexes 1-4. Total concentration of each siRNA in the pool is 25 nM. Total concentration=4×25=100 nM.

FIG. 11 demonstrates the in vivo functionality of 48 individual siRNAs, selected using Formula VIII (most of them will meet the criteria incorporated by Formula IX as well) targeting 12 genes. Various cell lines were transfected with siRNA duplexes (Dup1-4) or pools of siRNA duplexes (Pool), and the cells were lysed 3 days after transfection with the exception of CALM (2 days) and 2 (4 days).

Note a β1-adaptin band (part of AP-1 Golgi adaptor complex) that runs slightly slower than β2 adaptin. CALM has two splice variants, 66 and 72 kD. The full-length Eps15R (a doublet of ~130 kD) and several truncated spliced forms of ~100 kD and ~70 kD were detected in Eps15R immunoprecipitates (shown by arrows). The cells were lysed 3 days after transfection. Equal amounts of lysates were resolved by electrophoresis and blotted with the antibody specific to a targeted protein (GFP antibody for YFP fusion proteins) and the antibody specific to unrelated proteins PP1 phosphatase or α-actinin, and TSG101. The amount of protein in each specific band was normalized to the amount of non-specific proteins in each lane of the gel. Nearly all of them appear to be functional, which establishes that Formula VIII and IX can be used to predict siRNAs' functionality in general in a genome wide manner.

To generate the fusion of yellow fluorescent protein (YFP) with Rab5b or Rab5c (YFP-Rab5b or YFP-Rab5c), a DNA fragment encoding the full-length human Rab5b or Rab5c was obtained by PCR using Pfu polymerase (Stratagene) with a SacI restriction site introduced into the 5' end and a KpnI site into the 3' end and cloned into pEYFP-C1 vector (CLONTECH, Palo Alto, Calif., USA). GFP-CALM and YFP-Rab5a were described previously (Tebar, Bohlander, & Sorkin (1999) Clathrin Assembly Lymphoid Myeloid Leukemia (CALM) Protein: Localization in Endocytic-coated Pits, Interactions with Clathrin, and the Impact of Overexpression on Clathrin-mediated Traffic, *Mol. Biol. Cell* 10:2687).

Example IV

Validation of the Algorithm Using Eg5, GADPH, ATE1, MEK2, MEK1, QB, LaminA/C, C-myc, Human Cyclophilin, and Mouse Cyclophilin A number of genes have been identified as playing potentially important roles in disease etiology. Expression profiles of normal and diseased kidneys has implicated Edg5 in immunoglobulin A neuropathy, a common renal glomerular disease. Myc1, MEK1/2 and other related kinases have been associated with one or more cancers, while lamins have been implicated in muscular dystrophy and other diseases. For these reasons, siRNA directed against the genes encoding these classes of molecules would be important research and therapeutic tools.

Figure 12:
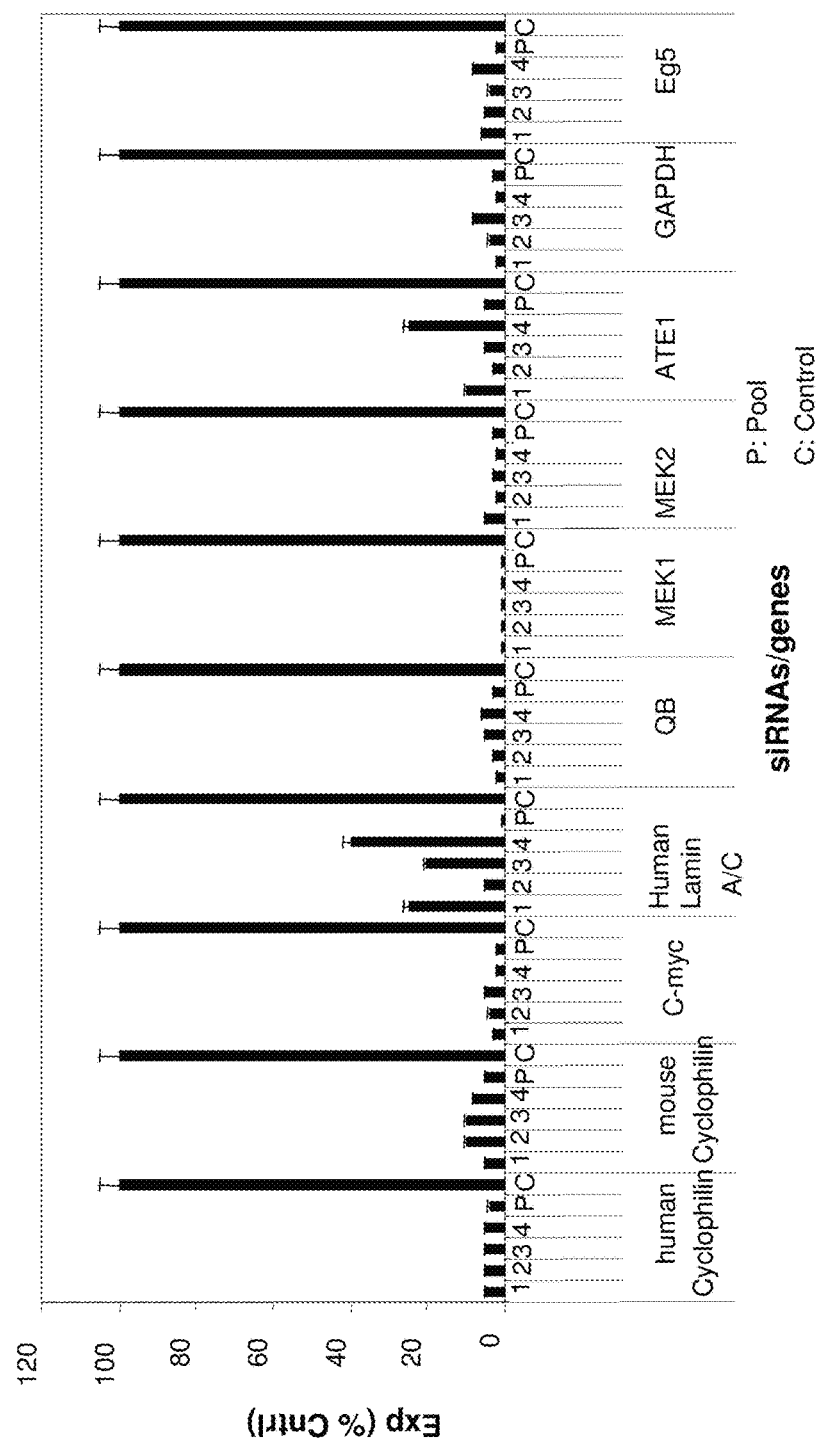
FIG. 12 is a representation of the gene silencing capabilities of rationally-selected siRNA directed against ten different genes (human and mouse cyclophilin, C-myc, human lamin A/C, QB (ubiquinol-cytochrome c reductase core protein I), MEK1 and MEK2, ATE1 (arginyl-tRNA protein transferase), GAPDH, and Eg5). The Y-axis is the percent expression of the control. Numbers 1, 2, 3 and 4 represent individual rationally selected siRNA. "Pool" represents a mixture of the four individual siRNA.

FIG. 12 illustrates four siRNAs targeting 10 different genes (Table V for sequence and accession number information) that were selected according to the Formula VIII and assayed as individuals and pools in HEK293 cells. The level of siRNA induced silencing was measured using the B-DNA assay. These studies demonstrated that thirty-six out of the forty individual SMART-selected siRNA tested are functional (90%) and all 10 pools are fully functional.

Example V

Validation of the Algorithm Using Bcl2

Bcl-2 is a ~25kD, 205-239 amino acid, anti-apoptotic protein that contains considerable homology with other members of the BCL family including BCLX, MCL1, BAX, BAD, and BIK. The protein exists in at least two forms (Bcl2a, which has a hydrophobic tail for membrane anchorage, and Bcl2b, which lacks the hydrophobic tail) and is predominantly localized to the mitochondrial membrane. While Bcl2 expression is widely distributed, particular interest has focused on the expression of this molecule in B and T cells. Bcl2 expression is down-regulated in normal germinal center B cells yet in a high percentage of follicular lymphomas, Bcl2 expression has been observed to be elevated. Cytological studies have identified a common translocation ((14;18)(q32;q32)) amongst a high percentage (>70%) of these lymphomas. This genetic lesion places the Bcl2 gene in juxtaposition to immunoglobulin heavy chain gene (IgH) encoding sequences and is believed to enforce inappropriate levels of gene expression, and resistance to programmed cell death in the follicle center B cells. In other cases, hypomethylation of the Bcl2 promoter leads to enhanced expression and again, inhibition of apoptosis. In addition to cancer, dysregulated expression of Bcl-2 has been correlated with multiple sclerosis and various neurological diseases.

The correlation between Bcl-2 translocation and cancer makes this gene an attractive target for RNAi. Identification of siRNA directed against the bcl2 transcript (or Bcl2-IgH fusions) would further our understanding Bcl2 gene function and possibly provide a future therapeutic agent to battle diseases that result from altered expression or function of this gene.

In Silico Identification of Functional siRNA

To identify functional and hyperfunctional siRNA against the Bcl2 gene, the sequence for Bcl-2 was downloaded from the NCBI Unigene database and analyzed using the Formula VIII algorithm. As a result of these procedures, both the sequence and SMARTSCORES™, or siRNA rankings of the Bcl2 siRNA were obtained and ranked according to their functionality. Subsequently, these sequences were BLAST'ed (database) to insure that the selected sequences were specific and contained minimal overlap with unrelated genes. The SMARTSCORES™, or siRNA rankings for the top 10 Bcl-2 siRNA are identified in FIG. 13.

In Vivo Testing of Bcl2 SiRNA

Bcl-2 siRNAs having the top ten SMARTSCORES™, or siRNA rankings were selected and tested in a functional assay to determine silencing efficiency. To accomplish this, each of the ten duplexes were synthesized using 2'-O-ACE chemistry and transfected at 100 nM concentrations into cells. Twenty-four hours later assays were performed on cell extracts to assess the degree of target silencing. Controls used in these experiments included mock transfected cells, and cells that were transfected with a non-specific siRNA duplex.

Figure 14:
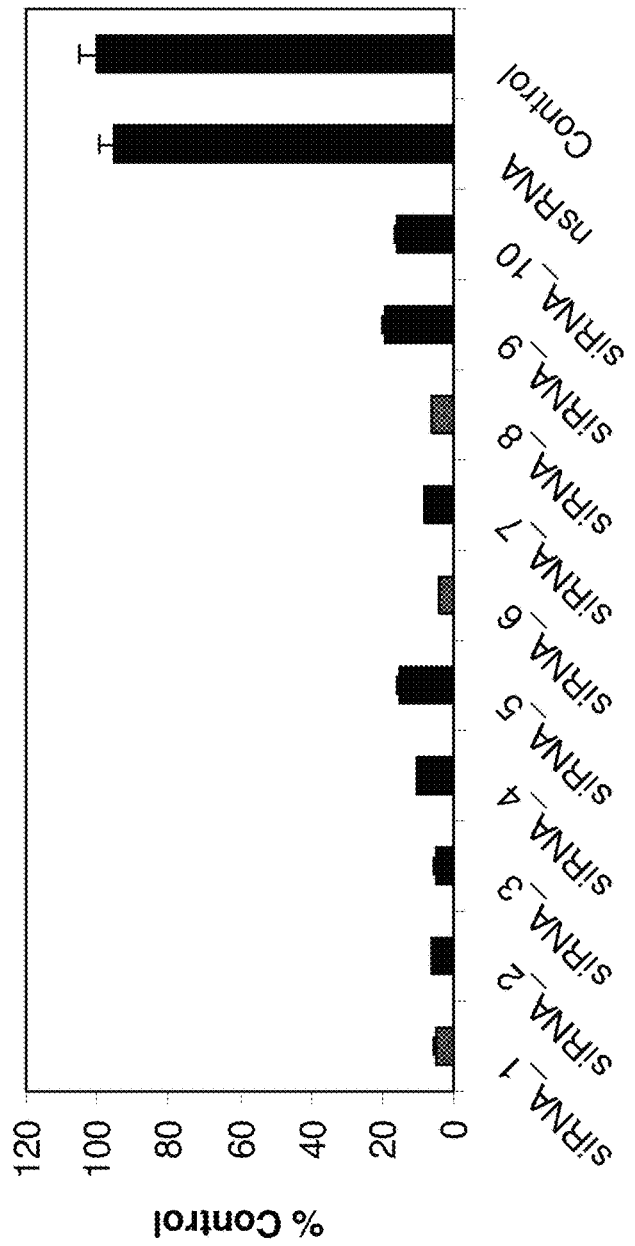
FIG. 14 is the knockdown by the top ten Bcl2 siRNAs at 100 nM concentrations. The Y-axis represents the amount of expression relative to the non-specific (ns) and transfection mixture control.

The results of these experiments are presented below (and in FIG. 14) and show that all ten of the selected siRNA induce 80% or better silencing of the Bcl2 message at 100 nM concentrations. These data verify that the algorithm successfully identified functional Bcl2 siRNA and provide a set of functional agents that can be used in experimental and therapeutic environments.

|  |  |
|---|---|
| siRNA 1 | SEQ. ID NO. 302<br>GGGAGAUAGUGAUGAAGUA |
| siRNA 2 | SEQ. ID NO. 303<br>GAAGUACAUCCAUUAUAAG |
| siRNA 3 | SEQ. ID NO. 304<br>GUACGACAACCGGGAGAUA |
| siRNA 4 | SEQ. ID NO. 305<br>AGAUAGUGAUGAAGUACAU |
| siRNA 5 | SEQ. ID NO. 306<br>UGAAGACUCUGCUCAGUUU |
| siRNA 6 | SEQ. ID NO. 307<br>GCAUGCGGCCUCUGUUUGA |
| siRNA 7 | SEQ. ID NO. 308<br>UGCGGCCUCUGUUUGAUUU |
| siRNA 8 | SEQ. ID NO. 309<br>GAGAUAGUGAUGAAGUACA |
| siRNA 9 | SEQ. ID NO. 310<br>GGAGAUAGUGAUGAAGUAC |
| siRNA 10 | SEQ. ID NO. 311<br>GAAGACUCUGCUCAGUUUG |

Bcl2 siRNA: Sense Strand, 5'ÿ 3'

Example VI

Sequences Selected By the Algorithm

Sequences of the siRNAs selected using Formulas (Algorithms) VIII and IX with their corresponding ranking, which have been evaluated for the silencing activity in vivo in the present study (Formula VIII and IX, respectively) are shown in Table V. It should be noted that the "t" residues in Table V, and elsewhere, when referring to siRNA, should be replaced by "u" residues.

TABLE V (SEQ ID NOS 312-426, 301 and 428-437, respectively, in order of appearance)

| GENE | Name | ACCESSION NUMBER | FTLLSEQTENCE | FORMULA VIII | FORMULA IX |
|---|---|---|---|---|---|
| CLTC | NM_004859 | 0428 | GAAAGAATCTGTAGAGAAA | 76 | 94.2 |
| CLTC | NM_004859 | 0429 | GCAATGAGCTGTTTGAAGA | 65 | 39.9 |
| CLTC | NM_004859 | 0430 | TGACAAAGGTGGATAAATT | 57 | 38.2 |
| CLTC | NM_004859 | 0431 | GGAAATGGATCTCTTTGAA | 54 | 49.4 |

TABLE V-continued (SEQ ID NOS 312-426, 301 and 428-437, respectively, in order of appearance)

| GENE | Name | ACCESSION NUMBER | FTLLSEQTENCE | FORMULA VIII | FORMULA IX |
|---|---|---|---|---|---|
| CLTA | NM_001833 | 0432 | GGAAAGTAATGGTCCAACA | 22 | 55.5 |
| CLTA | NM_001833 | 0433 | AGACAGTTATGCAGCTATT | 4 | 22.9 |
| CLTA | NM_001833 | 0434 | CCAATTCTCGGAAGCAAGA | 1 | 17 |
| CLTA | NM_001833 | 0435 | GAAAGTAATGGTCCAACAG | -1 | -13 |
| CLTB | NM_001834 | 0436 | GCGCCAGAGTGAACAAGTA | 17 | 57.5 |
| CLTB | NM_001834 | 0437 | GAAGGTGGCCCAGCTATGT | 15 | -8.6 |
| CLTB | NM_001834 | 0311 | GGAACCAGCGCCAGAGTGA | 13 | 40.5 |
| CLTB | NM_001834 | 0312 | GAGCGAGATTGCAGGCATA | 20 | 61.7 |
| CALM | U45976 | 0313 | GTTAGTATCTGATGACTTG | 36 | -34.6 |
| CALM | U45976 | 0314 | GAAATGGAACCACTAAGAA | 33 | 46.1 |
| CALM | U45976 | 0315 | GGAAATGGAACCACTAAGA | 30 | 61.2 |
| CALM | U45976 | 0316 | CAACTACACTTTCCAATGC | 28 | 6.8 |
| EPS15 | NM_001981 | 0317 | CCACCAAGATTTCATGATA | 48 | 25.2 |
| EPS15 | NM_001981 | 0318 | GATCGGAACTCCAACAAGA | 43 | 49.3 |
| EPS15 | NM_001981 | 0319 | AAACGGAGCTACAGATTAT | 39 | 11.5 |
| EPS15 | NM_001981 | 0320 | CCACACAGCATTCTTGTAA | 33 | -23.6 |
| EPS15R | NM_021235 | 0321 | GAAGTTACCTTGAGCAATC | 48 | 33 |
| EPS15R | NM_021235 | 0322 | GGACTTGGCCGATCCAGAA | 27 | 33 |
| EPS15R | NM_021235 | 0323 | GCACTTGGATCGAGATGAG | 20 | 1.3 |
| EPS15R | NM_021235 | 0324 | CAAAGACCAATTCGCGTTA | 17 | 27.7 |
| DNM2 | NM_004945 | 0325 | CCGAATCAATCGCATCTTC | 6 | -29.6 |
| DNM2 | NM_004945 | 0326 | GACATGATCCTGCAGTTCA | 5 | -14 |
| DNM2 | NM_004945 | 0327 | GAGCGAATCGTCACCACTT | 5 | 24 |
| DNM2 | NM_004945 | 0328 | CCTCCGAGCTGGCGTCTAC | -4 | -63.6 |
| ARF6 | AF93885 | 0329 | TCACATGGTTAACCTCTAA | 27 | -21.1 |
| ARF6 | AF93885 | 0330 | GATGAGGGACGCCATAATC | 7 | -38.4 |
| ARF6 | AF93885 | 0331 | CCTCTAACTACAAATCTTA | 4 | 16.9 |
| ARF6 | AF93885 | 0332 | GGAAGGTGCTATCCAAAAT | 4 | 11.5 |
| RAB5A | BC001267 | 0333 | GCAAGCAAGTCCTAACATT | 40 | 25.1 |
| RAB5A | BC001267 | 0334 | GGAAGAGGAGTAGACCTTA | 17 | 50.1 |
| RAB5A | BC001267 | 0335 | AGGAATCAGTGTTGTAGTA | 16 | 11.5 |
| RAB5A | BC001267 | 0336 | GAAGAGGAGTAGACCTTAC | 12 | 7 |
| RAB5B | NM_002868 | 0337 | GAAAGTCAAGCCTGGTATT | 14 | 18.1 |
| RAB5B | NM_002868 | 0338 | AAAGTCAAGCCTGGTATTA | 6 | -17.8 |
| RAB5B | NM_002868 | 0339 | GCTATGAACGTGAATGATC | 3 | -21.1 |
| RAB5B | NM_002868 | 0340 | CAAGCCTGGTATTACGTTT | -7 | -37.5 |
| RAB5C | AF141304 | 0341 | GGAACAAGATCTGTCAATT | 38 | 51.9 |
| RAB5C | AF141304 | 0342 | GCAATGAACGTGAACGAAA | 29 | 43.7 |
| RAB5C | AF141304 | 0343 | CAATGAACGTGAACGAAAT | 18 | 43.3 |
| RAB5C | AF141304 | 0344 | GGACAGGAGCGGTATCACA | 6 | 18.2 |
| EEA1 | XM_018197 | 0345 | AGACAGAGCTTGAGAATAA | 67 | 64.1 |
| EEA1 | XM_018197 | 0346 | GAGAAGATCTTTATGCAAA | 60 | 48.7 |
| EEA1 | XM_018197 | 0347 | GAAGAGAAATCAGCAGATA | 58 | 45.7 |
| EEA1 | XM_018197 | 0348 | GCAAGTAACTCAACTAACA | 56 | 72.3 |
| AP2B1 | NM_001282 | 0349 | GAGCTAATCTGCCACATTG | 49 | -12.4 |
| AP2B1 | NM_001282 | 0350 | GCAGATGAGTTACTAGAAA | 44 | 48.9 |
| AP2B1 | NM_001282 | 0351 | CAACTTAATTGTCCAGAAA | 41 | 28.2 |
| AP2B1 | NM_001282 | 0352 | CAACACAGGATTCTGATAA | 33 | -5.8 |
| PLK | NM_005030 | 0353 | AGATTGTGCCTAAGTCTCT | -35 | -3.4 |
| PLK | NM_005030 | 0354 | ATGAAGATCTGGAGGTGAA | 0 | -4.3 |
| PLK | NM_005030 | 0355 | TTTGAGACTTCTTGCCTAA | -5 | -27.7 |
| PLK | NM_005030 | 0356 | AGATCACCCTCCTTAAATA | 15 | 72.3 |
| GAPDH | NM_002046 | 0357 | CAACGGATTTGGTCGTATT | 27 | -2.8 |
| GAPDH | NM_002046 | 0358 | GAAATCCCATCACCATCTT | 24 | 3.9 |
| GAPDH | NM_002046 | 0359 | GACCTCAACTACATGGTTT | 22 | -22.9 |
| GAPDH | NM_002046 | 0360 | TGGTTTACATGTTCCAATA | 9 | 9.8 |
| c-Myc | | 0361 | GAAGAAATCGATGTTGTTT | 31 | -11.7 |
| c-Myc | | 0362 | ACACAAACTTGAACAGCTA | 22 | 51.3 |
| c-Myc | | 0363 | GGAAGAAATCGATGTTGTT | 18 | 26 |
| c-Myc | | 0364 | GAAACGACGAGAACAGTTG | 18 | -8.9 |

TABLE V-continued (SEQ ID NOS 312-426, 301 and 428-437, respectively, in order of appearance)

| GENE | Name | ACCESSION NUMBER | FTLLSEQTENCE | FORMULA VIII | FORMULA IX |
|---|---|---|---|---|---|
| MAP2K1 | NM_002755 | 0365 | GCACATGGATGGAGGTTCT | 26 | 16 |
| MAP2K1 | NM_002755 | 0366 | GCAGAGAGAGCAGATTTGA | 16 | 0.4 |
| MAP2K1 | NM_002755 | 0367 | GAGGTTCTCTGGATCAAGT | 14 | 15.5 |
| MAP2K1 | NM_002755 | 0368 | GAGCAGATTTGAAGCAACT | 14 | 18.5 |
| MAP2K2 | NM_030662 | 0369 | CAAAGACGATGACTTCGAA | 37 | 26.4 |
| MAP2K2 | NM_030662 | 0370 | GATCAGCATTTGCATGGAA | 24 | -0.7 |
| MAP2K2 | NM_030662 | 0371 | TCCAGGAGTTTGTCAATAA | 17 | -4.5 |
| MAP2K2 | NM_030662 | 0372 | GGAAGCTGATCCACCTTGA | 16 | 59.2 |
| KNSL1(EG5) | NM_004523 | 0373 | GCAGAAATCTAAGGATATA | 53 | 35.8 |
| KNSL1(EG5) | NM_004523 | 0374 | CAACAAGGATGAAGTCTAT | 50 | 18.3 |
| KNSL1(EG5) | NM_004523 | 0375 | CAGCAGAAATCTAAGGATA | 41 | 32.7 |
| KNSL1(EG5) | NM_004523 | 0376 | CTAGATGGCTTTCTCAGTA | 39 | 3.9 |
| CyclophilinA | NM_021130 | 0377 | AGACAAGGTCCCAAAGACA | -16 | 58.1 |
| CyclophilinA | NM_021130 | 0378 | GGAATGGCAAGACCAGCAA | -6 | 36 |
| CyclophilinA | NM_021130 | 0379 | AGAATTATTCCAGGGTTTA | -3 | 16.1 |
| CyclophilinA | NM_021130 | 0380 | GCAGACAAGGTCCCAAAGA | 8 | 8.9 |
| LAMIN A/C | NM_170707 | 0381 | AGAAGCAGCTTCAGGATGA | 31 | 38.8 |
| LAMIN A/C | NM_170707 | 0382 | GAGCTTGACTTCCAGAAGA | 33 | 22.4 |
| LAMIN A/C | NM_170707 | 0383 | CCACCGAAGTTCACCCTAA | 21 | 27.5 |
| LAMIN A/C | NM_170707 | 0384 | GAGAAGAGCTCCTCCATCA | 55 | 30.1 |
| CyclophilinB | M60857 | 0385 | GAAAGAGCATCTACGGTGA | 41 | 83.9 |
| CyclophilinB | M60857 | 0386 | GAAAGGATTTGGCTACAAA | 53 | 59.1 |
| CyclophilinB | M60857 | 0387 | ACAGCAAATTCCATCGTGT | -20 | 28.8 |
| CyclophilinB | M60857 | 0388 | GGAAAGACTGTTCCAAAAA | 2 | 27 |
| DBI1 | NM_020548 | 0389 | CAACACGCCTCATCCTCTA | 27 | -7.6 |
| DBI2 | NM_020548 | 0390 | CATGAAAGCTTACATCAAC | 25 | -30.8 |
| DBI3 | NM_020548 | 0391 | AAGATGCCATGAAAGCTTA | 17 | 22 |
| DBI4 | NM_020548 | 0392 | GCACATACCGCCTGAGTCT | 15 | 3.9 |
| rLUC1 | | 0393 | GATCAAATCTGAAGAAGGA | 57 | 49.2 |
| rLUC2 | | 0394 | GCCAAGAAGTTTCCTAATA | 50 | 13.7 |
| rLUC3 | | 0395 | CAGCATATCTTGAACCATT | 41 | -2.2 |
| rLUC4 | | 0396 | GAACAAAGGAAACGGATGA | 39 | 29.2 |
| SeAP1 | NM_031313 | 0397 | CGGAAACGGTCCAGGCTAT | 6 | 26.9 |
| SeAP2 | NM_031313 | 0398 | GCTTCGAGCAGACATGATA | 4 | -11.2 |
| SeAP3 | NM_031313 | 0399 | CCTACACGGTCCTCCTATA | 4 | 4.9 |
| SeAP4 | NM_031313 | 0400 | GCCAAGAACCTCATCATCT | 1 | -9.9 |
| fLUC1 | | 0401 | GATATGGGCTGAATACAAA | 54 | 40.4 |
| fLUC2 | | 0402 | GCACTCTGATTGACAAATA | 47 | 54.7 |
| fLUC3 | | 0403 | TGAAGTCTCTGATTAAGTA | 46 | 34.5 |
| fLUC4 | | 0404 | TCAGAGAGATCCTCATAAA | 40 | 11.4 |
| mCyclo_1 | NM_008907 | 0405 | GCAAGAAGATCACCATTTC | 52 | 46.4 |
| mCyclo_2 | NM_008907 | 0406 | GAGAGAAATTTGAGGATGA | 36 | 70.7 |
| mCyclo_3 | NM_008907 | 0407 | GAAAGGATTTGGCTATAAG | 35 | -1.5 |
| mCyclo_4 | NM_008907 | 0408 | GAAAGAAGGCATGAACATT | 27 | 10.3 |
| BCL2_1 | NM_000633 | 0409 | GGGAGATAGTGATGAAGTA | 21 | 72 |
| BCL2_2 | NM_000633 | 0410 | GAAGTACATCCATTATAAG | 1 | 3.3 |
| BCL2_3 | NM_000633 | 0411 | GTACGACAACCGGGAGATA | 1 | 35.9 |
| BCL2_4 | NM_000633 | 0412 | AGATAGTGATGAAGTACAT | -12 | 22.1 |
| BCL2_5 | NM_000633 | 0413 | TGAAGACTCTGCTCAGTTT | 36 | 19.1 |
| BCL2_6 | NM_000633 | 0414 | GCATGCGGCCTCTGTTTGA | 5 | -9.7 |
| QB1 | NM_003365.1 | 0415 | GCACACAGCUUACUACAUC | 52 | -4.8 |
| QB2 | NM_003365.1 | 0416 | GAAAUGCCCUGGUAUCUCA | 49 | 22.1 |
| QB3 | NM_003365.1 | 0417 | GAAGGAACGUGAUGUGAUC | 34 | 22.9 |
| QB4 | NM_003365.1 | 0418 | GCACUACUCCUGUGUGUGA | 28 | 20.4 |
| ATE1-1 | NM_007041 | 0419 | GAACCCAGCUGGAGAACUU | 45 | 15.5 |
| ATE1-2 | NM_007041 | 0420 | GAUAUACAGUGUGAUCUUA | 40 | 12.2 |
| ATE1-3 | NM_007041 | 0421 | GUACUACGAUCCUGAUUAU | 37 | 32.9 |
| ATE1-4 | NM_007041 | 0422 | GUGCCGACCUUUACAAUUU | 35 | 18.2 |
| EGFR-1 | NM_005228 | 0423 | GAAGGAAACUGAAUUCAAA | 68 | 79.4 |
| EGFR-1 | NM_005228 | 0424 | GGAAAUAUGUACUACGAAA | 49 | 49.5 |

TABLE V-continued (SEQ ID NOS 312-426, 301 and 428-437, respectively, in order of appearance)

| GENE | Name | ACCESSION NUMBER | FTLLSEQTENCE | FORMULA VIII | FORMULA IX |
|---|---|---|---|---|---|
| EGFR-1 | NM_005228 | 0425 | CCACAAAGCAGTGAATTTA | 41 | 7.6 |
| EGFR-1 | NM_005228 | 0426 | GTAACAAGCTCACGCAGTT | 40 | 25.9 |

Many of the genes to which the described siRNA are directed play critical roles in disease etiology. For this reason, the siRNAs listed in the sequence listing may potentially act as therapeutic agents. A number of prophetic examples follow and should be understood in view of the siRNA that are identified in the sequence listing. To isolate these siRNAs, the appropriate message sequence for each gene is analyzed using one of the before mentioned formulas (preferably formula VIII) to identify potential siRNA targets. Subsequently these targets are BLAST'ed to eliminate homology with potential off-targets.

Example VII

Evidence for the Benefits of Pooling

Evidence for the benefits of pooling have been demonstrated using the reporter gene, luciferase. Ninety siRNA duplexes were synthesized using Dharmacon proprietary ACE® chemistry against one of the standard reporter genes: firefly luciferase. The duplexes were designed to start two base pairs apart and to cover approximately 180 base pairs of the luciferase gene (see sequences in Table IV). Subsequently, the siRNA duplexes were co-transfected with a luciferase expression reporter plasmid into HEK293 cells using standard transfection protocols and luciferase activity was assayed at 24 and 48 hours.

Figure 15:
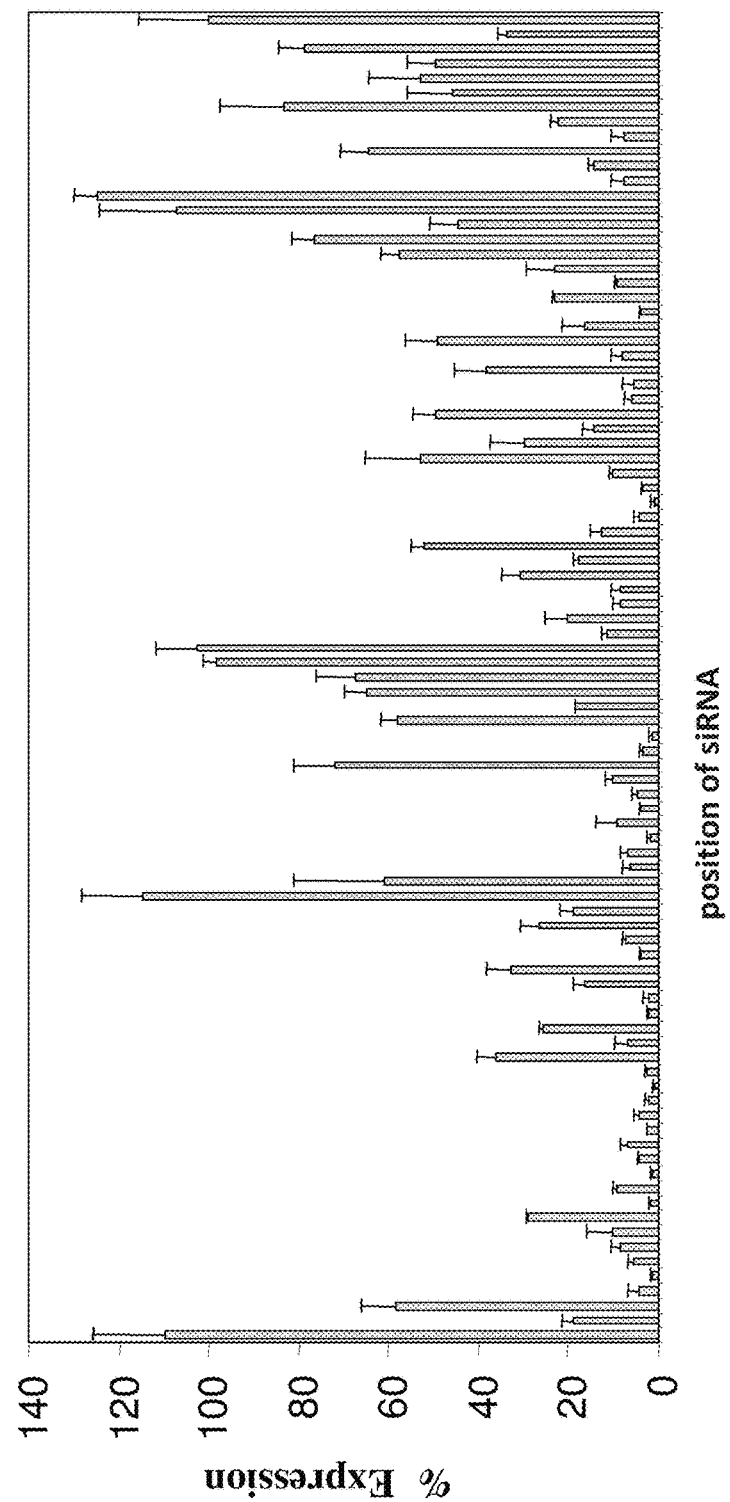
FIG. 15 represents a functional walk where siRNA beginning on every other base pair of a region of the luciferase gene are tested for the ability to silence the luciferase gene. The Y-axis represents the percent expression relative to a control. The X-axis represents the position of each individual siRNA. Reading from left to right across the X-axis, the position designations are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid.
Figure 17B:
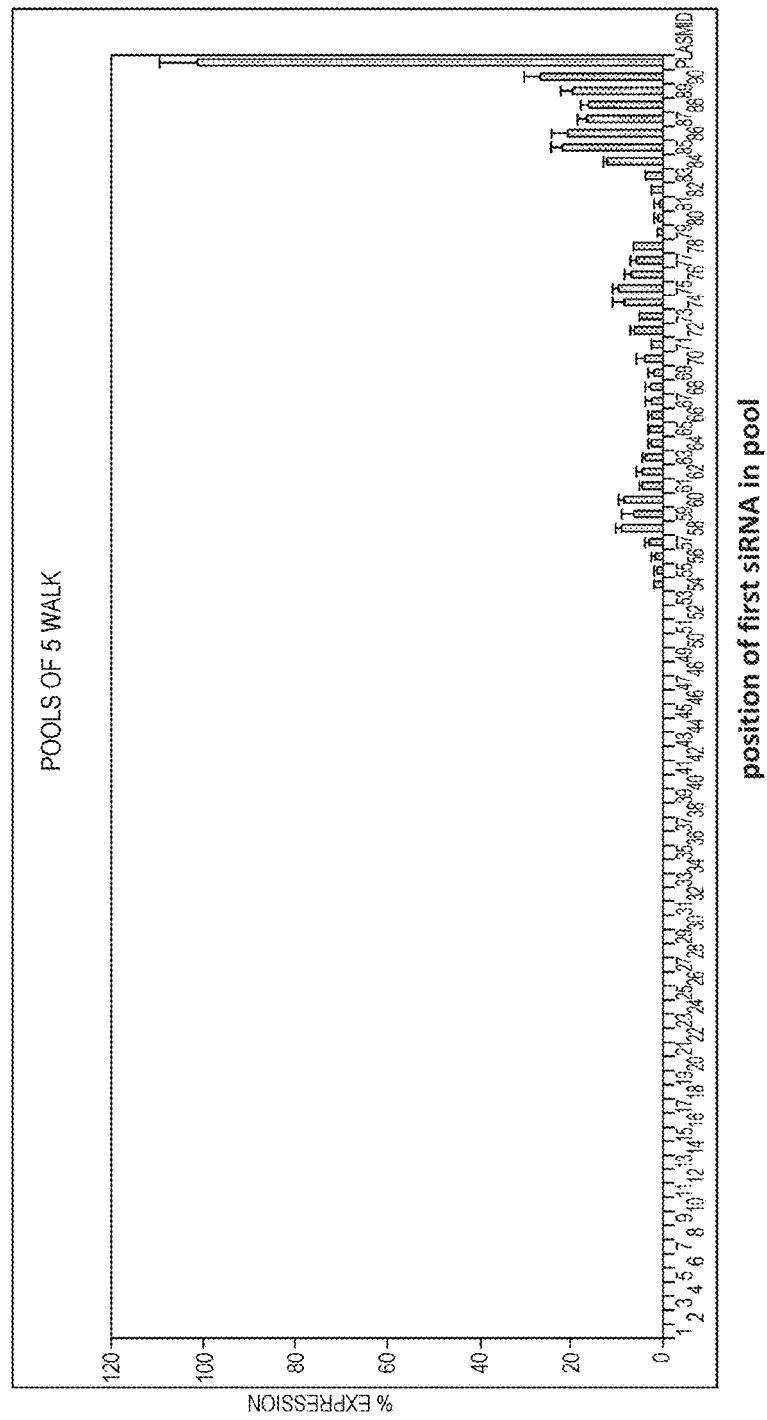

Transfection of individual siRNAs showed standard distribution of inhibitory effect. Some duplexes were active, while others were not. FIG. 15 represents a typical screen of ninety siRNA duplexes (SEQ. ID NO. 0032-0120) positioned two base pairs apart. As the figure suggests, the functionality of the siRNA duplex is determined more by a particular sequence of the oligonucleotide than by the relative oligonucleotide position within a gene or excessively sensitive part of the mRNA, which is important for traditional anti-sense technology.

Figure 18B:
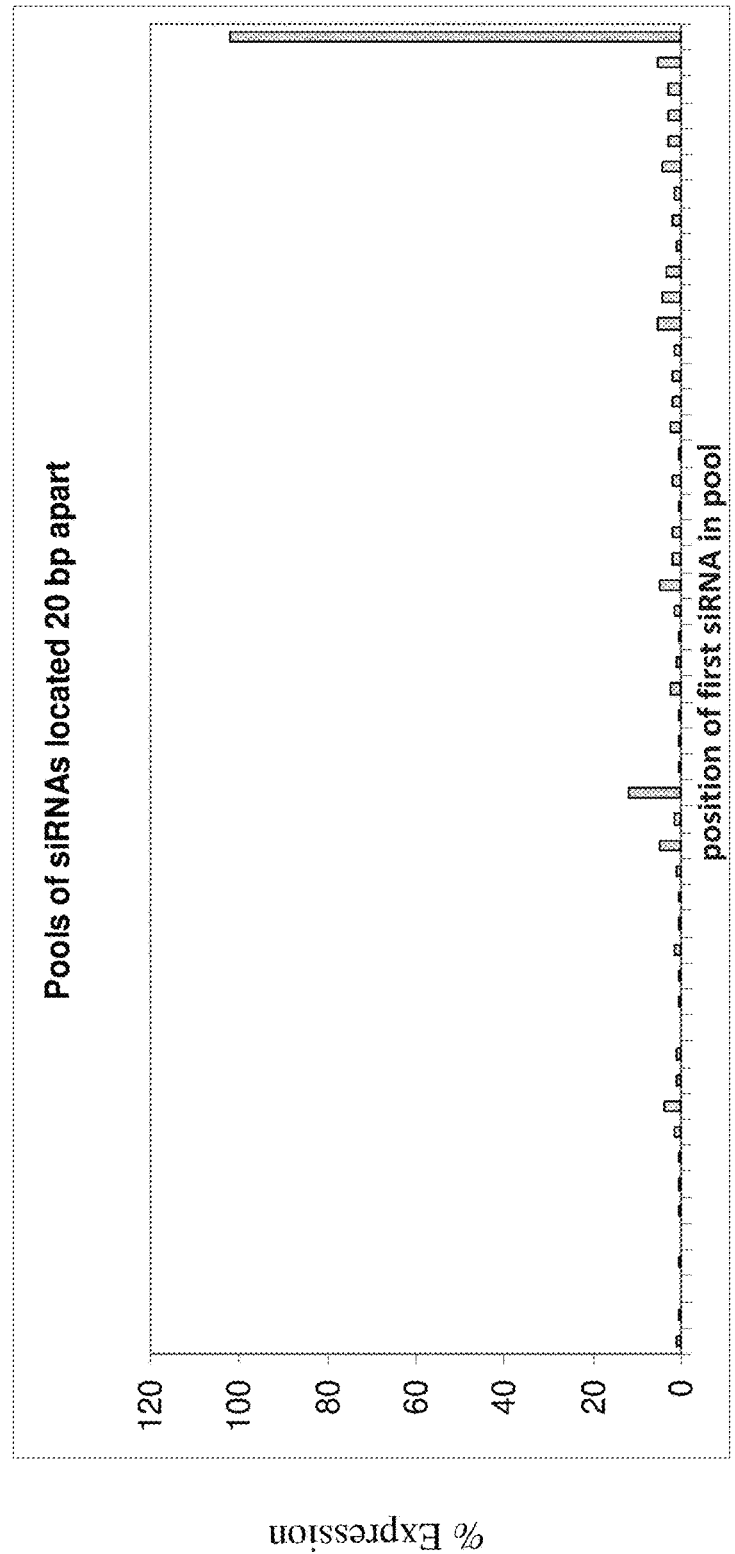

When two continuous oligonucleotides were pooled together, a significant increase in gene silencing activity was observed (see FIGS. 16A and B). A gradual increase in efficacy and the frequency of pools functionality was observed when the number of siRNAs increased to 3 and 4 (FIGS. 16A, 16B, 17A, and 17B). Further, the relative positioning of the oligonucleotides within a pool did not determine whether a particular pool was functional (see FIGS. 18A and 18B, in which 100% of pools of oligonucleotides distanced by 2, 10 and 20 base pairs were functional).

However, relative positioning may nonetheless have an impact. An increased functionality may exist when the siRNA are positioned continuously head to toe (5' end of one directly adjacent to the 3' end of the others).

Figure 19:
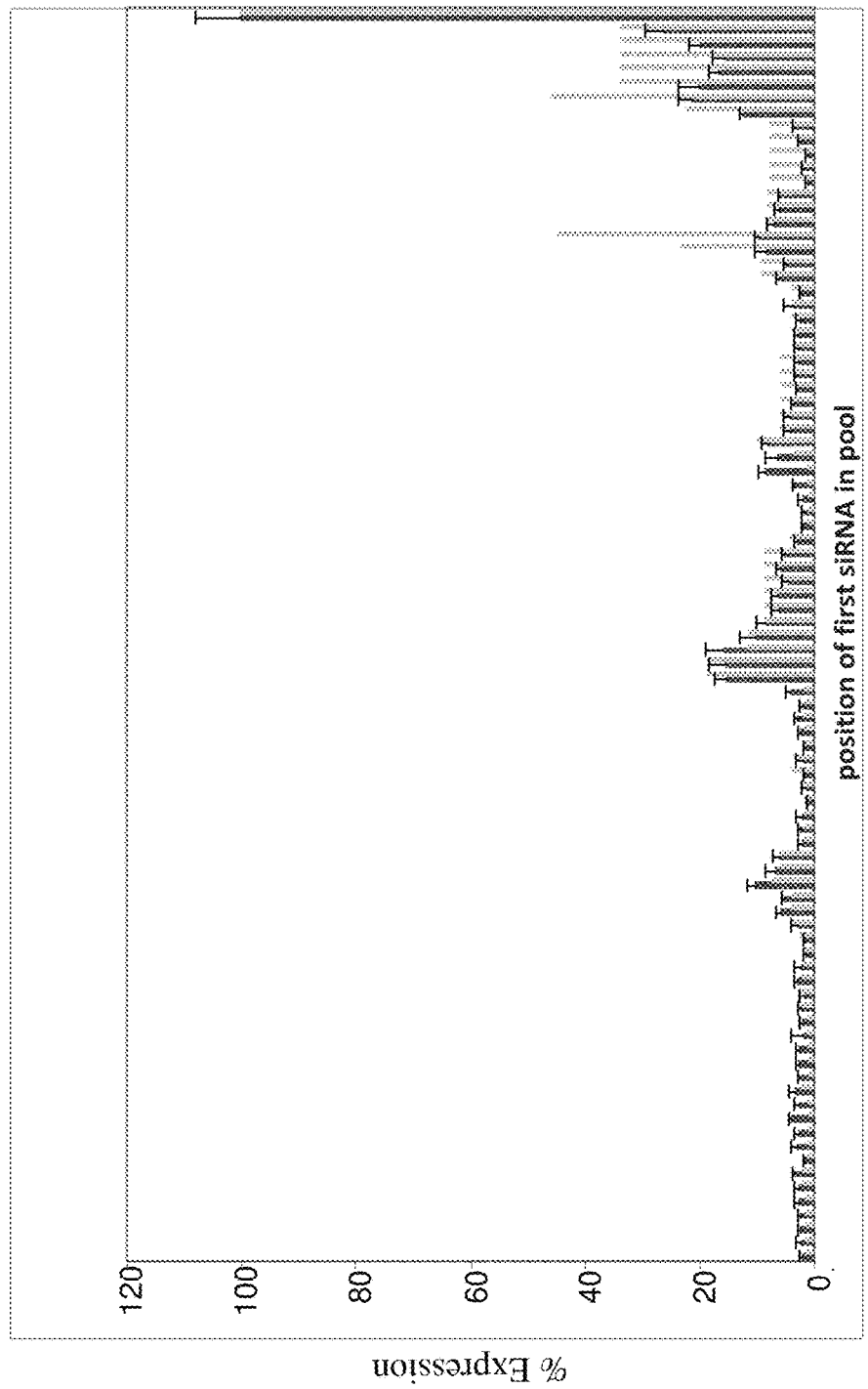
FIG. 19 shows that pools of siRNAs (dark gray bar) work as well (or better) than the best siRNA in the pool (light gray bar). The Y-axis represents the percent expression relative to a control. The X-axis represents the position of the first siRNA in each pool. The X-axis from left to right designations are-1, 2, 3, 4, 5, 6, 7, 8, 9, 10, 11, 12, 13, 14, 15, 16, 17, 18, 19, 20, 21, 22, 23, 24, 25, 26, 2 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and Plasmid
Figure 21A:
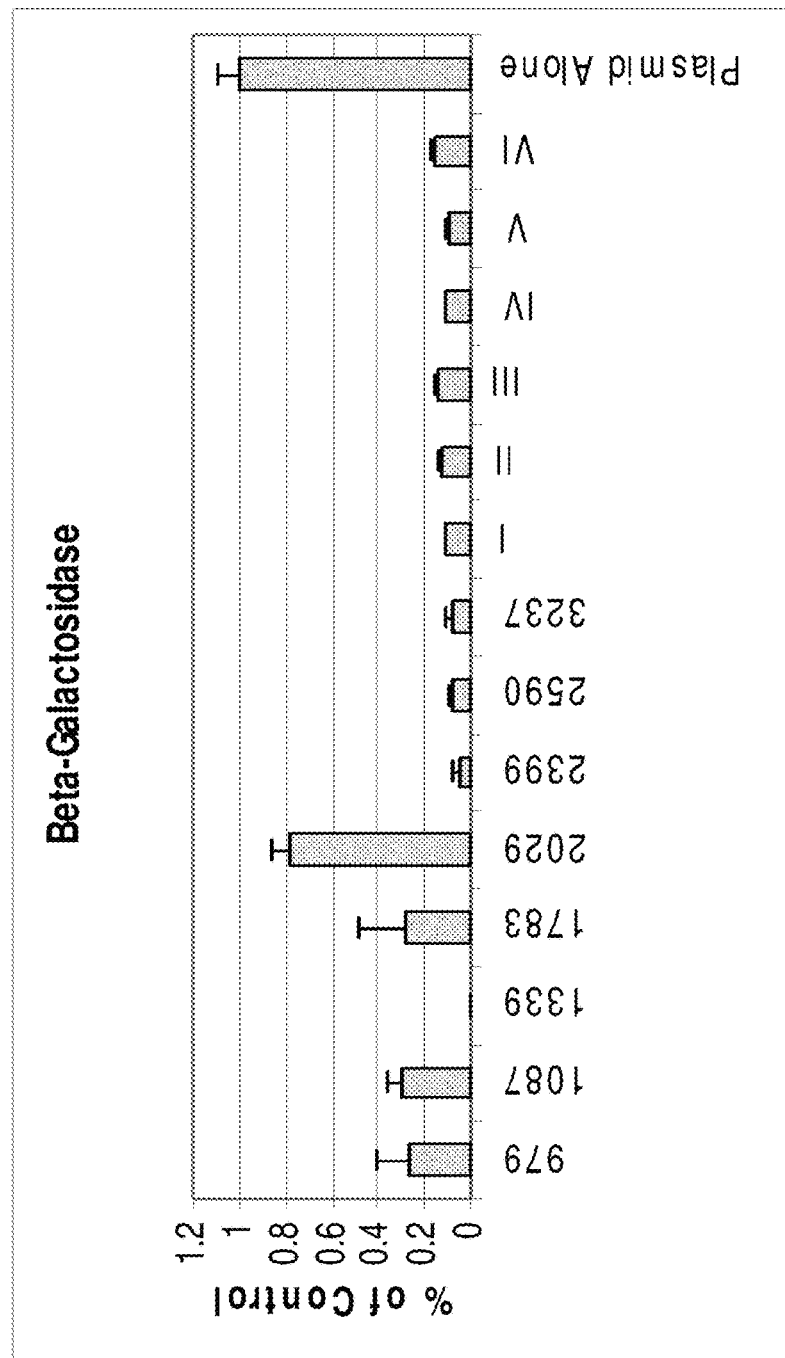
Figure 21B:
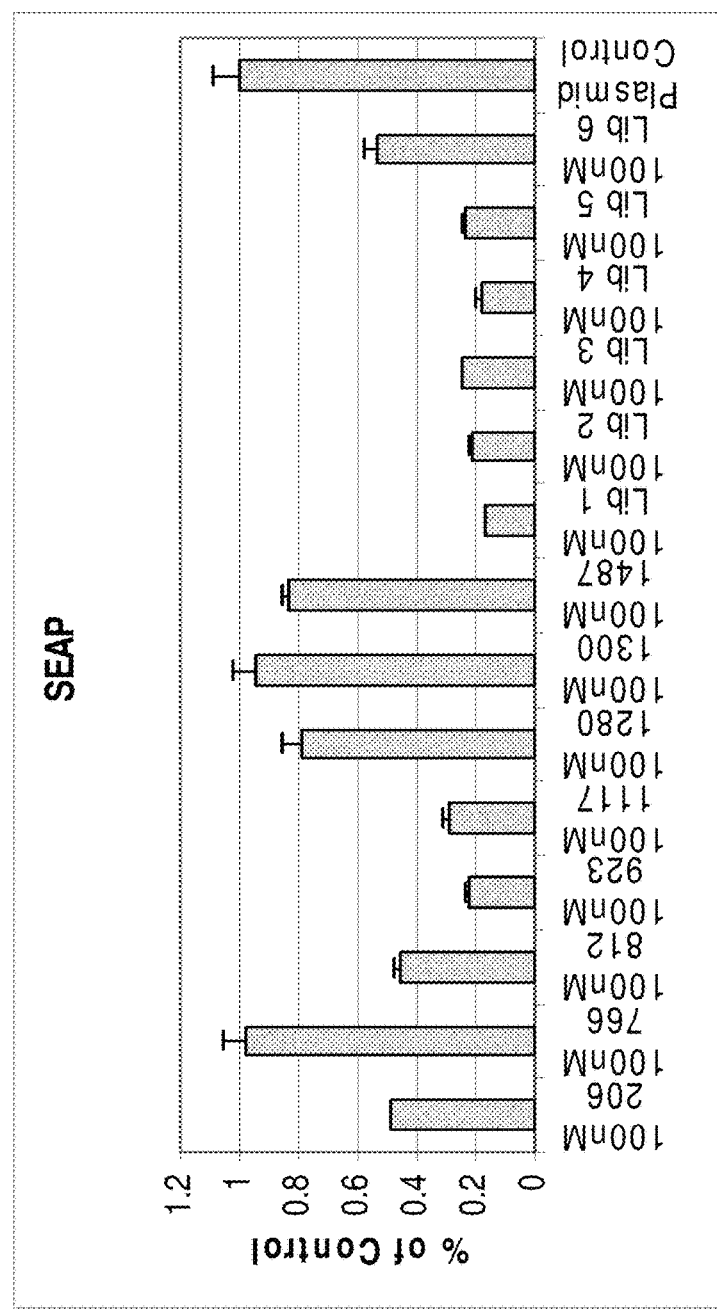

Additionally, siRNA pools that were tested performed at least as well as the best oligonucleotide in the pool, under the experimental conditions whose results are depicted in FIG. 19. Moreover, when previously identified non-functional and marginally (semi) functional siRNA duplexes were pooled together in groups of five at a time, a significant functional cooperative action was observed (see FIG. 20). In fact, pools of semi-active oligonucleotides were 5 to 25 times more functional than the most potent oligonucleotide in the pool. Therefore, pooling several siRNA duplexes together does not interfere with the functionality of the most potent siRNAs within a pool, and pooling provides an unexpected significant increase in overall functionality Example VIII Additional Evidence of the Benefits of Pooling Experiments were performed on the following genes: β-galactosidase, *Renilla* luciferase, and Secreted alkaline phosphatase, which demonstrates the benefits of pooling. (see FIGS. 21A, 21B and 21C). Individual and pools of siRNA (described in Figure legends 21A-C) were transfected into cells and tested for silencing efficiency. Approximately 50% of individual siRNAs designed to silence the above-specified genes were functional, while 100% of the pools that contain the same siRNA duplexes were functional.

Example IX

Highly Functional siRNA

Pools of five siRNAs in which each two siRNAs overlap to 10-90% resulted in 98% functional entities (>80% silencing). Pools of siRNAs distributed throughout the mRNA that were evenly spaced, covering an approximate 20-2000 base pair range, were also functional. When the pools of siRNA were positioned continuously head to tail relative to mRNA sequences and mimicked the natural products of Dicer cleaved long double stranded RNA, 98% of the pools evidenced highly functional activity (>95% silencing).

Example X

Human Cyclophilin B

Table IV above lists the siRNA sequences for the human cyclophilin B protein. A particularly functional siRNA may be selected by applying these sequences to any of Formula I to VII above.

Alternatively, one could pool 2, 3, 4, 5 or more of these sequences to create a kit for silencing a gene. Preferably, within the kit there would be at least one sequence that has a relatively high predicted functionality when any of Formulas I-VII is applied.

EXAMPLE XI

Sample Pools of siRNAS and Their Application to Human Disease

The genetic basis behind human disease is well documented and siRNA may be used as both research or diagnostic tools and therapeutic agents, either individually or in pools. Genes involved in signal transduction, the immune response, apoptosis, DNA repair, cell cycle control, and a variety of other physiological functions have clinical relevance and therapeutic agents that can modulate expression of these genes may alleviate some or all of the associated symptoms. In some instances, these genes can be described as a member of a family or class of genes and siRNA (randomly, conventionally, or rationally designed) can be directed against one or multiple members of the family to induce a desired result.

To identify rationally designed siRNA to each gene, the sequence was analyzed using Formula VIII or Formula X to identify rationally designed siRNA. To confirm the activity of these sequences, the siRNA are introduced into a cell type of choice (e.g., HeLa cells, HEK293 cells) and the levels of the appropriate message are analyzed using one of several art proven techniques. siRNA having heightened levels of potency can be identified by testing each of the before mentioned duplexes at increasingly limiting concentrations. Similarly, siRNA having increased levels of longevity can be identified by introducing each duplex into cells and testing functionality at 24, 48, 72, 96, 120, 144, 168, and 192 hours after transfection. Agents that induce >95% silencing at sub-nanomolar concentrations and/or induce functional levels of silencing for >96 hours are considered hyperfunctional.

Example XII

Validation of Multigene Knockout Using Rab5 and Eps

Two or more genes having similar, overlapping functions often leads to genetic redundancy. Mutations that knockout only one of, e.g., a pair of such genes (also referred to as homologs) results in little or no phenotype due to the fact that the remaining intact gene is capable of fulfilling the role of the disrupted counterpart. To fully understand the function of such genes in cellular physiology, it is often necessary to knockout or knockdown both homologs simultaneously. Unfortunately, concomitant knockdown of two or more genes is frequently difficult to achieve in higher organisms (e.g., mice) thus it is necessary to introduce new technologies dissect gene function. One such approach to knocking down multiple genes simultaneously is by using siRNA. For example, FIG. 11 showed that rationally designed siRNA directed against a number of genes involved in the clathrin-mediated endocytosis pathway resulted in significant levels of protein reduction (e.g., >80%). To determine the effects of gene knockdown on clathrin-related endocytosis, internalization assays were performed using epidermal growth factor and transferrin. Specifically, mouse receptor-grade EGF (Collaborative Research Inc.) and iron-saturated human transferrin (Sigma) were iodinated as described previously (Jiang, X., Huang, F., Marusyk, A. & Sorkin, A. (2003) *Mol Biol Cell* 14, 858-70). HeLa cells grown in 12-well dishes were incubated with $^{125}$I-EGF (1 ng/ml) or 125I-transferrin (1 g/ml) in binding medium (DMEM, 0.1% bovine serum albumin) at 37C, and the ratio of internalized and surface radioactivity was determined during 5-min time course to calculate specific internalization rate constant $k_e$ as described previously (Jiang, X et al.). The measurements of the uptakes of radiolabeled transferrin and EGF were performed using short time-course assays to avoid influence of the recycling on the uptake kinetics, and using low ligand concentration to avoid saturation of the clathrin-dependent pathway (for EGF Lund, K. A., Opresko, L. K., Strarbuck, C., Walsh, B. J. & Wiley, H. S. (1990) *J. Biol. Chem.* 265, 15713-13723).

Figure 22:
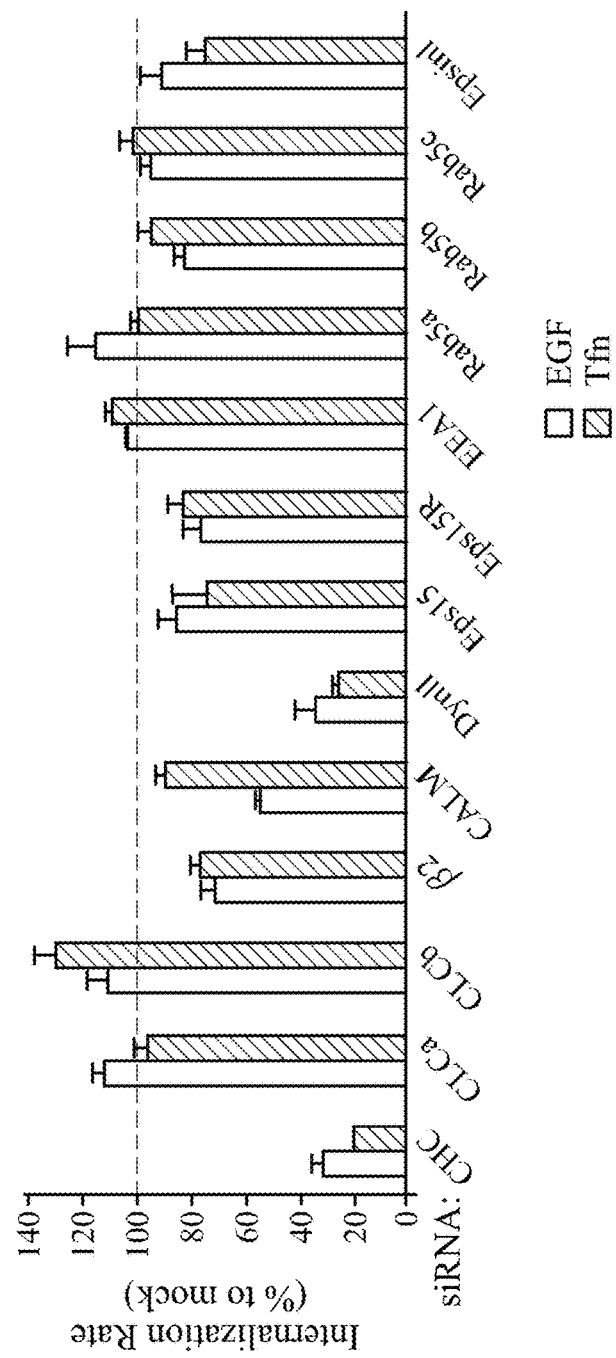
FIG. 22 shows the results of an EGFR and TfuR internalization assay when single gene knockdowns are performed. The Y-axis represents percent internalization relative to control.
Figure 23:
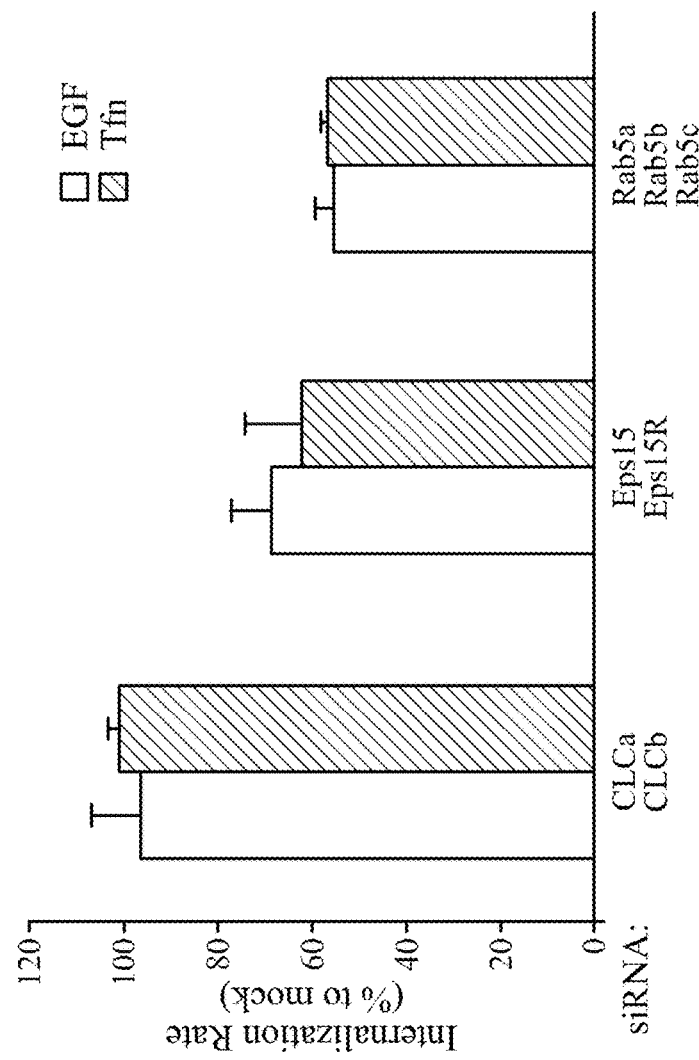
FIG. 23 shows the results of an EGFR and TfuR internalization assay when multiple genes are knocked down (e.g., Rab5a, b, c). The Y-axis represents the percent internalization relative to control.

The effects of knocking down Rab5a, 5b, 5c, Eps, or Eps 15R (individually) are shown in FIG. 22 and demonstrate that disruption of single genes has little or no effect on EGF or Tfn internalization. In contrast, simultaneous knock down of Rab5a, 5b, and 5c, or Eps and Eps 15R, leads to a distinct phenotype (note: total concentration of siRNA in these experiments remained constant with that in experiments in which a single siRNA was introduced, see FIG. 23). These experiments demonstrate the effectiveness of using rationally designed siRNA to knockdown multiple genes and validates the utility of these reagents to override genetic redundancy.

Example XIII

Validation of Multigene Targeting Using G6PD, GAPDH, PLK, AND UQC

Figure 24:
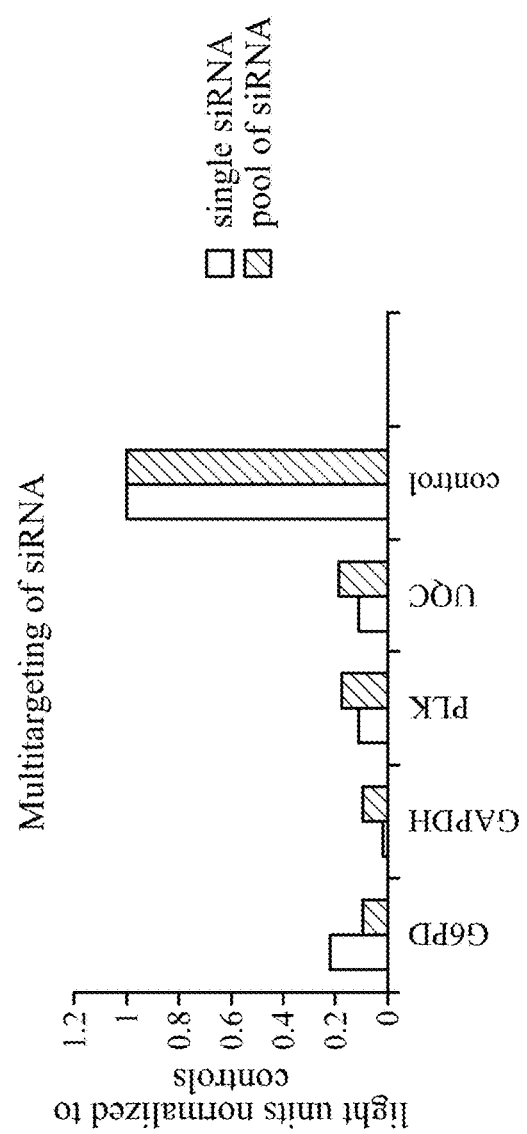
FIG. 24 shows the simultaneous knockdown of four different genes. siRNAs directed against G6PD, GAPDH, PLK, and UQC were simultaneously introduced into cells. Twenty-four hours later, cultures were harvested and assayed for mRNA target levels for each of the four genes. A comparison is made between cells transfected with individual siRNAs vs. a pool of siRNAs directed against all four genes.

Further demonstration of the ability to knock down expression of multiple genes using rationally designed siRNA was performed using pools of siRNA directed against four separate genes. To achieve this, siRNA were transfected into cells (total siRNA concentration of 100 nM) and assayed twenty-four hours later by B-DNA. Results shown in FIG. 24 show that pools of rationally designed molecules are capable of simultaneously silencing four different genes.

Example XIV

Validation of Multigene Knockouts as Demonstrated by Gene Expression Profiling, a Prophetic Example To further demonstrate the ability to concomitantly knockdown the expression of multiple gene targets, single siRNA or siRNA pools directed against a collection of genes (e.g., 4, 8, 16, or 23 different targets) are simultaneously transfected into cells and cultured for twenty-four hours. Subsequently, mRNA is harvested from treated (and untreated) cells and labeled with one of two fluorescent probes dyes (e.g., a red fluorescent probe for the treated cells, a green fluorescent probe for the control cells.). Equivalent amounts of labeled RNA from each sample is then mixed together and hybridized to sequences that have been linked to a solid support (e.g., a slide, "DNA CHIP"). Following hybridization, the slides are washed and analyzed to assess changes in the levels of target genes induced by siRNA.

Example XV

Identifying Hyperfunctional siRNA

Identification of Hyperfunctional Bcl-2 siRNA

Figure 25:
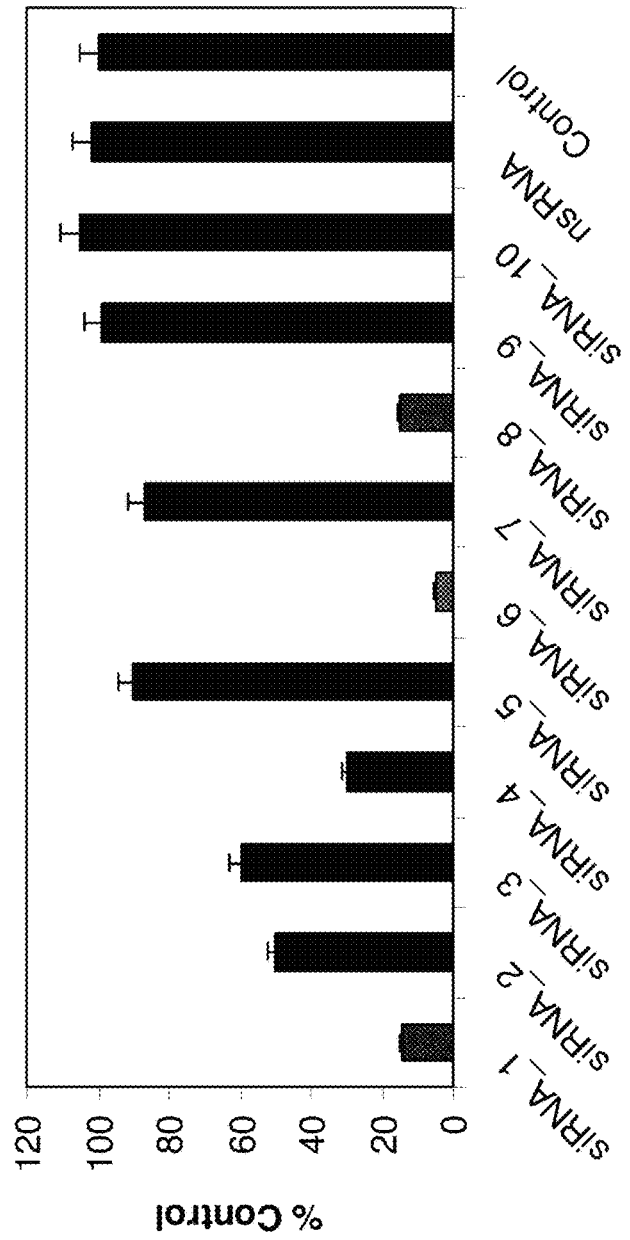
FIG. 25 shows the functionality of ten siRNAs at 0.3 nM concentrations.

The ten rationally designed Bcl2 siRNA (identified in FIG. 13, 14) were tested to identify hyperpotent reagents. To accomplish this, each of the ten Bcl-2 siRNA were individually transfected into cells at a 300 pM (0.3 nM) concentrations. Twenty-four hours later, transcript levels were assessed by B-DNA assays and compared with relevant controls. As shown in FIG. 25, while the majority of Bcl-2 siRNA failed to induce functional levels of silencing at this concentration, siRNA 1 and 8 induced >80% silencing, and siRNA 6 exhibited greater than 90% silencing at this sub-nanomolar concentration.

By way of prophetic examples, similar assays could be performed with any of the groups of rationally designed genes described in the Examples. Thus for instance, rationally designed siRNA sequences directed against a gene of interest could be introduced into cells at increasingly limiting concentrations to determine whether any of the duplexes are hyperfunctional.

Example XVI

Gene Silencing: Prophetic Example

Below is an example of how one might transfect a cell.

Select a cell line. The selection of a cell line is usually determined by the desired application. The most important feature to RNAi is the level of expression of the gene of interest. It is highly recommended to use cell lines for which siRNA transfection conditions have been specified and validated.

Plate the cells. Approximately 24 hours prior to transfection, plate the cells at the appropriate density so that they will be approximately 70-90% confluent, or approximately $1\times10^5$ cells/ml at the time of transfection. Cell densities that are too low may lead to toxicity due to excess exposure and uptake of transfection reagent-siRNA complexes. Cell densities that are too high may lead to low transfection efficiencies and little or no silencing. Incubate the cells overnight. Standard incubation conditions for mammalian cells are 37° C. in 5% $CO_2$. Other cell types, such as insect cells, require different temperatures and $CO_2$ concentrations that are readily ascertainable by persons skilled in the art. Use conditions appropriate for the cell type of interest.

siRNA re-suspension. Add 20 μl siRNA universal buffer to each siRNA to generate a final concentration of 50 μM.

siRNA-lipid complex formation. Use RNase-free solutions and tubes. Using the following table, Table VI:

TABLE VI

|  | 96-WELL | 24-WELL |
| --- | --- | --- |
| MIXTURE 1 (TRANSIT-TKO-PLASMID DILUTION MIXTURE) | | |
| Opti-MEM | 9.3 μl | 46.5 μl |
| TransIT-TKO (1 μg/μl) | 0.5 μl | 2.5 μl |
| MIXTURE 1 FINAL VOLUME | 10.0 μl | 50.0 μl |
| MIXTURE 2 (SIRNA DILUTION MIXTURE) | | |
| Opti-MEM | 9.0 μl | 45.0 μl |
| siRNA (1 μM) | 1.0 μl | 5.0 μl |
| MIXTURE 2 FINAL VOLUME | 0.0 μl | 50.0 μl |
| MIXTURE 3 (SIRNA-TRANSFECTION REAGENT MIXTURE) | | |
| Mixture 1 | 10 μl | 50 μl |
| Mixture 2 | 10 μl | 50 μl |
| MIXTURE 3 FINAL VOLUME | 20 μl | 100 μl |
| Incubate 20 minutes at room temperature | | |
| MIXTURE 4 (MEDIA-SIRNA/TRANSFECTION REAGENT MIXTURE) | | |
| Mixture 3 | 20 μl | 100 μl |
| Complete media | 80 μl | 400 μl |
| MIXTURE 4 FINAL VOLUME | 100 μl | 500 μl |
| Incubate 48 hours at 37° C. | | |

Transfection. Create a Mixture 1 by combining the specified amounts of OPTI-MEM serum free media and transfection reagent in a sterile polystyrene tube. Create a Mixture 2 by combining specified amounts of each siRNA with OPTI-MEM media in sterile 1 ml tubes. Create a Mixture 3 by combining specified amounts of Mixture 1 and Mixture 2. Mix gently (do not vortex) and incubate at room temperature for 20 minutes. Create a Mixture 4 by combining specified amounts of Mixture 3 to complete media. Add appropriate volume to each cell culture well. Incubate cells with transfection reagent mixture for 24-72 hours at 37° C. This incubation time is flexible. The ratio of silencing will remain consistent at any point in the time period. Assay for gene silencing using an appropriate detection method such as RT-PCR, Western blot analysis, immunohistochemistry, phenotypic analysis, mass spectrometry, fluorescence, radioactive decay, or any other method that is now known or that comes to be known to persons skilled in the art and that from reading this disclosure would be seen as being useful with the present invention. The optimal window for observing a knockdown phenotype is related to the mRNA turnover of the gene of interest, although 24-72 hours is standard. Final Volume reflects amount needed in each well for the desired cell culture format. When adjusting volumes for a Stock Mix, an additional 10% should be used to accommodate variability in pipetting, etc. Duplicate or triplicate assays should be carried out when possible.

Example XVII siRNAs That Target TTR siRNAs that target nucleotide sequences for TTR (NCBI accession number NM_000371.3) and having sequences generated in silico by the algorithms herein, are provided. In various embodiments, the siRNAs are rationally designed. In various embodiments, the siRNAs are functional or hyperfunctional. These siRNA that have been generated by the algorithms of the present invention include:

| siRNA Sense Sequence | Sequence ID Number |
| --- | --- |
| GGGAUGGGAUUUCAUGUAA | 438 |
| GGAAAUAGACACCAAAUCU | 439 |
| GAAAUAGACACCAAAUCUU | 440 |
| GAAUCCAAGUGUCCUCUGA | 441 |
| CAACUGAGGAGGAAUUUGU | 442 |
| UAGAAGGGAUAUACAAAGU | 443 |
| UAACCAAGAGUAUUCCAUU | 444 |
| GGAAUUUGUAGAAGGGAUA | 445 |
| GGUCAAAGUUCUAGAUGCU | 446 |
| CAGAAAGGCUGCUGAUGAC | 447 |
| AACCAAGAGUAUUCCAUUU | 448 |
| GACGAGGGAUGGGAUUUCA | 449 |
| UCACCAAUCCCAAGGAAUG | 450 |
| GAGGAGGAAUUUGUAGAAG | 451 |
| GUGCAUGUGUUCAGAAAGG | 452 |
| GCAGAGACAAUAAAACAUU | 453 |

-continued

| siRNA Sense Sequence | Sequence ID Number |
|---|---|
| GGAUAUACAAAGUGGAAAU | 454 |
| UCACAACUGAGGAGGAAUU | 455 |
| GUAGAAGGGAUAUACAAAG | 456 |
| UGAGGAGGAAUUUGUAGAA | 457 |
| CAAUAAAACAUUCCUGUGA | 458 |
| CGUCACCAAUCCCAAGGAA | 459 |
| CAUGUAACCAAGAGUAUUC | 460 |
| GAUGGGAUUUCAUGUAACC | 461 |
| GGACGAGGGAUGGGAUUUC | 462 |
| CUGCCUUGCUGGACUGGUA | 463 |
| UUGCUGGACUGGUAUUUGU | 464 |
| GAUUUCAUGUAACCAAGAG | 465 |
| CCAAGUGUCCUCUGAUGGU | 466 |
| CGAGGGAUGGGAUUUCAUG | 467 |
| CCGUGCAUGUGUUCAGAAA | 468 |
| GAUGGUCAAAGUUCUAGAU | 469 |
| GGAUUUCAUGUAACCAAGA | 470 |
| GCAUGCAGAGGUGGUAUUC | 471 |
| GGCCGUGCAUGUGUUCAGA | 472 |
| GACUGGUAUUUGUGUCUGA | 473 |
| GUCCAGGCAGAGACAAUAA | 474 |
| GGAUGGGAUUUCAUGUAAC | 475 |
| GAAUUUGUAGAAGGGAUAU | 476 |
| CCUCUGAUGGUCAAAGUUC | 477 |
| UCAAUGUGGCCGUGCAUGU | 478 |
| UUUCAUGUAACCAAGAGUA | 479 |
| CAAUGUGGCCGUGCAUGUG | 480 |
| AAGUGGAAAUAGACACCAA | 481 |

Thus, consistent with Example XVII, the present invention provides an siRNA that targets a nucleotide sequence for TTR, wherein the siRNA is selected from the group consisting of SEQ ID NOs: 438-481.

In another embodiment, an siRNA is provided, said siRNA comprising a sense region and an antisense region, wherein said sense region and said antisense region are at least 90% complementary, said sense region and said antisense region together form a duplex region comprising 18-30 base pairs, and said sense region comprises a sequence that is at least 90% similar to a sequence selected from the group consisting of: SEQ. ID NOs 438-481.

In another embodiment, an siRNA is provided wherein the siRNA comprises a sense region and an antisense region, wherein said sense region and said antisense region are at least 90% complementary, said sense region and said antisense region together form a duplex region comprising 18-30 base pairs, and said sense region comprises a sequence that is identical to a contiguous stretch of at least 18 bases of a sequence selected from the group consisting of: SEQ. ID NOs 438-481.

In another embodiment, an siRNA is provided wherein the siRNA comprises a sense region and an antisense region, wherein said sense region and said antisense region are at least 90% complementary, said sense region and said antisense region together form a duplex region comprising 19-30 base pairs, and said sense region comprises a sequence that is identical to a contiguous stretch of at least 18 bases of a sequence selected from the group consisting of: SEQ. ID NOs 438-481.

In another embodiment, a pool of at least two siRNAs is provided, wherein said pool comprises a first siRNA and a second siRNA, said first siRNA comprises a duplex region of length 18-30 base pairs that has a first sense region that is at least 90% similar to 18 bases of a first sequence selected from the group consisting of: SEQ ID NOS: 438-481 and said second siRNA comprises a duplex region of length 18-30 base pairs that has a second sense region that is at least 90% similar to 18 bases of a second sequence selected from the group consisting of: SEQ. ID NOs 438-481 and wherein said first sense region and said second sense region are not identical.

In another embodiment, a pool of at least two siRNAs is provided, wherein said pool comprises a first siRNA and a second siRNA, said first siRNA comprises a duplex region of length 18-30 base pairs that has a first sense region that is identical to at least 18 bases of a sequence selected from the group consisting of: SEQ. ID NOs 438-481 and wherein the second siRNA comprises a second sense region that comprises a sequence that is identical to at least 18 bases of a sequence selected from the group consisting of: SEQ. ID NOs 438-481.

In another embodiment, a pool of at least two siRNAs is provided, wherein said pool comprises a first siRNA and a second siRNA, said first siRNA comprises a duplex region of length 19-30 base pairs and has a first sense region comprising a sequence that is at least 90% similar to a sequence selected from the group consisting of: SEQ. ID NOs 438-481 and said duplex of said second siRNA is 19-30 base pairs and comprises a second sense region that comprises a sequence that is at least 90% similar to a sequence selected from the group consisting of: SEQ. ID NOs 438-481.

In another embodiment, a pool of at least two siRNAs is provided, wherein said pool comprises a first siRNA and a second siRNA, said first siRNA comprises a duplex region of length 19-30 base pairs and has a first sense region comprising a sequence that is identical to at least 18 bases of a sequence selected from the group consisting of: SEQ. ID NOs 438-481 and said duplex of said second siRNA is 19-30 base pairs and comprises a second sense region comprising a sequence that is identical to a sequence selected from the group consisting of: SEQ. ID NOs 438-481.

In each of the aforementioned embodiments, preferably the antisense region is at least 90% complementary to a contiguous stretch of bases of one of the NCBI sequences identified in Example XVII; each of the recited NCBI sequences is incorporated by reference as if set forth fully herein. In some embodiments, the antisense region is 100% complementary to a contiguous stretch of bases of one of the NCBI sequences identified in Example XVII.

Further, in some embodiments that are directed to siRNA duplexes in which the antisense region is 20-30 bases in length, preferably there is a stretch of 19 bases that is at least 90%, more preferably 100% complementary to the recited sequence id number and the entire antisense region is at least 90% and more preferably 100% complementary to a contiguous stretch of bases of one of the NCBI sequences identified in Example XVII.

While the invention has been described in connection with specific embodiments thereof, it will be understood that it is capable of further modifications and this application is intended to cover any variations, uses, or adaptations of the invention following, in general, the principles of the invention and including such departure from the present disclosure as come within known or customary practice within the art to which the invention pertains and as may be applied to the essential features hereinbefore set forth and as follows in the scope of the appended claims.

We claim:

1. An siRNA molecule, wherein said siRNA molecule consists of: (a) a duplex region; and
    (b) either no overhang regions or at least one overhang region, wherein each overhang region contains six or fewer nucleotides, wherein the duplex region consists of a sense region and an antisense region, wherein said sense region and said antisense region together form said duplex region and said sense region and said antisense region are each 19-30 nucleotides in length and said antisense region comprises a sequence that is the complement of SEQ ID NO:463.

2. The siRNA molecule of claim 1, wherein said antisense region and said sense region are each 19-25 nucleotides in length.

3. The siRNA molecule of claim 2, wherein said antisense region and said sense region are each 19 nucleotides in length.

4. The siRNA molecule of claim 1, wherein said siRNA molecule has at least one overhang region.

5. The siRNA molecule of claim 1, wherein said siRNA molecule has no overhang regions.

6. The siRNA molecule of claim 2, wherein said siRNA molecule has at least one overhang region.

7. The siRNA molecule of claim 2, wherein said siRNA molecule has no overhang regions.

8. The siRNA molecule of claim 3, wherein said siRNA molecule has at least one overhang region.

9. The siRNA molecule of claim 3, wherein said siRNA molecule has no overhang regions.

10. A chemically synthesized double stranded siRNA molecule, wherein:
    (a) each strand of said double stranded siRNA molecule is between 19 and 30 nucleotides in length; and
    (b) one strand of said siRNA molecule comprises a sequence that is the complement of SEQ ID NO:463.

11. The chemically synthesized double stranded siRNA molecule of claim 10, wherein each strand of said siRNA molecule is 19-25 nucleotides in length.

12. The chemically synthesized double stranded siRNA molecule of claim 11, wherein each strand of said siRNA molecule is 19 nucleotides in length.

* * * * *